(12) United States Patent
Schilling et al.

(10) Patent No.: US 8,129,160 B2
(45) Date of Patent: Mar. 6, 2012

(54) METHOD OF SCREENING FOR INHIBITORS OF GLUTAMINYL CYCLASE ACTIVITY

(75) Inventors: Stephan Schilling, Halle/Saale (DE); Holger Cynis, Halle/Saale (DE); Jens-Ulrich Rahfeld, Lieskau (DE); Hans-Ulrich Demuth, Halle/Saale (DE)

(73) Assignee: Probiodrug AG, Halle (Salle) (DE)

( * ) Notice: Subject to any disclaimer, the term of this patent is extended or adjusted under 35 U.S.C. 154(b) by 0 days.

(21) Appl. No.: 12/497,082

(22) Filed: Jul. 2, 2009

(65) Prior Publication Data

US 2010/0009337 A1 Jan. 14, 2010

Related U.S. Application Data

(62) Division of application No. 11/859,217, filed on Sep. 21, 2007, now abandoned.

(60) Provisional application No. 60/846,244, filed on Sep. 21, 2006, provisional application No. 60/947,780, filed on Jul. 3, 2007.

(51) Int. Cl.
*C12N 9/00* (2006.01)
*C12N 9/10* (2006.01)
*C12N 1/20* (2006.01)
*C12N 15/00* (2006.01)
*C07H 21/04* (2006.01)

(52) U.S. Cl. ............... 435/183; 435/193; 435/252.3; 435/320.1; 536/23.2

(58) Field of Classification Search ............... None
See application file for complete search history.

(56) References Cited

U.S. PATENT DOCUMENTS

| | | |
|---|---|---|
| 7,304,086 B2 | 12/2007 | Schilling |
| 7,371,871 B2 | 5/2008 | Schilling |
| 7,381,537 B2 | 6/2008 | Demuth |
| 7,462,599 B2 | 12/2008 | Schilling |
| 2004/0006011 A1 | 1/2004 | Gour et al. |
| 2004/0224875 A1 | 11/2004 | Schilling et al. |
| 2005/0137142 A1 | 6/2005 | Schultz |
| 2005/0171112 A1 | 8/2005 | Schultz |
| 2006/0100253 A1 | 5/2006 | Niestroj |
| 2007/0191366 A1 | 8/2007 | Hoffmann |
| 2008/0153892 A1 | 6/2008 | Schilling |
| 2008/0260688 A1 | 10/2008 | Buchholz et al. |
| 2008/0286810 A1 | 11/2008 | Demuth |
| 2009/0018087 A1 | 1/2009 | Schilling |
| 2009/0068699 A1 | 3/2009 | Schilling |
| 2009/0149394 A1 | 6/2009 | Schilling |

FOREIGN PATENT DOCUMENTS

| | | |
|---|---|---|
| DE | 293584 | 5/1991 |
| WO | 01/09090 | 2/2001 |
| WO | 01/53331 | 7/2001 |
| WO | 03/045321 | 6/2003 |
| WO | 2004/098591 | 11/2004 |
| WO | 2004/098625 | 11/2004 |
| WO | 2005/039548 | 5/2005 |
| WO | 2005/049025 | 6/2005 |
| WO | 2005/075436 | 8/2005 |
| WO | 2008/034891 | 3/2008 |
| WO | 2008/055947 | 5/2008 |

OTHER PUBLICATIONS

Whisstock et al. Q Rev Biophys. Aug. 2003;36(3):307-40.*
Chica et al. Curr Opin Biotechnol. Aug. 2005;16(4):378-84.*
Sen et al. Appl Biochem Biotechnol. Dec. 2007;143(3):212-23.*
Buchholz et al., The First Potent Inhibitors for Human Glutaminyl Cyclase: Synthesis and Structure—Activity Relationship, J Medicinal Chemistry 2006, 49, 664-677.
Suzuki et al., *Homo sapiens* mRNA for glutaminyl-peptide cyclotransferase-like variant. clone: CBLO3904., EMBL 2006.
Suzuki et al., Glutaminyl-peptide cyclotransferase-like variant (fragment), UniProt 2006.
Penn et al., Human Genome Derived Single Exon Probe, GENSEQ 2004.
Schilling et al., Identification of Human Glutaminyl Cyclase as a Metalloenzyme, Potent Inhibition by Imidazole Derivatives and Hetercyclic Chelators, The Journal of Biological Chemistry, vol. 278, No. 50, Dec. 12, 2003, pp. 49773-49779.
Ohsugi et al. Anti-platelet Aggregation and Anti-blood Coagulation Activities of Dipicolinic Acid, A Sporal Component of *Bacillus subtilis* Natto, Chemical Abstracts Service 2005.
Chica et al., Semi-rational approaches to engineering enzyme activity: combining the benefits of directed evolution and rational design, Curr Opin Biotechnol 2005 16(4) pp. 378-384.
Sen et al, Developments in directed evolution for improving enzyme functions, Appl Biotechnol 2007 143(3) pp. 212-223.
Karim et al. Accession AAL61267 Sep. 22, 2003.
Jansen et al., Hydantoin-Substituted 4,6-Dichloroindole-2-carboxylic Acids as Ligands with High Affinity for the Glycine Binding Site of the NMDA receptor, J Med Chem, 2003, 46:64-73.
Werbel and Elslager, Antischistosomal Effects of 5-(2,4,5-Trichlorophenyl)hydantoin and Related Compounds, J Med Chem, 1977, 20:1569-72.

* cited by examiner

*Primary Examiner* — Christian Fronda
(74) *Attorney, Agent, or Firm* — SNR Denton US LLP

(57) ABSTRACT

Novel glutaminyl-peptide cyclotransferase-like proteins (QPCTLs), which are isoenzymes of glutaminyl cyclase (QC, EC 2.3.2.5), and to isolated nucleic acids coding for these isoenzymes, all of which are useful for the discovery of new therapeutic agents, for measuring cyclase activity, and for determining the inhibitory activity of compounds against these glutaminyl cyclase isoenzymes.

19 Claims, 34 Drawing Sheets

Figure 1

```
hQC       ---------------MAGGRHRRVVGTLHLL----LLVAALPWASRG--VSPSASAWPE--
hisoQC    MRSGGRGRPRLRLGERGLMEPLLPPKRRLLPRVRLLP-LLLALAVGSAFYTIWSGWHRRT
mQC       ---------------MAGSEDKLVVGTLHLL----LLQATVLSLTAGN-LSLVSAAWTQ--
misoQC    MSPGSRGRPRQRLEDRGLMKPPSLSKRRLLPRVQFLPLLLLALAMGLAFYIVWNSWHPGV
                         *  .     .:**  :*  :  .:*  .    .* hQC       -----EKNYHQPAI--LNSSALRQIAEGTSISEMWQNDLQPLLIERYPGSPGSYAARQHI
hisoQC    EELPLGRELRVPLIGSLPEARLRRVVGQLDPQRLWSTYLRPLLVVRTPGSPGNLQVRKFL
mouse     -----EKNHHQPAH--LNSSSLQQVAEGTSISEMWQNDLRPLLIERYPGSPGSYSARQHI
misoQC    EEMSRSRDLRVPLIGSLSEAKLRLVVGQLDPQRLWGTFLRPLLIVRPPGSSGNLQVRKFL
               ::  :*      * .: *:  .    ...:*  .  *;***:  *  ***.*.  .*:.:

hQC       MQRIQRLQADWVLEIDTFLSQTPYGYRSFSNIISTLNPTAKRHLVLACHYDSKYFSHWNN
hisoQC    EATLRSLTAGWHVELDPFTASTPLGPVDFGNVVATLDPRAARHLTLACHYDSKLFPPG-S
mouse     MQRIQRLQAEWVVEVDTFLSRTPYGYRSFSNIISTLNPEAKRHLVLACHYDSKYFPRWDS
misoQC    EATLQSLSAGWHVELDPFTASTPLGPLDFGNVVATLDPGAARHLTLACHYDSKFFPPG-L
          ::  *  *  :*:*.*  :  **  *    .*.*::**:* *  *** *******  *.

hQC       RVFVGATDSAVPCAMMLELARALDKKLLSLKTVSDSKPDLSLQLIFFDGEEAFLHWSPQD
hisoQC    TPFVGATDSAVPCALLLELAQALDLELSRAK--KQAAP-VTLQLLFLDGEEALKEWGPKD
mouse     RVFVGATDSAVPCAMMLELARALDKKLHSLKDVSGSKPDLSLRLIFFDGEEAFHHWSPQD
misoQC    PPFVGATDSAVPCALLLELVQALDAMLSRIK--QQAAP-VTLQLLFL-GEEALKEWGPKD
           *********:;*  :  ***    *   .  : *   :*:*:*: ****:  .*.*:* hQC       SLYGSRHLAAKMASTPHPPGARGTSQLHGMDLLVLLDLIGAPNPTFPNFFPNSARWFERL
hisoQC    SLYGSRHLAQLMESIPHSPG---PTRIQAIELFMLLDLLGAPNPTFYSHFPRTVRWFHRL
mouse     TLYGSRHLAQKMASSPHPPGSRGTNQLDGMDLLVLLDLIGAANPTFPNFFPKTTRWFNRL
misoQC    SLYGSRHLAQIMESIPHSPG---PTRIQAIELFVLLDLLGASSPIFFSHFPRTARWFQRL
          :********  *  *  **.**    ..:;..::*::****:**.. *  ..** :  ***:**

hQC       QAIEHELHELGLLKDHSLEGRYFQNYSYGGVIQDDHIPFLRRGVPVLHLIPSPFPEVWHT
hisoQC    RSIEKRLHRLNLLQSHPQEVMYFQPGEPSGSVEDDHIPFLRRGVPVLHLISTPFPAVWHT
mouse     QAIEKELYELGLLKDHSLERKYFQNFGYGNIIQDDHIPFLRKGVPVLHLIASPSPEVWHT
misoQC    RSIEKRLHRLNLLQSHPQEVMYFQPGEPPGPVEDDHIPFLRRGVPVLHLIATPFPAVLHT
          ::**:.*:.*.**:*. *   *       . ;:******.:*******:* *  * ** hQC       MDDNEENLDESTIDNLNKILQVFVLEYLHL
hisoQC    PADTEVNLHPPTVHNLCRILAVFLAEYLGL
mouse     MDDNEENLHASTIDNLNKIIQVFVLEYLHL
misoQC    PADTEANLHPPTVHNLSRILAVFLAEYLGL
           *.* **, .*:.**  :*: **: *** *
```

Identity:   38.97%
Similarity  65.64%

Figure 2

```
hisoQC         MRSGGRGRPRLRLGERGLMEPLLPPKRRLLPRVRLLP-LLLALAVGSAFYTIWSGWHRRT
M_fascicularis MRSGGRGRPRLRLGERGVMEPLLPPKRRLLPRVRLLP-LLLALAVGSAFYTIWSGWHRRT
M_mulatta      MRSGGRGRPRLRLGERGVMEPLLPPKRRLLPRVRLLP-LLLALAVGSAFYTIWSGWHRRT
C_familiaris   MPSGGRGRSRLRLGERGLLEPPSPPKRRLLPRAHFLPLLLLALALASATYTIWSGWHHQT
R_norvegicus   MSPASRGRSRQRLGDRGLMKPPSLSKRRLLPRVQLLPLLLLALALGLAFYIVWNSWHPGV
M_musculus     MSPGSRGRPRQRLEDRGLMKPPSLSKRRLLPRVQFLPLLLLALAMGLAFYIVWNSWHPGV
B_taurus       MPSGGRGRPRLQVGERSLLERPSPPKRRLIPRAQLLPQLLLALTVASVFYTIWRIWHSQT
               * ...***.* :: :*.:::    .****:**.::** *****::. . * :*  **  .

hisoQC         EELPLGRELRVPLIGSLPEARLRRVVGQLDPQRLWSTYLRPLLVVRTPGSPGNLQVRKFL
M_fascicularis EELPLGRELRVPLIGSLPEARLRRVVGQLDPQRLWGTYLRPLLVVRTPGSPGNLQVRKFL
M_mulatta      EELPLGRELRVPLIGSLPEARLRRVVGQLDPQRLWGTYLRPLLVVRTPGSPGNLQVRKFL
C_familiaris   EELPRGRELRGRLIGSLSEARLRRVVGQLDPHRLWNTYLRPLLVVRTPGSPGNLQVRKFL
R_norvegicus   EEVSRSRDLRVPLIGSLSEAKLRLVVGQLDPQRLWGTFLRPLLIVRPPGSPGNLQVRKFL
M_musculus     EEMSRSRDLRVPLIGSLSEAKLRLVVGQLDPQRLWGTFLRPLLIVRPPGSSGNLQVRKFL
B_taurus       EELPLGRELRGPLIGSLPEARVRRVVGQLDPHRLWNTFLRPLLVVRTPGSPGNLQVRKFL
               **:. .*: *.::* *****:*.*:***:.*.****** hisoQC         EATLRSLTAGWHVELDPFTASTPLGPVDFGNVVATLDPRAARHLTLACHYDSKLFPPGST
M_fascicularis EATLRSLTAGWHVELDPFTASTPLGPVDFGNVVATLDPGAARHLTLACHYDSKLFPPGST
M_mulatta      EATLRSLTAGWHVELDPFTASTPLGPVDFGNVVATLDPGAARHLTLACHYDSKLFPPGST
C_familiaris   EATLRTLTAGWHVELDPFTALTPLGPLDFGNVVATLDPGAARHLTLACHYDSKLFASESV
R_norvegicus   EATLQSLSAGWHVELDPFTASTPLGPLDFGNVVATLDPGAARHLTLACHYDSKFFPPGLP
M_musculus     EATLQSLSAGWHVELDPFTASTPLGPLDFGNVVATLDPGAARHLTLACHYDSKFFPPGLP
B_taurus       EATLRTLSAGWHIELDSFTASTPVGPLDFSNVVATLDPGAARHLTLACHYDSKLFPSDSA
               ****::*:****:***.*** **:**:**.********* *************:*..

hisoQC         PFVGATDSAVPCALLLELAQALDLELSRAKKQAAPVTLQLLFLDGEEALKEWGPKDSLYG
M_fascicularis PFVGATDSAVPCALLLELAQALDLELSRAKEQAAPVTLQLLFLDGEEALKEWGPKDSLYG
M_mulatta      PFVGATDSAVPCALLLELAQALDLELSRAKEQAAPVTLQLLFLDGEEALKEWGPKDSLYG
C_familiaris   PFVGATDSAVPCALLLELAQALDRELSRAKEQEAPVTLQLLFLDGEEALKEWGPTDSLYG
R_norvegicus   PFVGATDSAVPCALLLELVQALDVMLSRIKQQAAPVTLQLLFLDGEEALKEWGPKDSLYG
M_musculus     PFVGATDSAVPCALLLELVQALDAMLSRIKQQAAPVTLQLLFLDGEEALKEWGPKDSLYG
B_taurus       PFVGATDSAVPCSLLLELAQALDQELGKAKERAAPMTLQLIFLDGEEALKQWGPKDSLYG
               **********:*.** *.: *:: :*:***:*.*.*** hisoQC         SRHLAQLMESIPHSPGPTRIQAIELFMLLDLLGAPNPTFYSHFPRTVRWFHRLRSIEKRL
M_fascicularis SRHLAQLMESIPHSPGPTRIQAIELFMLLDLLGAPNPTFYSHFPRTVRWFHRLRSIEKRL
M_mulatta      SRHLAQLMESIPHSPGPTRIQAIELFMLLDLLGAPNPTFYSHFPRTVRWFHRLRSIEKRL
C_familiaris   SRHLAQLMESAPHSPGPTRIQAIELFMLLDLLGAPNPNFYSHFPHTARWFHRLRSIEKRL
R_norvegicus   SRHLAQIMESIPHSPGPTRIQAIELFVLLDLLGAPSPIFFSHFPRTARWFQRLRSIEKRL
M_musculus     SRHLAQIMESIPHSPGPTRIQAIELFVLLDLLGASSPIFFSHFPRTARWFQRLRSIEKRL
B_taurus       SRHLAQLMESTPHGLGSTRIQAIELFMLLDLLGAPNPTFYSHFPRTARWFHRLRSIEKRL
               ****:* **. *.*******:***..* *:****:*.*:****** hisoQC         HRLNLLQSHPQEVMYFQPGEPSGSVEDDHIPFLRRGVPVLHLISTPFPAVWHTPADTEVN
M_fascicularis HRLNLLQSHPQEVMYFQPGEPFGSVEDDHIPFLRRGVPVLHLISTPFPAVWHTPADTEAN
M_mulatta      HRLNLLQSHPQEVMYFQPGEPFGSVEDDHIPFLRRGVPVLHLISTPFPAVWHTPADTEAN
C_familiaris   HRMNLLQSHPQEVMYFQPGEPPGSVEDDHIPFLRRGVPVLHLISMPFPSVWHTPDDSEAN
R_norvegicus   HRLNLLQSHPQEVMYFQPGEPPGPVEDDHIPFLRRGVPVLHLIAMPFPAVWHTPADTEAN
M_musculus     HRLNLLQSHPQEVMYFQPGEPPGPVEDDHIPFLRRGVPVLHLIATPFPAVWHTPADTEAN
B_taurus       HRLNLLQSHPWEVMYFQTGEPPGSVEDDHIPFLRRGVPVLHLIATPFPSVWHTSDDSEAN
               :*** **.* .*********:.*:***. *.*.* hisoQC         LHPPTVHNLCRILAVFLAEYLGL
M_fascicularis LHPPTVHNLSRILAVFLAEYLGL
M_mulatta      LHPPTVHNLSRILAVFLAEYLGL
C_familiaris   LHPPTVHNLSRILAVFLAEYLGL
R_norvegicus   LHPPTVHNLSRILAVFLAEYLGL
M_musculus     LHPPTVHNLSRILAVFLAEYLGL
B_taurus       LHPPTVHNLSRILAVFLAEYLGL
               *********.*************
```

Identity:    71.28%

Similarity   90.86%

Figure 3

```
hQC      --MAGGRHRRVVGTLHLLLLVAALP--------WASRGVSPSASAWPEEKNYHQPAILNS
hisoQC   MEPLLPPKRRLLPRVRLLPLLLALAVGSAFYTIWSGWHRRTEELPLGRELRVPLIGSLPE
SgAP     ------------------------------------------------------APDIPL
VpAP     ----MPPITQQATVTAWLPQVDASQITGT-------------------------------IS hQC      SALRQIAEGTSISEMWQNDLQPLLIERYPGSPGSYAARQHIMQR---IQRLQADWVLEID
hisoQC   ARLRRVVGQLDPQRLWSTYLRPLLVVRTPGSPGNLQVRKFLEAT---LRSLTAGWHVELD
SGAP     ANVKAHLTQL------STIAANNGGNRAHGRPGYKASVDYVKAK---LDA--AGYTTTLQ
VpAP     ------------------SLESFTNRFYTTTSGAQASDWIASEWQALSA--SLPNASVK
                            *      ..    .:        :       :      :.

hQC      TFLSQTPYGYRSFSNIISTLNPT-AKRHLVLACHYDSKYFSHWNNR-VFVGATDSAVPCA
hisoQC   PFTASTPLGPVDFGNVVATLDPR-AARHLTLACHYDSKLFPP-GST-PFVGATDSAVPCA
SGAP     QFTSGGATGYNLIAN---WPGGD-PNKVLMAGAHLDSVS--------SGAGINDNGSGSA
VpAP     QVSHSGYNQ---KSVVMTITGSEAPDEWIVGGHLDSTIGSHTNEQSVAPGADDDDASGIA
             .               .   .   . .:  .  * **         *  *..    * hQC      MMLELARALDKKLLSLKTVSDSKPDLSLQLIFFDGEEAFLHWSPQDSLYGSRHLAAKMAS
hisoQC   LLLELAQALD---LELSRAKKQAAPVTLQLLFLDGEEALKEWGPKDSLYGSRHLAQLMES
SGAP     AVLETALAVSR--------AGYQPDKHLRFAWWGAEEL--------GLIGSKFYVNNLPS
VpAP     AVTEVIRVLSE--------NNFQPKRSIAFMAYAAFEEV--------GLRGSQDLANQYKS
         : *   .:.          .   : :   .*_*          .* **:   .     * hQC      TPHPPGARGTSQLHGMDLLVLLDLI---GAPNPTFPNFFPNSARWFERLQAIEHELHELG
hisoQC   IPHSP---GPTRIQAIELFMLLDLL---GAPNPTFYSHFPRTVRWFHRLRSIEKRLHRLN
SGAP     ADRS---------KLAGYLNFDMI---GSPNPGYFVYDDDPV--------IEKTFKNYF
VpAP     EGKN----------VVSALQLDMTNYKGSAQDVVFITDYTDS--------NFTQYLTQ-
          :                :  :*:    *:..:

hQC      LLKDHSLEGRYFQNY----SYGGVIQDDHIPFLRRGVPVLHLIP----------------
hisoQC   LLQSHPQEVMYFQPG----EPSGSVEDDHIPFLRRGVPVLHLIS----------------
SGAP     AGLNVPTEI---------ETEGDGRSDHAPFKNVGVPVGGLFTGAGYTKSAAQAQKWGG
VpAP     ------LMDEYLPSLTYGFDTCGYACSDHASWHNAGYPAAMPFE----------------
                .    *    .** .:  .   *  *.      :

hQC      ---SPF----PEVWHTMDDNEENLDESTIDNLNKILQVFVLEYLHL--------------
hisoQC   ---TPF----PAVWHTPADTEVNLHPPTVHNLCRILAVFLAEYLGL--------------
SGAP     TAGQAF----DRCYHSSCDSLSNINDTALDR-NSDAAAHAIWTLSS--GTGEPPT----
VpAP     ---SKFNDYNPRI-HTTQDTLANSDPTGSHA-KKFTQLGLAYAIEMGSATGDTPTPGNQ
                   *:  *. *  ...    .             :
```

Figure 4

```
hisoQC    MRSGGRGRPRLRLGERGLMEPLLPPKRRLLPVRLLPLLLALAVGSAFYTIWSGWHRRTE
hQC       MAGG-------R-------------HRRVVGTLHLLLLVAALPWAS--R----GVSPSAS
          *  .*       *               :**::   ::** *: **. .*    *    :.

hisoQC    ELPLGRELRVPLIGSLPEARLRRVVGQLDPQRLWSTYLRPLLVVRTPGSPGNLQVRKFLE
hQC       AWPEEKNYHQPAI--LNSSALRQIAEGTSISEMWQNDLQPLLIERYPGSPGSYAARQHIM
             *    ::  :  * *    * .:  **::.    . ..:*.. *:***: * ***** .  .*:.:

hisoQC    ATLRSLTAGWHVELDPFTASTPLGPVDFGNVVATLDPRAARHLTLACHYDSKLFPPGS-T
hQC       QRIQRLQADWVLEIDTFLSQTPYGYRSFSNIISTLNPTAKRHLVLACHYDSKYFSHWNNR
           ::  *  *.*  :*:*.*  :.** *   .*.*::**:* * ***.******** *.  .

hisoQC    PFVGATDSAVPCALLLELAQALDLELSRAKKQAAP---VTLQLLFLDGEEALKEWGPKDS
hQ        VFVGATDSAVPCAMMLELARALDKKLLSLKTVSDSKPDLSLQLIFFDGEEAFLHWSPQDS
           **********:.:****.*** :**  :* *. :  .    :.:***:*:*****: .*.*:**

hisoQC    LYGSRHLAQLMESIPHSP---GPTRIQAIELFMLLDLLGAPNPTFYSHFPRTVRWFHRLR
hQC       LYGSRHLAAKMASTPHPPGARGTSQLHGMDLLVLLDLIGAPNPTFPNFFPNSARWFERLQ
          ********  * * **.*    *.:::..::*:::**** ..**:..***.**:

hisoQC    SIEKRLHRLNLLQSHPQEVMYFQPGEPSGSVEDDHIPFLRRGVPVLHLISTPFPAVWHTP
hQC       AIEHELHELGLLKDHSLEGRYFQNYSYGGVIQDDHIPFLRRGVPVLHLPSPFPEVWHTM
          ::..*.**:.*.  *   ***   . .* ::****************.:* **** hisoQC    ADTEVNLHPPTVHNLCRILAVFLAEYLGL
hQC       DDNEENLDESTIDNLNKILQVFVLEYLHL
          *.* **.  .*:.**  :** **:  *** *
```

Identity:    45.24%

Similarity   71.98%

Figure 5

```
hQC        ---MAGGRHRRVVGTLHLLLLVAALP--------WASRGVSPSASAWPEEKNYHQPAILNS
hisoQC     MEPLLPPKRRLLPRVRLLPLLLALAVGSAFYTIWSGWHRRTEELPLGRELRVPLIGSLPE
            :   ::* :  . * **:*              *:.    .. . .* .   . * .

hQC        SALRQIAEGTSISEMWQNDLQPLLIERYPGSPGSYAARQHIMQRIQRLQADWVLEIDTFL
hisoQC     ARLRRVVGQLDPQRLWSTYLRPLLVVRTPGSPGNLQVRKFLEATLRSLTAGWHVELDPFT
            : **::.    . ..:*.. *:***: * *****.  .*:.:    :: * *.* :*:*.* hQC        SQTPYGYRSFSNIISTLNPTAKRHLVLACHYDSKYFSHWNNRVFVGATDSAVPCAMMLEL
hisoQC     ASTPLGPVDFGNVVATLDPRAARHLTLACHYDSKLFPPGS-TPFVGATDSAVPCALLLEL
           :.** *  .*.*:::**:* * ***.********* *.  .   *****.*******::***
                                                        _         _ hQC        ARALDKKLLSLKTVSDSKPDLSLQLIFFDGEEAFLHWSPQDSLYGSRHLAAKMASTPHPP
hisoQC     AQALDLELSRAKKQAAP---VTLQLLFLDGEEALKEWGPKDSLYGSRHLAQLMESIPHSP
           *:*** :*   *. : .    ::***:*:****:*  .*.*:********** * * **.*
                                         _                                   _ hQC        GARGTSQLHGMDLLVLLDLIGAPNPTFPNFFPNSARWFERLQAIEHELHELGLLKDHSLE
hisoQC     ---GPTRIQAIELFMLLDLLGAPNPTFYSHFPRTVRWFHRLRSIEKRLHRLNLLQSHPQE
              *.:::.:.:*::**:*** ...:.*.:.::..*.**:..*. * hQC        GRYFQNYSYGGVIQDDHIPFLRRGVPVLHLIPSPFPEVWHTMDDNEENLDESTIDNLNKI
hisoQC     VMYFQPGEPSGSVEDDHIPFLRRGVPVLHLISTPFPAVWHTPADTEVNLHPPTVHNLCRI
           ***  .  .* ::*****************.:*** **** *.*  **. .*::** :*
                                                        _          _ hQC        LQVFVLEYLHL
hisoQC     LAVFLAEYLGL
           * **: *** *
```

Figure 10
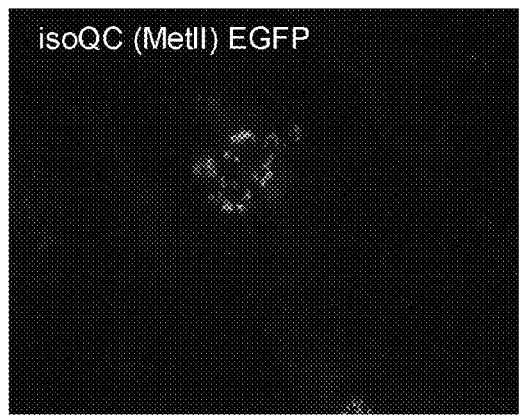
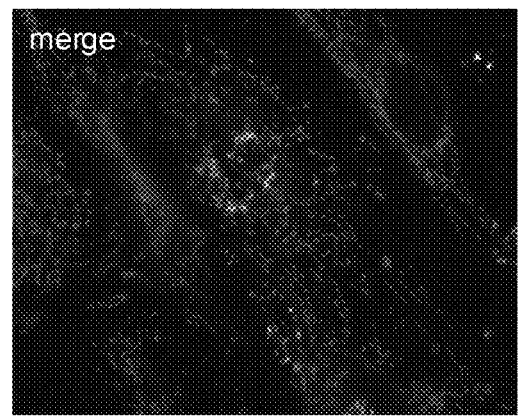
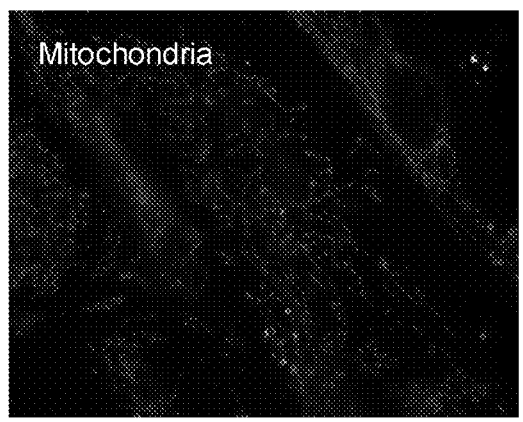

Figure 26
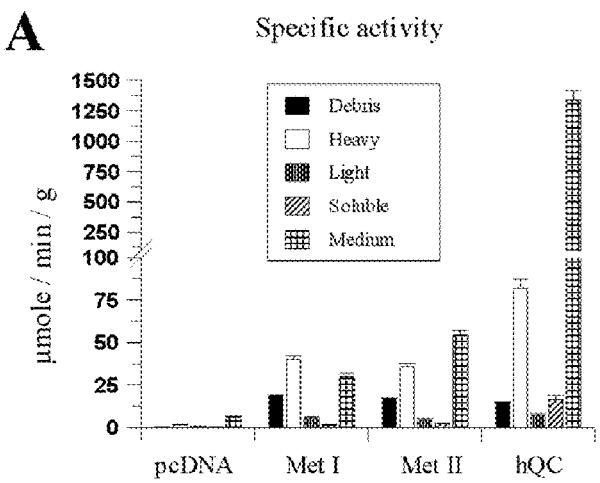
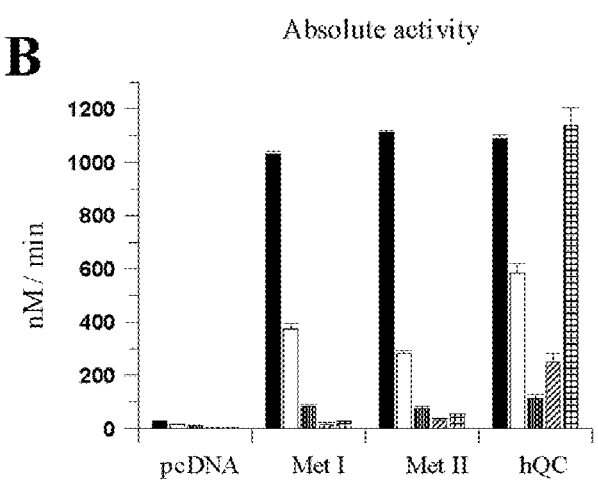
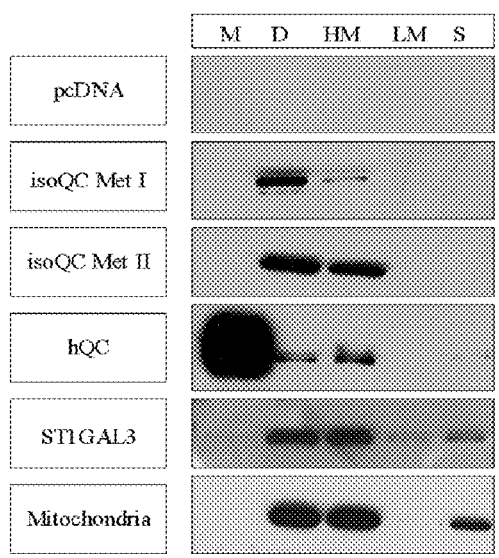

Figure 27
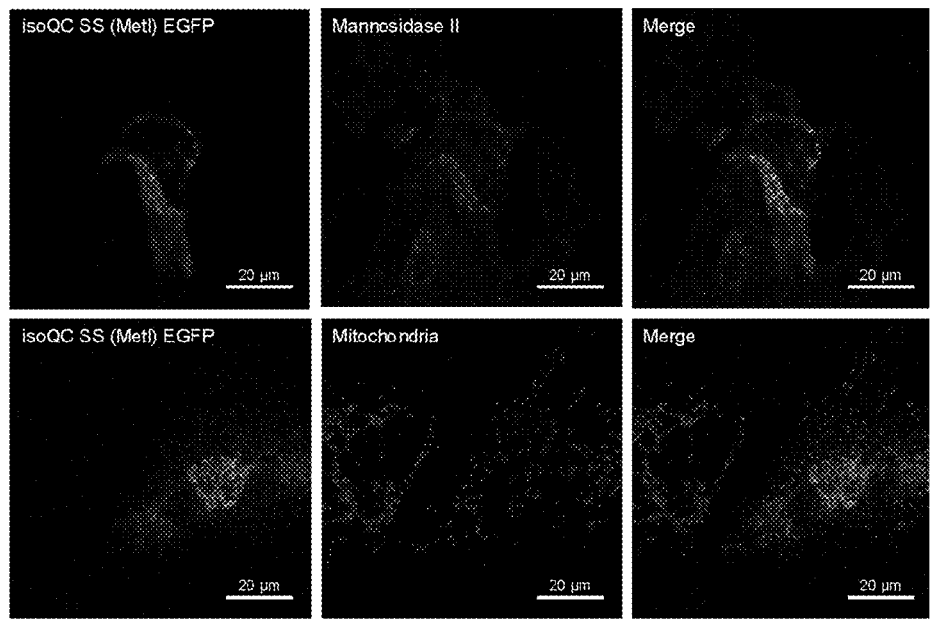
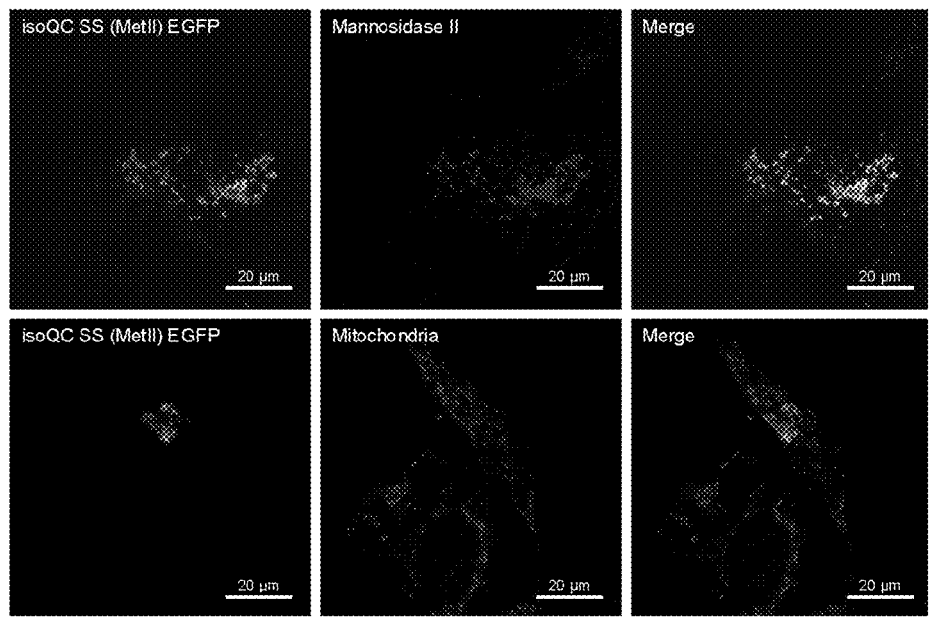

SEQUENCE LISTING

<160> NUMBER OF SEQ ID NOS: 121

<210> SEQ ID NO 1
<211> LENGTH: 1086
<212> TYPE: DNA
<213> ORGANISM: human

<400> SEQUENCE: 1

```
atggcaggcg gaagacaccg gcgcgtcgtg ggcaccctcc acctgctgct gctggtggcc      60
gccctgccct gggcatccag gggggtcagt ccgagtgcct cagcctggcc agaggagaag     120
aattaccacc agccagccat tttgaattca tcggctcttc ggcaaattgc agaaggcacc     180
agtatctctg aaatgtggca aaatgactta cagccattgc tgatagagcg atacccggga     240
tcccctggaa gctatgctgc tcgtcagcac atcatgcagc gaattcagag gcttcaggct     300
gactgggtct tggaaataga caccttcttg agtcagacac cctatgggta ccggtctttc     360
tcaaatatca tcagcaccct caatcccact gctaaacgac atttggtcct cgcctgccac     420
tatgactcca agtattttc ccactggaac aacagagtgt tgtaggagc cactgattca     480 gccgtgccat gtgcaatgat gttggaactt gctcgtgcct tagacaagaa actcctttcc     540
ttaaagactg tttcagactc caagccagat tgtcactcc agctgatctt ctttgatggt     600
gaagaggctt tcttcactg gtctcctcaa gattctctct atgggtctcg acacttagct     660
gcaaagatgg catcgacccc gcacccacct ggagcgagag gcaccagcca actgcatggc     720
atggatttat tggtcttatt ggatttgatt ggagctccaa acccaacgtt tcccaatttt     780
tttccaaact cagccaggtg gttcgaaaga cttcaagcaa ttgaacatga acttcatgaa     840 tgggtttgc tcaaggatca ctctttggag gggcggtatt tccagaatta cagttatgga     900
ggtgtgattc aggatgacca tattccattt taagaagag gtgttccagt tctgcatctg     960
ataccgtctc ctttccctga agtctggcac accatggatg acaatgaaga aaatttggat    1020
gaatcaacca ttgacaatct aaacaaaatc ctacaagtct tgtgttgga atatcttcat    1080 ttgtaa                                                               1086
```

```
<210> SEQ ID NO 2
<211> LENGTH: 1149
<212> TYPE: DNA
<213> ORGANISM: human

<400> SEQUENCE: 2
atgcgttccg ggggccgcgg gcgaccccgc ctgcggctgg gggaacgtgg cctcatggag      60
ccactcttgc cgccgaagcg ccgcctgcta ccgcgggttc ggctcttgcc tctgttgctg     120
gcgctggccg tgggctcggc gttctacacc atttggagcg gctggcaccg caggactgag     180
gagctgccgc tgggccggga gctgcgggtc ccattgatcg gaagcctccc cgaagcccgg     240
ctgcggaggg tggtgggaca actggatcca cagcgtctct ggagcactta tctgcgcccc     300
ctgctggttg tgcgaacccc gggcagcccg ggaaatctcc aagtcagaaa gttcctggag     360 ccacgctgc ggtccctgac agcaggttgg cacgtggagc tggatccctt cacagcctca      420
acacccctgg ggccagtgga cttttggcaat gtggtggcca cactggaccc aagggctgcc    480
cgtcacctca cccttgcctg ccattatgac tcgaagctct ccccaccgg atcgaccccc      540 tttgtagggg ccacggattc ggctgtgccc tgtgccctgc tgctggagct ggcccaagca     600
cttgacctgg agctgagcag ggccaaaaaa caggcagccc cggtgaccct gcaactgctc     660
ttcttggatg gtgaagaggc gctgaaggag tggggaccca aggactccct ttacggttcc     720
cggcacctgg cccagctcat ggagtctata cctcacagcc ccggcccac caggatccag      780 gctattgagc tctttatgct tcttgatctc ctgggagccc ccaatcccac cttctacagc     840
cacttccctc gcacggtccg ctggttccat cggctgagga gcattgagaa gcgtctgcac     900
cgtttgaacc tgctgcagtc tcatccccag gaagtgatgt acttccaacc cggggagccc     960
tttggctctg tggaagacga ccacatcccc ttcctccgca gaggggtacc cgtgctccat    1020
ctcatctcca cgcccttccc tgctgtctgg cacacccctg cggacaccga ggtcaatctc    1080
cacccaccca cggtacacaa cttgtgccgc attctcgctg tgttcctggc tgaatacctg    1140
gggctctag                                                             1149

<210> SEQ ID NO 3
<211> LENGTH: 1145
<212> TYPE: DNA
<213> ORGANISM: human

<400> SEQUENCE: 3
atgcgttccg ggggccgcgg gcgaccccgc ctgcggctgg gggaacgtgg atggagccac      60
tcttgccgcc gaagcgccgc ctgctaccgc gggttcggct cttgcctctg ttgctggcgc     120
tggccgtggg ctcggcgttc tacaccattt ggagcggctg gcaccgcagg actgaggagc     180
tgccgctggg ccgggagctg cgggtcccat tgatcggaag cctccccgaa gcccggctgc     240
ggagggtggt gggacaactg gatccacagc gtctctggag cacttatctg cgccccctgc     300
tggttgtgcg aaccccgggc agcccgggaa atctccaagt cagaaagttc ctggaggcca     360
cgctgcggtc cctgacagca ggttggcacg tggagctgga tcccttcaca gcctcaacac     420
ccctggggcc agtggacttt ggcaatgtgg tggcacact ggacccaagg gctgcccgtc      480
acctcaccct tgcctgccat tatgactcga agctcttccc accggatcg acccccttg      540 taggggccac ggattcggct gtgccctgtg ccctgctgct ggagctggcc caagcacttg     600
acctggagct gagcagggcc aaaaaacagg cagccccggt gaccctgcaa ctgctcttct     660
tggatggtga gaggcgctg aaggagtggg gacccaagga ctccctttac ggttcccggc      720
acctggccca gctcatggag tctataccte acagccccgg ccccaccagg atccaggcta    780
```

| | |
|---|---|
| ttgagctctt tatgcttctt gatctcctgg gagcccccaa tcccaccttc tacagccact | 840 |
| tccctcgcac ggtccgctgg ttccatcggc tgaggagcat tgagaagcgt ctgcaccgtt | 900 |
| tgaacctgct gcagtctcat ccccaggaag tgatgtactt ccaacccggg agccctttg | 960 |
| gctctgtgga agacgaccac atccccttcc tccgcagagg ggtacccgtg ctccatctca | 1020 |
| tctccacgcc cttccctgct gtctggcaca cccctgcgga caccgaggtc aatctccacc | 1080 |
| cacccacggt acacaacttg tgccgcattc tcgctgtgtt cctggctgaa tacctggggc | 1140 |
| tctag | 1145 |

<210> SEQ ID NO 4
<211> LENGTH: 1149
<212> TYPE: DNA
<213> ORGANISM: Macaca fascicularis

<400> SEQUENCE: 4

| | |
|---|---|
| atgcgttccg ggggccgcgg gcggccccgc ctgcggctag ggaacgtggc cgttatggag | 60 |
| ccactcttgc ccccgaagcg ccgcctgcta ccgcgggttc ggctcttgcc cctgttgctg | 120 |
| gcgctggccg tgggctcggc gttctacacc atttggagcg ctggcaccg caggactgag | 180 |
| gagctgccgc tgggccggga gctgcgggtc ccgttgatcg gaagccttcc cgaagcccgg | 240 |
| ctgcggaggg tggtgggaca actggaccca cagcgtctct ggggcactta tctgcgcccc | 300 |
| ctgctggttg tgcgaacccc aggcagcccg ggaaatctcc aagtcagaaa gttcctggag | 360 |
| gccacgctgc ggtccctgac agcaggttgg cacgtggagc tggatccctt cacagcctcg | 420 |
| acgcccctgg ggccagtgga ctttggcaat gtggtggcca cgctggaccc ggggctgcc | 480 |
| cgtcacctca cccttgcctg ccattatgac tcgaagctct tcccacccgg atcgaccccg | 540 |
| tttgtagggg ccacggactc ggctgtgccc tgtgccctgc tgctggagct ggcccaggca | 600 |
| cttgacctgg agctgagcag ggccaaagaa caggcagccc cggtgaccct gcaactgctc | 660 |
| ttcctggatg gtgaagaggc gctgaaggag tggggaccca aggactccct ttacggttcc | 720 |
| cggcacctgg cccagctcat ggagtctata cctcatagcc ccggcccac caggatccag | 780 |
| gctattgagc tctttatgct tcttgatctc ctgggagccc caatcccac cttctacagc | 840 |
| cacttccctc gcacggtccg ctggttccat cggctgagaa gcattgagaa gcgtctgcac | 900 |
| cgtttgaacc tgctgcagtc tcatccccag gaagtgatgt acttccaacc cggggagccc | 960 |
| ttcggctctg tggaagacga ccacatcccc ttcctccgca gggggtccc cgtgctccat | 1020 |
| ctcatctcta cgcccttccc tgctgtctgg cacaccctg cggacacaga ggccaatctc | 1080 |
| cacccgccca cggtacacaa cttaagccgc attctggccg tgttcctggc tgaatacctg | 1140 |
| gggctctag | 1149 |

<210> SEQ ID NO 5
<211> LENGTH: 1149
<212> TYPE: DNA
<213> ORGANISM: Macaca mulatta

<400> SEQUENCE: 5

| | |
|---|---|
| atgcgttccg ggggccgcgg gcggccccgc ctgcggctag ggaacgtggc cgttatggag | 60 |
| ccactcttgc ccccgaagcg ccgcctgcta ccgcgggttc ggctcttgcc cctgttgctg | 120 |
| gcgctggccg tgggctcggc gttctacacc atttggagcg ctggcaccg caggactgag | 180 |
| gagctgccgc tgggccggga gctgcgggtc ccgttgatcg gaagccttcc cgaagcccgg | 240 |
| ctgcggaggg tggtgggaca actggaccca cagcgtctct ggggcactta tctgcgcccc | 300 |

```
ctgctggttg tgcgaacccc aggcagcccg ggaaatctcc aagtcagaaa gttcctggag    360
gccacgctgc ggtccctgac agcaggttgg cacgtggagc tggatcccct cacagcctcg    420
acgcccctgg gcccagtgga ctttggcaat gtggtggcca cgctggaccc ggggctgcc     480
cgtcacctca cccttgcctg ccattatgac tcgaagctct ccccaccgg atcgaccccg     540
tttgtagggg ccacagactc ggctgtgccc tgtgccctgc tgctggagct ggcccaggca    600
cttgacctgg agctgagcag ggccaaagaa caggcagccc cggtgaccct gcaactgctc    660
ttcctggatg gtgaagaggc gctgaaggag tggggaccca aggactccct ttacggttcc    720
cggcacctgg cccagctcat ggagtctata cctcatagcc ccggcccac caggatccag     780
gctattgagc tctttatgct tcttgatctc ctgggagccc caatcccac cttctacagc     840
cacttccctc gcacggtccg ctggttccat cggctgagaa gcattgagaa gcgtctgcac    900
cgtttgaacc tgctgcagtc tcatccccag gaagtgatgt acttccaacc cggggagccc    960
tttggctctg tggaagacga ccacatcccc ttcctccgca gaggggtccc cgtgctccat   1020
ctcatctcta cgcccttccc tgctgtctgg cacacccctg cggacacaga ggccaatctc   1080
cacccgccca cggtacacaa cttaagccgc attctggccg tgttcctggc tgaatacctg   1140
gggctctag                                                           1149

<210> SEQ ID NO 6
<211> LENGTH: 1152
<212> TYPE: DNA
<213> ORGANISM: Canis familiaris

<400> SEQUENCE: 6
atgccttccg ggggccgcgg gcggtcccgg ctacggctcg gggaacgtgg cctcttggag     60
ccgccctccc cgcccaagcg ccgcctgctc ccgcgggcgc acttcttgcc tctgcttctg    120
ctggccctgg ccctggcttc ggcgacctac accatctgga gcggctggca ccaccagact    180
gaggagctgc cgcggggccg ggagctgcgg ggccgcttga tcggaagcct ctccgaagcc    240
cggctgcggc gggtggtggg gcaactggac ccacaccgtc tctggaacac ttatctgcgc    300
cccctgctgg ttgtgcggac cccgggcagc cccggcaatc tccaagtcag aaagttcctg    360
gaggctacac tacggacctt gacagcaggc tggcatgtgg aactggaccc cttcacagcc    420
ttgacacccc tggggccact ggactttggc aatgtggtgg ccacgctgga cccagggct    480
gcccgtcacc tcacccttgc ctgccattat gactccaagc tcttcgcatc tgagtcggtt    540
cccttgtgg gggcaacaga ttcggctgta ccttgcgccc tgctgctgga gctggctcag    600
gccctcgaca gggagttgag tagggccaag gagcaggaag ccccggtgac tctgcagctg    660
ctcttttgg atggtgaaga agcactgaag gagtggggac ccacagactc cctctatggc    720
tcccggcacc tggcccagct catggagtct gcaccccaca gcccgggccc caccaggatc    780
caggctatcg agctcttcat gctccttgat ctcctgggtg ccccgaatcc aaacttctac    840
agtcacttcc ctcatacagc ccgctggttc atcggctga ggagcatcga gaagcgcctt    900
caccgcatga acctgctgca gtctcatccc caggaagtga tgtacttcca gcccggggag    960
cccctggtt ctgtggaaga tgaccacatc cccttcctcc gccgagggt ccctgtgctc    1020
cacctcatct ccatgccctt ccctccgtc tggcacaccc ccgatgactc tgaggccaac   1080
ctgcacccac ccaccgtaca caatctgagc cgcatcctgc ccgtgttcct ggccgaatat   1140
ctggggctct ag                                                      1152
```

```
<210> SEQ ID NO 7
<211> LENGTH: 1152
<212> TYPE: DNA
<213> ORGANISM: Rattus norvegicus

<400> SEQUENCE: 7
atgagtccgg ccagccgcgg gcggtctcgg cagcggctcg gggatcgcgg cctcatgaaa      60
ccaccctcac tttccaagcg ccgtcttctg ccgcggtgc agctcctgcc cctgctgctg      120
ctggcgctgg ccctgggctt ggcttttat atcgtctgga atagctggca ccctggggtt      180
gaggaggtat cacggagccg ggatctgcgg gtcccgctga tcggaagcct ttcagaagcc      240
aagctgcggc ttgtggtagg gcagctggat ccacagcgtc tctggggaac tttttctgcgt     300
cccttgttga ttgtacgacc cccaggtagt cctggcaatc tccaagtgag aaagttcctg      360
gaggctacgt tgcagtccct atcggcaggc tggcacgtgg aactggaccc attcacagcc      420
tcaaccccct ggggccacct ggacttcggg aacgtggtgg ccaccttga cccaggagct      480
gcccgtcacc tcaccctcgc ctgccattat gactctaagt tcttccctcc tgggttaccc      540
cccctttgtgg gggccacaga ttcagccgtg ccctgtgccc tgcttctgga gttagtccag      600
gcccttgatg tcatgctgag cagaatcaag cagcaggcag caccagtgac cctgcagctg      660
ctcttcttgg acggggagga ggcactgaag gagtggggac caaaggactc cctctatggt      720
tcccggcacc tagctcagat catggagtct ataccgcaca gccctggccc caccaggatc      780
caggctattg agctctttgt ccttcttgac cttctgggag cgcccagtcc aatcttcttc      840
agtcacttcc cccgcacagc ccgctggttc aacgactgc ggagcatcga aagcgcctt       900
caccgtctga acctactgca gtctcacccc caggaagtga tgtacttcca acccggggag      960
ccccctggcc ctgtggaaga tgaccacatc cccttccttc gcagagggt cccggtgctc      1020
cacctcattg cgatgccctt ccctgccgtg tggcacacac ctgctgacac tgaggctaac      1080
ctccacccgc ccacggtgca caacctgagc cgcatcctcg ccgtgttcct ggctgagtac      1140
ctgggtctct ag                                                         1152

<210> SEQ ID NO 8
<211> LENGTH: 1152
<212> TYPE: DNA
<213> ORGANISM: Mus musculus

<400> SEQUENCE: 8
atgagtcccg ggagccgcgg gcggcccccgg cagcggctcg aggatcgtgg cctcatgaaa    60
ccaccctcac tttccaagcg ccgtcttctg ccgcgagtgc agttcctgcc cctgctgctg    120
ctggcgctgg ctatgggctt ggcttttctat atcgtctgga acagctggca ccctggggtt   180
gaggagatgt cacggagccg ggatctgcgg gtcccgctga tcggaagcct ttcagaagcc    240
aagctgcggc tggtggtagg gcagctggat ccgcagcgtc tctggggaac tttcctgcgt    300
cccttattga ttgtgcgacc cccgggtagt tctggcaatc tccaagtgag aaagttcctg    360
gaggctacgt tgcagtccct gtcggcaggc tggcatgttg aactggaccc attcacggcc    420
tcaaccccct ggggccact ggacttcggg aacgtggtgg ccacacttga cccaggagct    480
gcccgtcacc tcaccctcgc ctgccattat gactctaagt tcttccctcc ggggttgccc    540
cccctttgtgg gggccacaga ttcagctgtg ccctgtgccc tgcttctgga gttggtccag    600
gcccttgatg ccatgctgag cagaatcaag cagcaggcag caccggtgac cctgcagctg    660
cttttcttgg atggggagga ggcactgaag gagtggggac caaaggactc cctctatggc    720
tcccggcacc tagctcagat catggagtct ataccacaca gccctggccc caccaggatc    780
```

```
caggctattg agctctttgt cctcctcgac cttctgggag catccagtcc gatcttcttc    840
agtcacttcc ctcgcacagc ccgctggttc cagcgactga ggagcattga gaagcgcctt    900
caccggctga acctactgca gtctcacccc caggaagtga tgtacttcca acccggggag    960
ccccccggcc ctgtggaaga tgaccacatc cccttccttc gcagagdggt cccggtgctc   1020
cacctcattg ccacgccctt ccctgctgtg tggcacacac ctgctgacac cgaggccaac   1080
ctccacccac ccactgtgca taacctgagc cgcatccttg ctgtgttcct ggccgagtac   1140
ctgggactct ag                                                       1152

<210> SEQ ID NO 9
<211> LENGTH: 1152
<212> TYPE: DNA
<213> ORGANISM: Bos taurus

<400> SEQUENCE: 9
atgccttccg ggggccgcgg gcggccccgg ctccaggtcg gggaacgcag ccttttggag     60
cgaccctcac cgcccaagcg ccgcctgata ccgcgggcac agctgttgcc ccagctgctg    120
ctggctctga cggtagcctc ggtgttctat accatttgga ggatctggca tagccagact    180
gaagagctac cgctggggcg ggagctgcgg ggccctttga tcggaagcct ccccgaagct    240
cgggtgcgga gggtagtggg gcaactggac cctcaccgtc tctggaacac ttcctgcgc    300 cctctgctgg ttgtacggac tccgggcagc ccgggcaatc tccaagtgag aaagttcctg    360
gaggctacgt gcggacact tcagcaggc tggcatatag aactcgactc cttcactgcc    420
tccacacccg tggggccatt ggacttcagc aatgtggtgg ccacgctgga cccaggggct    480
gcccgccacc ttaccctttgc ctgccattat gactccaagc tcttcccatc tgactcagcc    540 cccttttgtgg gggccacgga ttcggcagtg ccttgctccc tgctactgga gctggcccaa    600
gcccttgacc aggagctggg caaagccaag gagagggcag cgccaatgac cttgcagctg    660
atcttcctgg atggtgaaga ggcactgaag cagtggggac ccaaggactc gctttatggc    720 tccccggcacc tggcccagct catggagtct acacccacg gctgggctc caccaggatc    780 caggctattg agctctttat gcttcttgat ctcctgggag ccccaaccc gaccttctac    840 agtcacttcc ctcgcacggc ccgctggttc catcggctca ggagcattga gaagcgcctg    900
caccgtctga acctcctgca gtctcatcct tgggaagtga tgtacttcca gaccggggag    960
ccccccggct ccgtggaaga cgaccacatc ccgttcctcc gccgaggagt tcccgtgctc   1020
cacctcatcg ccacacccctt cccctctgtc tggcacacgt ccgatgactc cgaggccaac   1080
ctgcacccac ccacggtaca aacctgagc cgcatcctgg ccgtgttcct ggctgagtac   1140
ctggggctct ag                                                       1152

<210> SEQ ID NO 10
<211> LENGTH: 361
<212> TYPE: PRT
<213> ORGANISM: human

<400> SEQUENCE: 10

Met Ala Gly Gly Arg His Arg Val Val Gly Thr Leu His Leu Leu
1               5                   10                  15

Leu Leu Val Ala Ala Leu Pro Trp Ala Ser Arg Gly Val Ser Pro Ser
                20                  25                  30

Ala Ser Ala Trp Pro Glu Glu Lys Asn Tyr His Gln Pro Ala Ile Leu
        35                  40                  45
```

-continued

Asn Ser Ser Ala Leu Arg Gln Ile Ala Glu Gly Thr Ser Ile Ser Glu
        50                  55                  60

Met Trp Gln Asn Asp Leu Gln Pro Leu Leu Ile Glu Arg Tyr Pro Gly
 65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln
            100                 105                 110

Thr Pro Tyr Gly Tyr Arg Ser Phe Ser Asn Ile Ile Ser Thr Leu Asn
        115                 120                 125

Pro Thr Ala Lys Arg His Leu Val Leu Ala Cys His Tyr Asp Ser Lys
    130                 135                 140

Tyr Phe Ser His Trp Asn Asn Arg Val Phe Val Gly Ala Thr Asp Ser
145                 150                 155                 160

Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser
            180                 185                 190

Leu Gln Leu Ile Phe Phe Asp Gly Glu Glu Ala Phe Leu His Trp Ser
        195                 200                 205

Pro Gln Asp Ser Leu Tyr Gly Ser Arg His Leu Ala Ala Lys Met Ala
    210                 215                 220

Ser Thr Pro His Pro Pro Gly Ala Arg Gly Thr Ser Gln Leu His Gly
225                 230                 235                 240

Met Asp Leu Leu Val Leu Leu Asp Leu Ile Gly Ala Pro Asn Pro Thr
                245                 250                 255

Phe Pro Asn Phe Phe Pro Asn Ser Ala Arg Trp Phe Glu Arg Leu Gln
            260                 265                 270

Ala Ile Glu His Glu Leu His Glu Leu Gly Leu Leu Lys Asp His Ser
        275                 280                 285

Leu Glu Gly Arg Tyr Phe Gln Asn Tyr Ser Tyr Gly Gly Val Ile Gln
    290                 295                 300

Asp Asp His Ile Pro Phe Leu Arg Arg Gly Val Pro Val Leu His Leu
305                 310                 315                 320

Ile Pro Ser Pro Phe Pro Glu Val Trp His Thr Met Asp Asp Asn Glu
                325                 330                 335

Glu Asn Leu Asp Glu Ser Thr Ile Asp Asn Leu Asn Lys Ile Leu Gln
            340                 345                 350

Val Phe Val Leu Glu Tyr Leu His Leu
        355                 360

<210> SEQ ID NO 11
<211> LENGTH: 382
<212> TYPE: PRT
<213> ORGANISM: human

<400> SEQUENCE: 11

Met Arg Ser Gly Gly Arg Gly Arg Pro Arg Leu Arg Leu Gly Glu Arg
 1               5                  10                  15

Gly Leu Met Glu Pro Leu Leu Pro Pro Lys Arg Arg Leu Leu Pro Arg
                20                  25                  30

Val Arg Leu Leu Pro Leu Leu Leu Ala Leu Ala Val Gly Ser Ala Phe
            35                  40                  45

Tyr Thr Ile Trp Ser Gly Trp His Arg Arg Thr Glu Glu Leu Pro Leu
        50                  55                  60

```
Gly Arg Glu Leu Arg Val Pro Leu Ile Gly Ser Leu Pro Glu Ala Arg
 65                  70                  75                  80

Leu Arg Arg Val Val Gly Gln Leu Asp Pro Gln Arg Leu Trp Ser Thr
                 85                  90                  95

Tyr Leu Arg Pro Leu Leu Val Arg Thr Pro Gly Ser Pro Gly Asn
            100                 105                 110

Leu Gln Val Arg Lys Phe Leu Glu Ala Thr Leu Arg Ser Leu Thr Ala
            115                 120                 125

Gly Trp His Val Glu Leu Asp Pro Phe Thr Ala Ser Thr Pro Leu Gly
            130                 135                 140

Pro Val Asp Phe Gly Asn Val Val Ala Thr Leu Asp Pro Arg Ala Ala
145                 150                 155                 160

Arg His Leu Thr Leu Ala Cys His Tyr Asp Ser Lys Leu Phe Pro Pro
                165                 170                 175

Gly Ser Thr Pro Phe Val Gly Ala Thr Asp Ser Ala Val Pro Cys Ala
                180                 185                 190

Leu Leu Leu Glu Leu Ala Gln Ala Leu Asp Leu Glu Leu Ser Arg Ala
                195                 200                 205

Lys Lys Gln Ala Ala Pro Val Thr Leu Gln Leu Leu Phe Leu Asp Gly
210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
                245                 250                 255

Thr Arg Ile Gln Ala Ile Glu Leu Phe Met Leu Leu Asp Leu Leu Gly
                260                 265                 270

Ala Pro Asn Pro Thr Phe Tyr Ser His Phe Pro Arg Thr Val Arg Trp
                275                 280                 285

Phe His Arg Leu Arg Ser Ile Glu Lys Arg Leu His Arg Leu Asn Leu
                290                 295                 300

Leu Gln Ser His Pro Gln Glu Val Met Tyr Phe Gln Pro Gly Glu Pro
305                 310                 315                 320

Phe Gly Ser Val Glu Asp Asp His Ile Pro Phe Leu Arg Arg Gly Val
                325                 330                 335

Pro Val Leu His Leu Ile Ser Thr Pro Phe Pro Ala Val Trp His Thr
                340                 345                 350

Pro Ala Asp Thr Glu Val Asn Leu His Pro Pro Thr Val His Asn Leu
                355                 360                 365

Cys Arg Ile Leu Ala Val Phe Leu Ala Glu Tyr Leu Gly Leu
                370                 375                 380

<210> SEQ ID NO 12
<211> LENGTH: 364
<212> TYPE: PRT
<213> ORGANISM: human

<400> SEQUENCE: 12

Met Glu Pro Leu Leu Pro Pro Lys Arg Leu Leu Pro Arg Val Arg
 1               5                  10                  15

Leu Leu Pro Leu Leu Leu Ala Leu Ala Val Gly Ser Ala Phe Tyr Thr
                 20                  25                  30

Ile Trp Ser Gly Trp His Arg Arg Thr Glu Glu Leu Pro Leu Gly Arg
             35                  40                  45

Glu Leu Arg Val Pro Leu Ile Gly Ser Leu Pro Glu Ala Arg Leu Arg
 50                  55                  60
```

```
Arg Val Val Gly Gln Leu Asp Pro Gln Arg Leu Trp Ser Thr Tyr Leu
 65                  70                  75                  80

Arg Pro Leu Leu Val Arg Thr Pro Gly Ser Pro Gly Asn Leu Gln
                 85                  90                  95

Val Arg Lys Phe Leu Glu Ala Thr Leu Arg Ser Leu Thr Ala Gly Trp
            100                 105                 110

His Val Glu Leu Asp Pro Phe Thr Ala Ser Thr Pro Leu Gly Pro Val
        115                 120                 125

Asp Phe Gly Asn Val Val Ala Thr Leu Asp Pro Arg Ala Ala Arg His
    130                 135                 140

Leu Thr Leu Ala Cys His Tyr Asp Ser Lys Leu Phe Pro Pro Gly Ser
145                 150                 155                 160

Thr Pro Phe Val Gly Ala Thr Asp Ser Ala Val Pro Cys Ala Leu Leu
                165                 170                 175

Leu Glu Leu Ala Gln Ala Leu Asp Leu Glu Leu Ser Arg Ala Lys Lys
            180                 185                 190

Gln Ala Ala Pro Val Thr Leu Gln Leu Leu Phe Leu Asp Gly Glu Glu
        195                 200                 205

Ala Leu Lys Glu Trp Gly Pro Lys Asp Ser Leu Tyr Gly Ser Arg His
    210                 215                 220

Leu Ala Gln Leu Met Glu Ser Ile Pro His Ser Pro Gly Pro Thr Arg
225                 230                 235                 240

Ile Gln Ala Ile Glu Leu Phe Met Leu Leu Asp Leu Leu Gly Ala Pro
                245                 250                 255

Asn Pro Thr Phe Tyr Ser His Phe Pro Arg Thr Val Arg Trp Phe His
            260                 265                 270

Arg Leu Arg Ser Ile Glu Lys Arg Leu His Arg Leu Asn Leu Leu Gln
        275                 280                 285

Ser His Pro Gln Glu Val Met Tyr Phe Gln Pro Gly Glu Pro Phe Gly
    290                 295                 300

Ser Val Glu Asp Asp His Ile Pro Phe Leu Arg Arg Gly Val Pro Val
305                 310                 315                 320

Leu His Leu Ile Ser Thr Pro Phe Pro Ala Val Trp His Thr Pro Ala
                325                 330                 335

Asp Thr Glu Val Asn Leu His Pro Pro Thr Val His Asn Leu Cys Arg
            340                 345                 350

Ile Leu Ala Val Phe Leu Ala Glu Tyr Leu Gly Leu
        355                 360

<210> SEQ ID NO 13
<211> LENGTH: 382
<212> TYPE: PRT
<213> ORGANISM: Macaca fascicularis

<400> SEQUENCE: 13

Met Arg Ser Gly Gly Arg Gly Arg Pro Arg Leu Arg Leu Gly Glu Arg
 1               5                  10                  15

Gly Val Met Glu Pro Leu Leu Pro Pro Lys Arg Arg Leu Leu Pro Arg
                20                  25                  30

Val Arg Leu Leu Pro Leu Leu Leu Ala Leu Ala Val Gly Ser Ala Phe
            35                  40                  45

Tyr Thr Ile Trp Ser Gly Trp His Arg Arg Thr Glu Glu Leu Pro Leu
        50                  55                  60

Gly Arg Glu Leu Arg Val Pro Leu Ile Gly Ser Leu Pro Glu Ala Arg
 65                  70                  75                  80
```

```
Leu Arg Arg Val Val Gly Gln Leu Asp Pro Gln Arg Leu Trp Gly Thr
                85                  90                  95

Tyr Leu Arg Pro Leu Leu Val Val Arg Thr Pro Gly Ser Pro Gly Asn
            100                 105                 110

Leu Gln Val Arg Lys Phe Leu Glu Ala Thr Leu Arg Ser Leu Thr Ala
            115                 120                 125

Gly Trp His Val Glu Leu Asp Pro Phe Thr Ala Ser Thr Pro Leu Gly
            130                 135                 140

Pro Val Asp Phe Gly Asn Val Val Ala Thr Leu Asp Pro Gly Ala Ala
145                 150                 155                 160

Arg His Leu Thr Leu Ala Cys His Tyr Asp Ser Lys Leu Phe Pro Pro
                165                 170                 175

Gly Ser Thr Pro Phe Val Gly Ala Thr Asp Ser Ala Val Pro Cys Ala
            180                 185                 190

Leu Leu Leu Glu Leu Ala Gln Ala Leu Asp Leu Glu Leu Ser Arg Ala
            195                 200                 205

Lys Glu Gln Ala Ala Pro Val Thr Leu Gln Leu Leu Phe Leu Asp Gly
            210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
                245                 250                 255

Thr Arg Ile Gln Ala Ile Glu Leu Phe Met Leu Leu Asp Leu Leu Gly
            260                 265                 270

Ala Pro Asn Pro Thr Phe Tyr Ser His Phe Pro Arg Thr Val Arg Trp
            275                 280                 285

Phe His Arg Leu Arg Ser Ile Glu Lys Arg Leu His Arg Leu Asn Leu
            290                 295                 300

Leu Gln Ser His Pro Gln Glu Val Met Tyr Phe Gln Pro Gly Glu Pro
305                 310                 315                 320

Phe Gly Ser Val Glu Asp Asp His Ile Pro Phe Leu Arg Arg Gly Val
                325                 330                 335

Pro Val Leu His Leu Ile Ser Thr Pro Phe Pro Ala Val Trp His Thr
            340                 345                 350

Pro Ala Asp Thr Glu Ala Asn Leu His Pro Pro Thr Val His Asn Leu
            355                 360                 365

Ser Arg Ile Leu Ala Val Phe Leu Ala Glu Tyr Leu Gly Leu
            370                 375                 380

<210> SEQ ID NO 14
<211> LENGTH: 382
<212> TYPE: PRT
<213> ORGANISM: Macaca mulatta

<400> SEQUENCE: 14

Met Arg Ser Gly Gly Arg Gly Arg Pro Arg Leu Arg Leu Gly Glu Arg
1               5                   10                  15

Gly Val Met Glu Pro Leu Leu Pro Pro Lys Arg Arg Leu Leu Pro Arg
            20                  25                  30

Val Arg Leu Leu Pro Leu Leu Leu Ala Leu Ala Val Gly Ser Ala Phe
            35                  40                  45

Tyr Thr Ile Trp Ser Gly Trp His Arg Arg Thr Glu Glu Leu Pro Leu
            50                  55                  60

Gly Arg Glu Leu Arg Val Pro Leu Ile Gly Ser Leu Pro Glu Ala Arg
65                  70                  75                  80
```

Leu Arg Arg Val Val Gly Gln Leu Asp Pro Gln Arg Leu Trp Gly Thr
            85                  90                  95

Tyr Leu Arg Pro Leu Leu Val Val Arg Thr Pro Gly Ser Pro Gly Asn
                100                 105                 110

Leu Gln Val Arg Lys Phe Leu Glu Ala Thr Leu Arg Ser Leu Thr Ala
            115                 120                 125

Gly Trp His Val Glu Leu Asp Pro Phe Thr Ala Ser Thr Pro Leu Gly
        130                 135                 140

Pro Val Asp Phe Gly Asn Val Val Ala Thr Leu Asp Pro Gly Ala Ala
145                 150                 155                 160

Arg His Leu Thr Leu Ala Cys His Tyr Asp Ser Lys Leu Phe Pro Pro
                165                 170                 175

Gly Ser Thr Pro Phe Val Gly Ala Thr Asp Ser Ala Val Pro Cys Ala
                180                 185                 190

Leu Leu Leu Glu Leu Ala Gln Ala Leu Asp Leu Glu Leu Ser Arg Ala
            195                 200                 205

Lys Glu Gln Ala Ala Pro Val Thr Leu Gln Leu Leu Phe Leu Asp Gly
        210                 215                 220

Glu Glu Ala Leu Lys Glu Trp Gly Pro Lys Asp Ser Leu Tyr Gly Ser
225                 230                 235                 240

Arg His Leu Ala Gln Leu Met Glu Ser Ile Pro His Ser Pro Gly Pro
                245                 250                 255

Thr Arg Ile Gln Ala Ile Glu Leu Phe Met Leu Leu Asp Leu Leu Gly
                260                 265                 270

Ala Pro Asn Pro Thr Phe Tyr Ser His Phe Pro Arg Thr Val Arg Trp
            275                 280                 285

Phe His Arg Leu Arg Ser Ile Glu Lys Arg Leu His Arg Leu Asn Leu
        290                 295                 300

Leu Gln Ser His Pro Gln Glu Val Met Tyr Phe Gln Pro Gly Glu Pro
305                 310                 315                 320

Phe Gly Ser Val Glu Asp Asp His Ile Pro Phe Leu Arg Arg Gly Val
                325                 330                 335

Pro Val Leu His Leu Ile Ser Thr Pro Phe Pro Ala Val Trp His Thr
                340                 345                 350

Pro Ala Asp Thr Glu Ala Asn Leu His Pro Pro Thr Val His Asn Leu
            355                 360                 365

Ser Arg Ile Leu Ala Val Phe Leu Ala Glu Tyr Leu Gly Leu
        370                 375                 380

<210> SEQ ID NO 15
<211> LENGTH: 383
<212> TYPE: PRT
<213> ORGANISM: Canis familiaris

<400> SEQUENCE: 15

Met Pro Ser Gly Gly Arg Gly Arg Ser Arg Leu Arg Leu Gly Glu Arg
1               5                   10                  15

Gly Leu Leu Glu Pro Pro Ser Pro Pro Lys Arg Arg Leu Leu Pro Arg
            20                  25                  30

Ala His Phe Leu Pro Leu Leu Leu Ala Leu Ala Leu Ala Ser Ala
        35                  40                  45

Thr Tyr Thr Ile Trp Ser Gly Trp His His Gln Thr Glu Glu Leu Pro
    50                  55                  60

Arg Gly Arg Glu Leu Arg Gly Arg Leu Ile Gly Ser Leu Ser Glu Ala
65                  70                  75                  80

```
Arg Leu Arg Arg Val Val Gly Gln Leu Asp Pro His Arg Leu Trp Asn
                85                  90                  95

Thr Tyr Leu Arg Pro Leu Leu Val Val Arg Thr Pro Gly Ser Pro Gly
            100                 105                 110

Asn Leu Gln Val Arg Lys Phe Leu Glu Ala Thr Leu Arg Thr Leu Thr
        115                 120                 125

Ala Gly Trp His Val Glu Leu Asp Pro Phe Thr Ala Leu Thr Pro Leu
    130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Leu Phe Ala
                165                 170                 175

Ser Glu Ser Val Pro Phe Val Gly Ala Thr Asp Ser Ala Val Pro Cys
            180                 185                 190

Ala Leu Leu Leu Glu Leu Ala Gln Ala Leu Asp Arg Glu Leu Ser Arg
        195                 200                 205

Ala Lys Glu Gln Glu Ala Pro Val Thr Leu Gln Leu Leu Phe Leu Asp
    210                 215                 220

Gly Glu Glu Ala Leu Lys Glu Trp Gly Pro Thr Asp Ser Leu Tyr Gly
225                 230                 235                 240

Ser Arg His Leu Ala Gln Leu Met Glu Ser Ala Pro His Ser Pro Gly
                245                 250                 255

Pro Thr Arg Ile Gln Ala Ile Glu Leu Phe Met Leu Leu Asp Leu Leu
            260                 265                 270

Gly Ala Pro Asn Pro Asn Phe Tyr Ser His Phe Pro His Thr Ala Arg
        275                 280                 285

Trp Phe His Arg Leu Arg Ser Ile Glu Lys Arg Leu His Arg Met Asn
    290                 295                 300

Leu Leu Gln Ser His Pro Gln Glu Val Met Tyr Phe Gln Pro Gly Glu
305                 310                 315                 320

Pro Pro Gly Ser Val Glu Asp Asp His Ile Pro Phe Leu Arg Arg Gly
                325                 330                 335

Val Pro Val Leu His Leu Ile Ser Met Pro Phe Pro Ser Val Trp His
            340                 345                 350

Thr Pro Asp Asp Ser Glu Ala Asn Leu His Pro Pro Thr Val His Asn
        355                 360                 365

Leu Ser Arg Ile Leu Ala Val Phe Leu Ala Glu Tyr Leu Gly Leu
    370                 375                 380

<210> SEQ ID NO 16
<211> LENGTH: 383
<212> TYPE: PRT
<213> ORGANISM: Rattus norvegicus

<400> SEQUENCE: 16

Met Ser Pro Ala Ser Arg Gly Arg Ser Arg Gln Arg Leu Gly Asp Arg
1               5                   10                  15

Gly Leu Met Lys Pro Pro Ser Leu Ser Lys Arg Arg Leu Leu Pro Arg
            20                  25                  30

Val Gln Leu Leu Pro Leu Leu Leu Ala Leu Ala Leu Gly Leu Ala
        35                  40                  45

Phe Tyr Ile Val Trp Asn Ser Trp His Pro Gly Val Glu Glu Val Ser
    50                  55                  60

Arg Ser Arg Asp Leu Arg Val Pro Leu Ile Gly Ser Leu Ser Glu Ala
65                  70                  75                  80
```

```
Lys Leu Arg Leu Val Val Gly Gln Leu Asp Pro Gln Arg Leu Trp Gly
                85                  90                  95

Thr Phe Leu Arg Pro Leu Leu Ile Val Arg Pro Pro Gly Ser Pro Gly
            100                 105                 110

Asn Leu Gln Val Arg Lys Phe Leu Glu Ala Thr Leu Gln Ser Leu Ser
        115                 120                 125

Ala Gly Trp His Val Glu Leu Asp Pro Phe Thr Ala Ser Thr Pro Leu
    130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
                165                 170                 175

Pro Gly Leu Pro Pro Phe Val Gly Ala Thr Asp Ser Ala Val Pro Cys
            180                 185                 190

Ala Leu Leu Leu Glu Leu Val Gln Ala Leu Asp Val Met Leu Ser Arg
        195                 200                 205

Ile Lys Gln Gln Ala Ala Pro Val Thr Leu Gln Leu Leu Phe Leu Asp
    210                 215                 220

Gly Glu Glu Ala Leu Lys Glu Trp Gly Pro Lys Asp Ser Leu Tyr Gly
225                 230                 235                 240

Ser Arg His Leu Ala Gln Ile Met Glu Ser Ile Pro His Ser Pro Gly
                245                 250                 255

Pro Thr Arg Ile Gln Ala Ile Glu Leu Phe Val Leu Asp Leu Asp Leu
            260                 265                 270

Gly Ala Pro Ser Pro Ile Phe Ser His Phe Pro Arg Thr Ala Arg
        275                 280                 285

Trp Phe Gln Arg Leu Arg Ser Ile Glu Lys Arg Leu His Arg Leu Asn
290                 295                 300

Leu Leu Gln Ser His Pro Gln Glu Val Met Tyr Phe Gln Pro Gly Glu
305                 310                 315                 320

Pro Pro Gly Pro Val Glu Asp Asp His Ile Pro Phe Leu Arg Gly
                325                 330                 335

Val Pro Val Leu His Leu Ile Ala Met Pro Phe Pro Ala Val Trp His
            340                 345                 350

Thr Pro Ala Asp Thr Glu Ala Asn Leu His Pro Pro Thr Val His Asn
        355                 360                 365

Leu Ser Arg Ile Leu Ala Val Phe Leu Ala Glu Tyr Leu Gly Leu
    370                 375                 380

<210> SEQ ID NO 17
<211> LENGTH: 383
<212> TYPE: PRT
<213> ORGANISM: Mus musculus

<400> SEQUENCE: 17

Met Ser Pro Gly Ser Arg Gly Arg Pro Arg Gln Arg Leu Glu Asp Arg
1               5                   10                  15

Gly Leu Met Lys Pro Pro Ser Leu Ser Lys Arg Arg Leu Leu Pro Arg
            20                  25                  30

Val Gln Phe Leu Pro Leu Leu Leu Ala Leu Ala Met Gly Leu Ala
        35                  40                  45

Phe Tyr Ile Val Trp Asn Ser Trp His Pro Gly Val Glu Glu Met Ser
    50                  55                  60

Arg Ser Arg Asp Leu Arg Val Pro Leu Ile Gly Ser Leu Ser Glu Ala
65                  70                  75                  80
```

```
Lys Leu Arg Leu Val Val Gly Gln Leu Asp Pro Gln Arg Leu Trp Gly
                85                  90                  95

Thr Phe Leu Arg Pro Leu Leu Ile Val Arg Pro Pro Gly Ser Ser Gly
            100                 105                 110

Asn Leu Gln Val Arg Lys Phe Leu Glu Ala Thr Leu Gln Ser Leu Ser
            115                 120                 125

Ala Gly Trp His Val Glu Leu Asp Pro Phe Thr Ala Ser Thr Pro Leu
        130                 135                 140

Gly Pro Leu Asp Phe Gly Asn Val Val Ala Thr Leu Asp Pro Gly Ala
145                 150                 155                 160

Ala Arg His Leu Thr Leu Ala Cys His Tyr Asp Ser Lys Phe Phe Pro
                165                 170                 175

Pro Gly Leu Pro Pro Phe Val Gly Ala Thr Asp Ser Ala Val Pro Cys
            180                 185                 190

Ala Leu Leu Leu Glu Leu Val Gln Ala Leu Asp Ala Met Leu Ser Arg
        195                 200                 205

Ile Lys Gln Gln Ala Ala Pro Val Thr Leu Gln Leu Leu Phe Leu Asp
        210                 215                 220

Gly Glu Glu Ala Leu Lys Glu Trp Gly Pro Lys Asp Ser Leu Tyr Gly
225                 230                 235                 240

Ser Arg His Leu Ala Gln Ile Met Glu Ser Ile Pro His Ser Pro Gly
                245                 250                 255

Pro Thr Arg Ile Gln Ala Ile Glu Leu Phe Val Leu Leu Asp Leu Leu
            260                 265                 270

Gly Ala Ser Ser Pro Ile Phe Ser His Phe Pro Arg Thr Ala Arg
        275                 280                 285

Trp Phe Gln Arg Leu Arg Ser Ile Glu Lys Arg Leu His Arg Leu Asn
        290                 295                 300

Leu Leu Gln Ser His Pro Gln Glu Val Met Tyr Phe Gln Pro Gly Glu
305                 310                 315                 320

Pro Pro Gly Pro Val Glu Asp Asp His Ile Pro Phe Leu Arg Arg Gly
                325                 330                 335

Val Pro Val Leu His Leu Ile Ala Thr Pro Phe Pro Ala Val Trp His
            340                 345                 350

Thr Pro Ala Asp Thr Glu Ala Asn Leu His Pro Thr Val His Asn
        355                 360                 365

Leu Ser Arg Ile Leu Ala Val Phe Leu Ala Glu Tyr Leu Gly Leu
        370                 375                 380

<210> SEQ ID NO 18
<211> LENGTH: 383
<212> TYPE: PRT
<213> ORGANISM: Bos taurus

<400> SEQUENCE: 18

Met Pro Ser Gly Gly Arg Gly Arg Pro Arg Leu Gln Val Gly Glu Arg
1               5                   10                  15

Ser Leu Leu Glu Arg Pro Ser Pro Pro Lys Arg Arg Leu Ile Pro Arg
            20                  25                  30

Ala Gln Leu Leu Pro Gln Leu Leu Leu Ala Leu Thr Val Ala Ser Val
        35                  40                  45

Phe Tyr Thr Ile Trp Arg Ile Trp His Ser Gln Thr Glu Glu Leu Pro
    50                  55                  60

Leu Gly Arg Glu Leu Arg Gly Pro Leu Ile Gly Ser Leu Pro Glu Ala
65                  70                  75                  80
```

```
Arg Val Arg Arg Val Val Gly Gln Leu Asp Pro His Arg Leu Trp Asn
                85                  90                  95
Thr Phe Leu Arg Pro Leu Leu Val Val Arg Thr Pro Gly Ser Pro Gly
            100                 105                 110
Asn Leu Gln Val Arg Lys Phe Leu Glu Ala Thr Leu Arg Thr Leu Ser
        115                 120                 125
Ala Gly Trp His Ile Glu Leu Asp Ser Phe Thr Ala Ser Thr Pro Val
130                 135                 140
Gly Pro Leu Asp Phe Ser Asn Val Val Ala Thr Leu Asp Pro Gly Ala
145                 150                 155                 160
Ala Arg His Leu Thr Leu Ala Cys His Tyr Asp Ser Lys Leu Phe Pro
                165                 170                 175
Ser Asp Ser Ala Pro Phe Val Gly Ala Thr Asp Ser Ala Val Pro Cys
            180                 185                 190
Ser Leu Leu Leu Glu Leu Ala Gln Ala Leu Asp Gln Glu Leu Gly Lys
        195                 200                 205
Ala Lys Glu Arg Ala Ala Pro Met Thr Leu Gln Leu Ile Phe Leu Asp
210                 215                 220
Gly Glu Glu Ala Leu Lys Gln Trp Gly Pro Lys Asp Ser Leu Tyr Gly
225                 230                 235                 240
Ser Arg His Leu Ala Gln Leu Met Glu Ser Thr Pro His Gly Leu Gly
                245                 250                 255
Ser Thr Arg Ile Gln Ala Ile Glu Leu Phe Met Leu Leu Asp Leu Leu
            260                 265                 270
Gly Ala Pro Asn Pro Thr Phe Tyr Ser His Phe Pro Arg Thr Ala Arg
        275                 280                 285
Trp Phe His Arg Leu Arg Ser Ile Glu Lys Arg Leu His Arg Leu Asn
290                 295                 300
Leu Leu Gln Ser His Pro Trp Glu Val Met Tyr Phe Gln Thr Gly Glu
305                 310                 315                 320
Pro Pro Gly Ser Val Glu Asp Asp His Ile Pro Phe Leu Arg Arg Gly
                325                 330                 335
Val Pro Val Leu His Leu Ile Ala Thr Pro Phe Pro Ser Val Trp His
            340                 345                 350
Thr Ser Asp Asp Ser Glu Ala Asn Leu His Pro Pro Thr Val His Asn
        355                 360                 365
Leu Ser Arg Ile Leu Ala Val Phe Leu Ala Glu Tyr Leu Gly Leu
370                 375                 380

<210> SEQ ID NO 19
<211> LENGTH: 1457
<212> TYPE: DNA
<213> ORGANISM: human

<400> SEQUENCE: 19
gtctggtaca ggtttcaggg caaagcggcc atgcgttccg ggggccgcgg gcgaccccgc      60
ctgcggctgg gggaacgtgg cctcatggag ccactcttgc cgccgaagcg ccgcctgcta     120
ccgcgggttc ggctcttgcc tctgttgctg gcgctggccg tgggctcggc gttctacacc     180
atttggagcg gctggcaccg caggactgag gagctgccgc tgggccggga gctgcgggtc     240
ccattgatcg gaagcctccc cgaagcccgg ctgcggaggg tggtgggaca actggatcca     300
cagcgtctct ggagcactta tctgcgcccc tgctggttg tgcgaacccc gggcagcccg      360
ggaaatctcc aagtcagaaa gttcctggag gccacgctgc ggtccctgac agcaggttgg     420
cacgtggagc tggatcccct tacagcctca acacccctgg ggccagtgga ctttggcaat     480
```

| | | |
|---|---|---|
| gtggtggcca cactggaccc aagggctgcc cgtcacctca cccttgcctg ccattatgac | 540 | |
| tcgaagctct tcccacccgg atcgacccccc tttgtagggg ccacggattc ggctgtgccc | 600 | |
| tgtgccctgc tgctggagct ggcccaagca cttgacctgg agctgagcag gccaaaaaa | 660 | |
| caggcagccc cggtgaccct gcaactgctc ttcttggatg gtgaagaggc gctgaaggag | 720 | |
| tggggaccca aggactccct ttacggttcc cggcacctgg cccagctcat ggagtctata | 780 | |
| cctcacagcc ccggccccac caggatccag gctattgagc tctttatgct tcttgatctc | 840 | |
| ctggagcccc caatcccac cttctacagc cacttccctc gcacggtccg ctggttccat | 900 | |
| cggctgagga gcattgagaa gcgtctgcac cgtttgaacc tgctgcagtc tcatcccag | 960 | |
| gaagtgatgt acttccaacc cggggagccc tttggctctg tggaagacga ccacatcccc | 1020 | |
| ttcctccgca gaggggtacc cgtgctccat ctcatctcca cgcccttccc tgctgtctgg | 1080 | |
| cacaccccctg cggacaccga ggtcaatctc cacccaccca cggtacacaa cttgtgccgc | 1140 | |
| attctcgctg tgttcctggc tgaataccctg ggctctagc gtgcttggcc aatgactgtg | 1200 | |
| gagaggactg tgagagagaa ggtcccagcg ggggccagtg aagctcaggc aggatctgcc | 1260 | |
| tagggtgtgc tggtttgtcc ttttcatacc tttgtctcct aattgtgcta caattggaag | 1320 | |
| accttctttc ttttgattgt ctcaagctgc caccccttcaa ggacagggaa gagaccactg | 1380 | |
| tgggatgaca gccagaggaa taagaacttg ctccctcccc agaggtaaac acttggtcca | 1440 | |
| aaggtttgca gggacca | 1457 | |

<210> SEQ ID NO 20
<211> LENGTH: 1088
<212> TYPE: DNA
<213> ORGANISM: human

<400> SEQUENCE: 20

| | | |
|---|---|---|
| agcggccatg cgttccgggg gccgcgggcg accccgcctg cggctggggg aacgtggcct | 60 | |
| catggagcca ctcttgccgc cgaagcgccg cctgctaccg cgggttcggc tcttgcctct | 120 | |
| gttgctggcg ctggccgtgg gctcggcgtt ctacaccatt tggagcggct ggcaccgcag | 180 | |
| gactgaggag ctgccgctgg gccggagct gcgggtccca ttgatcggaa gcctccccga | 240 | |
| agcccggctg cggagggtgg tgggacaact ggatccacag cgtctctgga gcacttatct | 300 | |
| gcgcccctg ctggttgtgc gaaccccggg cagcccggga aatctccaag tcagaaaggc | 360 | |
| agccccggtg accctgcaac tgctcttctt ggatggtgaa gaggcgctga aggagtgggg | 420 | |
| acccaaggac tcccctttacg gttcccggca cctggcccag ctcatggagt ctataccctca | 480 | |
| cagccccggc cccaccagga tccaggctat tgagctcttt atgcttcttg atctcctggg | 540 | |
| agcccccaat cccaccttct acagccactt ccctcgcacg gtccgctggt tccatcggct | 600 | |
| gaggagcatt gagaagcgtc tgcaccgttt gaacctgctg cagtctcatc ccaggaagt | 660 | |
| gatgtacttc caacccgggg agccctttgg ctctgtggaa gacgaccaca tcccctcct | 720 | |
| ccgcagaggg gtaccgtgc tccatctcat ctccacgccc ttccctgctg tctggcacac | 780 | |
| ccctgcggac accgaggtca atctccaccc acccacggta cacaacttgt gccgcattct | 840 | |
| cgctgtgttc ctggctgaat acctgggggct agcgtgct tggccaatga ctgtggagag | 900 | |
| gactgtgaga gagaaggtcc cagcggggc cagtgaagct caggcaggat ctgcctaggg | 960 | |
| tgtgctggtt tgtccttttc ataccttttgt ctcctaattg tgctacaatt ggaagacctt | 1020 | |
| cttttcttttg attgtctcaa gctgccaccc ttcaaggaca gggaagagac cactgtggga | 1080 | |
| tgacagcc | 1088 | |

<210> SEQ ID NO 21
<211> LENGTH: 481
<212> TYPE: PRT
<213> ORGANISM: human

<400> SEQUENCE: 21

```
Val Trp Tyr Arg Phe Gln Gly Lys Ala Ala Met Arg Ser Gly Gly Arg
1               5                   10                  15

Gly Arg Pro Arg Leu Arg Leu Gly Glu Arg Gly Leu Met Glu Pro Leu
            20                  25                  30

Leu Pro Pro Lys Arg Arg Leu Leu Pro Arg Val Arg Leu Leu Pro Leu
        35                  40                  45

Leu Leu Ala Leu Ala Val Gly Ser Ala Phe Tyr Thr Ile Trp Ser Gly
50                  55                  60

Trp His Arg Arg Thr Glu Glu Leu Pro Leu Gly Arg Glu Leu Arg Val
65                  70                  75                  80

Pro Leu Ile Gly Ser Leu Pro Glu Ala Arg Leu Arg Arg Val Val Gly
                85                  90                  95

Gln Leu Asp Pro Gln Arg Leu Trp Ser Thr Tyr Leu Arg Pro Leu Leu
            100                 105                 110

Val Val Arg Thr Pro Gly Ser Pro Gly Asn Leu Gln Val Arg Lys Phe
        115                 120                 125

Leu Glu Ala Thr Leu Arg Ser Leu Thr Ala Gly Trp His Val Glu Leu
130                 135                 140

Asp Pro Phe Thr Ala Ser Thr Pro Leu Gly Pro Val Asp Phe Gly Asn
145                 150                 155                 160

Val Val Ala Thr Leu Asp Pro Arg Ala Ala Arg His Leu Thr Leu Ala
                165                 170                 175

Cys His Tyr Asp Ser Lys Leu Phe Pro Pro Gly Ser Thr Pro Phe Val
            180                 185                 190

Gly Ala Thr Asp Ser Ala Val Pro Cys Ala Leu Leu Leu Glu Leu Ala
        195                 200                 205

Gln Ala Leu Asp Leu Glu Leu Ser Arg Ala Lys Lys Gln Ala Ala Pro
210                 215                 220

Val Thr Leu Gln Leu Leu Phe Leu Asp Gly Glu Glu Ala Leu Lys Glu
225                 230                 235                 240

Trp Gly Pro Lys Asp Ser Leu Tyr Gly Ser Arg His Leu Ala Gln Leu
                245                 250                 255

Met Glu Ser Ile Pro His Ser Pro Gly Pro Thr Arg Ile Gln Ala Ile
            260                 265                 270

Glu Leu Phe Met Leu Leu Asp Leu Leu Gly Ala Pro Asn Pro Thr Phe
        275                 280                 285

Tyr Ser His Phe Pro Arg Thr Val Arg Trp Phe His Arg Leu Arg Ser
290                 295                 300

Ile Glu Lys Arg Leu His Arg Leu Asn Leu Leu Gln Ser His Pro Gln
305                 310                 315                 320

Glu Val Met Tyr Phe Gln Pro Gly Glu Pro Phe Gly Ser Val Glu Asp
                325                 330                 335

Asp His Ile Pro Phe Leu Arg Arg Gly Val Pro Val Leu His Leu Ile
            340                 345                 350

Ser Thr Pro Phe Pro Ala Val Trp His Thr Pro Ala Asp Thr Glu Val
        355                 360                 365

Asn Leu His Pro Pro Thr Val His Asn Leu Cys Arg Ile Leu Ala Val
370                 375                 380
```

```
Phe Leu Ala Glu Tyr Leu Gly Leu Arg Ala Trp Pro Met Thr Val Glu
385                 390                 395                 400

Arg Thr Val Arg Glu Lys Val Pro Ala Gly Ala Ser Glu Ala Gln Ala
                405                 410                 415

Gly Ser Ala Gly Val Leu Val Cys Pro Phe His Thr Phe Val Ser Leu
            420                 425                 430

Cys Tyr Asn Trp Lys Thr Phe Phe Leu Leu Ile Val Ser Ser Cys His
            435                 440                 445

Pro Ser Arg Thr Gly Lys Arg Pro Leu Trp Asp Asp Ser Gln Arg Asn
            450                 455                 460

Lys Asn Leu Leu Pro Pro Gln Arg Thr Leu Gly Pro Lys Val Cys Arg
465                 470                 475                 480

Asp

<210> SEQ ID NO 22
<211> LENGTH: 359
<212> TYPE: PRT
<213> ORGANISM: human

<400> SEQUENCE: 22

Ala Ala Met Arg Ser Gly Gly Arg Gly Pro Arg Leu Arg Leu Gly
1               5                   10                  15

Glu Arg Gly Leu Met Glu Pro Leu Leu Pro Pro Lys Arg Arg Leu Leu
                20                  25                  30

Pro Arg Val Arg Leu Leu Pro Leu Leu Ala Leu Ala Val Gly Ser
                35                  40                  45

Ala Phe Tyr Thr Ile Trp Ser Gly Trp His Arg Arg Thr Glu Glu Leu
50                  55                  60

Pro Leu Gly Arg Glu Leu Arg Val Pro Leu Ile Gly Ser Leu Pro Glu
65                  70                  75                  80

Ala Arg Leu Arg Arg Val Val Gly Gln Leu Asp Pro Gln Arg Leu Trp
                85                  90                  95

Ser Thr Tyr Leu Arg Pro Leu Leu Val Val Arg Thr Pro Gly Ser Pro
                100                 105                 110

Gly Asn Leu Gln Val Arg Lys Ala Ala Pro Val Thr Leu Gln Leu Leu
            115                 120                 125

Phe Leu Asp Gly Glu Glu Ala Leu Lys Glu Trp Gly Pro Lys Asp Ser
130                 135                 140

Leu Tyr Gly Ser Arg His Leu Ala Gln Leu Met Glu Ser Ile Pro His
145                 150                 155                 160

Ser Pro Gly Pro Thr Arg Ile Gln Ala Ile Glu Leu Phe Met Leu Leu
                165                 170                 175

Asp Leu Leu Gly Ala Pro Asn Pro Thr Phe Tyr Ser His Phe Pro Arg
            180                 185                 190

Thr Val Arg Trp Phe His Arg Leu Arg Ser Ile Glu Lys Arg Leu His
            195                 200                 205

Arg Leu Asn Leu Leu Gln Ser His Pro Gln Glu Val Met Tyr Phe Gln
210                 215                 220

Pro Gly Glu Pro Phe Gly Ser Val Glu Asp Asp His Ile Pro Phe Leu
225                 230                 235                 240

Arg Arg Gly Val Pro Val Leu His Leu Ile Ser Thr Pro Phe Pro Ala
                245                 250                 255

Val Trp His Thr Pro Ala Asp Glu Val Asn Leu His Pro Pro Thr
                260                 265                 270
```

```
Val His Asn Leu Cys Arg Ile Leu Ala Val Phe Leu Ala Glu Tyr Leu
        275                 280                 285

Gly Leu Arg Ala Trp Pro Met Thr Val Glu Arg Thr Val Arg Glu Lys
    290                 295                 300

Val Pro Ala Gly Ala Ser Glu Ala Gln Ala Gly Ser Ala Gly Val Leu
305                 310                 315                 320

Val Cys Pro Phe His Thr Phe Val Ser Leu Cys Tyr Asn Trp Lys Thr
                325                 330                 335

Phe Phe Leu Leu Ile Val Ser Ser Cys His Pro Ser Arg Thr Gly Lys
                340                 345                 350

Arg Pro Leu Trp Asp Asp Ser
        355

<210> SEQ ID NO 23
<211> LENGTH: 42
<212> TYPE: PRT
<213> ORGANISM: Homo sapiens

<400> SEQUENCE: 23

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 24
<211> LENGTH: 40
<212> TYPE: PRT
<213> ORGANISM: Homo sapiens

<400> SEQUENCE: 24

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 25
<211> LENGTH: 40
<212> TYPE: PRT
<213> ORGANISM: Homo sapiens

<400> SEQUENCE: 25

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 26
<211> LENGTH: 38
<212> TYPE: PRT
<213> ORGANISM: Homo sapiens

<400> SEQUENCE: 26

Glu Phe Arg His Asp Ser Gly Tyr Glu Val His His Gln Lys Leu Val
1               5                   10                  15
```

```
Phe Phe Ala Glu Asp Val Gly Ser Asn Lys Gly Ala Ile Ile Gly Leu
            20                  25                  30

Met Val Gly Gly Val Val
        35
```

<210> SEQ ID NO 27
<211> LENGTH: 32
<212> TYPE: PRT
<213> ORGANISM: artificial sequence
<220> FEATURE:
<223> OTHER INFORMATION: synthetic peptide

<400> SEQUENCE: 27

```
Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
            20                  25                  30
```

<210> SEQ ID NO 28
<211> LENGTH: 30
<212> TYPE: PRT
<213> ORGANISM: artificial sequence
<220> FEATURE:
<223> OTHER INFORMATION: synthetic peptide

<400> SEQUENCE: 28

```
Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30
```

<210> SEQ ID NO 29
<211> LENGTH: 40
<212> TYPE: PRT
<213> ORGANISM: human
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 29

```
Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40
```

<210> SEQ ID NO 30
<211> LENGTH: 38
<212> TYPE: PRT
<213> ORGANISM: human
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 30

```
Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35
```

<210> SEQ ID NO 31
<211> LENGTH: 32
<212> TYPE: PRT
<213> ORGANISM: human
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 31

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Ile Ala
            20                  25                  30

<210> SEQ ID NO 32
<211> LENGTH: 30
<212> TYPE: PRT
<213> ORGANISM: human
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 32

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30

<210> SEQ ID NO 33
<211> LENGTH: 34
<212> TYPE: PRT
<213> ORGANISM: Homo sapiens

<400> SEQUENCE: 33

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Arg

<210> SEQ ID NO 34
<211> LENGTH: 34
<212> TYPE: PRT
<213> ORGANISM: Homo sapiens

<400> SEQUENCE: 34

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Arg

<210> SEQ ID NO 35
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 35

```
Gln Gly Pro Trp Leu Glu Glu Glu Glu Ala Tyr Gly Trp Met Asp
1               5                   10                  15

Phe

<210> SEQ ID NO 36
<211> LENGTH: 34
<212> TYPE: PRT
<213> ORGANISM: human

<400> SEQUENCE: 36

Gln Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe

<210> SEQ ID NO 37
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 37

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Arg

<210> SEQ ID NO 38
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 38

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Arg

<210> SEQ ID NO 39
<211> LENGTH: 17
<212> TYPE: PRT
<213> ORGANISM: human
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 39

Gln Gly Pro Trp Leu Glu Glu Glu Glu Ala Tyr Gly Trp Met Asp
1               5                   10                  15

Phe

<210> SEQ ID NO 40
```

```
<211> LENGTH: 34
<212> TYPE: PRT
<213> ORGANISM: human
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 40
```

Gln Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe

```
<210> SEQ ID NO 41
<211> LENGTH: 13
<212> TYPE: PRT
<213> ORGANISM: Homo sapiens

<400> SEQUENCE: 41
```

Gln Leu Tyr Glu Asn Lys Pro Arg Arg Pro Tyr Ile Leu
1               5                   10

```
<210> SEQ ID NO 42
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 42
```

Gln His Trp Ser Tyr Gly Leu Arg Pro Gly
1               5                   10

```
<210> SEQ ID NO 43
<211> LENGTH: 97
<212> TYPE: PRT
<213> ORGANISM: Homo sapiens

<400> SEQUENCE: 43
```

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
            20                  25                  30

Lys Ala Leu Asn Cys His Leu Pro Ala Ile Ile Phe Val Thr Lys Arg
        35                  40                  45

Asn Arg Glu Val Cys Thr Asn Pro Asn Asp Asp Trp Val Gln Glu Tyr
    50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                85                  90                  95

Gln

```
<210> SEQ ID NO 44
<211> LENGTH: 76
<212> TYPE: PRT
<213> ORGANISM: Homo sapiens

<400> SEQUENCE: 44
```

```
Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
50                  55                  60

Lys His Leu Asp Gln Ile Phe Gln Asn Leu Lys Pro
65                  70                  75

<210> SEQ ID NO 45
<211> LENGTH: 76
<212> TYPE: PRT
<213> ORGANISM: Homo sapiens

<400> SEQUENCE: 45

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr
65                  70                  75

<210> SEQ ID NO 46
<211> LENGTH: 68
<212> TYPE: PRT
<213> ORGANISM: Homo sapiens

<400> SEQUENCE: 46

Gln Val Gly Thr Asn Lys Glu Leu Cys Cys Leu Val Tyr Thr Ser Trp
1               5                   10                  15

Gln Ile Pro Gln Lys Phe Ile Val Asp Tyr Ser Glu Thr Ser Pro Gln
                20                  25                  30

Cys Pro Lys Pro Gly Val Ile Leu Leu Thr Lys Arg Gly Arg Gln Ile
            35                  40                  45

Cys Ala Asp Pro Asn Lys Lys Trp Val Gln Lys Tyr Ile Ser Asp Leu
50                  55                  60

Lys Leu Asn Ala
65

<210> SEQ ID NO 47
<211> LENGTH: 373
<212> TYPE: PRT
<213> ORGANISM: Homo sapiens

<400> SEQUENCE: 47

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
                20                  25                  30

Ser Cys Gly Lys Arg Ala Ile Ile Leu Glu Thr Arg Gln His Arg Leu
            35                  40                  45

Phe Cys Ala Asp Pro Lys Glu Gln Trp Val Lys Asp Ala Met Gln His
50                  55                  60
```

```
Leu Asp Arg Gln Ala Ala Leu Thr Arg Asn Gly Gly Thr Phe Glu
 65                  70                  75                  80

Lys Gln Ile Gly Glu Val Lys Pro Arg Thr Thr Pro Ala Ala Gly Gly
                 85                  90                  95

Met Asp Glu Ser Val Val Leu Glu Pro Glu Ala Thr Gly Glu Ser Ser
            100                 105                 110

Ser Leu Glu Pro Thr Pro Ser Ser Gln Glu Ala Gln Arg Ala Leu Gly
        115                 120                 125

Thr Ser Pro Glu Leu Pro Thr Gly Val Thr Gly Ser Ser Gly Thr Arg
130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
        195                 200                 205

Ser Pro Ala Pro Glu Glu Asn Ala Pro Ser Glu Gly Gln Arg Val Trp
210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Val Pro Val Ser Ser Glu Gly Thr
            260                 265                 270

Pro Ser Arg Glu Pro Val Ala Ser Gly Ser Trp Thr Pro Lys Ala Glu
        275                 280                 285

Glu Pro Ile His Ala Thr Met Asp Pro Gln Arg Leu Gly Val Leu Ile
290                 295                 300

Thr Pro Val Pro Asp Ala Gln Ala Ala Thr Arg Arg Gln Ala Val Gly
305                 310                 315                 320

Leu Leu Ala Phe Leu Gly Leu Leu Phe Cys Leu Gly Val Ala Met Phe
                325                 330                 335

Thr Tyr Gln Ser Leu Gln Gly Cys Pro Arg Lys Met Ala Gly Glu Met
            340                 345                 350

Ala Glu Gly Leu Arg Tyr Ile Pro Arg Ser Cys Gly Ser Asn Ser Tyr
        355                 360                 365

Val Leu Val Pro Val
370

<210> SEQ ID NO 48
<211> LENGTH: 76
<212> TYPE: PRT
<213> ORGANISM: Homo sapiens

<400> SEQUENCE: 48

Gln Pro Val Gly Ile Asn Thr Ser Thr Thr Cys Cys Tyr Arg Phe Ile
 1               5                  10                  15

Asn Lys Lys Ile Pro Lys Gln Arg Leu Glu Ser Tyr Arg Arg Thr Thr
                20                  25                  30

Ser Ser His Cys Pro Arg Glu Ala Val Ile Phe Lys Thr Lys Leu Asp
            35                  40                  45

Lys Glu Ile Cys Ala Asp Pro Thr Gln Lys Trp Val Gln Asp Phe Met
 50                  55                  60
```

Lys His Leu Asp Lys Lys Thr Gln Thr Pro Lys Leu
65                  70                  75

<210> SEQ ID NO 49
<211> LENGTH: 33
<212> TYPE: PRT
<213> ORGANISM: Homo sapiens

<400> SEQUENCE: 49

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu

<210> SEQ ID NO 50
<211> LENGTH: 11
<212> TYPE: PRT
<213> ORGANISM: Homo sapiens

<400> SEQUENCE: 50

Arg Pro Lys Pro Gln Gln Phe Phe Gly Leu Met
1               5                   10

<210> SEQ ID NO 51
<211> LENGTH: 5
<212> TYPE: PRT
<213> ORGANISM: artificial sequence
<220> FEATURE:
<223> OTHER INFORMATION: ynthetic peptide

<400> SEQUENCE: 51

Gln Tyr Asn Ala Asp
1               5

<210> SEQ ID NO 52
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 52

Gln Tyr Asn Ala Asp
1               5

<210> SEQ ID NO 53
<211> LENGTH: 26
<212> TYPE: DNA
<213> ORGANISM: artificial sequence
<220> FEATURE:
<223> OTHER INFORMATION: synthetic nucleotide

<400> SEQUENCE: 53
ggtctacacc atttggagcg gctggc                                            26

<210> SEQ ID NO 54
<211> LENGTH: 27
<212> TYPE: DNA
<213> ORGANISM: artificial sequence
<220> FEATURE:
<223> OTHER INFORMATION: synthtic nucleotide

<400> SEQUENCE: 54
gggttggaag tacatcactt cctgggg                                        27

<210> SEQ ID NO 55
<211> LENGTH: 24
<212> TYPE: DNA
<213> ORGANISM: artificial sequence
<220> FEATURE:
<223> OTHER INFORMATION: synthetic nucleotide

<400> SEQUENCE: 55
accatgcgtt ccgggggccg cggg                                           24

<210> SEQ ID NO 56
<211> LENGTH: 27
<212> TYPE: DNA
<213> ORGANISM: artificial sequence
<220> FEATURE:
<223> OTHER INFORMATION: synthetic nucleotide

<400> SEQUENCE: 56
acgctagagc cccaggtatt cagccag                                        27

<210> SEQ ID NO 57
<211> LENGTH: 30
<212> TYPE: DNA
<213> ORGANISM: artificial sequence
<220> FEATURE:
<223> OTHER INFORMATION: synthetic nucleotide

<400> SEQUENCE: 57
atatatgaat tcatgcgttc cggggccgc                                      30

<210> SEQ ID NO 58
<211> LENGTH: 33
<212> TYPE: DNA
<213> ORGANISM: artificial sequence
<220> FEATURE:
<223> OTHER INFORMATION: synthetic nucleotide

<400> SEQUENCE: 58
atatatgaat tcatggagcc actcttgccg ccg                                 33

<210> SEQ ID NO 59
<211> LENGTH: 33
<212> TYPE: DNA
<213> ORGANISM: artificial sequence
<220> FEATURE:
<223> OTHER INFORMATION: synthetic nucleotide

<400> SEQUENCE: 59
atatatgtcg acgagcccca ggtattcagc cag                                 33

<210> SEQ ID NO 60
<211> LENGTH: 44
<212> TYPE: DNA
<213> ORGANISM: artificial sequence
<220> FEATURE:
<223> OTHER INFORMATION: synthetic nucleotide

<400> SEQUENCE: 60
atatactagt gatgacgacg acaagttcta caccatttgg agcg                     44

<210> SEQ ID NO 61
<211> LENGTH: 49

```
<212> TYPE: DNA
<213> ORGANISM: artificial sequence
<220> FEATURE:
<223> OTHER INFORMATION: synthetic nucleotide

<400> SEQUENCE: 61
tatagaattc ctagtgatgg tgatggtgat ggagccccag gtattcagc          49

<210> SEQ ID NO 62
<211> LENGTH: 28
<212> TYPE: DNA
<213> ORGANISM: artificial sequence
<220> FEATURE:
<223> OTHER INFORMATION: PCR primer

<400> SEQUENCE: 62
atatgaattc ttctacacca tttggagc                                 28

<210> SEQ ID NO 63
<211> LENGTH: 49
<212> TYPE: DNA
<213> ORGANISM: artificial sequence
<220> FEATURE:
<223> OTHER INFORMATION: PCR primer

<400> SEQUENCE: 63
atatgaattc catcaccatc accatcactt ctacaccatt tggagcggc          49

<210> SEQ ID NO 64
<211> LENGTH: 35
<212> TYPE: DNA
<213> ORGANISM: artificial sequence
<220> FEATURE:
<223> OTHER INFORMATION: PCR primer

<400> SEQUENCE: 64
atatatgcgg ccgcctagag ccccaggtat tcagc                         35

<210> SEQ ID NO 65
<211> LENGTH: 20
<212> TYPE: DNA
<213> ORGANISM: artificial sequence
<220> FEATURE:
<223> OTHER INFORMATION: PCR primer

<400> SEQUENCE: 65
ccaggatcca ggctattgag                                          20

<210> SEQ ID NO 66
<211> LENGTH: 56
<212> TYPE: DNA
<213> ORGANISM: artificial sequence
<220> FEATURE:
<223> OTHER INFORMATION: PCR primer

<400> SEQUENCE: 66
atatatgcgg ccgcctagtg atggtgatgg tgatggagcc ccaggtattc agccag  56

<210> SEQ ID NO 67
<211> LENGTH: 19
<212> TYPE: DNA
<213> ORGANISM: artificial sequence
<220> FEATURE:
<223> OTHER INFORMATION: PCR primer

<400> SEQUENCE: 67
ttccacaggg ccgggggggc                                          19
```

<210> SEQ ID NO 68
<211> LENGTH: 18
<212> TYPE: DNA
<213> ORGANISM: artificial sequence
<220> FEATURE:
<223> OTHER INFORMATION: PCR primer

<400> SEQUENCE: 68
atgagtcccg ggagccgc                                                   18

<210> SEQ ID NO 69
<211> LENGTH: 18
<212> TYPE: DNA
<213> ORGANISM: artificial sequence
<220> FEATURE:
<223> OTHER INFORMATION: PCR primer

<400> SEQUENCE: 69
ctagagtccc aggtactc                                                   18

<210> SEQ ID NO 70
<211> LENGTH: 20
<212> TYPE: DNA
<213> ORGANISM: artificial sequence
<220> FEATURE:
<223> OTHER INFORMATION: PCR primer

<400> SEQUENCE: 70
agttcctgcc cctgctgctg                                                 20

<210> SEQ ID NO 71
<211> LENGTH: 20
<212> TYPE: DNA
<213> ORGANISM: artificial sequence
<220> FEATURE:
<223> OTHER INFORMATION: PCR primer

<400> SEQUENCE: 71
atcaagaggc accaaccaac                                                 20

<210> SEQ ID NO 72
<211> LENGTH: 19
<212> TYPE: DNA
<213> ORGANISM: artificial sequence
<220> FEATURE:
<223> OTHER INFORMATION: PCR primer

<400> SEQUENCE: 72
ctggataata tttccatag                                                  19

<210> SEQ ID NO 73
<211> LENGTH: 19
<212> TYPE: DNA
<213> ORGANISM: artificial sequence
<220> FEATURE:
<223> OTHER INFORMATION: PCR primer

<400> SEQUENCE: 73
acagctggga atctgagtc                                                  19

<210> SEQ ID NO 74
<211> LENGTH: 21
<212> TYPE: DNA
<213> ORGANISM: artificial sequence
<220> FEATURE:
<223> OTHER INFORMATION: PCR primer

<400> SEQUENCE: 74
gagcagaata gcttccgggc g         21

<210> SEQ ID NO 75
<211> LENGTH: 33
<212> TYPE: DNA
<213> ORGANISM: artificial sequence
<220> FEATURE:
<223> OTHER INFORMATION: PCR primer

<400> SEQUENCE: 75
ctgcgggtcc cattgaacgg aagcctcccc gaa         33

<210> SEQ ID NO 76
<211> LENGTH: 33
<212> TYPE: DNA
<213> ORGANISM: artificial sequence
<220> FEATURE:
<223> OTHER INFORMATION: PCR primer

<400> SEQUENCE: 76
ttcggggagg cttccgttca atgggacccg cag         33

<210> SEQ ID NO 77
<211> LENGTH: 33
<212> TYPE: DNA
<213> ORGANISM: artificial sequence
<220> FEATURE:
<223> OTHER INFORMATION: PCR primer

<400> SEQUENCE: 77
acggtacaca acttggcccg cattctcgct gtg         33

<210> SEQ ID NO 78
<211> LENGTH: 33
<212> TYPE: DNA
<213> ORGANISM: artificial sequence
<220> FEATURE:
<223> OTHER INFORMATION: PCR primer

<400> SEQUENCE: 78
cacagcgaga atgcgggcca agttgtgtac cgt         33

<210> SEQ ID NO 79
<211> LENGTH: 362
<212> TYPE: PRT
<213> ORGANISM: Mus musculus

<400> SEQUENCE: 79

Met Ala Gly Ser Glu Asp Lys Leu Val Val Gly Thr Leu His Leu Leu
1               5                   10                  15

Leu Leu Gln Ala Thr Val Leu Ser Leu Thr Ala Gly Asn Leu Ser Leu
            20                  25                  30

Val Ser Ala Ala Trp Thr Gln Glu Lys Asn His His Gln Pro Ala His
        35                  40                  45

Leu Asn Ser Ser Ser Leu Gln Gln Val Ala Glu Gly Thr Ser Ile Ser
    50                  55                  60

Glu Met Trp Gln Asn Asp Leu Arg Pro Leu Leu Ile Glu Arg Tyr Pro
65                  70                  75                  80

Gly Ser Pro Gly Ser Tyr Ser Ala Arg Gln His Ile Met Gln Arg Ile
                85                  90                  95

Gln Arg Leu Gln Ala Glu Trp Val Val Glu Val Asp Thr Phe Leu Ser

```
                    100                 105                 110
Arg Thr Pro Tyr Gly Tyr Arg Ser Phe Ser Asn Ile Ile Ser Thr Leu
            115                 120                 125

Asn Pro Glu Ala Lys Arg His Leu Val Leu Ala Cys His Tyr Asp Ser
130                 135                 140

Lys Tyr Phe Pro Arg Trp Asp Ser Arg Val Phe Val Gly Ala Thr Asp
145                 150                 155                 160

Ser Ala Val Pro Cys Ala Met Met Leu Glu Leu Ala Arg Ala Leu Asp
                165                 170                 175

Lys Lys Leu His Ser Leu Lys Asp Val Ser Gly Ser Lys Pro Asp Leu
            180                 185                 190

Ser Leu Arg Leu Ile Phe Phe Asp Gly Glu Glu Ala Phe His His Trp
            195                 200                 205

Ser Pro Gln Asp Ser Leu Tyr Gly Ser Arg His Leu Ala Gln Lys Met
        210                 215                 220

Ala Ser Ser Pro His Pro Pro Gly Ser Arg Gly Thr Asn Gln Leu Asp
225                 230                 235                 240

Gly Met Asp Leu Leu Val Leu Leu Asp Leu Ile Gly Ala Ala Asn Pro
                245                 250                 255

Thr Phe Pro Asn Phe Phe Pro Lys Thr Thr Arg Trp Phe Asn Arg Leu
                260                 265                 270

Gln Ala Ile Glu Lys Glu Leu Tyr Glu Leu Gly Leu Leu Lys Asp His
            275                 280                 285

Ser Leu Glu Arg Lys Tyr Phe Gln Asn Phe Gly Tyr Gly Asn Ile Ile
            290                 295                 300

Gln Asp Asp His Ile Pro Phe Leu Arg Lys Gly Val Pro Val Leu His
305                 310                 315                 320

Leu Ile Ala Ser Pro Phe Pro Glu Val Trp His Thr Met Asp Asp Asn
                325                 330                 335

Glu Glu Asn Leu His Ala Ser Thr Ile Asp Asn Leu Asn Lys Ile Ile
            340                 345                 350

Gln Val Phe Val Leu Glu Tyr Leu His Leu
            355                 360

<210> SEQ ID NO 80
<211> LENGTH: 284
<212> TYPE: PRT
<213> ORGANISM: Strepromyces griseus

<400> SEQUENCE: 80

Ala Pro Asp Ile Pro Leu Ala Asn Val Lys Ala His Leu Thr Gln Leu
1               5                   10                  15

Ser Thr Ile Ala Ala Asn Asn Gly Gly Asn Arg Ala His Gly Arg Pro
            20                  25                  30

Gly Tyr Lys Ala Ser Val Asp Tyr Val Lys Ala Lys Leu Asp Ala Ala
        35                  40                  45

Gly Tyr Thr Thr Thr Leu Gln Gln Phe Thr Ser Gly Gly Ala Thr Gly
    50                  55                  60

Tyr Asn Leu Ile Ala Asn Trp Pro Gly Gly Asp Pro Asn Lys Val Leu
65              70                  75                  80

Met Ala Gly Ala His Leu Asp Ser Val Ser Ser Gly Ala Gly Ile Asn
                85                  90                  95

Asp Asn Gly Ser Gly Ser Ala Ala Val Leu Glu Thr Ala Leu Ala Val
            100                 105                 110

Ser Arg Ala Gly Tyr Gln Pro Asp Lys His Leu Arg Phe Ala Trp Trp
```

```
            115                 120                 125
Gly Ala Glu Glu Leu Gly Leu Ile Gly Ser Lys Phe Tyr Val Asn Asn
130                 135                 140

Leu Pro Ser Ala Asp Arg Ser Lys Leu Ala Gly Tyr Leu Asn Phe Asp
145                 150                 155                 160

Met Ile Gly Ser Pro Asn Pro Gly Tyr Phe Tyr Asp Asp Pro
                165                 170                 175

Val Ile Glu Lys Thr Phe Lys Asn Tyr Phe Ala Gly Leu Asn Val Pro
            180                 185                 190

Thr Glu Ile Glu Thr Glu Gly Asp Gly Arg Ser Asp His Ala Pro Phe
        195                 200                 205

Lys Asn Val Gly Val Pro Val Gly Gly Leu Phe Thr Gly Ala Gly Tyr
    210                 215                 220

Thr Lys Ser Ala Ala Gln Ala Gln Lys Trp Gly Gly Thr Ala Gly Gln
225                 230                 235                 240

Ala Phe Asp Arg Cys Tyr His Ser Ser Cys Asp Ser Leu Ser Asn Ile
                245                 250                 255

Asn Asp Thr Ala Leu Asp Arg Asn Ser Asp Ala Ala His Ala Ile
            260                 265                 270

Trp Thr Leu Ser Ser Gly Thr Gly Glu Pro Pro Thr
            275                 280

<210> SEQ ID NO 81
<211> LENGTH: 299
<212> TYPE: PRT
<213> ORGANISM: Vibrio proteolyticus

<400> SEQUENCE: 81

Met Pro Pro Ile Thr Gln Gln Ala Thr Val Thr Ala Trp Leu Pro Gln
1               5                   10                  15

Val Asp Ala Ser Gln Ile Thr Gly Thr Ile Ser Ser Leu Glu Ser Phe
            20                  25                  30

Thr Asn Arg Phe Tyr Thr Thr Thr Ser Gly Ala Gln Ala Ser Asp Trp
        35                  40                  45

Ile Ala Ser Glu Trp Gln Ala Leu Ser Ala Ser Leu Pro Asn Ala Ser
50                  55                  60

Val Lys Gln Val Ser His Ser Gly Tyr Asn Gln Lys Ser Val Val Met
65                  70                  75                  80

Thr Ile Thr Gly Ser Glu Ala Pro Asp Glu Trp Ile Val Ile Gly Gly
                85                  90                  95

His Leu Asp Ser Thr Ile Gly Ser His Thr Asn Glu Gln Ser Val Ala
            100                 105                 110

Pro Gly Ala Asp Asp Ala Ser Gly Ile Ala Ala Val Thr Glu Val
        115                 120                 125

Ile Arg Val Leu Ser Glu Asn Asn Phe Gln Pro Lys Arg Ser Ile Ala
130                 135                 140

Phe Met Ala Tyr Ala Ala Glu Glu Val Gly Leu Arg Gly Ser Gln Asp
145                 150                 155                 160

Leu Ala Asn Gln Tyr Lys Ser Glu Gly Lys Asn Val Val Ser Ala Leu
                165                 170                 175

Gln Leu Asp Met Thr Asn Tyr Lys Gly Ser Ala Gln Asp Val Val Phe
            180                 185                 190

Ile Thr Asp Tyr Thr Asp Ser Asn Phe Thr Gln Tyr Leu Thr Gln Leu
        195                 200                 205

Met Asp Glu Tyr Leu Pro Ser Leu Thr Tyr Gly Phe Asp Thr Cys Gly
```

```
            210                 215                 220
Tyr Ala Cys Ser Asp His Ala Ser Trp His Asn Ala Gly Tyr Pro Ala
225                 230                 235                 240

Ala Met Pro Phe Glu Ser Lys Phe Asn Asp Tyr Asn Pro Arg Ile His
                245                 250                 255

Thr Thr Gln Asp Thr Leu Ala Asn Ser Asp Pro Thr Gly Ser His Ala
            260                 265                 270

Lys Lys Phe Thr Gln Leu Gly Leu Ala Tyr Ala Ile Glu Met Gly Ser
        275                 280                 285

Ala Thr Gly Asp Thr Pro Thr Pro Gly Asn Gln
    290                 295

<210> SEQ ID NO 82
<211> LENGTH: 30
<212> TYPE: DNA
<213> ORGANISM: Artificial sequence
<220> FEATURE:
<223> OTHER INFORMATION: Cloning primer

<400> SEQUENCE: 82
atatataagc ttatggcagg cggaagacac                                    30

<210> SEQ ID NO 83
<211> LENGTH: 31
<212> TYPE: DNA
<213> ORGANISM: Artificial sequence
<220> FEATURE:
<223> OTHER INFORMATION: Cloning primer

<400> SEQUENCE: 83
atatgcggcc gcttacaaat gaagatattc c                                  31

<210> SEQ ID NO 84
<211> LENGTH: 35
<212> TYPE: DNA
<213> ORGANISM: Artificial sequence
<220> FEATURE:
<223> OTHER INFORMATION: PCR primer

<400> SEQUENCE: 84
atatatgcgg ccgcctagag ccccaggtat tcagc                              35

<210> SEQ ID NO 85
<211> LENGTH: 31
<212> TYPE: DNA
<213> ORGANISM: Artificial sequence
<220> FEATURE:
<223> OTHER INFORMATION: PCR primer

<400> SEQUENCE: 85
atatctcgag tccatcgcca ccatggtgag c                                  31

<210> SEQ ID NO 86
<211> LENGTH: 31
<212> TYPE: DNA
<213> ORGANISM: Artificial sequence
<220> FEATURE:
<223> OTHER INFORMATION: PCR primer

<400> SEQUENCE: 86
atatctcgag ttacttgtac agctcgtcca t                                  31

<210> SEQ ID NO 87
<211> LENGTH: 41
```

```
<212> TYPE: DNA
<213> ORGANISM: artificial sequence
<220> FEATURE:
<223> OTHER INFORMATION: PCR primer

<400> SEQUENCE: 87
atatgcggcc gcatgtcgac gctccaaatg gtgtagaacg c                    41

<210> SEQ ID NO 88
<211> LENGTH: 57
<212> TYPE: DNA
<213> ORGANISM: Artificial sequence
<220> FEATURE:
<223> OTHER INFORMATION: PCR primer

<400> SEQUENCE: 88
atatgcggcc gcttacttgt catcgtcatc cttgtaatcc aaatgaagat attccaa    57

<210> SEQ ID NO 89
<211> LENGTH: 57
<212> TYPE: DNA
<213> ORGANISM: Artificial sequence
<220> FEATURE:
<223> OTHER INFORMATION: PCR primer

<400> SEQUENCE: 89
atatgcggcc gcctacttgt catcgtcatc cttgtaatcg agccccaggt attcagc    57

<210> SEQ ID NO 90
<211> LENGTH: 20
<212> TYPE: DNA
<213> ORGANISM: Artificial sequence
<220> FEATURE:
<223> OTHER INFORMATION: PCR primer

<400> SEQUENCE: 90
gcctccagca tgaaagtctc                                            20

<210> SEQ ID NO 91
<211> LENGTH: 20
<212> TYPE: DNA
<213> ORGANISM: Artificial sequence
<220> FEATURE:
<223> OTHER INFORMATION: CAGATCTCCTTGGCCACAAT

<400> SEQUENCE: 91
cagatctcct tggccacaat                                            20

<210> SEQ ID NO 92
<211> LENGTH: 20
<212> TYPE: DNA
<213> ORGANISM: Artificial sequence
<220> FEATURE:
<223> OTHER INFORMATION: PCR primer

<400> SEQUENCE: 92
atgaaagcct ctgcagcact                                            20

<210> SEQ ID NO 93
<211> LENGTH: 20
<212> TYPE: DNA
<213> ORGANISM: artificial sequence
<220> FEATURE:
<223> OTHER INFORMATION: PCR primer

<400> SEQUENCE: 93
tggctactgg tggtccttct                                            20
```

<210> SEQ ID NO 94
<211> LENGTH: 20
<212> TYPE: DNA
<213> ORGANISM: artificial sequence
<220> FEATURE:
<223> OTHER INFORMATION: PCR primer

<400> SEQUENCE: 94
tcacctgctg ctttaacgtg                                              20

<210> SEQ ID NO 95
<211> LENGTH: 20
<212> TYPE: DNA
<213> ORGANISM: Artificial sequence
<220> FEATURE:
<223> OTHER INFORMATION: PCR primer

<400> SEQUENCE: 95
atccctgacc catctctcct                                              20

<210> SEQ ID NO 96
<211> LENGTH: 20
<212> TYPE: DNA
<213> ORGANISM: artificial sequence
<220> FEATURE:
<223> OTHER INFORMATION: PCR primer

<400> SEQUENCE: 96
atctccttgc agaggctgaa                                              20

<210> SEQ ID NO 97
<211> LENGTH: 20
<212> TYPE: DNA
<213> ORGANISM: artificial sequence
<220> FEATURE:
<223> OTHER INFORMATION: PCR primer

<400> SEQUENCE: 97
agaagaggag gccagaggag                                              20

<210> SEQ ID NO 98
<211> LENGTH: 20
<212> TYPE: DNA
<213> ORGANISM: artificial sequence
<220> FEATURE:
<223> OTHER INFORMATION: PCR primer

<400> SEQUENCE: 98
cacagaaatg gccttgtgaa                                              20

<210> SEQ ID NO 99
<211> LENGTH: 20
<212> TYPE: DNA
<213> ORGANISM: artificial sequence
<220> FEATURE:
<223> OTHER INFORMATION: PCR primer

<400> SEQUENCE: 99
ccaagcaggt cataggtggt                                              20

<210> SEQ ID NO 100
<211> LENGTH: 20
<212> TYPE: DNA
<213> ORGANISM: artificial sequence
<220> FEATURE:
<223> OTHER INFORMATION: PCR primer

```
<400> SEQUENCE: 100
tcctttcatc ctggaacctg                                              20

<210> SEQ ID NO 101
<211> LENGTH: 20
<212> TYPE: DNA
<213> ORGANISM: artificial sequence
<220> FEATURE:
<223> OTHER INFORMATION: PCR primer

<400> SEQUENCE: 101
cgcctcttct gtttcacctc                                              20

<210> SEQ ID NO 102
<211> LENGTH: 20
<212> TYPE: DNA
<213> ORGANISM: artificial sequence
<220> FEATURE:
<223> OTHER INFORMATION: PCR primer

<400> SEQUENCE: 102
aagcgctgtt tgccagttat                                              20

<210> SEQ ID NO 103
<211> LENGTH: 20
<212> TYPE: DNA
<213> ORGANISM: artificial sequence
<220> FEATURE:
<223> OTHER INFORMATION: PCR primer

<400> SEQUENCE: 103
cacacgtgag gcgctattta                                              20

<210> SEQ ID NO 104
<211> LENGTH: 20
<212> TYPE: DNA
<213> ORGANISM: artificial sequence
<220> FEATURE:
<223> OTHER INFORMATION: PCR primer

<400> SEQUENCE: 104
gtcaacagat cctccccaga                                              20

<210> SEQ ID NO 105
<211> LENGTH: 20
<212> TYPE: DNA
<213> ORGANISM: artificial sequence
<220> FEATURE:
<223> OTHER INFORMATION: PCR primer

<400> SEQUENCE: 105
cagcatttct gcctttgtga                                              20

<210> SEQ ID NO 106
<211> LENGTH: 20
<212> TYPE: DNA
<213> ORGANISM: artificial sequence
<220> FEATURE:
<223> OTHER INFORMATION: PCR primer

<400> SEQUENCE: 106
aggtggagag cctgaggaat                                              20

<210> SEQ ID NO 107
<211> LENGTH: 20
```

<212> TYPE: DNA
<213> ORGANISM: artificial sequence
<220> FEATURE:
<223> OTHER INFORMATION: PCR primer

<400> SEQUENCE: 107
ctcgggtcct acttgtcagc                                          20

<210> SEQ ID NO 108
<211> LENGTH: 20
<212> TYPE: DNA
<213> ORGANISM: artificial sequence
<220> FEATURE:
<223> OTHER INFORMATION: PCR primer

<400> SEQUENCE: 108
aagcgaggtt ctcgttctga                                          20

<210> SEQ ID NO 109
<211> LENGTH: 20
<212> TYPE: DNA
<213> ORGANISM: artificial sequence
<220> FEATURE:
<223> OTHER INFORMATION: PCR primer

<400> SEQUENCE: 109
tgacctcttg ctctccctgt                                          20

<210> SEQ ID NO 110
<211> LENGTH: 20
<212> TYPE: DNA
<213> ORGANISM: artificial sequence
<220> FEATURE:
<223> OTHER INFORMATION: PCR primer

<400> SEQUENCE: 110
cttcaagctc tcctgctgct                                          20

<210> SEQ ID NO 111
<211> LENGTH: 20
<212> TYPE: DNA
<213> ORGANISM: artificial sequence
<220> FEATURE:
<223> OTHER INFORMATION: PCR primer

<400> SEQUENCE: 111
cgaccctgac ttcctggtta                                          20

<210> SEQ ID NO 112
<211> LENGTH: 20
<212> TYPE: DNA
<213> ORGANISM: artificial sequence
<220> FEATURE:
<223> OTHER INFORMATION: PCR primer

<400> SEQUENCE: 112
gctcatcggc tgttggtatt                                          20

<210> SEQ ID NO 113
<211> LENGTH: 20
<212> TYPE: DNA
<213> ORGANISM: artificial sequence
<220> FEATURE:
<223> OTHER INFORMATION: PCR primer

<400> SEQUENCE: 113
ataagcaggt ggagcattgg                                          20

<210> SEQ ID NO 114
<211> LENGTH: 20
<212> TYPE: DNA
<213> ORGANISM: artificial sequence
<220> FEATURE:
<223> OTHER INFORMATION: PCR primer

<400> SEQUENCE: 114
atgcttcgga aactggacat                                               20

<210> SEQ ID NO 115
<211> LENGTH: 20
<212> TYPE: DNA
<213> ORGANISM: artificial sequence
<220> FEATURE:
<223> OTHER INFORMATION: PCR primer

<400> SEQUENCE: 115
atggttcgat gcagctttct                                               20

<210> SEQ ID NO 116
<211> LENGTH: 20
<212> TYPE: DNA
<213> ORGANISM: artificial sequence
<220> FEATURE:
<223> OTHER INFORMATION: PCR primer

<400> SEQUENCE: 116
tacggcgtaa tcctggaaac                                               20

<210> SEQ ID NO 117
<211> LENGTH: 20
<212> TYPE: DNA
<213> ORGANISM: artificial sequence
<220> FEATURE:
<223> OTHER INFORMATION: PCR primer

<400> SEQUENCE: 117
attgtgcatg ctgctttgag                                               20

<210> SEQ ID NO 118
<211> LENGTH: 20
<212> TYPE: DNA
<213> ORGANISM: artificial sequence
<220> FEATURE:
<223> OTHER INFORMATION: PCR primer

<400> SEQUENCE: 118
ccgaaacaca gtggaaggtt                                               20

<210> SEQ ID NO 119
<211> LENGTH: 20
<212> TYPE: DNA
<213> ORGANISM: artificial sequence
<220> FEATURE:
<223> OTHER INFORMATION: PCR primer

<400> SEQUENCE: 119
tctgtgaagg tgtgcaggag                                               20

<210> SEQ ID NO 120
<211> LENGTH: 20
<212> TYPE: DNA
<213> ORGANISM: artificial sequence
<220> FEATURE:
<223> OTHER INFORMATION: PCR primer

```
<400> SEQUENCE: 120
ggttcctttc ttccctccag                                              20

<210> SEQ ID NO 121
<211> LENGTH: 20
<212> TYPE: DNA
<213> ORGANISM: artificial sequence
<220> FEATURE:
<223> OTHER INFORMATION: PCR primer

<400> SEQUENCE: 121
aaccaaagcc accagtgttc                                              20
```

METHOD OF SCREENING FOR INHIBITORS OF GLUTAMINYL CYCLASE ACTIVITY

CROSS REFERENCE TO RELATED APPLICATIONS

This application is a Divisional Application of U.S. Nonprovisional application Ser. No. 11/859,217, filed on Sep. 21, 2007, which claims benefit of U.S. Provisional Patent Application Ser. No. 60/846,244, filed on Sep. 21, 2006, and U.S. Provisional Patent Application Ser. No. 60/947,780, filed on Jul. 3, 2007. All of these applications are incorporated herein by reference in their entireties to the extent permitted by law.

INCORPORATION-BY-REFERENCE OF MATERIAL SUBMITTED IN COMPUTER READABLE FORM

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The present invention relates to novel glutaminyl-peptide cyclotransferase-like proteins (QPCTLs), which are isoenzymes of glutaminyl cyclase (QC, EC 2.3.2.5), and to isolated nucleic acids coding for these isoenzymes, all of which are useful for the discovery of new therapeutic agents, for measuring cyclase activity, and for determining the inhibitory activity of compounds against these glutaminyl cyclase isoenzymes.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

EP 02 011 349.4 discloses polynucleotides encoding insect glutaminyl cyclase, as well as polypeptides encoded thereby. This application further provides host cells comprising expression vectors comprising polynucleotides of the invention. Isolated polypeptides and host cells comprising insect QC are useful in methods of screening for agents that reduce glutaminyl cyclase activity. Such agents are useful as pesticides.

Inhibitors of QC, which also could be useful as inhibitors of QC isoenzymes, are described in WO 2004/098625, WO 2004/098591, WO 2005/039548 and WO 2005/075436, which are incorporated herein in their entirety, especially with regard to the structure of the inhibitors, their use and their production.

DEFINITIONS

Enzyme Inhibitors

Reversible enzyme inhibitors: comprise competitive inhibitors, non-competitive reversible inhibitors, slow-binding or tight-binding inhibitors, transition state analogs and multisubstrate analogs.

Competitive Inhibitors Show
 i) non-covalent interactions with the enzyme,
 ii) compete with substrate for the enzyme active site, The principal mechanism of action of a reversible enzyme inhibitor and the definition of the dissociation constant can be visualized as follows:

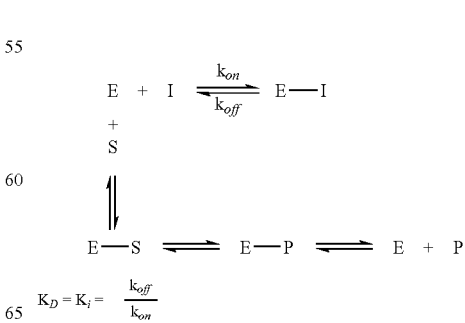

The formation of the enzyme-inhibitor [E-I] complex prevents binding of substrates, therefore the reaction cannot proceed to the normal physiological product, P. A larger inhibitor concentration [I] leads to larger [E-I], leaving less free enzyme to which the substrate can bind.

Non-competitive Reversible Inhibitors
  i) bind at a site other than active site (allosteric binding site)
  ii) cause a conformational change in the enzyme which decreases or stops catalytic activity.

Slow-binding or Tight-binding Inhibitors
  i) are competitive inhibitors where the equilibrium between inhibitor and enzyme is reached slowly,
  ii) ($k_{on}$ is slow), possibly due to conformational changes that must occur in the enzyme or inhibitor
    a) are often transition state analogs
    b) are effective at concentrations similar to the enzyme conc. (subnanomolar $K_D$ values)
    c) due to $k_{off}$ values being so low these types of inhibitors are "almost" irreversible Transition State Analogs
  are competitive inhibitors which mimic the transition state of an enzyme catalyzed reaction. Enzyme catalysis occurs due to a lowering of the energy of the transition state, therefore, transition state binding is favored over substrate binding.

Multisubstrate Analogs
  For a reaction involving two or more substrates, a competitive inhibitor or transition state analog can be designed which contains structural characteristics resembling two or more of the substrates.

Irreversible enzyme inhibitors: drive the equilibrium between the unbound enzyme and inhibitor and enzyme inhibitor complex (E+I<- - - >E-I) all the way to the right with a covalent bond (~100 kcal/mole), making the inhibition irreversible.

Affinity Labeling Agents
  Active-site directed irreversible inhibitors (competitive irreversible inhibitor) are recognized by the enzyme (reversible, specific binding) followed by covalent bond formation, and
    i) are structurally similar to substrate, transition state or product allowing for specific interaction between drug and target enzyme,
    ii) contain reactive functional group (e.g. a nucleophile, —COCH$_2$Br) allowing for covalent bond formation The reaction scheme below describes an active-site directed reagent with its target enzyme where $K_D$ is the dissociation constant and $k_{inactivation}$ is the rate of covalent bond formation.

Mechanism-based enzyme inactivators (also called suicide inhibitors) are active-site directed reagents (unreactive) which binds to the enzyme active site where it is transformed to a reactive form (activated) by the enzyme's catalytic capabilities. Once activated, a covalent bond between the inhibitor and the enzyme is formed.

The reaction scheme below shows the mechanism of action of a mechanism based enzyme inactivator, where $K_D$ is the dissociation complex, $k_2$ is the rate of activation of the inhibitor once bound to the enzyme, $k_3$ is the rate of dissociation of the activated inhibitor, P, from the enzyme (product can still be reactive) from the enzyme and $k_4$ is the rate of covalent bond formation between the activated inhibitor and the enzyme.

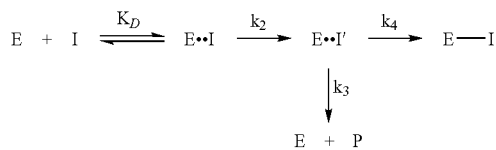

Inactivation (covalent bond formation, $k_4$) must occur prior to dissociation ($k_3$) otherwise the now reactive inhibitor is released into the environment. Partition ratio, $k_3/k_4$: ratio of released product to inactivation should be minimized for efficient inactivation of the system and minimal undesirable side reactions. A large partition ratio (favors dissocation) leads to nonspecific reactions.

Uncompetitive enzyme inhibitors: From the definition of uncompetitive inhibitor (an inhibitor which binds only to ES complexes) the following equilibria can be written:

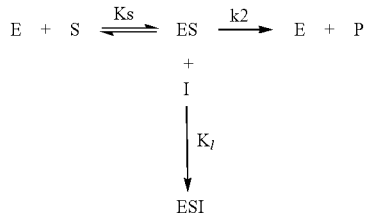

The ES complex dissociates the substrate with a dissociation constant equal to Ks, whereas the ESI complex does not dissociate it (i.e has a Ks value equal to zero). The $K_m$'s of Michaelis-Menten type enzymes are expected to be reduced. Increasing substrate concentration leads to increasing ESI concentration (a complex incapable of progressing to reaction products), therefore the inhibition can not be removed.

Preferred according to the present invention are competitive enzyme inhibitors. Most preferred are competitive reversible enzyme inhibitors.

The terms "$k_i$" or "$K_I$" and "$K_D$" are binding constants, which describe the binding of an inhibitor to and the subsequent release from an enzyme. Another measure is the "IC$_{50}$" value, which reflects the inhibitor concentration, which at a given substrate concentration results in 50% enzyme activity.

The term "QC" as used herein comprises glutaminyl cyclase (QC), which is synonymous to glutaminyl-peptide cyclotransferase (QPCT); and QC-like enzymes, which are synonymous to glutaminyl-peptide cyclotransferase-like proteins (QPCTLs). QC and QC-like enzymes have identical or similar enzymatic activity, further defined as QC activity. In this regard, QC-like enzymes can fundamentally differ in their molecular structure from QC.

"QC-activity" is defined as the catalytic activity of glutaminyl cyclase (QC, QPCT) and QC-like enzymes (QPCTLs). These enzymes are found in various tissues of the body of a mammal including kidney, liver, intestine, brain and body fluids such as CSF, where they cyclize glutamine or glutamate at the N-terminus of biologically active peptides with a high specificity.

In particular, the term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

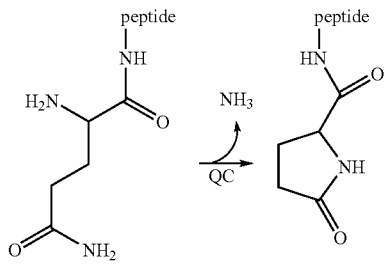

Scheme 2: Cyclization of L-homoglutamine by QC

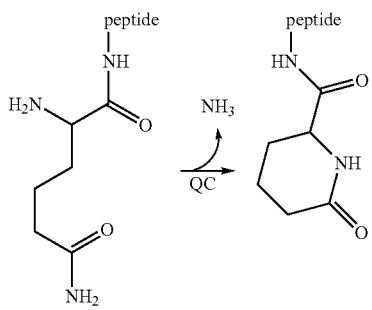

The term "EC" as used herein comprises the side activity of glutaminyl cyclase (QC, QPCT) and QC-like enzymes (QPCTLs) as glutamate cyclase (EC), further defined as EC activity.

The term "EC activity" as used herein is defined as intramolecular cyclization of N-terminal glutamate residues into pyroglutamic acid (pGlu*) by glutaminyl cyclase (QC, QPCT) and QC-like enzymes (QPCTLs). See therefore scheme 3.

Scheme 3: N-terminal cyclization of uncharged glutamyl peptides by QC (EC)

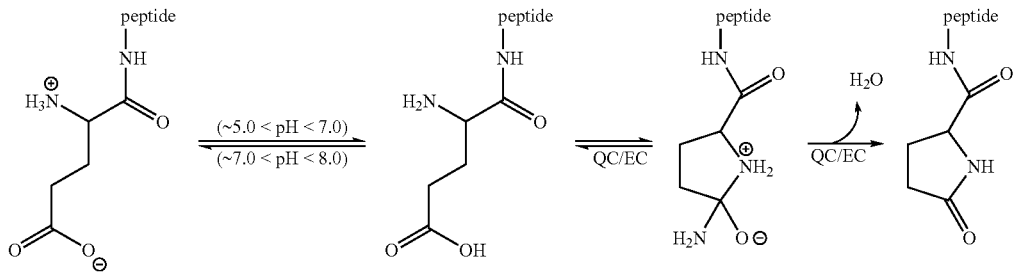

The term "QC-inhibitor" or "glutaminyl cyclase inhibitor" is generally known to a person skilled in the art and means enzyme inhibitors, which inhibit the catalytic activity of glutaminyl cyclase (QC, QPCT) or QC-like enzymes (QPCTLs) or their glutamyl cyclase (EC) activity, preferably by direct interaction of the inhibitor with the enzyme.

Ther term "selective QC-inhibitor" as defined herein means enzyme inhibitors, which inhibit the catalytic activity of glutaminyl cyclase (QC, QPCT) but do not or with a lower potency inhibit at least one QC-like enzymes (QPCTLs). Preferred are selective QC-inhibitors, which inhibit glutaminyl cyclase (QC, QPCT) with an ki-value, which is one order of magnitude lower than its ki-value for the inhibition of at least one QC-like enzyme (QPCTL). More preferably, the ki-value of said selective QC-inhibitor for the inhibition of glutaminyl cyclase (QC, QPCT) is two orders of magnitude lower than its ki-value for the inhibition of at least one QC-like enzyme (QPCTL). Even more preferred are selective QC-inhibitors, wherein their ki-value for the inhibition of glutaminyl cyclase (QC, QPCT) is three orders of magnitude lower than their ki-value for the inhibition of at least one QC-like enzyme (QPCTL). Most preferred are selective QC-inhibitors, which do not inhibit QC-like enzymes (QPCTLs).

Ther term "selective QPCTL-inhibitor" as defined herein means enzyme inhibitors, which inhibit the catalytic activity of at least one QC-like enzyme (QPCTL), but do not or with a lower potency inhibit the activity of glutaminyl cyclase (QC, QPCT). Preferred are selective QPCTL-inhibitors, which inhibit at least one QC-like enzyme (QPCTL) with an ki-value, which is one order of magnitude lower than its ki-value for the inhibition of glutaminyl cyclase (QC, QPCT). More preferably, the ki-value of said selective QPCTL-inhibitor for the inhibition of at least one QC-like enzyme (QPCTL) is two orders of magnitude lower than its ki-value for the inhibition of glutaminyl cyclase (QC, QPCT). Even more preferred are selective QPCTL-inhibitors, wherein their ki-value for the inhibition of at least one QC-like enzyme (QPCTL) is three orders of magnitude lower than their ki-value for the inhibition of glutaminyl cyclase (QC, QPCT). Most preferred are selective QPCTL-inhibitors, which do not inhibit the activity of glutaminyl cyclase (QC, QPCT).

Potency of QC Inhibition

In light of the correlation with QC inhibition, in preferred embodiments, the subject method and medical use utilize an agent with a $K_i$ for QC inhibition of 10 μM or less, more preferably of 1 μM or less, even more preferably of 0.1 μM or less or 0.01 μM or less, or most preferably 0.01 μM or less. Indeed, inhibitors with $K_i$ values in the lower micromolar, preferably the nanomolar and even more preferably the picomolar range are contemplated. Thus, while the active agents are described herein, for convience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 1000 g/mole or less, 500 g/mole or less, preferably of 400 g/mole or less, and even more preferably of 350 g/mole or less and even of 300 g/mole or less.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: for example the term "pharmaceutically acceptable" embraces a veterinarily acceptable compound or a compound acceptable in human medicine and health care.

Guillain-Barré Syndrome (GBS)

Alternative names are Landry-Guillain-Barré syndrome, Acute idiopathic polyneuritis, Infectious polyneuritis or Acute inflammatory polyneuropathy.

Guillain-Barré syndrome is a serious disorder that occurs when the body's defense (immune) system mistakenly attacks part of the nervous system. This leads to nerve inflammation that causes muscle weakness, which continues to get worse.

Guillain-Barré syndrome is an autoimmune disorder. The exact cause of Guillain-Barré syndrome is unknown. The syndrome may occur at any age, but is most common in people of both sexes between the ages 30 and 50. It often follows a minor infection, usually a respiratory (lung) infection or gastrointestinal (gut) infection. Usually, signs of the original infection have disappeared before the symptoms of Guillain-Barré begin. Guillain-Barré syndrome causes inflammation that damages parts of nerves. This nerve damage causes tingling, muscle weakness, and paralysis. The inflammation usually affects the nerve's covering (myelin sheath). Such damage is called demyelination. Demyelination slows nerve signaling. Damage to other parts of the nerve can cause the nerve to stop working.

Symptoms of Guillain-Barré get worse very quickly. It may take only a few hours to reach the most severe symptoms. Muscle weakness or the loss of muscle function (paralysis) affects both sides of the body. If the muscle weakness starts in the legs and then spreads to the arms, it is called ascending paralysis.

Patients may notice tingling, foot or hand pain, and clumsiness. As the loss of muscle function gets worse, the patient may need breathing assistance.

There is no cure for Guillain-Barré syndrome. However, many treatments are available to help reduce symptoms, treat complications, and speed up recovery. When symptoms are severe, the patient will need to go to the hospital for breathing help, treatment, and physical therapy. A method called plasmaphoresis is used to remove a person's blood and replace it with intravenous fluids or donated blood that is free of antibodies. High-dose immunoglobulin therapy is another procedure used to reduce the severity and length of Guillain-Barré symptoms. Other treatments are directed at preventing complications.

Chronic Inflammatory Demyelinizing Polyradiculoneuropathy (CIDP)

A disease, which resembles GBS but is characterized by a chronic course is called chronic inflammatory demyelinizing polyradiculoneuropathy (CIDP). There is as yet no generally applicable definition for CIDP with the exception of the observation that in contrast to GBS, the progressive phase lasts longer than four weeks, often longer than six months, and that deficiencies often remain in the patient. The mechanism, which causes the severe paresis with GBS and CIDP possibly includes an immune reaction and inflammation mediated by T lymphocytes, which follows demyelination of peripheral neurons. This assumption is confirmed by increased amounts of complement compounds and cytokines observed in the serum and cerebrospinal fluid of GBS patients. The process of demyelinization, especially in the region of the nerve roots, is currently regarded as the decisive mechanism in the development of nerve conduction block. One theory is based on a disorder of the blood/cerebrospinal fluid (CSF) barrier as a relatively early important step in the development of the disease. Another theory claims that leaks develop in the blood/CSF barrier as a consequence of the disease and cause the increased protein content in the CSF. At any rate, non-specific serum constituents without direct reference to the immune system could penetrate into the CSF from the blood, cause neuronal or glial dysfunctions and/or modify neuronal activity. An alternative mechanism is a reduced flow rate of the CSF, which could explain the increased protein content of the CSF. This interpretation requires no impairment or modified selectivity of the blood/CSF barrier. Although all the effects mentioned could be of importance for the course of GBS and CIDP, their actual contribution to the symptoms has not yet been clarified. It has not been possible to establish a connection between the increased protein concentrations in the CSF and specific electrophysiological findings or the clinical picture. Factors in the CSF of GBS patients and multiple sclerosis patients, which interact with potential-dependent sodium channels have recently been described (Wüz et al. 1995, Muscle and Nerve 18, 772-781). Brinkmeier (Brinkmeier et al. 1996, Muscle and Nerve 19, 54-62) report that the factors have a molecular weight of less than three kDa, and under more stringent test conditions of less than one kDa. On the basis of this observation and the fact that the activity of the factors was not substantially reduced even after incubation of CSF with proteases, the authors concluded that the factors were neither antibodies nor cytokines.

Multiple Sclerosis (MS)

Multiple sclerosis is an autoimmune disease that affects the central nervous system (the brain and spinal cord). Multiple sclerosis usually affects woman more than men. The disorder most commonly begins between ages 20 and 40, but can strike at any age. The exact cause is not known, but MS is believed to result from damage to the myelin sheath, the protective material, which surrounds nerve cells. It is a progressive disease, meaning the damage gets worse over time. Inflammation destroys the myelin, leaving multiple areas of scar tissue (sclerosis). The inflammation occurs when the body's own immune cells attack the nervous system. The inflammation causes nerve impulses to slow down or become blocked, leading to the symptoms of MS. Repeated episodes, or flare ups, of inflammation can occur along any area of the brain and spinal cord. Symptoms vary because the location and extent of each attack varies. Usually episodes that last days, weeks, or months alternate with times of reduced or no symptoms (remission). Recurrence (relapse) is common although nonstop progression without periods of remission may also occur.

It is not clear what triggers an attack. Patients with MS typically have a higher number of immune cells than a healthy person, which suggests that an immune response might play a role. The most common theories point to a virus or genetic defect, or a combination of both. There also appears to be a genetic link to the disease. MS is more likely to occur in northern Europe, the northern United States, southern Australia, and New Zealand than in other areas. Geographic studies indicate there may be an environmental factor involved. People with a family history of MS and those who live in a geographical area with a higher incidence rate for MS have a higher risk of the disease.

There is no known cure for multiple sclerosis at this time. However, there are a number of therapies that may slow the disease. The goal of treatment is to control symptoms and maintain a normal quality of life.

SUMMARY OF THE INVENTION

The present invention provides proteins with glutaminyl cyclase activities that constitute novel members of a family of proteins related to glutaminyl cyclase, including the full-length proteins, alternative splice forms, subunits, and mutants, as well as nucleotide sequences encoding the same. The present invention also provides methods of screening for substrates, interacting proteins, agonists, antagonists or inhibitors of the above proteins, and furthermore to pharmaceutical compositions comprising the proteins and/or mutants, derivatives and/or analogues thereof and/or ligands thereto.

These novel proteins having significant sequence similarity to glutaminyl cyclase (nucleic acid sequence of SEQ ID NO 1, protein sequence of SEQ ID NO 10) are proteins (QPCTLs) from human (further named as human isoQC) (GenBank accession no. NM_017659), mouse (GenBank accession no. NM_027455), Macaca fascicularis (GenBank accession no. AB168255), Macaca mulatta (GenBank accession no. XM_001110995), cat (GenBank accession no. XM_541552), rat (GenBank accession no. XM_001066591), cow (GenBank accession no. BT026254) or an analogue thereof having at least 50%/75% sequence identity/similarity, preferably 70%/85% sequence identity/similarity, more preferably 90%/95% sequence identity/similarity, most preferably 99% sequence identity/similarity.

The protein sequences are given in SEQ. ID NOS: 11 to 18. Further disclosed are nucleic acid sequences coding for these proteins (SEQ. ID NOS: 2 to 9). Table 1 illustrates the similarity between the novel proteins and the known glutaminyl cyclase. Table 2 illustrates the identity between the novel proteins and the known glutaminyl cyclase.

TABLE 1

Similarity of the protein sequences of the novel glutaminyl-peptide cyclotransferase-like proteins with glutaminyl cyclase

| QPCTL source | human isoQC (SEQ ID NO 11) | human QC (SEQ ID NO 10) |
| --- | --- | --- |
| human isoQC (SEQ ID NO 11) | — | 71.98% |
| M_fascicularis (SEQ ID NO 13) | 99.48% | 72.24% |
| M_mulatta (SEQ ID NO 14) | 99.48% | 72.24% |
| C_familiaris (SEQ ID NO 15) | 95.82% | 72.31% |
| R_norvegicus (SEQ ID NO 16) | 95.30% | 70.77% |
| M_musculus (SEQ ID NO 17) | 95.04% | 70.77% |
| B_taurus (SEQ ID NO 18) | 96.08% | 72.31% |

TABLE 2

Identity of the protein sequences of the novel glutaminyl-peptide cyclotransferase-like proteins with glutaminyl cyclase

| QPCTL source | human isoQC (SEQ ID NO 11) | human QC (SEQ ID NO 10) |
| --- | --- | --- |
| human isoQC (SEQ ID NO 11) | — | 45.24% |
| M_fascicularis (SEQ ID NO 13) | 98.17% | 44.99% |
| M_mulatta (SEQ ID NO 14) | 98.17% | 44.99% |
| C_familiaris (SEQ ID NO 15) | 88.51% | 45.13% |
| R_norvegicus (SEQ ID NO 16) | 84.33% | 45.38% |
| M_musculus (SEQ ID NO 17) | 84.07% | 44.62% |
| B_taurus (SEQ ID NO 18) | 84.60% | 45.64% |

There is a high similarity of 95 to 99% and a high identity of 84 to 98% between the QPCTLs from different sources (see FIG. 2). On the basis of sequence similarity with human and murine glutaminyl cyclase (see FIG. 1), one might predict that these QPCTLs would have functions that include, but are not limited to, roles as enzymes. Cloning, expression, biochemical and molecular characterization have confirmed this hypothesis.

The expression pattern of the QPCTLs in brain, prostate and lung tissue is consistent with a role in the diseases described below. The enzymatic activity as glutaminyl cyclase demonstrates that QPCTLs-activating or inhibiting molecules will have numerous therapeutic applications as described below.

QPCTL activities described herein and their expression patterns are compatible with their functional roles as physiological regulators of the immune and neuroendocrine systems through the enzymatic modification of biochemical mediators like hormones, peptides and chemokines. The numerous functions previously described for QC based upon the use of inhibitors may be due in part to its action and that of similar proteins, like the QPCTLs. Therefore, the discovery of selective and potent inhibitors of QC, of the QPCTLs and of other related enzymes is considered central to achieving effective and safe pharmaceutical use of these and any newly identified glutaminyl-peptide cyclotransferases, as well as other active compounds that modify the function(s) of such proteins.

The invention thus provides novel proteins or polypeptides, the nucleic acids coding therefore, cells which have been modified with the nucleic acid so as to express these proteins, antibodies to these proteins, a screening method for the discovery of new therapeutic agents which are inhibitors of the activity of these proteins (or which are inhibitors of QC and not of the proteins), and therapeutic agents discovered by such screening methods. The novel proteins and the nucleic acids coding therefore can be used to discover new therapeutic agents for the treatment of certain diseases, such as for example, neurodegenerative, reproductive, inflammatory and metabolic disorders and also in the preparation of antibodies with therapeutic or diagnostic value.

In accordance with one aspect of the present invention, there are provided novel, mature, biologically active proteins, preferably of human origin. Such proteins may be isolated in small quantities from suitable animal (including human) tissue or biological fluids by standard techniques; however, larger quantities are more conveniently prepared in cultures of cells genetically modified so as to express the protein.

In accordance with another aspect of the present invention, there are provided isolated nucleic acid molecules encoding polypeptides of the present invention including mRNAs, DNAs, cDNAs, genomic DNAs thereof.

In accordance with a further aspect of the present invention, nucleic acid probes are also provided comprising nucleic acid molecules of sufficient length to specifically hybridize to a nucleic acid sequence of the present invention.

In accordance with a still further aspect of the present invention, processes utilizing recombinant techniques are provided for producing such polypeptides useful for in vitro scientific research, for example, synthesis of DNA and manufacture of DNA vectors. Processes for producing such polypeptides include culturing recombinant prokaryotic and/or eukaryotic host cells that have been transfected with DNA vectors containing a nucleic acid sequence encoding such a polypeptide and/or the mature protein under conditions promoting expression of such protein and subsequent recovery of such protein or a fragment of the expressed product.

In accordance with still another aspect, the invention provides methods for using QPCTL polypeptides and polynucleotides for the treatment of diseases.

In accordance with yet another aspect of the present invention, there is provided a process for utilizing such polypeptides, or polynucleotides encoding such polypeptides, for the discovery of compounds that inhibit the biological activity of the mature proteins, e.g. the QC activity or the EC activity, and such inhibitors are thus also provided.

In accordance with a more specific aspect, the invention provides an isolated nucleic acid which encodes (a) a QPCTL polypeptide, selected from SEQ ID NOS: 11 to 18, or (b) having an amino acid sequence that is at least about 75% similar thereto and exhibits the same biological function, or which is an alternative splice variant of one of SEQ ID NOS: 2 to 9, or which is a probe comprising at least 14 contiguous nucleotides from said nucleic acid encoding (a) or (b), or which is complementary to any one of the foregoing.

In accordance with another specific aspect, the invention provides a polypeptide which may be optionally glycosylated, and which (a) has the amino acid sequence of a mature protein set forth in any one of SEQ ID NOS: 10 to 18; preferably of a mature protein set forth in any one of SEQ ID NOS: 11 to 18 (b) has the amino acid sequence of a mature protein having at least about 75% similarity to one of the mature proteins of (a) and which exhibits the same biological function; (c) has the amino acid sequence of a mature protein having at least about 50% identity with a mature protein of any of SEQ ID NOS: 10 to 18; preferably of a mature protein set forth in any one of SEQ ID NOS: 11 to 18 or (d) is an immunologically reactive fragment of (a).

In accordance with still another specific aspect, the invention provides a method of screening for a compound capable of inhibiting the enzymatic activity of at least one mature protein according to the present invention, preferably selected from the proteins of SEQ ID NOS: 11 to 18, which method comprises incubating said mature protein and a suitable substrate for said mature protein in the presence of one or more test compounds or salts thereof, measuring the enzymatic activity of said mature protein, comparing said activity with comparable activity determined in the absence of a test compound, and selecting the test compound or compounds that reduce the enzymatic activity.

Further, the present invention pertains to diagnostic kits and methods based on the use of a QC-inhibitor, selective QC-inhibitor or selective QPCTL-inhibitor.

These and other aspects of the present invention should be apparent to those skilled in the art from the detailed description, which follows.

BRIEF DESCRIPTION OF THE DRAWINGS

FIG. 1 shows the sequence alignment of human QC (hQC), human isoQC (hisoQC), murine QC (mQC) and murine isoQC (misoQC). Multiple sequence alignment was performed using ClustalW at PBIL (Pôle Bioinformatique Lyonnais) (http://npsa-pbil.ibcp.fr) with default settings. The conservation of the zinc-ion ligating residues is shown for human QC (hQC; GenBank X71125, SEQ ID NO: 10), human isoQC (hisoQC, GenBank NM_017659, SEQ ID NO: 11), murine QC (mQC, GenBank NM_027455, SEQ ID NO: 79) and murine isoQC (misoQC, GenBank BC058181, SEQ ID NO: 17) in bold and underlined.

FIG. 2 shows the sequence alignment of isoQC from *Homo sapiens* (hisoQC, GenBank NM_017659, SEQ ID NO: 11), *Macaca fascicularis* (M_fascicularis, GenBank AB168255, SEQ ID NO: 13), *Macaca mulatta* (M_mulatta, GenBank XM_001110995, SEQ ID NO: 14), *Canis familiaris* (C_familiaris, GenBank XM_541552, SEQ ID NO: 15), *Rattus norvegicus* (R_norvegicus, GenBank XM_001066591, SEQ ID NO: 16), *Mus musculus* (M_musculus, GenBank BC058181, SEQ ID NO: 17) and *Bos taurus* (B_taurus, GenBank BT026254, SEQ ID NO: 18). Multiple sequence alignment was performed using ClustalW at PBIL (Pole Bioinformatique Lyonnais) (http://npsa-pbil.ibcp.fr) with default settings. The amino acids of the conserved zinc-ion ligating residues are underlined and typed in bold.

FIG. 3 shows the sequence alignment of human QC (hQC, SEQ ID NO: 10) and human isoQC (hisoQC, SEQ ID NO: 12) and other M28 family members of the metallopeptidase Clan MH. Multiple sequence alignment was performed using ClustalW at ch.EMBnet.org with default settings. The conservation of the amino acid residues ligating the single zinc-ion within the human QC (hQC; Swiss-Prot Q16769, SEQ ID NO: 10), is shown for the human isoQC (isoQC; Swiss-Prot Q53HE4, SEQ ID NO: 12) (residues 19-382), the Zn-dependent aminopeptidase from *Streptomyces griseus* (SGAP; Swiss-Prot P80561, SEQ ID NO: 80) and the mature Zn-dependent leucyl-aminopeptidase from *Vibrio proteolyticus* (VpAP; Swiss-Prot Q01693, SEQ ID NO: 81). The respective amino acid residues are underlined and typed in bold.

FIG. 4 shows the sequence alignment of human QC (hQC, SEQ ID NO: 10) and human isoQC (hisoQC, SEQ ID NO: 11), showing two putative tranlational starts (methionine I—bold, underlined; methionine II—bold). Multiple sequence alignment was performed using ClustalW at PBIL (Pole Bioinformatique Lyonnais) http://npsa-pbil.ibcp.fr with default settings. The transmembrane domain, present in human isoQC, is indicated by the black bar.

FIG. 5 shows the sequence alignment of human QC (hQC, SEQ ID NO: 10) and human isoQC (hisoQC, SEQ ID NO: 12), starting with methionine II (bold). Multiple sequence alignment was performed using ClustalW at ch.EMBnet.org with default settings. The amino acids involved in metal binding are underlined and typed in bold. The transmembrane domain, present in human isoQC, is indicated by the black bar.

FIG. 10 shows the analysis of isoQC (Met II, SEQ ID NO: 12) subcellular localization by immunhistochemistry. Human isoQC starting at methionine II was expressed as a fusion protein with EGFP (isoQC (MetII) EGFP) in LN 405. Mitochondrial counterstaining was performed using MAB1273 (Chemicon). Merge represents the overlay of isoQC (MetII)-EGFP and mitochondrial staining.

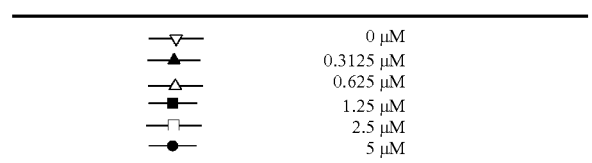

The determined $K_i$-value was 240±8 nM.

Figure 16:
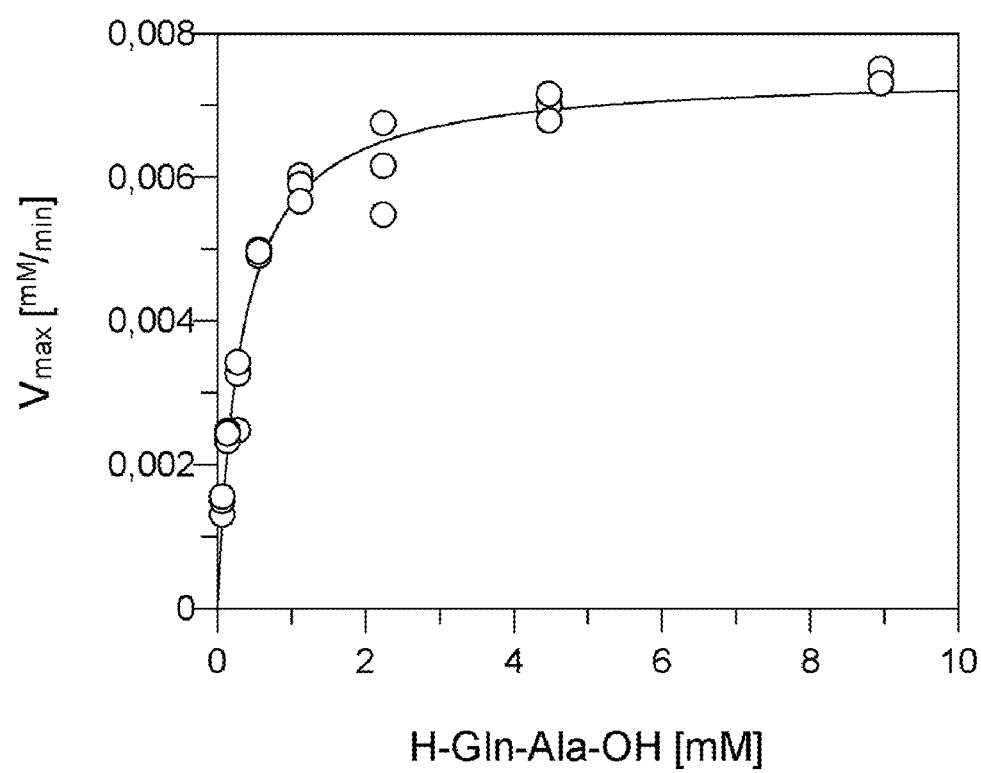

FIG. 16 shows the human isoQC-catalyzed conversion of H-Gln-Ala-OH into pGlu-Ala-OH determined using a spectrophotometric assay. The data were evaluated according to Michaelis-Menten kinetics. The kinetic parameters were 324±28 µM and 7.4±0.2 nM/min for the $K_M$ and $V_{max}$-value, respectively.

Figure 17:
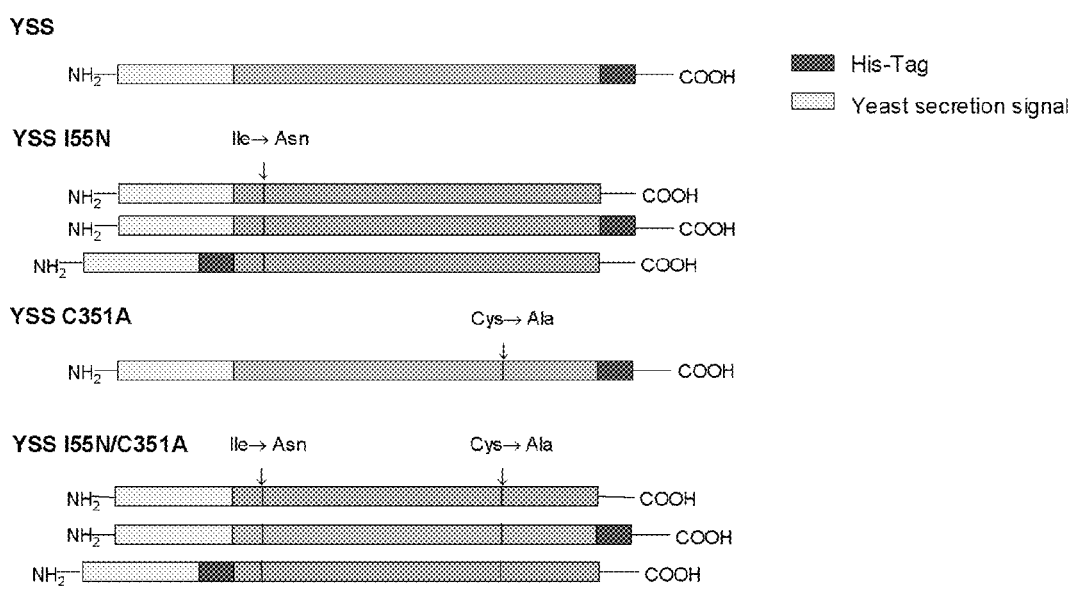

FIG. 17 provides a schematic representation of the human isoQC protein constructs that were expressed hetereologously in the yeast P. pastoris. Two mutations were introduced in some proteins, leading to a glycosylation site at position 55 (I55N) and a mutated cystein residue at position 351 (C351A). For expression, the N-terminus including the transmembrane domain was replaced by a secretion signal of yeast (YSS). The constructs containing the N-terminal secretion signal should be efficiently secreted into the medium.

Figure 18:
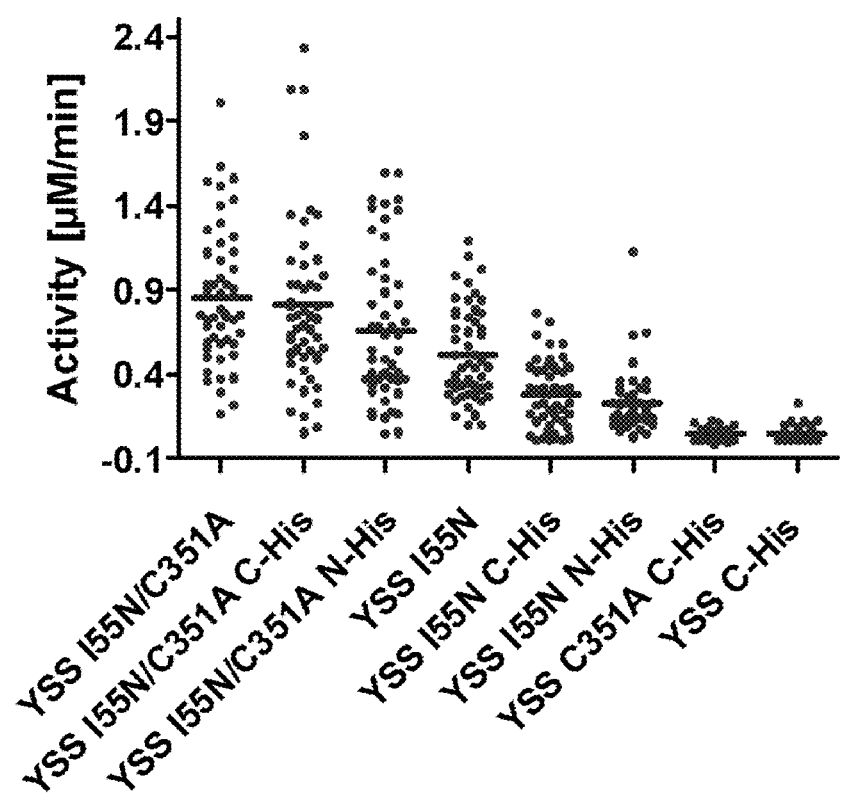

FIG. 18 shows the QC activity, which was determined in the medium of expressing yeast cells. Due to the transmembrane domain, the native constructs were not secreted into the medium (not implemented). Caused by glycosylation (I55N), proteins are most efficiently secreted. The mutation C351A resulted also in higher QC activity detected in the medium. The constructs are described in FIG. 17.

Figure 19:
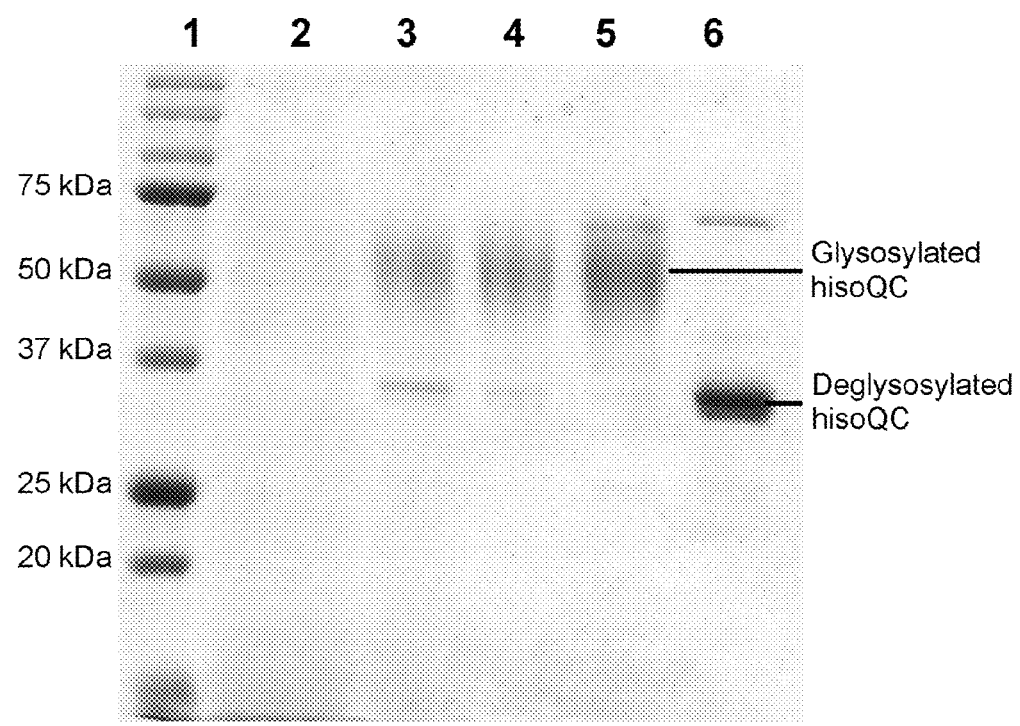

FIG. 19 shows the purification of the human isoQC, based on construct YSShisoQCI55NC351A C-His, from the medium of a transgenic P. pastoris strain. The QC was purified by a combination of IMAC (immobilized metal affinity chromatography, lane 3), HIC (hydrophobic interaction chromatography, lane 4) and desalting (lane 5). The glycosylation of the enzyme was evidence by enzymatic deglycosalytion, which results in a shift in migration of the protein (lane 6). Lane 1, protein standard: Lane 2, medium prior to purification.

Figure 20:
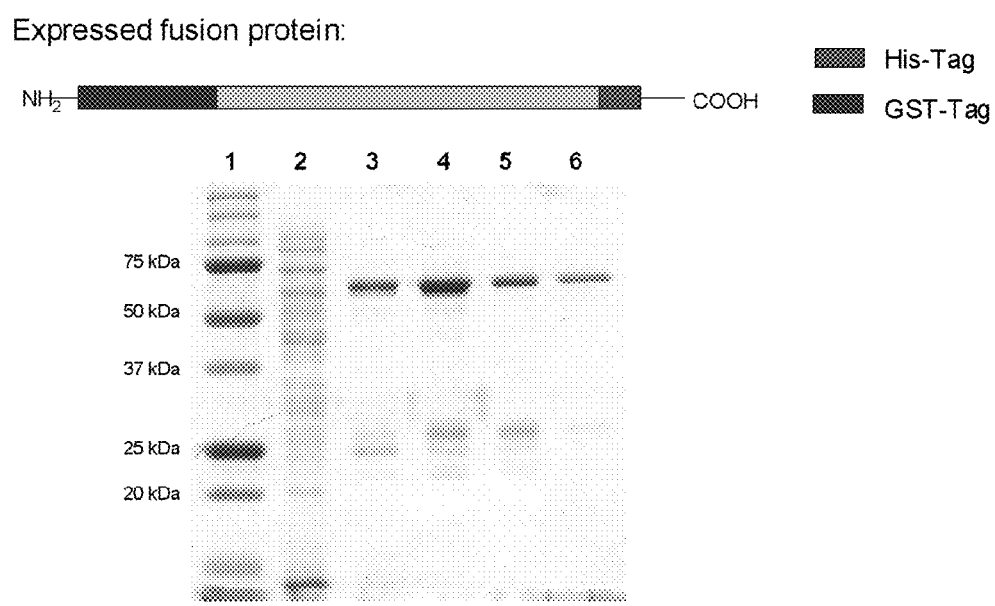

FIG. 20 shows the purification of the human isoQC, based on construct GST-hisoQC C-His, from the cell homogenate of transformed E. coli. The isoQC was purified by a combination of IMAC (immobilized metal affinity chromatography, lane 3), GST-affinity (lane 4), desalting (lane 5) and ion exchange chromatography (lane 6). Lane 1, protein standard: Lane 2, cell homogenate prior to purification. The difference in the molecular mass between the hisoQC which was expressed in yeast and E. coli is caused by the N-terminal GST-tag fusion. The expressed construct is provided schematically in the upper part of the figure.

Figure 21:
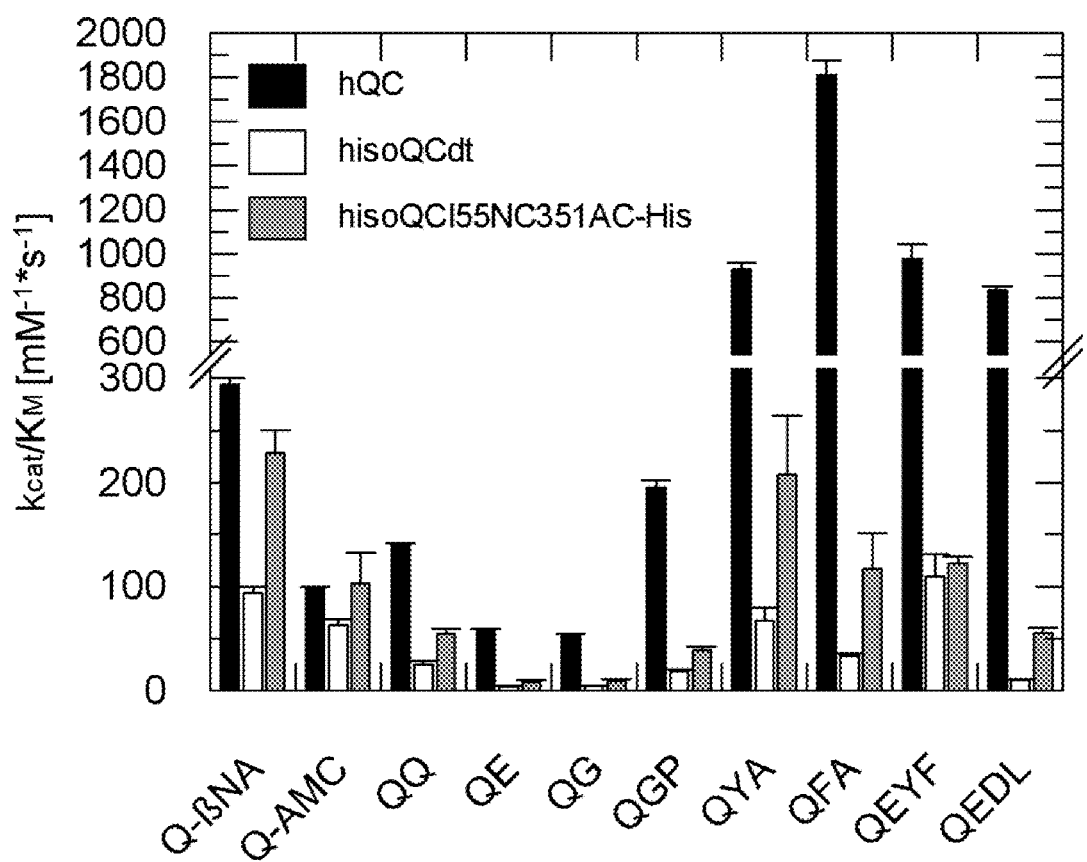

FIG. 21 shows the specificity constants for conversion of dipeptide-surrogates, dipeptides and oligopeptides by human isoQC(YSShisoQCI55NC351A C-His; compare FIG. 17), GST-hisoQC and human QC. The specificity of GST-hisoQC was the lowest, followed by YSShisoQCI55NC351A C-His. The highest specificity displayed human QC, indicating a higher overall enzymatic activity.

Figure 22:
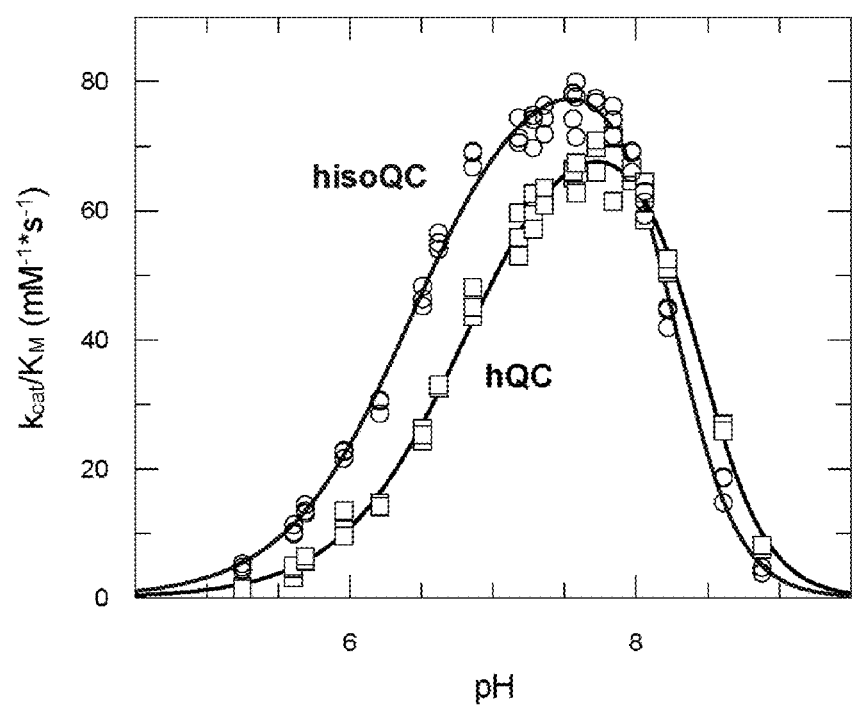

FIG. 22 shows the pH-dependency of catalysis, investigated with human isoQC (hisoQC), which was expressed in yeast, and human QC (hQC). Both proteins display a pH-optimum between pH 7 and 8. The fitted curve is based on three dissociating groups that influence catalysis, one at acidic pH, two at basic pH.

Figure 23:
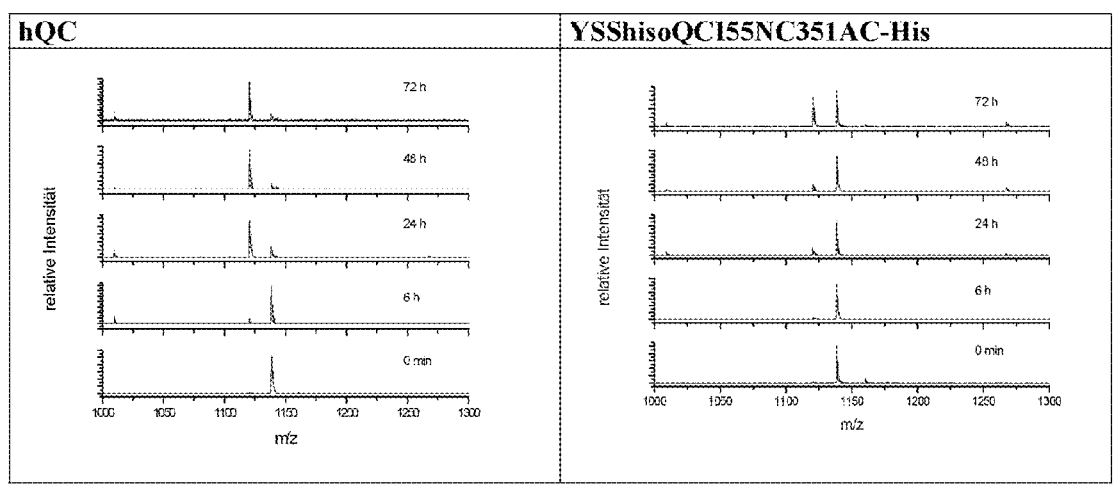

FIG. 23 shows the analysis of conversion of glutamic acid, which is present at the N-terminus of the amyloid-β related peptide Aβ(3-11). The analysis was performed using Maldi-T of mass spectrometry, the substrate and product differ in their molecular mass/charge ratio of the single chared molecule by about 18 Da, which is the mass of the released water. In both cases, the same protein concentration was present in the samples, clearly suggesting that human isoQC also converts N-terminal glutamic acid, but slower than the human QC.

Figure 24:
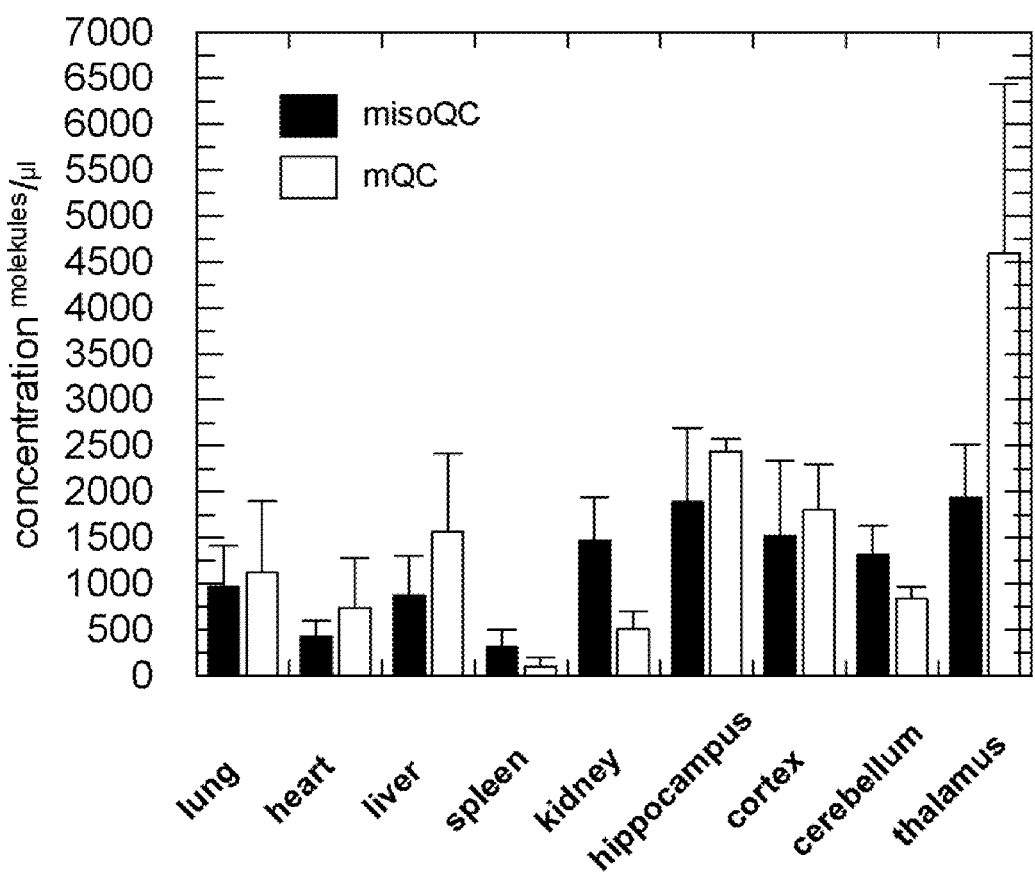

FIG. 24 shows the tissue distribution of murine QC (mQC, SEQ ID NO: 79) and its isoenzyme misoQC (SEQ ID NO: 17), analyzed using real-time PCR. Both enzymes are expressed in the tested organs. However, the expression level of mQC was higher in the brain compared with the peripheral organs. In contrats, misoQC was expressed in all tested organs and tissues at a more similar level, indicating a ubiquitous, "house-keeping" protein.

Figure 25:
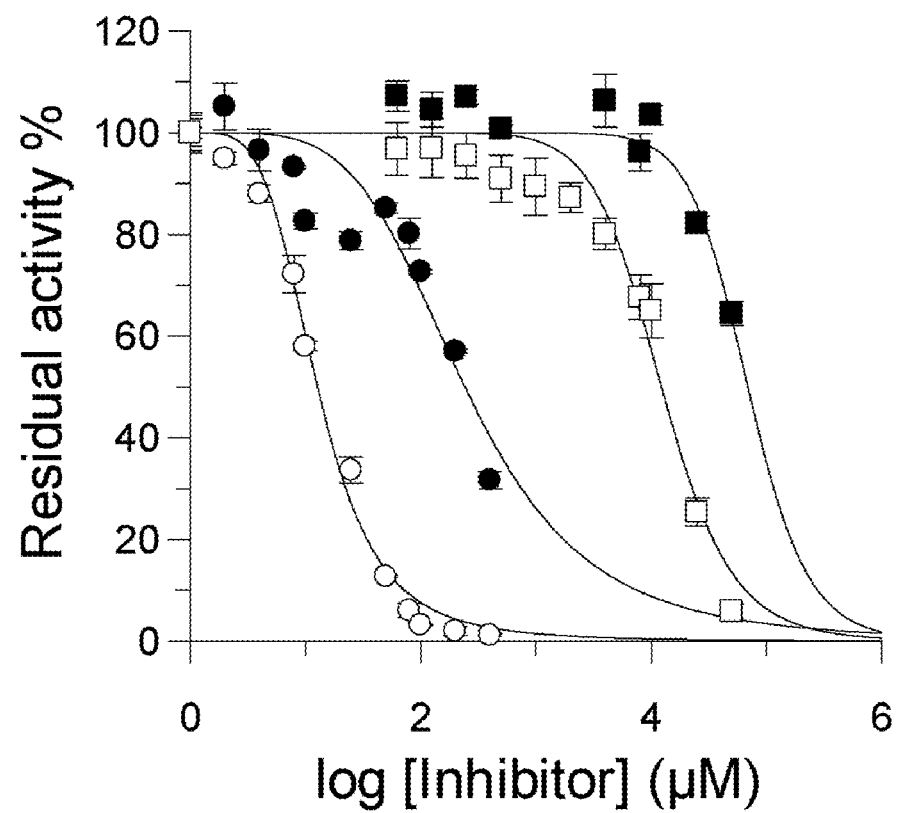

FIG. 25 shows the time-dependent inhibition of human isoQC (hisoQC) by metal-chelating compounds 1,10-phenanthroline (circles) and EDTA (squares). Residual hisoQC activity was determined directly after addition (closed symbols) or preincubation of hisoQC with respective reagent for 15 min at 30° C. (open symbols).

FIG. 26 shows the biochemical analysis of the subcellular localization of QC activity after expression of pcDNA and the native enzymes hisoQC (Met I, SEQ ID NO: 11), hisoQC (Met II, SEQ ID NO: 12) and hQC (SEQ ID NO: 10) in HEK293 cells. (A) specific activity within the cell fractions in μmole/min/g. (B) absolute activity in nM/min. (C) Expression of h-isoQC (Met I, SEQ ID NO: 11), h-isoQC (Met II, SEQ ID NO: 12) and hQC (SEQ ID NO: 10) possessing a C-terminal FLAG-tag in HEK293 in comparison to vector-transfected control (pcDNA), followed by Western Blot analysis applying specific antibodies detecting either the FLAG-epitope (anti-DYKDDDDK-antibody, Cell Signaling), a 65 kDa protein of human mitochondria (anti-human mitochondria, Chemicon) or human Sialyltransferase ST1 GAL3 (Abnova).

FIG. 27 shows the subcellular localization of human isoQC (hisoQC) signal sequences (A) methionine I—serine 53 and (B) methionine II—serine 53, fused to EGFP. Golgi complex was stained using an anti-mannosidase II antibody and mitochondria were stained using an antibody detecting a 65 kDA protein of human mitochondria. Co-localization is shown by superimposition of EGFP fluorescence and Red X fluorescence (Merge).

Figure 28:
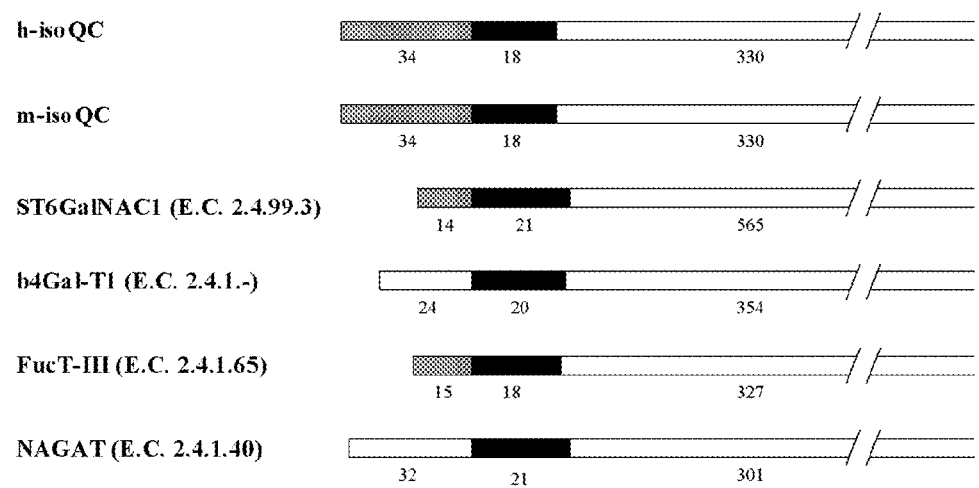

FIG. 28 shows the domain structure of human isoQC (hisoQC) and murine isoQC (misoQC) in comparison to published sequences of human glycosyltransferases: alpha-N-acetylgalactosaminide alpha-2,6-sialyl transferase 1 (ST6GalNAC1; E.C. 2.4.99.3); beta-1,4-galactosyltransferase 1 (b4Gal-T1, E.C. 2.4.1.-); Galactoside 3(4)-L-fucosyltransferase (FucT-III; E.C. 2.4.1.65) and Glycoprotein-fucosylgalactoside alpha-N-acetylgalactosaminyl transferase (NAGAT, E.C.2.4.1.40). The number of amino acids as listed below the columns. The cytosolic part is shaded, the transmembrane helix is black and luminal part is illustrated in white.

Figure 29:
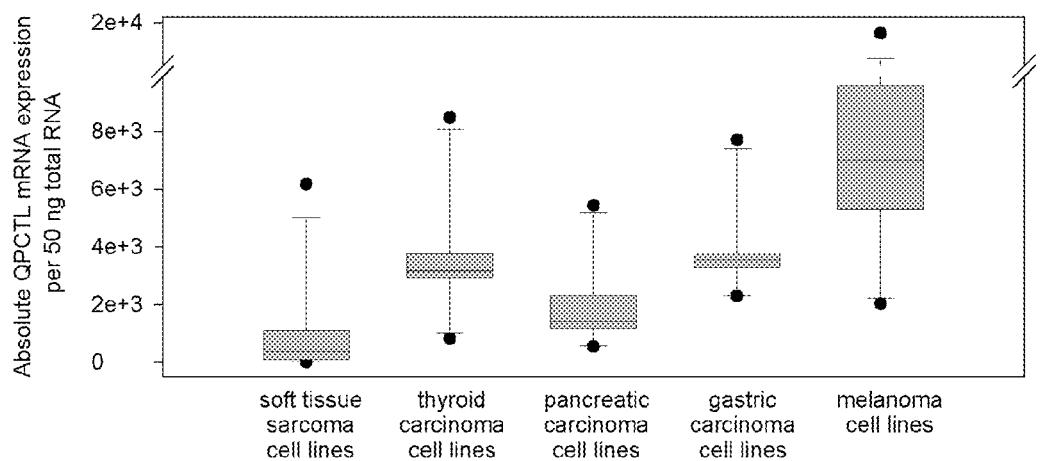

FIG. 29 shows the quantification of human isoQC (QPCTL) mRNA in different carcinoma cell lines. The QPCTL expression was normalized to 50 ng total-RNA. The black bar within the boxes represents the respective median.

Figure 30:
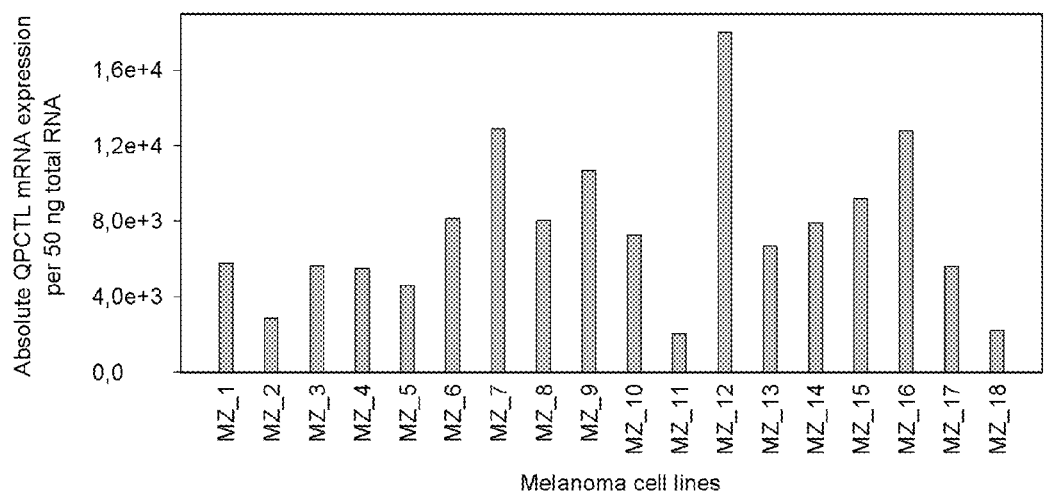

FIG. 30 shows the quantification of human isoQC (QPCTL) mRNA expression in different melanoma cell lines. The QPCTL expression was normalized to 50 ng total-RNA.

Figure 31:
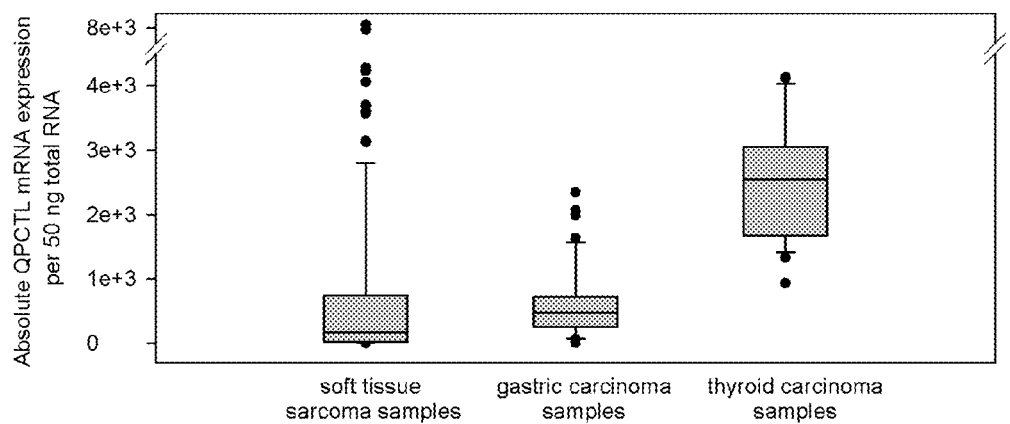

FIG. 31 shows the quantification of human isoQC (QPCTL) mRNA expression in samples from soft tissue carcinoma, gastric carcinoma and thyroid carcinoma from different patients. The QPCTL expression was normalized to 50 ng total-RNA. The black bar within the boxes represents the respective median.

Figure 32:
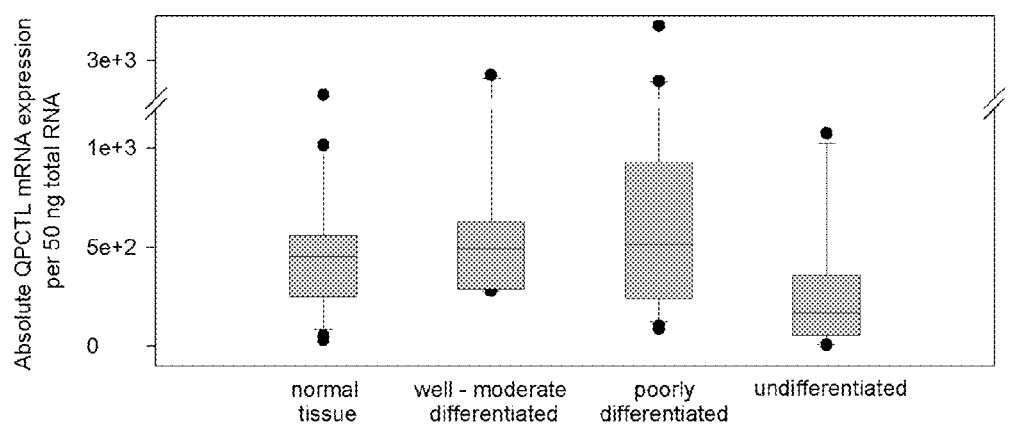

FIG. 32 shows the human isoQC (QPCTL) mRNA expression in different gastric carcinomas against their stage of differentiation. QPCTL expression was normalized to 50 ng total-RNA. The black bar within the boxes represents the respective median.

Figure 33:
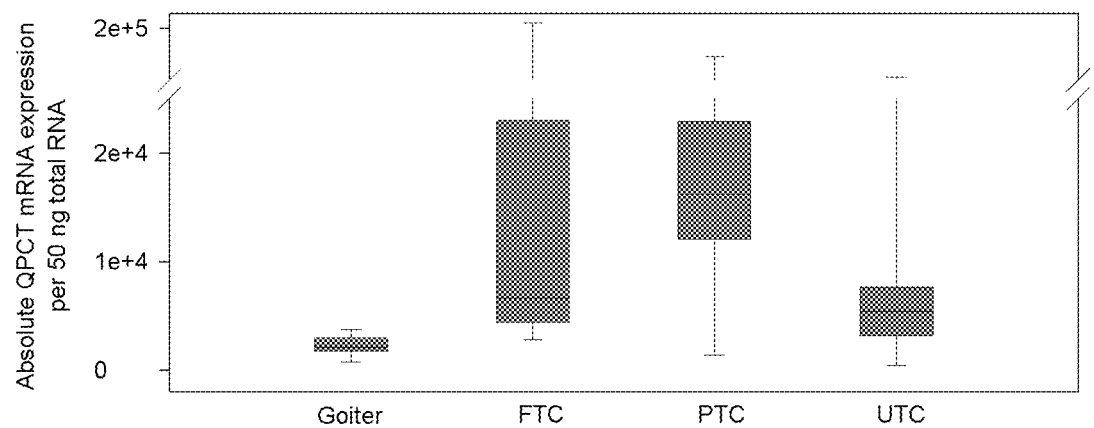

FIG. 33 shows a comparison of human QC (QPCT) mRNA expression in different thyroid carcinomas. QPCT expression was normalized to 50 ng total-RNA. The black bar within the boxes represents the respective median. (FTC: folicular thyroid carcinoma; PTC: papillary thyroid carcinoma; UTC: undifferentiated thyroid carcinoma).

Figure 34:
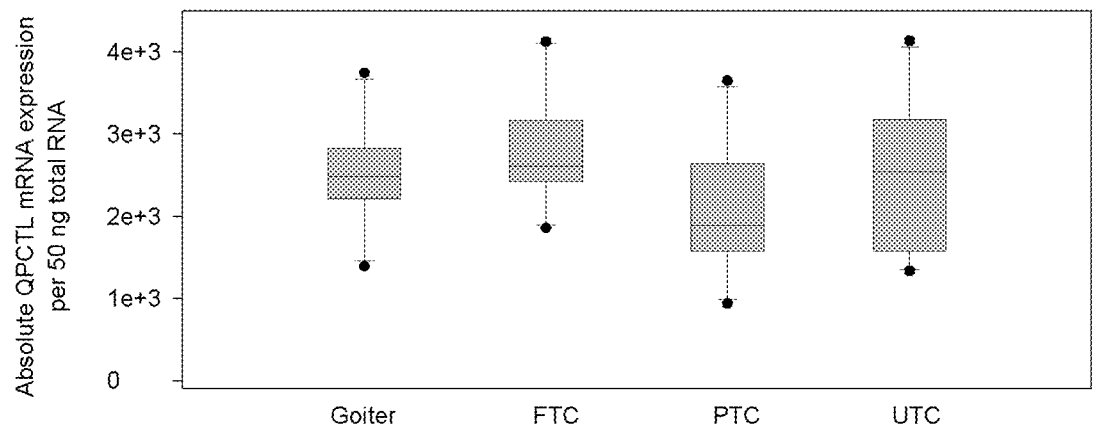

FIG. 34 shows a comparison of human isoQC (QPCTL) mRNA expression in different thyroid carcinomas. QPCTL expression was normalized to 50 ng total-RNA. The black bar within the boxes represents the respective median. (FTC: folicular thyroid carcinoma; PTC: papillary thyroid carcinoma; UTC: undifferentiated thyroid carcinoma).

Figure 35:
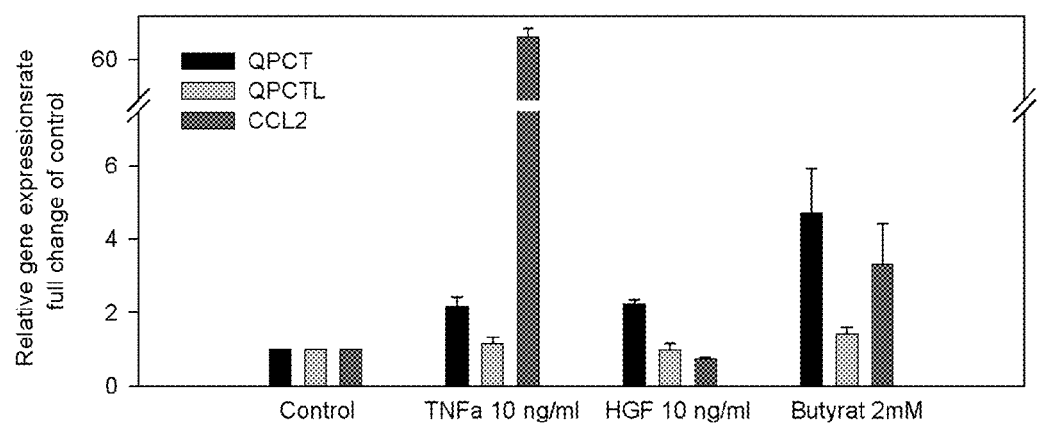

FIG. 35 shows the influence of different stimuli on mRNA expression of human QC (QPCT), human isoQC (QPCTL) and CCL2 in HEK293 cells. The amount of transcripts is depicted relating to basal expression without stimulus. The used concentration of stimulus is stated on the x-axis drawing.

Figure 36:
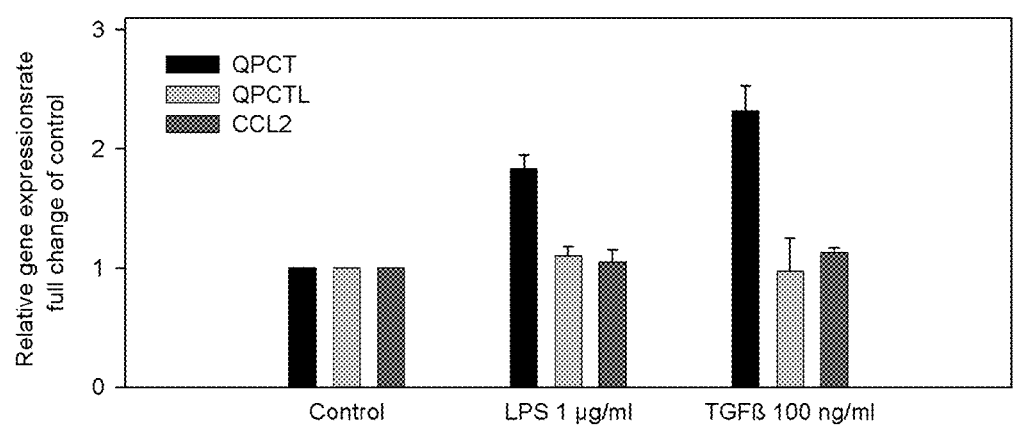

FIG. 36 shows the influence of different stimuli on mRNA expression of human QC (QPCT), human isoQC (QPCTL) and CCL2 in FTC-133 cells. The amount of transcripts is depicted relating to basal expression without stimulus. The used concentration of stimulus is stated on the x-axis drawing.

Figure 37:
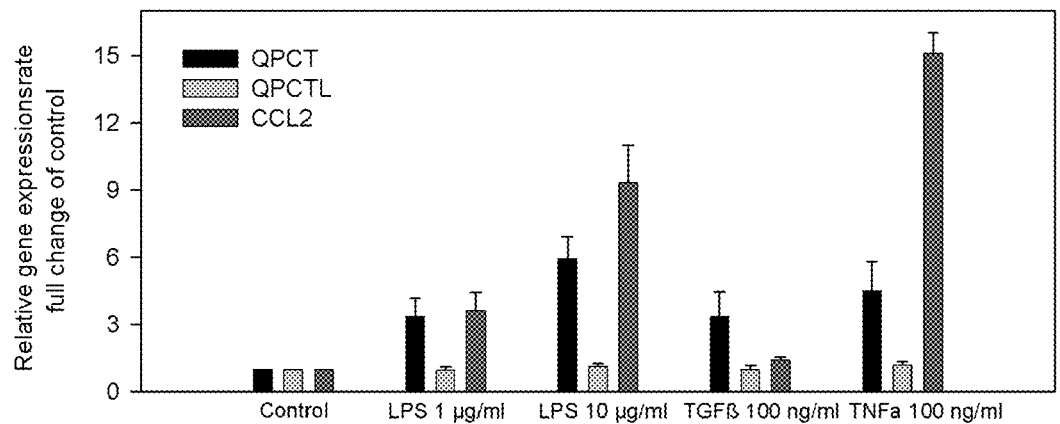

FIG. 37 shows the influence of different stimuli on mRNA expression of human QC (QPCT), human isoQC (QPCTL) and CCL2 in THP-1 cells. The amount of transcripts is depicted relating to basal expression without stimulus. The used concentration of stimulus is stated on the x-axis drawing.

Figure 38:
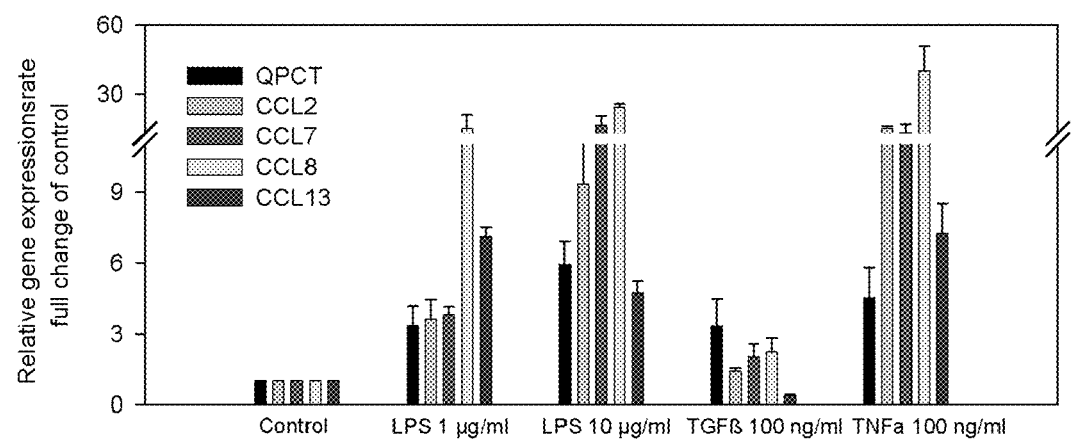

FIG. 38 shows the influence of different stimuli on mRNA expression of human QC (QPCT), CCL2, CCL7, CCL8 and CCL13 in THP-1 cells. The amount of transcripts is depicted relating to basal expression without stimulus. The used concentration of stimulus is stated on the x-axis drawing.

Figure 39:
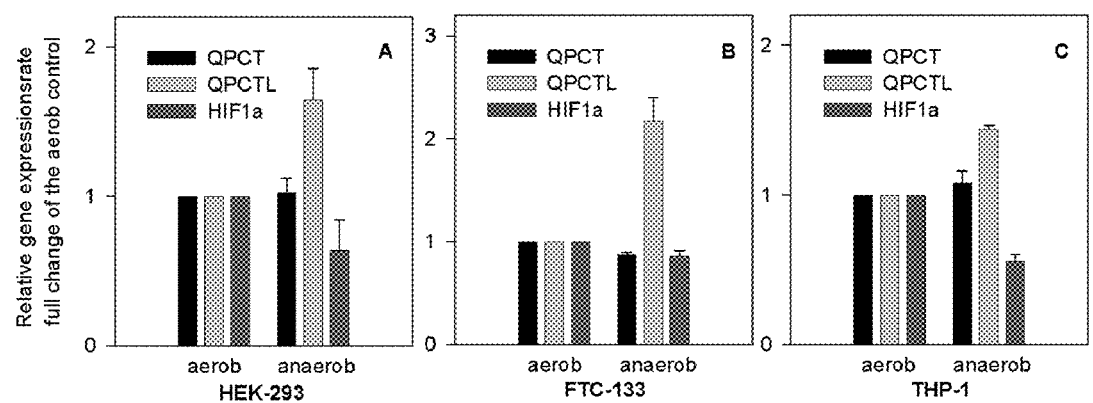

FIG. 39 shows the influence of hypoxia on the mRNA level of human QC (QPCT), human isoQC (QPCTL) and HIF1α in HEK293 (A), FTC-133 (b) and THP-1 (C).

LIST OF SEQUENCES

| SEQ ID NO | Description |
| --- | --- |
| 1 | human QC, nucleic acid |
| 2 | human isoQC Met I, nucleic acid |
| 3 | human isoQC Met II, nucleic acid |
| 4 | *Macaca fascicularis* QPCTL, nucleic acid |
| 5 | *Macaca mulatta* QPCTL, nucleic acid |

-continued

| SEQ ID NO | Description |
|---|---|
| 6 | *Canis familiaris* QPCTL, nucleic acid |
| 7 | rat QPCTL, nucleic acid |
| 8 | mouse QPCTL, nucleic acid |
| 9 | bovine QPCTL, nucleic acid |
| 10 | human QC, protein |
| 11 | human isoQC Met I, protein |
| 12 | human isoQC Met II, protein |
| 13 | *Macaca fascicularis* QPCTL, protein |
| 14 | *Macaca mulatta* QPCTL, protein |
| 15 | *Canis familiaris* QPCTL, protein |
| 16 | rat QPCTL, protein |
| 17 | mouse QPCTL, protein |
| 18 | bovine QPCTL, protein |
| 19 | human isoQC splice form 1, nucleic acid |
| 20 | human isoQC splice form 2, nucleic acid |
| 21 | human isoQC splice form 1, protein |
| 22 | human isoQC splice form 2, protein |
| 23 | Amyloid beta peptide (Abeta) (1-42) |
| 24 | Abeta (1-40) |
| 25 | Abeta (3-42) |
| 26 | Abeta (3-40) |
| 27 | Abeta (11-42) |
| 28 | Abeta (11-40) |
| 29 | pGlu$^3$-Abeta (3-42) |
| 30 | pGlu$^3$-Abeta (3-40) |
| 31 | pGlu$^3$-Abeta (11-42) |
| 32 | pGlu$^3$-Abeta (11-40) |
| 33 | ABri |
| 34 | ADan |
| 35 | Gastrin 17 |
| 36 | Gastrin 34 |
| 37 | pGlu-Abri |
| 38 | pGlu-ADan |
| 39 | pGlu-Gastrin 17 |
| 40 | pGlu-Gastrin 34 |
| 41 | Neurotensin |
| 42 | GnRH |
| 43 | CCL16 |
| 44 | CCL8 |
| 45 | CCL2 |
| 46 | CCL18 |
| 47 | Fractalkine |
| 48 | CCL7 |
| 49 | Orexin A |
| 50 | Substance P |
| 51 | QYNAD |
| 52 | pGlu-YNAD |
| 53 | human isoQC forward primer used for cell line screening |
| 54 | human isoQC reverse primer used for cell line screening |
| 55 | forward primer used for isolation of human isoQC |
| 56 | reverse primer used for isolation of human isoQC |
| 57 | forward primer used for cloning of human isoQC (isoform Met I) into vector pEGFP-N3 |
| 58 | forward primer used for cloning of human isoQC (isoform Met II) into vector pEGFP-N3 |
| 59 | reverse primer used for cloning of human isoQC (isoforms Met I and Met II) into vector pEGFP-N3 |
| 60 | forward primer used for cloning of human isoQC into vector pET41a |
| 61 | reverse primer used for cloning of human isoQC into vector pET41a |
| 62 | forward primer for cloning human isoQC into vector pPICZαA with a C-terminal histidine tag |
| 63 | forward primer for cloning human isoQC into vector pPICZαA with a N-terminal histidine tag |
| 64 | reverse primer for cloning human isoQC into vector pPICZαA with a N-terminal histidine tag |
| 65 | forward primer for real-time PCR analysis of isoQC |
| 66 | reverse primer for cloning human isoQC into vector pPICZαA with a C-terminal histidine tag |
| 67 | reverse primer for real-time PCR analysis of isoQC |
| 68 | Forward primer for cloning of murine isoQC cDNA |
| 69 | Reverse primer for cloning of murine isoQC cDNA |
| 70 | Forward primer for cloning of murine isoQC cDNA |
| 71 | forward primer for real-time PCR analysis of murine QC |
| 72 | reverse primer for real-time PCR analysis of murine QC |
| 73 | forward primer for real-time PCR analysis of murine QC |
| 74 | reverse primer for real-time PCR analysis of murine QC |
| 75 | forward primer for site-directed mutagenesis hisoQC I55N |
| 76 | reverse primer for site-directed mutagenesis hisoQC I55N |

| SEQ ID NO | Description |
| --- | --- |
| 77 | forward primer for site-directed mutagenesis hisoQC C351A |
| 78 | reverse primer for site-directed mutagenesis hisoQC C351A |
| 79 | Mouse glutaminyl cyclase protein |
| 80 | *Streptomyces griseus* SGAP |
| 81 | *Vibrio proteolyticus* VpAP |
| 82 | forward primer for insertion of native hQC into pcDNA 3.1 |
| 83 | reverse primer for insertion of native hQC into pcDNA 3.1 |
| 84 | reverse primer for amplification of hisoQC including the stop codon for insertion into pcDNA 3.1 |
| 85 | forward primer for amplification EGFP |
| 86 | reverse primer for amplification EGFP |
| 87 | Reverse primer for amplification of hisoQC N-terminal sequence for fusion with EGFP |
| 88 | Reverse primer for amplification hQC C-FLAG for insertion into pcDNA 3.1 |
| 89 | Reverse primer for amplification hisoQC C-FLAG for insertion into pcDNA 3.1 |

DETAILED DESCRIPTION OF THE INVENTION

In accordance with an aspect of the present invention, there are provided isolated nucleic acid sequences (polynucleotides) of SEQ ID NOS: 2 to 9, 19 and 20, which encode the mature polypeptides having the deduced amino acid sequences of the QPCTLs from different sources (SEQ ID NOS: 11 to 18, 21 and 22).

Preferred according to the present invention are isolated nucleic acid sequences (polynucleotides) of SEQ ID NOS: 2 and 3, 19 and 20, which encode the mature polypeptides having the deduced amino acid sequences of the QPCTLs from human (SEQ ID NOS: 11 and 12, 21 and 22).

More preferred according to the present invention are isolated nucleic acid sequences (polynucleotides) of SEQ ID NOS: 2 and 3, which encode the mature polypeptides having the deduced amino acid sequences of the human QPCTLs of SEQ ID NOS: 11 and 12.

Even preferred according to the present invention are isolated nucleic acid sequences (polynucleotides) of SEQ ID NOS: 19 and 20, which encode the mature polypeptides having the deduced amino acid sequences of alternative splice-forms of human QPCTLs of SEQ ID NOS: 21 and 22.

Most preferred according to the present invention is the isolated nucleic acid sequence (polynucleotide) of SEQ ID NO: 2, which encodes the mature polypeptide having the deduced amino acid sequence of the human QPCTL of SEQ ID NOS: 11.

Even most preferred according to the present invention is the isolated nucleic acid sequence (polynucleotide) of SEQ ID NO: 3, which encodes the mature polypeptide having the deduced amino acid sequence of the human QPCTL of SEQ ID NOS: 12.

The aforementioned embodiments and preferences apply to the QPCTL nucleic acids as well as QPCTL proteins and any desired method of use, diagnosing, treatment, screening, effectors, inhibitors and other uses and methods according to the present invention.

The polynucleotides of this invention were discovered by similarity search using Nucleotide BLAST at NCBI (http://www.ncbi.nlm.nih.gov/BLAST/) applying human QC as template. The search resulted in discovery of a putative QPCTL on chromosome 19, which is encoded in region 19q13.32. On basis of the search, primers for a cell line screening of human isoQC were designed (Table 4). The isolated cDNA for human QPCTL contains an open reading frame encoding a protein of 382 amino acids in length, which is related to human QC displaying 45.24% sequence identity, and 71.98% similarity. Applying different bioinformatic algorithms (www.expasy.ch) for prediction of the subcellular localization did not result in a reliable result. The prognosis, depending on the prediction program, was transfer to golgi-apparatus or mitochondria.

Amino acid sequence alignments of human QPCTL with other members of the M28 family members of the metallopeptidase Clan MH shows that human QPCTL protein has overall sequence and structural homology to human and murine QC (FIG. 1) and bacterial aminopeptidases (FIG. 3). A database search for additional human QPCTL-related genes revealed the presence of rodent, simian, cattle and dog QPCTLs. Alignment of these sequences with the novel human QPCTL shows that they display considerable homology with its human counterpart. The zinc-complexing residues of human QC (Asp-Glu-His) are conserved within QPCTLs from the different origins (FIG. 2).

Figure 6:
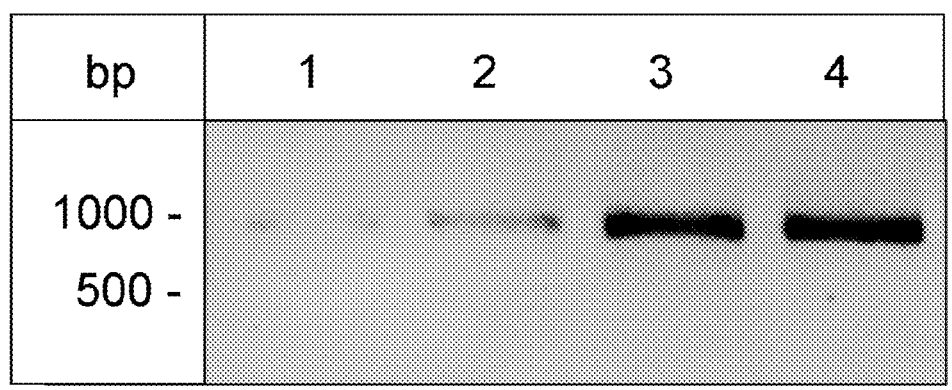
FIG. 6 shows the analysis of isoQC expression by RT-PCR. Detection in SH-SY5Y, LN405, HaCaT and Hep-G2. Lanes: bp, DNA standard; 1, amplified PCR product of human isoQC from SH-SY5Y; 2, amplified PCR product of human isoQC from LN405; 3, amplified PCR product of human isoQC from HaCaT; 4, amplified PCR product of human isoQC from Hep-G2.

The human isoQC gene contains at least 8 exons. The sequence coding for the human isoQC protein is located on exons 1 to 7. Human isoQC maps to chromosome 19 at position 19q13.32. A cell line screening for human isoQC revealed transcripts in cells origin from liver (Hep-G2, hepatocellular carcinoma), skin (HaCaT, keratinocyte) and neuronal tissues (LN405, astrocytoma; SH-SY5Y, neuroblastoma) (FIG. 6).

The isolated QPCTL-cDNA was tested on functional expression in several expression hosts. Expression in *P. pastoris*, which was successfully applied for human QC, did not result in an enzymatically active protein. Expression in mammalian cells resulted in detection of activity, however, expression levels were very low. Thus, the isolation of an enzymatically active protein was not possible with the knowledge of the skilled artisan. Enzymatically active protein was isolated only following expression of a GST-QPCTL fusion protein in *E. Coli*, applying very unusual expression conditions: Expression for 4 h at 37° C. in presence of 1% Glucose, induction of expression using 20 µM IPTG. The expression conditions result in a low-level expression in *E. Coli*, which is necessary for functional folding of the peptide chain.

In another embodiment, the present invention relates to QPCTL knockout animals, preferably rats or mice. The use of knockout mice in further analysis of the function of QPCTL genes is a valuable tool.

The polynucleotides of the present invention may be in the form of RNA or in the form of DNA; DNA should be understood to include cDNA, genomic DNA, and synthetic DNA.

The DNA may be double-stranded or single-stranded and, if single stranded, may be the coding strand or non-coding (antisense) strand. The coding sequence, which encodes the mature polypeptide may be identical to the coding sequence shown in SEQ ID NOS 2 to 9, or it may be a different coding sequence encoding the same mature polypeptide, as a result of the redundancy or degeneracy of the genetic code or a single nucleotide polymorphism. For example, it may also be an RNA transcript which includes the entire length of any one of SEQ ID NOS 11 to 18.

The polynucleotides which encode the mature proteins of SEQ ID NOS 2 to 9 may include but are not limited to the coding sequence for the mature protein alone; the coding sequence for the mature polypeptide plus additional coding sequence, such as a leader or secretory sequence or a proprotein sequence; and the coding sequence for the mature protein (and optionally additional coding sequence) plus non-coding sequence, such as introns or a non-coding sequence 5' and/or 3' of the coding sequence for the mature protein.

Thus, the term "polynucleotide encoding a polypeptide" or the term "nucleic acid encoding a polypeptide" should be understood to encompass a polynucleotide or nucleic acid which includes only coding sequence for the mature protein as well as one which includes additional coding and/or non-coding sequence. The terms polynucleotides and nucleic acid are used interchangeably.

The present invention also includes polynucleotides where the coding sequence for the mature protein may be fused in the same reading frame to a polynucleotide sequence which aids in expression and secretion of a polypeptide from a host cell; for example, a leader sequence which functions as a secretory sequence for controlling transport of a polypeptide from the cell may be so fused. The polypeptide having such a leader sequence is termed a preprotein or a preproprotein and may have the leader sequence cleaved, by the host cell to form the mature form of the protein. These polynucleotides may have a 5' extended region so that it encodes a proprotein, which is the mature protein plus additional amino acid residues at the N-terminus. The expression product having such a prosequence is termed a proprotein, which is an inactive form of the mature protein; however, once the prosequence is cleaved an active mature protein remains. Thus, for example, the polynucleotides of the present invention may encode mature proteins, or proteins having a prosequence, or proteins having both a prosequence and a presequence (leader sequence).

The polynucleotides of the present invention may also have the coding sequence fused in frame to a marker sequence which allows for purification of the polypeptides of the present invention. The marker sequence may be a polyhistidine tag, a hemagglutinin (HA) tag, a c-myc tag or a V5 tag when a mammalian host, e.g. COS-1 cells, is used.

The HA tag would correspond to an epitope derived from the influenza hemagglutinin protein (Wilson, I., et al., Cell, 37: 767 (1984)), and the c-myc tag may be an epitope from human Myc protein (Evans, G. I. et al., Mol. Cell. Biol. 5: 3610-3616 (1985)).

The term "gene" means the segment of DNA involved in producing a polypeptide chain; it includes regions preceding and following the coding region (leader and trailer) as well as intervening sequences (introns) between individual coding segments (exons).

The term "significant sequence homology" is intended to denote that at least 25%, preferably at least 40%, of the amino acid residues are conserved, and that, of the nonconserved residues, at least 40% are conservative substitutions.

Fragments of the full-length genes of the present invention may be used as a hybridization probe for a cDNA library to isolate full-length cDNA as well as to isolate other cDNAs, which have significant sequence homology to the gene and will encode proteins or polypeptides having similar biological activity or function. By similar biological activity or function, for purposes of this application, is meant the ability to form pyroglutamate from a N-terminal glutamine or glutamic acid of peptides, proteins, hormones or other substrates, defined as QC- and EC-activity, respectively. Such a probe of this type has at least 14 bases (at least 14 contiguous nucleotides from one of SEQ ID NOS: 2 to 9), preferably at least 30 bases, and such may contain, for example, 50 or more bases. Preferred are the probes of SEQ ID NOS 53 to 61. Such probe may also be used to identify a cDNA clone corresponding to a full-length transcript and/or a genomic clone or clones that contains the complete gene, including regulatory and promoter regions, exons, and introns. Labelled oligonucleotides having a sequence complementary to that of the gene of the present invention are useful to screen a library of human cDNA, genomic DNA or mRNA or similar libraries from other sources or animals to locate members of the library to which the probe hybridizes. As an example, a known DNA sequence may be used to synthesize an oligonucleotide probe, which is then used in screening a library to isolate the coding region of a gene of interest.

The present invention is considered to further provide polynucleotides which hybridize to the hereinabove-described sequences wherein there is at least about 70%, preferably at least about 90%, more preferably at least about 95%, and most preferably at least about 99% identity or similarity between the sequences, and thus encode proteins having similar biological activity. Moreover, as known in the art, there is "similarity" between two polypeptides when the amino acid sequences contain the same or conserved amino acid substitutes for each individual residue in the sequence. Identity and similarity may be measured using sequence analysis software (e.g., ClustalW at PBIL (Pôle Bioinformatique Lyonnais) http://npsa-pbil.ibcp.fr). The present invention particularly provides such polynucleotides, which hybridize under stringent conditions to the hereinabove-described polynucleotides. As herein used, the term "stringent conditions" means conditions which permit hybridization between polynucleotides sequences and the polynucleotide sequences of SEQ ID NOS: 2 to 9 where there is at least about 70% identity.

Suitably stringent conditions can be defined by, e.g., the concentrations of salt or formamide in the prehybridization and hybridization solutions, or by the hybridization temperature, and are well known in the art. In particular, stringency can be increased by reducing the concentration of salt, by increasing the concentration of formamide, and/or by raising the hybridization temperature.

For example, hybridization under high stringency conditions may employ about 50% formamide at about 37° C. to 42° C., whereas hybridization under reduced stringency conditions might employ about 35% to 25% formamide at about 30° C. to 35° C. One particular set of conditions for hybridization under high stringency conditions employs 42° C., 50% formamide, 5×. SSPE, 0.3% SDS, and 200 pg/ml sheared and denatured salmon sperm DNA. For hybridization under reduced stringency, similar conditions as described above may be used in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art. Preferably, hybridization should occur only if there is at least 95%, and more preferably at least 97%, identity between the sequences. The polynucleotides which hybridize to the hereinabove described polynucleotides in a preferred embodiment encode polypeptides which exhibit substantially the same biological function or activity as the mature protein encoded by one of the cDNAs of SEQ ID NOS: 2 to 9.

As mentioned, a suitable polynucleotide probe may have at least 14 bases, preferably 30 bases, and more preferably at least 50 bases, and will hybridize to a polynucleotide of the present invention, which has an identity thereto, as hereinabove described, and which may or may not retain activity. For example, such polynucleotides may be employed as a probe for hybridizing to the polynucleotides of SEQ ID NOS: 2 to 9 respectively, for example, for recovery of such a polynucleotide, or as a diagnostic probe, or as a PCR primer. Thus, the present invention includes polynucleotides having at least about a 70% identity, preferably at least about a 90% identity, and more preferably at least about a 95% identity, and most preferably at least about a 99% identity to a polynucleotide which encodes the polypeptides of SEQ ID NOS: 11 to 18 respectively, as well as fragments thereof, which fragments preferably have at least 30 bases and more preferably at least 50 bases, and to polypeptides encoded by such polynucleotides.

As is well known in the art, the genetic code is redundant in that certain amino acids are coded for by more than one nucleotide triplet (codon), and the invention includes those polynucleotide sequences which encode the same amino acids using a different codon from that specifically exemplified in the sequences herein. Such a polynucleotide sequence is referred to herein as an "equivalent" polynucleotide sequence. The present invention further includes variants of the hereinabove described polynucleotides which encode for fragments, such as part or all of the mature protein, analogs and derivatives of one of the polypeptides having the deduced amino acid sequence of any one of SEQ ID NOS: 11 to 18. The variant forms of the polynucleotides may be a naturally occurring allelic variant of the polynucleotides or a non-naturally occurring variant of the polynucleotides. For example, the variant in the nucleic acid may simply be a difference in codon sequence for the amino acid resulting from the degeneracy of the genetic code, or there may be deletion variants, substitution variants and addition or insertion variants. As known in the art, an allelic variant is an alternative form of a polynucleotide sequence, which may have a substitution, deletion or addition of one or more nucleotides that does not substantially alter the biological function of the encoded polypeptide.

The present invention further includes polypeptides, which have the deduced amino acid sequence of SEQ ID NOS: 11 to 18, as well as fragments, analogs and derivatives of such polypeptides. The terms "fragment", "derivative" and "analog", when referring to the polypeptides of SEQ ID NOS: 11 to 18, means polypeptides that retain essentially the same biological function or activity as such polypeptides. An analog might, for example, include a proprotein, which can be activated by cleavage of the proprotein portion to produce an active mature protein. The polypeptides of the present invention may be recombinant polypeptides, natural polypeptides or synthetic polypeptide; however, they are preferably recombinant polypeptides, glycosylated or unglycosylated.

The fragment, derivative or analog of a polypeptide of any one of SEQ ID NOS 11 to 18, may be (i) one in which one or more of the amino acid residues is substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the mature protein, such as a leader or secretory sequence or a sequence which is employed for purification of the mature polypeptide or a proprotein sequence. Such fragments, derivatives and analogs are deemed to be within the scope of those skilled in the art to provide upon the basis of the teachings herein.

The polypeptides and polynucleotides of the present invention should be in an isolated form, and preferably they are purified to substantial homogeneity or purity. By substantial homogeneity is meant a purity of at least about 85%.

The term "isolated" is used to mean that the material has been removed from its original environment (e.g., the natural environment if it is naturally occurring). For example, a naturally occurring polynucleotide or polypeptide present in a living animal is not considered to be isolated, but the same polynucleotide or polypeptide, when separated from substantially all of the coexisting materials in the natural system, is considered isolated. For DNA, the term includes, for example, a recombinant DNA which is incorporated into a vector, into an autonomously replicating plasmid or virus, or into the genomic DNA of a prokaryote or eukaryote; or which exists as a separate molecule (e. g., a cDNA or a genomic or cDNA fragment produced by polymerase chain reaction (PCR) or restriction endonuclease digestion) independent of other sequences. It also includes a recombinant DNA, which is part of a hybrid gene encoding additional polypeptide sequence, e.g., a fusion protein. Further included is recombinant DNA which includes a portion of the nucleotides shown in one of SEQ ID NOS 2 to 9 which encodes an alternative splice variant of the QPCTLs. Various alternative splice variants are exemplified in SEQ ID NOS: 19-22.

The polypeptides of the present invention include any one of the polypeptides of SEQ ID NOS 11 to 18 (in particular the mature proteins), as well as polypeptides which have at least 75% similarity (e.g. preferably at least 50% and more preferably at least 70% identity) to one of the polypeptides of SEQ ID NOS 11 to 18, more preferably at least 85% similarity (e.g. preferably at least 70% identity) to one of the polypeptides of SEQ ID NOS 11 to 18, and most preferably at least 95% similarity (e.g. preferably at least 90% identity) to any one of the polypeptides of SEQ ID NOS 11 to 18. Certain preferred embodiments can have at least about 95% sequence identity or more, including, for example, at least about 96% sequence identity, at least about 97% sequence identity, at least about 98% sequence identity, or at least about 99% sequence identity. Moreover, they should preferably include exact portions of such polypeptides containing a sequence of at least 30 amino acids, and more preferably at least 50 amino acids.

Fragments or portions of the polypeptides of the present invention may be employed as intermediates for producing the corresponding full-length polypeptides by peptide synthesis. Fragments or portions of the polynucleotides of the present invention may also be used to synthesize full-length polynucleotides of the present invention.

The present invention also includes vectors, which include such polynucleotides, host cells which are genetically engineered with such vectors and the production of polypeptides by recombinant techniques using the foregoing. Host cells are genetically engineered (transduced or transformed or transfected) with such vectors, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those commonly used with the host cell selected for expression, as well known to the ordinarily skilled artisan.

The polynucleotides of the present invention may be employed for producing polypeptides by recombinant techniques. Thus, for example, the polynucleotides may be included in any one of a variety of expression vectors for expressing polypeptides. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by any of a variety of procedures. In general, the DNA sequence is inserted into an appropriate restriction endonuclease site (s) by procedures well known in the art, which procedures are deemed to be within the scope of those skilled in this art.

The DNA sequence in the expression vector is operatively linked to an appropriate expression control sequence (s) (promoter) to direct mRNA synthesis. As representative examples of such promoters, there may be mentioned: LTR or SV40 promoter, the *E. coli* lac or trp, the phage lambda P.sub.L promoter and other promoters known to control expression of genes in prokaryotic or eukaryotic cells or their viruses.

The expression vector should also contain a ribosome binding site for translation initiation and a transcription terminator. The vector may also include appropriate sequences for amplifying expression. In addition, the expression vectors preferably contain one or more selectable marker genes to provide a phenotypic trait for selection of transformed host cells, such as dihydrofolate reductase or neomycin-resistance for eukaryotic cell culture, or such as tetracycline- or ampicillin-resistance in *E. coli*.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or Bowes melanoma; adenoviruses; plant cells, etc. The selection of an appropriate host is deemed to be within the scope of those skilled in the art from the teachings herein.

Synthetic production of nucleic acid sequences is well known in the art as is apparent from CLONTECH 95/96 Catalogue, pages 215-216, CLONTECH, 1020 East Meadow Circle, Palo Alto, Calif. 94303. Thus, the present invention also includes expression vectors useful for the production of the proteins of the present invention. The present invention further includes recombinant constructs comprising one or more of the sequences as broadly described above. The constructs may comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example: Bacterial: pQE70, pQE60, pQE-9 (Qiagen), pBS, pD10, phagescript, psiX174, pbluescript SK, pbsks, pNH8A, pNH16a, pNH18A, pNH46A (Stratagene), ptrc99a, pKK223-3, pKK233-3, pDR540 and pRIT5 (Pharmacia); and Eukaryotic: pWLNEO, pSV2CAT, pOG44, pXTI, pSG (Stratagene), pSVK3, pBPV, pMSG, and pSVL (Pharmacia). However, any other suitable plasmid or vector may be used as long as it is replicable and viable in the host.

Promoter regions can be selected from any desired gene using CAT (chloramphenicol acetyl transferase) vectors or other vectors with selectable markers.

Two appropriate vectors are pKK232-8 and pCM7. Particular named bacterial promoters include lacI, lacZ, T3, T7, gpt, lambda P.sub.R, P.sub.L and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Components of the expression vector may generally include: 1) a neomycin phosphotransferase (G418), or hygromycin B phosphotransferase (hyg) gene as a selection marker, 2) an *E. Coli* origin of replication, 3) a T7 and SP6 phage promoter sequence, 4) lac operator sequences, 5) the lactose operon repressor gene (lacIq) and 6) a multiple cloning site linker region. Such an origin of replication (oriC) may be derived from pUC19 (LTI, Gaithersburg, Md.).

A nucleotide sequence encoding one of the polypeptides of SEQ ID NOS: 2 to 9 having the appropriate restriction sites is generated, for example, according to the PCR protocol described in Examples 1 and 2 hereinafter, using PCR primers having restriction sites for EcoR I (as the 5' primer) and Sal I (as the 3'primer) for cloning of isoQC Met I and Met II into vector EGFP-N3, or sites for Spe I (as the 5' primer) and EcoR I (as the 3' primer) for cloning of isoQC into vector pET41a. The PCR inserts are gel-purified and digested with compatible restriction enzymes. The insert and vector are ligated according to standard protocols.

In a further embodiment, the present invention provides host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, lipofection or electroporation (Davis, L., Dibner, M., Battey, I., Basic Methods in Molecular Biology, (1986)).

Such constructs in host cells are preferably used in a conventional manner to produce the gene product encoded by the recombinant sequence. Alternatively, the polypeptides of the invention can be synthetically produced by conventional peptide synthesizers or by chemical ligation of suitable fragments thus prepared.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

Transcription of the DNA encoding the polypeptides of the present invention by higher eukaryotes is increased by inserting an enhancer sequence into the vector. Enhancers include cis-acting elements of DNA, usually about from 10 to 300 bp, that act on a promoter to increase its transcription. Examples include the SV40 enhancer on the late side of the replication origin bp 100 to 270, acytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. Coli and S. cerevisiae TRP1 gene, and a promoter derived from a highly expressed gene to direct transcription of a downstream structural sequence. Such promoters can be derived from operons encoding glycolytic enzymes, such as 3-phosphoglycerate kinase (PGK), alpha-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter.

The vector will comprise one or more phenotypic selectable markers and an origin of replication to ensure maintenance of the vector and to, if desired, provide amplification within the host. Suitable prokaryotic hosts for transformation include E. Coli, Bacillus subtilis, Salmonella typhimurium and various species within the genera Pseudomonas, Streptomyces and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction), and cells are cultured for an additional period.

Cells are typically harvested by centrifugation and then disrupted by physical or chemical means, with the resulting crude extract being retained for further purification.

Microbial cells employed in expression of proteins can be disrupted by any convenient method, including freeze-thaw cycling, sonication, mechanical disruption and use of cell-lysing agents; such methods are well known to those skilled in the art.

Various mammalian cell culture systems can also be employed to express a recombinant protein. Examples of mammalian expression systems include the COS-7 lines of monkey kidney fibroblasts, described by Gluzman, Cell, 23: 175 (1981). Other cell lines capable of expressing a compatible vector include, for example, the C127, 3T3, CHO, HeLa and BHK cell lines. Mammalian expression vectors will generally comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Recovery can be facilitated if the polypeptide is expressed at the surface of the cells, but such is not a prerequisite. Recovery may also be desirable of cleavage products that are cleaved following expression of a longer form of the polypeptide. Protein refolding steps as known in this art can be used, as necessary, to complete configuration of the mature protein. High performance liquid chromatography (HPLC) can be employed for final purification steps.

The polypeptides of the present invention may be purified natural products, or produced by recombinant techniques from a prokaryotic or eukaryotic host (for example, by bacterial, yeast, higher plant, insect or mammalian cells in culture). Depending upon the host employed in a recombinant production procedure, the polypeptides of the present invention may be glycosylated or may be non-glycosylated. Polypeptides of the invention may also include an initial methionine amino acid residue.

In a preferred embodiment, the proteins of the invention are isolated and purified so as to be substantially free of contamination from other proteins. For example, the proteins of the invention should constitute at least 80% by weight of the total protein present in a sample, more preferably at least 90%, even more preferably at least 95%, and most preferably at least 98% by weight of the total protein.

These proteins may be in the form of a solution in water, another suitable solvent, such as dimethyl sulphoxide (DMSO) or ethanol, or a mixture of suitable solvents.

Examples of mixtures of solvents include 10% (by weight) ethanol in water and 2% (by weight) DMSO in water. A solution may further comprise salts, buffering agents, chaotropic agents, detergents, preservatives and the like. Alternatively, the proteins may be in the form of a solid, such as a lyophilised powder or a crystalline solid, which may also comprise a residual solvent, a salt or the like.

As used herein, the term "antibodies" includes polyclonal antibodies, affinity-purified polyclonal antibodies, monoclonal antibodies, and antigen-binding fragments, such as F(ab')$_2$ and Fab'proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans should be reduced.

Alternative techniques for generating or selecting antibodies useful herein include in vitro exposure of lymphocytes to human isoQC protein or a peptide therefrom, and selection of antibody display libraries in phage or similar vectors (for instance, through use of immobilized or labeled human isoQC protein or peptide).

Genes encoding polypeptides having potential human isoQC polypeptide binding domains can be obtained by screening random peptide libraries displayed on phage (phage display) or on bacteria, such as *E. coli*. Nucleotide sequences encoding such polypeptides can be obtained in a number of ways well known in the art.

As would be evident to one of ordinary skill in the art, polyclonal antibodies can be generated from inoculating a variety of warm-blooded animals, such as horses, cows, goats, sheep, dogs, chickens, rabbits, mice and rats, with a human isoQC polypeptide or a fragment thereof. The immunogenicity of a human isoQC polypeptide may be increased through the use of an adjuvant, such as alum (aluminum hydroxide) or Freund's complete or incomplete adjuvant, or surface active substances, such as lysolecithin, pluronic polyols, polyanions, peptides, oil emulsions, KLH or dinitrophenol. Among adjuvants used in humans, BCG (bacilli Calmette-Guerin) and *Corynebacterium parvum* are especially preferable. Polypeptides useful for immunization also include fusion polypeptides, such as fusions of isoQC or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier, such as keyhole limpet hemocyanin (KLH), bovine serum albumin (BSA) or tetanus toxoid, for immunization. Antibodies to isoQC may also be generated using methods that are well known in the art. Such antibodies may include, but are not limited to, polyclonal, monoclonal, chimeric, and single chain antibodies, Fab fragments, and fragments produced by a Fab expression library.

Neutralizing antibodies (i.e., those which block or modify interactions at the active sites) are especially preferred for therapeutic use.

For the production of antibodies, binding proteins, or peptides which bind specifically to QPCTL, libraries of single chain antibodies, Fab fragments, other antibody fragments, non-antibody protein domains, or peptides may be screened. The libraries could be generated using phage display, other recombinant DNA methods, or peptide synthesis (Vaughan, T. J. et al. Nature Biotechnology 14: 309-314 (1966)). Such libraries would commonly be screened using methods, which are well known in the art to identify sequences which demonstrate specific binding to QPCTL.

It is preferred that the oligopeptides, peptides, or fragments used to induce antibodies to QPCTL have an amino acid sequence consisting of at least about 5 amino acids and, more preferably, of at least about 10 amino acids. It is also preferable that these oligopeptides, peptides, or fragments are identical to a portion of the amino acid sequence of the natural protein. Short stretches of QPCTL amino acids may also be fused with those of another protein, such as KLH, and antibodies to the chimeric molecule may be produced.

Monoclonal antibodies to QPCTL may be prepared using any well known technique which provides for the production of antibody molecules by continuous cell lines in culture. These include, but are not limited to, the hybridoma technique, the human B-cell hybridoma technique, and the EBV-hybridoma technique, although monoclonal antibodies produced by hybridoma cells may be preferred.

In addition, techniques developed for the production of "chimeric antibodies", such as the splicing of mouse antibody genes to human antibody genes to obtain a molecule with appropriate antigen specificity and biological activity, can be used, see Neuberger, M. S. et al. Nature 312: 604-608 (1984). Alternatively, techniques described for the production of single chain antibodies may be adapted, using methods known in the art, to produce QPCTL-specific single chain antibodies. Antibodies with related specificity, but of distinct idiotypic composition, may be generated by chain shuffling from random combinatorial immunoglobulin libraries. (Burton D. R. Proc. Natl. Acad. Sci. 88: 11120-11123 (1991)).

Antibodies may also be produced by inducing in vivo production in the lymphocyte population or by screening immunoglobulin libraries or panels of highly specific binding reagents as disclosed in the literature. (Orlandi, R. et al. Proc. Natl. Acad. Sci. 86: 3833-3837 (1989)).

Antibody fragments, which contain specific binding sites for QPCTL may also be generated. For example, such fragments include, but are not limited to, $F(ab')_2$ fragments produced by pepsin digestion of the antibody molecule and Fab fragments generated by reducing the disulfide bridges of the $F(ab')_2$ fragments. Alternatively, Fab expression libraries may be constructed to allow rapid and easy identification of monoclonal Fab fragments with the desired specificity. (Huse, W. D. et al. Science 254: 1275-1281 (1989)).

Various immunoassays may be used to identify antibodies having the desired specificity. Numerous protocols for competitive binding or immunoradiometric assays using either polyclonal or monoclonal antibodies with established specificities are well known in the art. Such immunoassays typically involve the measurement of complex formation between QPCTL and its specific antibody. A two-site, monoclonal-based immunoassay utilizing monoclonal antibodies reactive to two non-interfering QPCTL epitopes is preferred, but a competitive binding assay may also be employed.

As earlier mentioned, the QPCTLs can be used in treatment of the Diseases.

Pharmaceutical compositions suitable for use in this aspect of the invention include compositions wherein the active ingredients are contained in an effective amount to achieve the intended purpose relating to one of the Diseases. The determination of a therapeutically effective dose is well within the capability of those skilled in the art and can be estimated initially either in cell culture assays, e.g. of neoplastic cells, or in animal models, usually mice, rats, rabbits, dogs, or pigs. An animal model may also be used to determine the appropriate concentration range and route of administration, which information is then commonly used to determine useful doses and routes for administration in humans.

A therapeutically effective dose refers to that amount of active ingredient, e.g. a QPCTL or fragment thereof, antibodies of DPRP, or an agonist, antagonist or inhibitor of QPCTL, which ameliorates particular symptoms or conditions of the disease. For example, the amount to be administered may be effective to cyclise N-terminal Glu or Gln of a desired target substrate upon contact therewith. Therapeutic efficacy and toxicity may likewise be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

An exact dosage will normally be determined by the medical practitioner in light of factors related to the subject requiring treatment, with dosage and administration being adjusted to provide a sufficient level of the active moiety or to maintain a desired effect.

Factors to be taken into account include the severity of the disease state, the general health of the subject, the age, weight, and gender of the subject, diet, time and frequency of administration, drug combination (s), reaction sensitivities, and tolerance/response to therapy. Long-acting pharmaceutical compositions may be administered every 3 to 4 days, every week, or even once every two weeks, depending on the half-life and clearance rate of the particular formulation.

Yet another aspect of the invention provides polynucleotide molecules having sequences that are antisense to mRNA transcripts of a polynucleotide of SEQ ID NOS 2 to 9. Administration of an antisense polynucleotide molecule can block the production of the protein encoded by the QPCTL genes of SEQ ID NOS 2 to 9. The techniques for preparing antisense polynucleotide molecules and administering such molecules are known in the art. For example, antisense polynucleotide molecules can be encapsulated into liposomes for fusion with cells.

In particular, the expression of the QPCTL genes of SEQ ID NOS 2 to 9 in brain, prostate, lung, heart, liver, spleen and kidney tissue provides evidence for a potential role in the pathophysiology of the diseases described below. Therefore in a further aspect, the invention relates to diagnostic assays for detecting diseases associated with inappropriate QPCTL activity or expression levels. Antibodies that specifically bind QPCTL may be used for the diagnosis of disorders characterized by expression of QPCTL, or in assays to monitor patients being treated with QPCTL or with agonists or antagonists (inhibitors) of QPCTL. Antibodies useful for diagnostic purposes may be prepared in the same manner as those described above for therapeutics. Diagnostic assays for QPCTL include methods that utilize the antibody and a label to detect QPCTL in human body fluids or in extracts of cells or tissues. The antibodies may be used with or without modification, and they may be labeled by covalent or non-covalent joining with a reporter molecule. A wide variety of reporter molecules are known in the art. Recombinant QPCTL proteins that have been modified so as to be catalytically inactive can also be used as dominant negative inhibitors. Such modifications include, for example, mutation of the active site.

A variety of protocols for measuring QPCTL, including ELISAs, RIAs and FACS, are known in the art and provide a basis for diagnosing altered or abnormal levels of QPCTL expression. Normal or standard values for QPCTL expression are established by combining body fluids or cell extracts taken from normal mammalian subjects, preferably human, with antibody to QPCTL under conditions suitable for complex formation. The method for detecting QPCTL in a biological sample would comprise the steps of a) providing a biological sample; b) combining the biological sample and an anti-QPCTL antibody under conditions which are suitable for complex formation to occur between QPCTL and the antibody; and c) detecting complex formation between QPCTL and the antibody, thereby establishing the presence of QPCTL in the biological sample.

The amount of complex formation then may be quantified by various methods, preferably by photometric means. Quantities of QPCTL expressed in a subject, control, and disease samples from biopsied tissues are compared with the standard values. Deviation between standard and subject values establishes the parameters for diagnosing disease.

In another embodiment of the invention, the polynucleotides encoding QPCTL are used for diagnostic purposes, which polynucleotides may include oligonucleotide sequences, complementary RNA and DNA molecules, and PNAs. These polynucleotides may be used to detect and quantitate gene expression in biopsied tissues in which expression of QPCTL may be correlated with one of the diseases. The diagnostic assay may be used to distinguish between absence, presence, and excess expression of QPCTL and to monitor regulation of QPCTL levels during therapeutic intervention. Moreover, pharmacogenomic, single nucleotide polymorphisms (SNP) analysis of the QPCTL genes can be used as a method to screen for mutations that indicate predisposition to disease or modified response to drugs.

QPCTL polynucleotide and polypeptide sequences, fragments thereof, antibodies of QPCTLs, and agonists, antagonists or inhibitors of QPCTLs can be used as discovery tools to identify molecular recognition events and therefore proteins, polypeptides and peptides that interact with QPCTL proteins. A specific example is phage display peptide libraries where greater than 108 peptide sequences can be screened in a single round of panning. Such methods as well as others are known within the art and can be utilized to identify compounds that inhibit or enhance the activity of any one of the QPCTLs of SEQ ID NOS 11-18.

Coupled links represent functional interactions such as complexes or pathways, and proteins that interact with QPCTLs can be identified by a yeast two-hybrid system, proteomics (differential 2D gel analysis and mass spectrometry) and genomics (differential gene expression by microarray or serial analysis of gene expression SAGE).

Proteins identified as functionally linked to QPCTLs and the process of interaction form the basis of methods of screening for inhibitors, agonists and antagonists and modulators of these QPCTL-protein interactions.

The term "antagonist", as it is used herein, refers to an inhibitor molecule which, when bound to QPCTL, decreases the amount or the duration of the effect of the biological or immunological activity of QPCTL, e.g. decreasing the enzymatic activity of the peptidase to cyclise Glu- or Gln-residues at the N-termini of the QPCTL substrates. Antagonists may include proteins, nucleic acids, carbohydrates, antibodies, or any other molecules which decrease the effect of QPCTL; for example, they may include small molecules and organic compounds that bind to and inactivate QPCTLs by a competitive or non-competitive type mechanism. Preferred are small molecule inhibitors of QPCTL. Most preferred are competitive small molecule inhibitors of QPCTL.

Specific examples of QPCTL enzyme activity inhibitors are described in Example 4. Inhibitors can be, for example, inhibitors of the QPCTL cyclase activity, or alternatively inhibitors of the binding activity of the QPCTL to proteins with which they interact. Specific examples of such inhibitors can include, for example, anti-QPCTL antibodies, peptides, protein fragments, or small peptidyl protease inhibitors, or small non-peptide, organic molecule inhibitors which are formulated in a medium that allows introduction into the desired cell type. Alternatively, such inhibitors can be attached to targeting ligands for introduction by cell-mediated endocytosis and other receptor mediated events. Such methods are described further below and can be practiced by those skilled in the art given the QPCTL nucleotide and amino acid sequences described herein.

A further use of QPCTLs is for the screening of potential antagonists for use as therapeutic agents, for example, for inhibiting binding to QPCTL, as well as for screening for agonists. QPCTL, its immunogenic fragments, or oligopeptides thereof can be used for screening libraries of compounds which are prospective agonists or antagonists in any of a variety of drug screening techniques. The fragment employed in such screening may be free in solution, affixed to a solid support, borne on a cell surface, or located intracellularly. The formation of binding complexes between QPCTL and the agent being tested is then measured. Other assays to discover antagonists that will inhibit QPCTL are apparent from the disclosures of Patents Nos. WO 2004/098625, WO 2004/098591 and WO 2005/075436, which describe inhibitors of QC and which are incorporated herein in their entirety. Another worthwhile use of these QPCTLs is the screening of inhibitors of QC to show that they will not have undesired side effects by also inhibiting one or more of the QPCTLs.

A method provided for screening a library of small molecules to identify a molecule which binds QPCTL generally comprises: a) providing a library of small molecules; b) combining the library of small molecules with the polypeptide of either SEQ ID NOS 11 to 18, or with a fragment thereof, under conditions which are suitable for complex formation; and c) detecting complex formation, wherein the presence of such a complex identifies a small molecule, which binds to the QPCTL.

One method for identifying an antagonist comprises delivering a small molecule which binds QPCTL into extracts from cells transformed with a vector expressing QPCTL along with a chromogenic substrate (e.g. Ala-Pro-AFC or Ala-Pro-AMC) under conditions where cleavage would normally occur, and then assaying for inhibition of cleavage by the enzyme by monitoring changes in fluorescence, or UV light absorption, by spectrophotometry to identify molecules that inhibit cleavage. A reduced rate of reaction or total amount of fluorescence or UV light absorption, in the presence of the molecule, establishes that the small molecule is an antagonist, which reduces QPCTL catalytic/enzymatic activity. Once such molecules are identified, they may be administered to reduce or inhibit cyclisation of N-terminal Glu- or Gln-residues by a QPCTL.

In accordance with still another specific aspect, the invention provides a method of screening for a compound capable of inhibiting the enzymatic activity of at least one mature protein according to the present invention, preferably selected from the proteins of SEQ ID NOS: 11 to 18, which method comprises incubating said mature protein and a suitable substrate for said mature protein in the presence of one or more test compounds or salts thereof, measuring the enzymatic activity of said mature protein, comparing said activity with comparable activity determined in the absence of a test compound, and selecting the test compound or compounds that reduce the enzymatic activity.

Furthermore, the invention also provides a method of screening for a selective QC-inhibitor, i.e. a compound capable of inhibiting the enzymatic activity of QC, wherein said QC is preferably the protein of SEQ ID NO: 10, that does not inhibit the enzymatic activity of at least one mature protein according to the present invention, preferably selected from the proteins of SEQ ID NOS: 11 to 18, which method comprises incubating said mature protein and a suitable substrate in the presence of one or more inhibitors or salts thereof of QC, measuring the enzymatic activity of said mature protein, comparing said activity with comparable activity determined in the absence of the QC inhibitor, and selecting a compound that does not reduce the enzymatic activity of said mature protein.

Furthermore, the invention also provides a method of screening for a selective QPCTL-inhibitor, i.e. a compound capable of inhibiting the enzymatic activity of at least one QPCTL protein, which is preferably selected from the proteins of SEQ ID NOS: 11 to 18; that does not inhibit the enzymatic activity of QC, wherein said QC is preferably the protein of SEQ ID NO: 10, which method comprises incubating said QC in the presence of one or more inhibitors or salts thereof of a QPCTL, measuring the enzymatic activity of QC, comparing said activity with comparable activity determined in the absence of the QPCTL inhibitor, and selecting a compound that does not reduce the enzymatic activity of said QPCTL protein.

Useful inhibitors of QC, which also could be useful as inhibitors of QPCTLs, are described in WO 2004/098625, WO 2004/098591, WO 2005/039548 and WO 2005/075436, which are incorporated herein in their entirety, especially with regard to the structure of the inhibitors and their production.

Examples of QPCTL-inhibitors

Potential QPCTL-inhibitors, which are suitable for uses and methods according to the present invention are disclosed in WO 2005/075436, which is incorporated herein in its entirety with regard to the structure, synthesis and methods of use of the QC-inhibitors.

In particular:

A suitable compound is that of formula 1*:

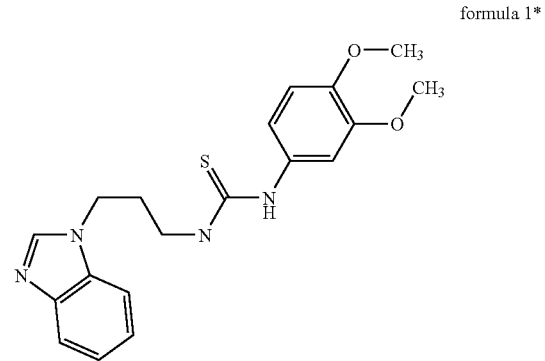

formula 1*

In a further embodiment, the inhibitors of QPCTL may be those of formula 1a,

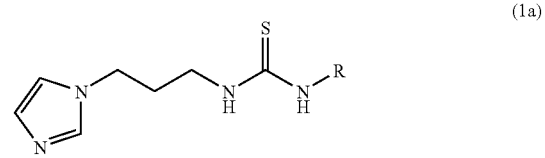

(1a)

wherein R is defined in examples 1 to 53.

| Example | R | ESI-MS (M + H) |
|---|---|---|
| 1 | Methyl | 199.3 |
| 2 | tert-Butyl | 241.4 |
| 3 | Benzyl | 275.4 |
| 4 | Phenyl | 261.4 |
| 5 | 4-(fluoro)-phenyl | 279.35 |

-continued

| Example | R | ESI-MS (M + H) |
|---|---|---|
| 6 | 4-(chloro)-phenyl | 295.80 |
| 7 | 4-(ethyl)-phenyl | 289.41 |
| 8 | 4-(trifluoromethyl)-phenyl | 329.4 |
| 9 | 4-(methoxy-carbonyl)-Phenyl | 319.4 |
| 10 | 4-(acetyl)-phenyl | 303.4 |
| 11 | 4-(methoxy)-phenyl | 291.4 |
| 12 | bicyclo[2.2.1]hept-5-en-2-yl | 277.5 |
| 13 | 3,4-(dimethoxy)-phenyl | 321.5 |
| 14 | 2,4-(dimethoxy)-phenyl | 321.5 |
| 15 | 3,5-(dimethoxy)-phenyl | 321.5 |
| 16 | 2-(methoxy-carbonyl)-Phenyl | 319.4 |
| 17 | 4-(oxazol-5-y)-phenyl | 328.5 |
| 18 | 4-(pyrazol-1-yl)-phenyl | 327.4 |
| 19 | 4-(isopropyl)-phenyl | 303.5 |
| 20 | 4-(piperidine-1-sulfonyl)-Phenyl | 408.6 |
| 21 | 4-(morpholin-4-yl)-phenyl | 346.5 |
| 22 | 4-(cyano)-phenyl | 286.4 |
| 23 | 2,3-dihydro-benzo[1,4]dioxin-6-yl | 319.4 |
| 24 | benzo[1,3]dioxol-5-yl | 305.4 |
| 25 | 3,4,5(trimethoxy)-phenyl | 351.5 |
| 26 | 3-(methoxy)-phenyl | 291.4 |
| 27 | 4-(ethoxy)-phenyl | 305.5 |
| 28 | 4-(benzyloxy)-phenyl | 367.5 |
| 29 | 4-(methoxy)-benzyl | 305.5 |
| 30 | 3,4-(dimethoxy)-benzyl | 335.5 |
| 31 | 2-(methoxy-carbonyl)-thiophene-3-yl | 325.5 |
| 32 | 3-(ethoxy-carbonyl)-4,5,6,7-tetrahydrobenzo[b]thiophene2-yl | 392.6 |
| 33 | 2-(methoxy-carbonyl)-4-(methyl)-thiophene-3-yl | 339.5 |
| 34 | Benzo[c][1,2,5]thiazol-4-yl | 319.5 |
| 35 | Benzo[c][1,2,5]thiazol-5-yl | 319.5 |
| 36 | 5-(methyl)-3-(phenyl)-isooxazol-4-yl | 342.5 |
| 37 | 3,5-(dimethyl)-isooxazol-4-yl | 280.4 |
| 38 | 4-(iodo)-phenyl | 387.3 |
| 39 | 4-(bromo)-phenyl | 340.3 |
| 40 | 4-(methyl)-phenyl | 275.4 |
| 41 | Naphthalen-1-yl | 311.5 |
| 42 | 4-(nitro)-phenyl | 306.4 |
| 43 | Butyl | 241.4 |
| 44 | Cyclooctyl | 295.5 |
| 45 | Furan-2-ylmethyl | 265.4 |
| 46 | Tetrahydrofuran-2-ylmethyl | 269.4 |
| 47 | Benzo[1,3]dioxol-5-ylmethyl | 319.4 |
| 48 | 2-(morpholin-4-yl)-ethyl | 298.5 |
| 49 | 4-(methylsulfanyl)-phenyl | 307.5 |
| 50 | 4-(dimethylamino)-phenyl | 304.5 |
| 51 | 4-(trifluoromethoxy)-phenyl | 345.4 |
| 52 | Benzoyl | 288.3 |
| 53 | Pyridin-4-yl | 261.1 |

Further suitable inhibitors of QPCTL may be those of formula 1b,

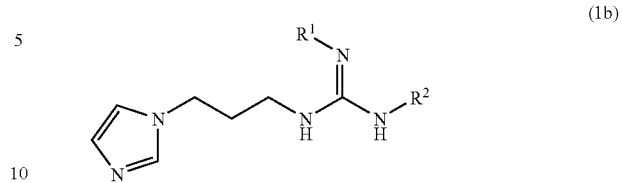

wherein $R^1$ and $R^2$ are defined in examples 54 to 95.

| Example | $R^1$ | $R^2$ |
|---|---|---|
| 54 | Cyano | Methyl |
| 55 | Cyano | 3,4-(dimethoxy)-phenyl |
| 56 | Cyano | 2,4-(dimethoxy)-phenyl |
| 57 | Cyano | 3,5-(dimethoxy)-phenyl |
| 58 | Cyano | 2,3-dihydrobenzo[b][1,4]dioxin-7-yl |
| 59 | Cyano | Benzo[d][1,3]dioxol-6-yl |
| 60 | Cyano | 3,4,5-(trimethoxy)-phenyl |
| 61 | Cyano | 3-(methoxy)-phenyl |
| 62 | Cyano | 4-(ethoxy)-phenyl |
| 63 | Cyano | 4-(benzyloxy)-phenyl |
| 64 | Cyano | Phenyl |
| 65 | Cyano | 4-(methoxy)-phenyl |
| 66 | Cyano | 4-(acetyl)-phenyl |
| 67 | Cyano | 4-(nitro)-phenyl |
| 68 | Cyano | Benzyl |
| 69 | Cyano | Naphthalen-1-yl |
| 70 | Cyano | 4-(fluoro)-phenyl |
| 71 | Cyano | 4-(iodo)-phenyl |
| 72 | Cyano | 4-(bromo)-phenyl |
| 73 | Cyano | Cyclooctyl |
| 74 | Cyano | tert-butyl |
| 75 | Cyano | 4-(methyl)-phenyl |
| 76 | Cyano | 4-(methylthio)-phenyl |
| 77 | Cyano | 4-(ethyl)-phenyl |
| 78 | Cyano | 4-(dimethylamino)-phenyl |
| 79 | Cyano | Butyl |
| 80 | Cyano | Trityl |
| 81 | Cyano | (Benzo[d][1,3]dioxol-6yl)methyl |
| 82 | Cyano | (tetrahydrofuran-2yl)methyl |
| 83 | Cyano | 4-(trifluoromethyl)-phenyl |
| 84 | Cyano | (furan-2-yl)methyl |
| 85 | Cyano | 2-(morpholin-4-yl)-ethyl |
| 86 | Cyano | 4-(oxazol-5yl)-phenyl |
| 87 | Cyano | Pyridin-3-yl |
| 88 | Cyano | 4-(cyano)-phenyl |
| 89 | Cyano | 4-(trifluoromethoxy)-phenyl |
| 90 | Cyano | 4-(piperidinosulfonyl)-phenyl |
| 91 | Cyano | 4-(1H-pyrazol-1-yl)phenyl |
| 92 | H | 3,4-(dimethoxy)-phenyl |
| 93 | Methyl | 3,4-(dimethoxy)-phenyl |
| 94 | Cyano | 2,3,4-(trimethoxy)-phenyl |
| 95 | Cyano | Cycloheptyl |

Further suitable inhibitors of QPCTL may be those of formula 1c,

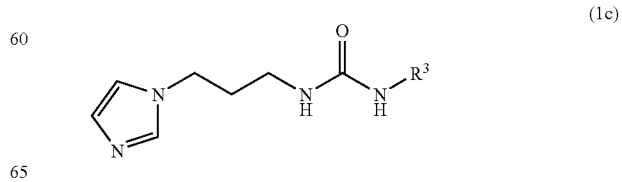

wherein $R^3$ is defined in examples 96 to 102.

| Example | R³ | ESI-MS (M + H) |
|---|---|---|
| 96 | Ethyl | 197.3 |
| 97 | 6-fluoro-4H-benzo[d][1,3]dioxin-8-yl | 321.4 |
| 98 | 3-(cylopentyloxy)-4-(methoxy)-phenyl | 359.4 |
| 99 | 4-(heptyloxy)-phenyl | 359.5 |
| 100 | 3,4-dihydro-2H-benzo[b][1,4]dioxepin-7-yl | 317.4 |
| 101 | 4-(butoxy)-phenyl | 317.4 |
| 102 | 3,4-(dimethoxy)-phenyl | 305.4 |

Further suitable inhibitors of QPCTL may be those of formula 1d,

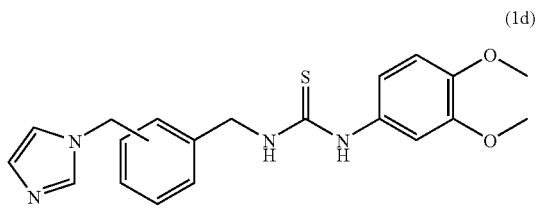
(1d)

wherein the position on the ring is defined in examples 103 to 105.

| Example | Position of the Benzyl-substitution | ESI-MS (M + H) |
|---|---|---|
| 103 | 2 | 383.5 |
| 104 | 3 | 383.5 |
| 105 | 4 | 383.5 |

Further suitable inhibitors of QPCTL may be those of formula 1e,

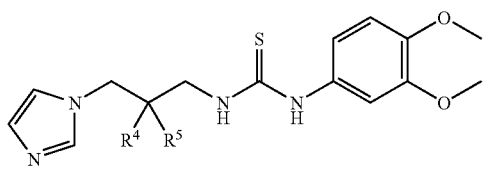
(1e)

wherein R⁴ and R⁵ are defined in examples 106 to 109.

| Example | R⁴ | R⁵ | ESI-MS (M + H) |
|---|---|---|---|
| 106(S) | H | Methyl | 335.5 |
| 107(R) | Methyl | H | 335.5 |
| 108 | Methyl | Methyl | 349.5 |
| 109 | —CH₂—CH₂— | | 347.5 |

Further suitable inhibitors of QPCTL may be those of formula 1f,

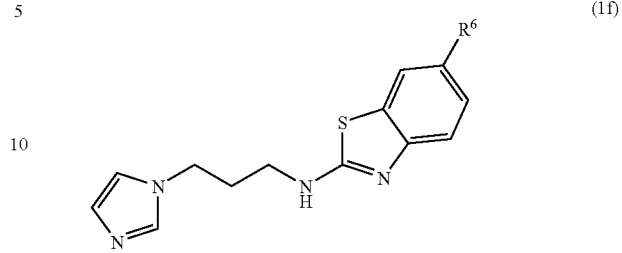
(1f)

wherein R⁶ is defined in examples 110 to 112.

| Example | R⁶ | ESI-MS (M + H) |
|---|---|---|
| 110 | H | 259.4 |
| 111 | Chloro | 293.8 |
| 112 | Methoxy | 289.4 |

Further suitable inhibitors of QPCTL may be those of formula 1g,

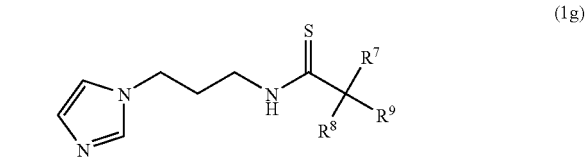
(1g)

wherein R⁷, R⁸ and R⁹ are defined in examples 113 to 132.

| Example | R⁷ | R⁸ | R⁹ | ESI-MS (M + H) |
|---|---|---|---|---|
| 113 | Phenyl | H | H | 260.4 |
| 114 | Thiophen-2-yl | H | H | 266.5 |
| 115(R) | Phenyl | Methyl | H | 274.5 |
| 116(S) | Phenyl | H | Methyl | 274.5 |
| 117 | Phenyl | H | Ethyl | 288.5 |
| 118 | Phenyl | H | Phenyl | 336.5 |
| 119 | 3,4-(dimethoxy)-Phenyl | H | H | 320.5 |
| 120 | 3,4-(dimethoxy)-Phenyl | Methyl | Methyl | 347.2 |
| 121 | 4-(chloro)-phenyl | —CH₂—CH₂—CH₂— | | 334.9 |
| 122 | 4-(chloro)-phenyl | —CH₂—C₂H₄—CH₂— | | 349.0 |
| 123 | 4-(methoxy)-phenyl | —CH₂—C₃H₆—CH₂— | | 358.6 |
| 124 | 4-(methoxy)-phenyl | —CH₂—CH₂— | | 316.5 |
| 125 | 3,4-(dimethoxy)-Phenyl | —CH₂—CH₂— | | 346.5 |
| 126 | 3,4,5-(trimethoxy)-Phenyl | —CH₂—CH₂— | | 376.6 |
| 127 | 2,3,4-(trimethoxy)-Phenyl | —CH₂—CH₂— | | 376.6 |
| 128 | 2-(methoxy)-phenyl | —CH₂—CH₂— | | 316.5 |
| 129 | 3-(methoxy)-phenyl | —CH₂—CH₂— | | 316.5 |
| 130 | 2,3-(dimethoxy)-Phenyl | —CH₂—CH₂— | | 346.5 |
| 131 | 3,5-(dimethoxy)-Phenyl | —CH₂—CH₂— | | 346.5 |
| 132 | 2,5-(dimethoxy)-Phenyl | —CH₂—CH₂— | | 346.5 |

Further suitable inhibitors of QPCTL may be are those of formula 1h,
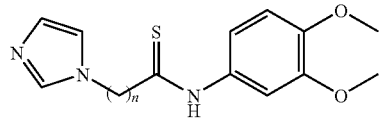
wherein n is defined in examples 133 to 135.
| Example | N | ESI-MS (M + H) |
|---|---|---|
| 133 | 3 | 306.4 |
| 134 | 4 | 320.5 |
| 135 | 5 | 334.5 |
Further suitable inhibitors of QPCTL may be those of formula 1i,
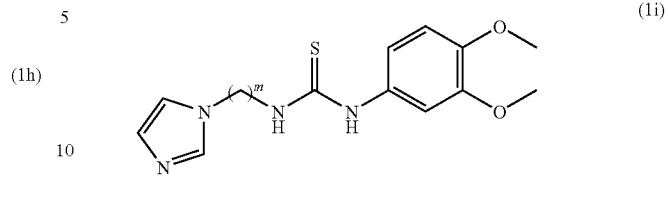
wherein m is defined in examples 136 and 137.
| Example | m | ESI-MS (M + H) |
|---|---|---|
| 136 | 2 | 307.4 |
| 137 | 4 | 335.5 |
Further suitable inhibitors of QPCTL may be those of formula 138 to 141.
| Example | Structure | ESI-MS (M + H) |
|---|---|---|
| 138 | 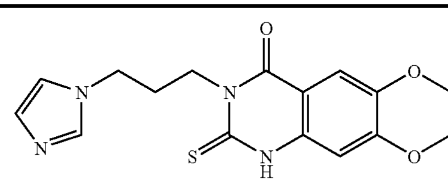 | 347.5 |
| 139 | 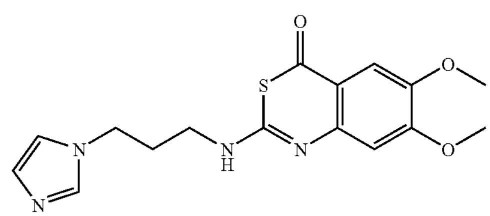 | 347.2 |
| 140 | 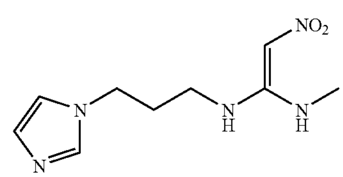 | 226.3 |
| 141 | 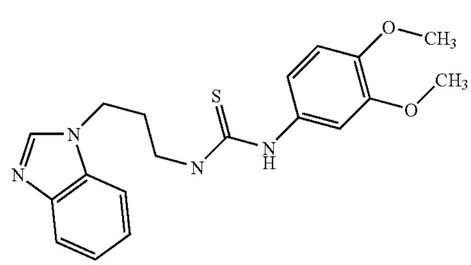 | 370.4 |

The term "agonist", as used herein, refers to a molecule which, when bound to QPCTL, increases or prolongs the duration of the effect of QPCTL. Agonists may include proteins, nucleic acids, carbohydrates, or any other molecules that bind to and modulate the effect of QPCTL. Although it is less likely that small molecules will prove to be effective QPCTL agonists, a method for identifying such a small molecule, which binds QPCTL as an agonist, comprises delivering a chromogenic form of a small molecule that binds QPCTL into cells transformed with a vector expressing QPCTL and assaying for fluorescence or UV light absorption changes by spectrophotometry. An increased amount of UV absorption or fluorescence would establish that the small molecule is an agonist that increases QPCTL activity.

Another technique for drug screening which may be used provides for high throughput screening of compounds having suitable binding affinity to the protein of interest as described in published PCT application W0 84/03564. In this method, large numbers of different small test compounds are synthesized on a solid substrate, such as plastic pins or some other surface. The test compounds are reacted with QPCTL, or with fragments thereof, and then washed. Bound QPCTL is then detected by methods well known in the art. Purified QPCTL can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding QPCTL specifically compete with a test compound for binding QPCTL. In this manner, antibodies can be used to detect the presence of any peptide that shares one or more antigenic determinants with QPCTL.

As indicated above, by investigating the binding sites, ligands may be designed that, for example, have more interactions with QPCTL than do its natural ligands. Such antagonist ligands will bind to QPCTL with higher affinity and so function as competitive ligands. Alternatively, synthetic or recombinant proteins homologous or analogous to the ligand binding site of native QPCTL may be designed, as may other molecules having high affinity for QPCTL. Such molecules should also be capable of displacing QPCTL and provide a protective effect.

As indicated above, the knowledge of the structures of QPCTL enables synthetic binding site homologues and analogues to be designed. Such molecules will facilitate greatly the use of the binding properties to target potential therapeutic agents, and they may also be used to screen potential therapeutic agents. Furthermore, they may be used as immunogens in the production of monoclonal antibodies, which antibodies may themselves be used in diagnosis and/or therapy as described hereinbefore.

Therapeutic Applications

It is known in the art that amyloid peptides, e.g. Abeta 1-42 (SEQ ID NO 23) and Abeta 1-40 (SEQ ID NO 24) become N-terminally truncated by proteolytic enzymes such as for example aminopeptidases or dipeptidyl aminopeptidases, resulting in the Abeta-peptides 3-42 (SEQ ID NO 25), 3-40 (SEQ ID NO 26), 11-42 (SEQ ID NO 27) and 11-40 (SEQ ID NO 28). These truncated Abeta peptides start with a glutamate residue at the N-terminus and are thus substrates for QC (see also WO 2004/09862) and possibly also for the QPCTLs of SEQ ID NOS 11-18, 21 and 22, preferably the human isoQCs of SEQ ID NOS 11, 12, 21 and 22, most preferably the human isoQCs of SEQ ID NOS 11 and 12. The resulting pGlu-Abeta peptides of SEQ ID NOS 29-32 are much more hydrophobic than the non-pyroglutamted peptides, are much more prone to form A-beta peptide aggregates, such as oligomers and fibrills, and were shown to by highly neurotoxic. Finally, the Abeta-peptides of SEQ ID NOS 29-32 play a crucial role in the development of Alzheimer's disease and Down Syndrome.

Accordingly, inhibitors of the QPCTLs of SEQ ID NOS 11-18, 21 and 22, preferably the human isoQCs of SEQ ID NOS 11, 12, 21 and 22, most preferably the human isoQCs of SEQ ID NOS 11 and 12, may be used for the treatment of amyloid peptide related diseases, especially neurodegenerative diseases, in particular Alzheimer's disease and Down Syndrome.

Other potential physiological substrates of QPTCLs in mammals are selected from the group consisting of $Glu^1$-ABri (SEQ ID NO 33), $Glu^1$-ADan (SEQ ID NO 34), and $Gln^1$-Gastrins (17 and 34) (SEQ ID NOS 35 and 36). Their pyroglutamated forms (SEQ ID NOS 37-40) cause pathologies such as those selected from the group consisting of duodenal cancer with or w/o *Helicobacter pylori* infections, colorectal cancer, Zolliger-Ellison syndrome, Familial British Dementia (FBD) and Familial Danish Dementia (FDD). Accordingly, inhibitors of QPCTLs can be used to treat these pathologies.

Further potential physiological substrates of QPCTLs are shown in table 3.

TABLE 3

Amino acid sequences of physiological active peptides with an N-terminal glutamine residue

| Peptide | Amino acid sequence | Function |
|---|---|---|
| Gastrin 17 (SEQ ID NO 35) Swiss-Prot: P01350 | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin (SEQ ID NO 41) Swiss-Prot: P30990 | QLYENKPRRP YIL | Neurotensin plays an endocrine or paracrine role in the regulation of fat metabolism. It causes contraction of smooth muscle. |

TABLE 3-continued

Amino acid sequences of physiological active peptides with an N-terminal glutamine residue

| Peptide | Amino acid sequence | Function |
| --- | --- | --- |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH<br>Swiss-Prot: P20396 | QHP amide | TRH functions as a regulator of the biosynthesis of TSH in the anterior pituitary gland and as a neurotransmitter/neuromodulator in the central and peripheral nervous systems. |
| GnRH<br>(SEQ ID NO 42)<br>Swiss-Prot: P01148 | QHWSYGL RP(G) amide | Stimulates the secretion of gonadotropins; it stimulates the secretion of both luteinizing and follicle-stimulating hormones. |
| CCL16 (small inducible cytokine A16)<br>(SEQ ID NO 43)<br>Swill-Prot: O15467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8)<br>(SEQ ID NO 44)<br>Swiss-Prot: P80075 | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind heparin. |
| CCL2 (small inducible cytokine A2)<br>(SEQ ID NO 45)<br>Swiss-Prot: P13500 | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18 (small inducible cytokine A18)<br>(SEQ ID NO 46)<br>Swiss-Prot: P55774 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated |

TABLE 3-continued

Amino acid sequences of physiological active peptides with an N-terminal glutamine residue

| Peptide | Amino acid sequence | Function |
|---|---|---|
| | | macrophages in lymph nodes, has chemotactic activity for naive T cells, CD4+ and CD8+ T cells and thus may play a role in both humoral and cell-mediated immunity responses. |
| Fractalkine (neurotactin) (SEQ ID NO 47) Swiss-Prot: P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane bound form promotes adhesion of those leukocytes to endothelial cells. May play a role in regulating leukocyte adhesion and migration processes at the endothelium. Binds to cx3cr1. |
| CCL7 (small inducible cytokine A7) (SEQ ID NO 48) Swiss-Prot: P80098 | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) (SEQ ID NO 49) Swiss-Prot O43612 | QPLPDCCRQK TCSCRLYELL HGAGNHAAGI LTL | Neuropeptide that plays a significant role in the regulation of food intake and sleep-wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high 7affinity. |
| Substance P (SEQ ID NO 50) | RPK PQQFFGLM | Belongs to the tachykinins. Tachykinins are active peptides which excite neurons, evoke behavioral responses, are potent vasodilators and secretagogues, and contract (directly or indirectly) many smooth muscles. |

The peptides $Gln^1$-Gastrin (17 and 34 amino acids in length), $Gln^1$-Neurotensin and $Gln^1$-FPP were identified as new physiological substrates of QPCTLs. Gastrin, Neurotensin and FPP comprise a pGlu residue in their N-terminal position. This N-terminal pGlu residue may be formed from N-terminal glutamine by QPCTL catalysis for all peptides. As a result, these peptides are activated in terms of their biological function upon conversion of the N-terminal glutamine residue to pGlu.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 *J Physiol* 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 *Regul Pept* 9337-44).

In a further embodiment, the present invention provides the use of activity increasing effectors of QPCTLs for the stimulation of gastrointestinal tract cell proliferation, especially gastric mucosal cell proliferation, epithelial cell proliferation, the differentiation of acid-producing parietal cells and histamine-secreting enterochromaffin-like (ECL) cells, and the expression of genes associated with histamine synthesis and storage in ECL cells, as well as for the stimulation of acute acid secretion in mammals by maintaining or increasing the concentration of active pGlu$^1$-Gastrin (SEQ ID NOS 39 and 40).

In a further embodiment, the present invention provides the use of inhibitors of QPCTLs for the treatment of duodenal ulcer disease and gastric cancer with or w/o *Helicobacter pylori* infections in mammals by decreasing the conversion rate of inactive Gln$^1$-Gastrin (SEQ ID NOS 35 and 36) to active pGlu$^1$-Gastrin (SEQ ID NOS 39 and 40).

Neurotensin (NT) (SEQ ID NO 41) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 *Biol Psychiatry* 50 856-872).

Accordingly, the present invention provides the use of activity increasing effectors of QPCTLs for the preparation of antipsychotic drugs and/or for the treatment of schizophrenia in mammals. The effectors of QPCTLs either maintain or increase the concentration of active pGlu$^1$-neurotensin.

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on," others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 *Vitam Horm* 63, 1-28).

In a further embodiment, the present invention provides the use of inhibitors of QPCTLs for the preparation of fertilization prohibitive drugs and/or to reduce the fertility in mammals. The inhibitors of QPCTLs decrease the concentration of active pGlu$^1$-FPP, leading to a prevention of sperm capacitation and deactivation of sperm cells. In contrast it could be shown that activity increasing effectors of QC are able to stimulate fertility in males and to treat infertility.

In a further embodiment, further physiological substrates of QPCTLs were identified within the present invention. These are Gln$^1$-CCL2 (SEQ ID NO 45), Gln$^1$-CCL7 (SEQ ID NO 48), Gln$^1$-CCL8 (SEQ ID NO 44), Gln$^1$-CCL16 (SEQ ID NO 43), Gln$^1$-CCL18 (SEQ ID NO 46) and Gln$^1$-fractalkine (SEQ ID NO 47). For details see Table 3. These polypeptides play an important role in pathophysiological conditions, such as suppression of proliferation of myeloid progenitor cells, neoplasia, inflammatory host responses, cancer, psoriasis, rheumatoid arthritis, atherosclerosis, humoral and cell-mediated immunity responses, leukocyte adhesion and migration processes at the endothelium.

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, *J Pept Res* 57(6):528-38.). Recently, it was found that also the enzyme glutaminyl cyclase (QC) is overexpressed in melanomas (Ross D. T et al., 2000, *Nat Genet.* 24:227-35.).

Accordingly, the present invention provides the use of inhibitors of QPCTLs for the preparation of a medicament for the treatment of pathophysiological conditions, such as suppression of proliferation of myeloid progenitor cells, neoplasia, inflammatory host responses, cancer, malign metastasis, melanoma, psoriasis, rheumatoid arthritis, atherosclerosis, impaired humoral and cell-mediated immunity responses, leukocyte adhesion and migration processes at the endothelium.

Furthermore, $Gln^1$-orexin A (SEQ ID NO 49) was identified as a physiological substrate of QPCTLs within the present invention. Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

In a further embodiment, the present invention provides the use of inhibitors of QPCTLs for the preparation of a medicament for the treatment of impaired food intake and sleep-wakefulness, impaired homeostatic regulation of energy metabolism, impaired autonomic function, impaired hormonal balance and impaired regulation of body fluids.

Polyglutamine expansions in several proteins lead to neurodegenerative disorders, such as Parkinson disease and Kennedy's disease. The mechanism therefore remains largely unknown. The biochemical properties of polyglutamine repeats suggest one possible explanation: endolytic cleavage at a glutaminyl-glutaminyl bond followed by pyroglutamate formation may contribute to the pathogenesis through augmenting the catabolic stability, hydrophobicity, amyloidogenicity, and neurotoxicity of the polyglutaminyl proteins (Saido, T; Med Hypotheses (2000) March; 54(3):427-9). Accordingly, the present invention provides therefore the use of inhibitors of QPCTLs for the preparation of a medicament for the treatment of Parkinson disease and Huntington's disease.

A further substrate of QPTCLs is the peptide QYNAD (SEQ ID NO 51). Its pyroglutamated form pGlu-Tyr-Asn-Ala-Asp (pEYNAD) (SEQ ID NO 52) is the effective agent with blocking activity of voltage-gated sodium channels. Sodium channels are expressed at high density in myelinated axons and play an obligatory role in conducting action potentials along axons within the mammalian brain and spinal cord. Therefore, it is speculated that they are involved in several aspects of the pathophysiology of multiple sclerosis (MS), the Guillain-Barré syndrome and chronic inflammatory demyelinizing polyradiculoneuropathy.

In a further embodiment, the present invention provides the use of inhibitors of QPCTLs for the preparation of a medicament for the treatment of inflammatory autoimmune diseases, especially for multiple sclerosis, the Guillain-Barré syndrome and chronic inflammatory demyelinizing polyradiculoneuropathy, wherein the formation of the voltage-gated sodium channel blocking peptide pEYNAD is inhibited.

Furthermore, the present invention provides a diagnostic assay, comprising a QC-inhibitor.

In another embodiment, the present invention provides a method of diagnosing any one of the aforementioned diseases and/or conditions, comprising the steps of collecting a sample from a subject who is suspected to be afflicted with said disease and/or condition, contacting said sample with a QC-inhibitor, and determining whether or not said subject is afflicted by said disease and/or condition.

Preferably, the sample in said diagnosing method is a blood sample, a serum sample, a sample of cerebrospinal liquor or a urine sample.

Preferably, the subject in said diagnosing method is a human being.

Preferably, the QC inhibitor in said diagnosing method is a selective QC inhibitor. Further preferred for the use in said diganostic assay are selective QPCTL inhibitors.

The present invention further pertains to a diagnostic kit for carrying out the diagnosing method comprising as detection means the aforementioned diagnostic assay and a determination means.

EXAMPLE 1

Preparation of Human isoQC

Cell Lines and Media

African green monkey kidney cell line COS-7, human neuroblastoma cell line SH-SY5Y, human asatrocytoma cell line LN405, human keratinocytoma cell line HaCaT and human hepatocellular carcinoma cell line Hep-G2 were cultured in appropriate cell culture media (DMEM, 10% FBS for Cos-7, SH-SY5Y, LN405, HaCaT), (RPMI1640, 10% FBS for Hep-G2), in a humidified atmosphere of 5% $CO_2$ (HaCaT, Hep-G2, COS-7) or 10% $CO_2$ (SH-SY5Y, LN405) at 37° C.

Analysis of Human isoQC Expression using RT-PCR

Total RNA was isolated from SH-SY5Y, LN405, HaCaT and Hep-G2 cells using the RNeasy Mini Kit (Qiagen) and reversely transcribed by SuperScript II (Invitrogen). Subsequently, human isoQC was amplified on a 1:12.5 dilution of generated cDNA product in a 25 µl reaction with Herculase Enhanced DNA-Polymerase (Stratagene) using primers iso-QCh-1 (sense, SEQ ID NO: 53) and isoQCh-2 (antisense, SEQ ID NO: 54). The PCR product of Hep-G2 was purified utilizing the Strataprep PCR Purification Kit (Stratagene) and confirmed by sequencing.

Results

Analysis of human isoQC Expression using RT-PCR

Transcripts of human isoQC were found to be present in cell lines SH-SY5Y (FIG. 6, lane 1), LN405 (FIG. 6, lane 2), HaCaT (FIG. 6, lane 3) and Hep-G2 (FIG. 6, lane 4). The PCR product of Hep-G2 was confirmed by sequencing.

Isolation of Human isoQC

Full-length cDNA of human isoQC was isolated from Hep-G2 cells using RT-PCR. Briefly, total RNA of Hep-G2 cells was reversely transcribed by SuperScript II (Invitrogen). Subsequently, human isoQC was amplified on a 1:12.5 dilution of generated cDNA product in a 25 µl reaction with Herculase Enhanced DNA-Polymerase (Stratagene) using primers iso-QChu-1 (sense, SEQ ID NO: 55) and isoQChu-2 (antisense, SEQ ID NO: 56). The resulting PCR-product was subcloned into vector pPCRScript CAM SK (+) (Stratagene) and confirmed by sequencing.

EXAMPLE 2

Preparation and Expression of Human isoQC in Mammalian Cell Culture

Molecular Cloning of Plasmid Vectors Encoding a Human isoQC-EGFP Fusion Protein

All cloning procedures were done applying standard molecular biology techniques. For expression of human isoQC-EGFP fusion protein in human cells, the vector pEGFP-N3 (Invitrogen) was used. The cDNA of the native human isoQC starting either at methionine I or at methionine II was fused N-terminally in frame with the plasmid encoded enhanced green fluorescent protein (EGFP). The primers isoQC EGFP-1 Met I (SEQ ID NO: 57) and isoQC EGFP-3 (SEQ ID NO: 59) were used for amplification of human isoQC starting with methionine I and primers isoQC EGFP-2 Met II (SEQ ID NO: 58) and isoQC EGFP-3 (SEQ ID NO: 59) were used for amplification of human isoQC starting with methionine 11. The fragments were inserted into vector pEGFP-N3 (Invitrogen) employing the restriction sites of EcoRI and SalI and the correct insertion was confirmed by sequencing. Subsequently, the vectors were isolated for cell culture purposes using the EndoFree Maxi Kit (Qiagen).

Cloning Procedure of the N-Terminal Sequences of hisoQC

In addition, the EGFP sequence of vector pEGFP-N3 (Invitrogen) was introduced into vector pcDNA 3.1 (Invitrogen) using EGFP-1 (sense) (SEQ ID NO: 85) and EGFP-2 (antisense) (SEQ ID NO: 86) for amplification. The fragment was introduced into XhoI site of pcDNA 3.1. The N-terminal sequences of hisoQC beginning with methionine I and II each ending at serine 53 were fused C-terminally with EGFP in vector pcDNA 3.1 using isoQC EGFP-1 Met I (sense, SEQ ID NO: 57) and hisoQC SS EGFP pcDNA as (antisense) (SEQ ID NO: 87) for the N-terminal fragment of hisoQC beginning with methionine I and isoQC EGFP-2 Met II (sense, SEQ ID NO: 58) and hisoQC SS EGFP pcDNA as (antisense) (SEQ ID NO: 87) for the N-terminal fragment of hisoQC beginning with methionine II. Fragments were inserted into EcoRI and NotI restriction sites of vector pcDNA 3.1. Subsequently, the vectors were isolated for cell culture purposes using the EndoFree Maxi Kit (Qiagen).

Cloning Procedure for Native Expression of hisoQC and hQC

Native hQC was inserted into HindIII and NotI restriction sites and native hisoQC was inserted into EcoRI and NotI restriction sites of vector pcDNA 3.1 (+) (Invitrogen) after amplification utilizing primers hQC-1 (sense) (SEQ ID NO: 82) and hQC-2 (antisense) (SEQ ID NO: 83) for hQC, isoQC EGFP-1 Met I (sense) (SEQ ID NO: 57) and hisoQC pcDNA as (antisense) (SEQ ID NO: 84) for hisoQC starting with methionine I and isoQC EGFP-2 Met II (sense) (SEQ ID NO: 58) and hisoQC pcDNA as (antisense) (SEQ ID NO: 84) for hisoQC starting with methionine II.

Cloning Procedure for FLAG-Tagged hisoQC and hQC

Human QC was cloned with a C-terminal FLAG-tag after amplification applying primers hQC-1 (sense) (SEQ ID NO: 82) and hQC C-FLAG pcDNA as (antisense) (SEQ ID NO: 88) into HindIII and NotI restriction sits of vector pcDNA 3.1. Human isoQC was inserted with a C-terminal FLAG-tag into pcDNA 3.1 after amplification using primers isoQC EGFP-1 Met I (sense) (SEQ ID NO: 57) and hisoQC C-FLAG pcDNA as (antisense) (SEQ ID NO: 89) for hisoQC starting with methionine I and primers isoQC EGFP-2 Met II (sense) (SEQ ID NO: 58) and hisoQC C-FLAG pcDNA as (antisense) (SEQ ID NO: 89) for hisoQC starting with methionine 2.

EXAMPLE 3

Immunhistochemical Staining of Human isoQC in Mammalian Cells

Transfection and histochemical staining of COS-7 and LN405 For expression of human isoQC-EGFP fusion proteins starting either with methionine I or methionine II, COS-7 and LN405 were cultured in 6-well dishes containing a cover slip. Cells were grown until 80% confluency, transfected using Lipofectamin2000 (Invitrogen) according to manufacturer's manual and incubated in the transfection solution for 5 hours. Afterwards, the solution was replaced by appropriate growth media and cells were grown over night.

The next day, cells were washed twice with D-PBS (Invitrogen) and fixed using ice-cold methanol for 10 min at −20° C., followed by 3 washing steps using D-PBS for 10 min at room temperature. For staining of the golgi-zone, COS-7 and LN405 were incubated with rabbit anti-mannosidase II polyclonal antibody (Chemicon) in a 1:50 dilution of antibody in D-PBS for 3 h. For staining of mitochondria in COS-7 and LN405, cells were incubated with mouse anti-human mitochondria monoclonal antibody (Chemicon) in a 1:100 dilution of antibody in D-PBS for 3 h at room temperature. Subsequently, the cells were washed 3 times with D-PBS for 10 min. Cells stained for golgi-zone were incubated with goat anti-rabbit IgG secondary antibody conjugated with Rhodamin-RedX (Dianova) for 45 min at room temperature in the dark. Cells stained for mitochondria were incubated with goat anti-mouse IgG secondary antibody conjugated with Rhodamin-RedX (Dianova) for 45 min at room temperature in the dark. Afterwards, cells were washed 3 times with D-PBS for 5 min at room temperature and at least, the cover slips were mounted on a microscope slide with citiflour. Cells were observed under a fluorescence microscope (Carl-Zeiss).

Results

1. Transfection and Histochemical Staining of LN405

Figure 7:
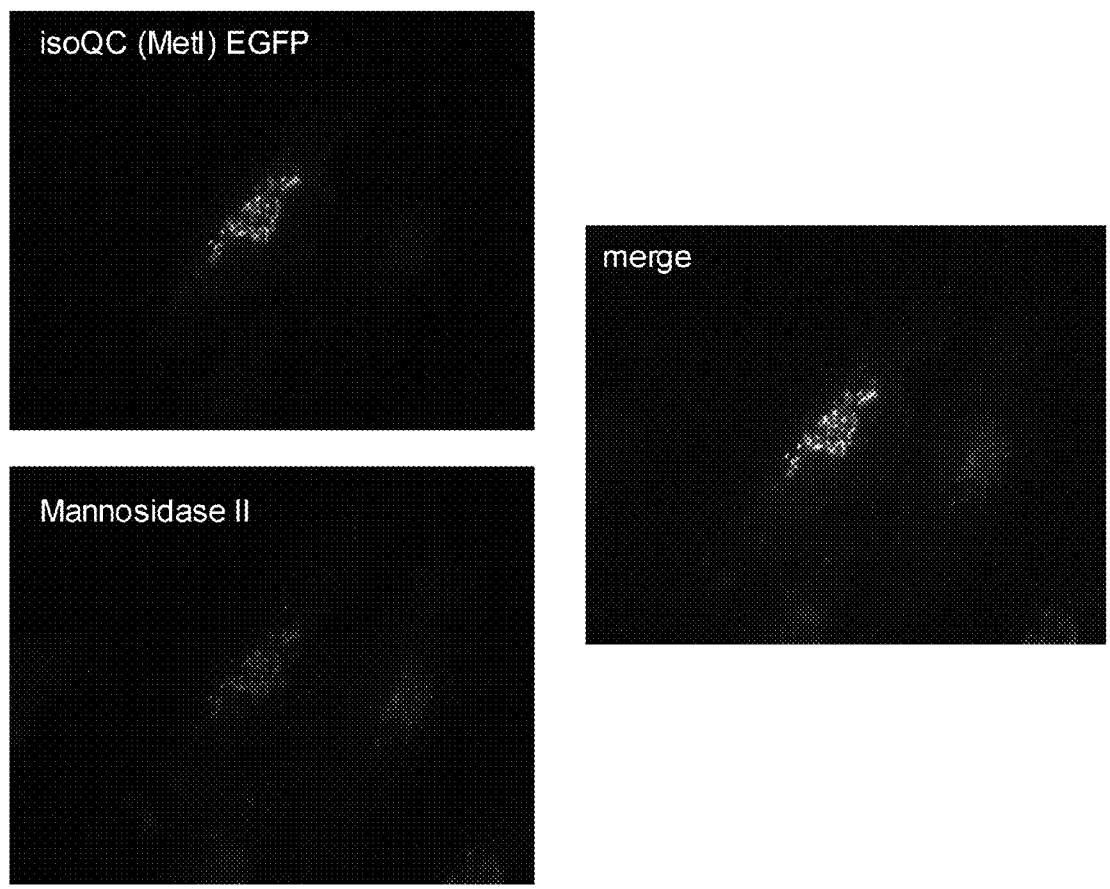
FIG. 7 shows the analysis of isoQC (Met I, SEQ ID NO: 11) subcellular localization by immunhistochemistry. Human isoQC starting at methionine I (see FIG. 5) was expressed as a fusion protein with EGFP (isoQC (MetI) EGFP) in LN 405. Mannosidase II counterstaining was performed using AB3712 (Chemicon). Merge represents the overlay of isoQC (MetI)-EGFP and Mannosidase II staining.
Figure 9:
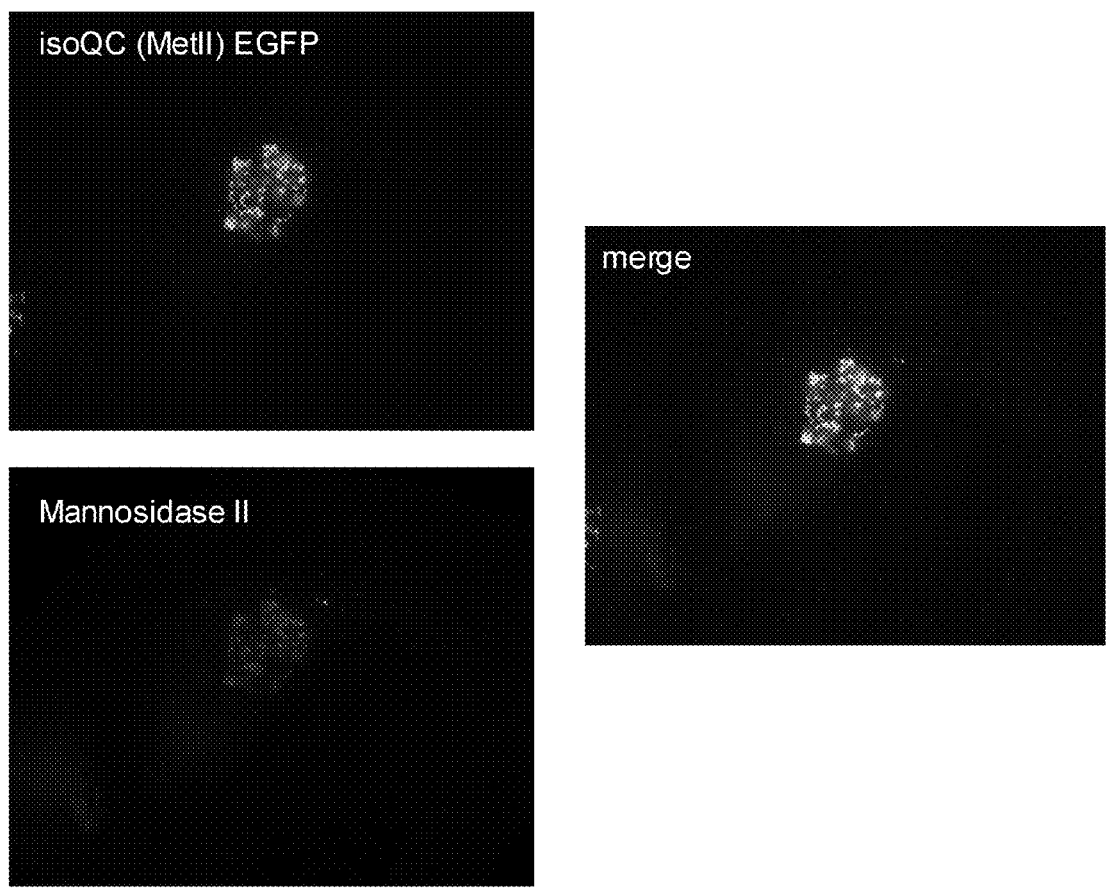
FIG. 9 shows the analysis of isoQC (Met II, SEQ ID NO: 12) subcellular localization by immunhistochemistry. Human isoQC starting at methionine II was expressed as a fusion protein with EGFP (isoQC (MetII) EGFP) in LN 405. Mannosidase II counterstaining was performed using AB3712 (Chemicon). Merge represents the overlay of isoQC (MetII)-EGFP and Mannosidase II staining.

The expression of human isoQC-EGFP fusion protein starting with methionine I and methionine II in cell line LN405 (green fluorescence) leads to a compartmentalization of the resulting protein. Counterstaining of the golgi-zone of LN405 using mannosidase 11 antibody (red fluorescence) and subsequent superimposition of human isoQC-EGFP with mannosidase 11 suggests a localization of human isoQC-EGFP fusion protein within the golgi-compartment (yellow coloration of the merged images) (FIGS. 7,9). Thereby, it is evident that human isoQC starting at methionine II is sufficient to generate a golgi-localization of the human isoQC fusion protein.

Figure 8:
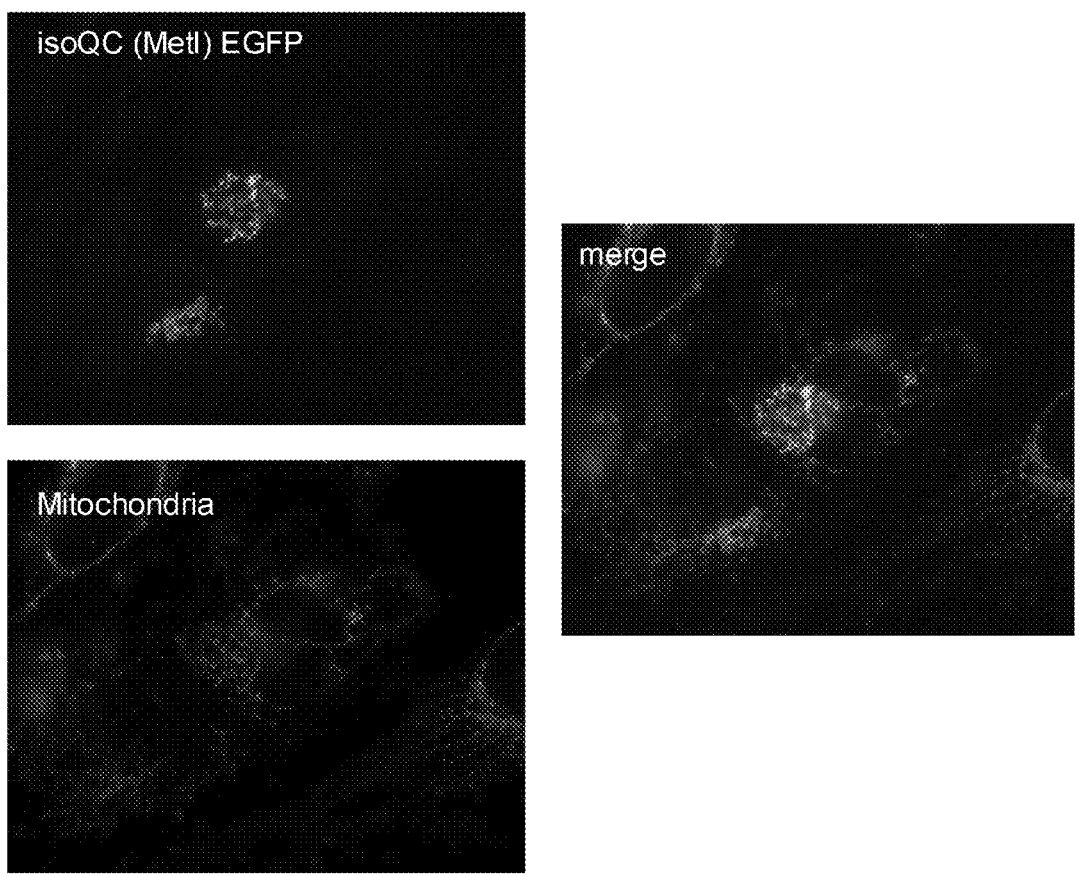
FIG. 8 shows the analysis of isoQC (Met I, SEQ ID NO: 11) subcellular localization by immunhistochemistry. Human isoQC starting at methionine I was expressed as a fusion protein with EGFP (isoQC (MetI) EGFP) in LN 405. Mitochondrial counterstaining was performed using MAB1273 (Chemicon). Merge represents the overlay of isoQC (MetI)-EGFP and mitochondrial staining.

The expression of human isoQC-EGFP fusion protein starting with methionine I and II (green fluorescence) and counterstaining for mitochondria (red fluorescence) did not reveal a localization of human isoQC-EGFP fusion protein starting with methionine I or II within the mitochondria due to the absence of a yellow coloration of the merged images after superimposition (FIGS. 8, 10).

2. Transfection and Histochemical Staining of COS-7

Figure 11:
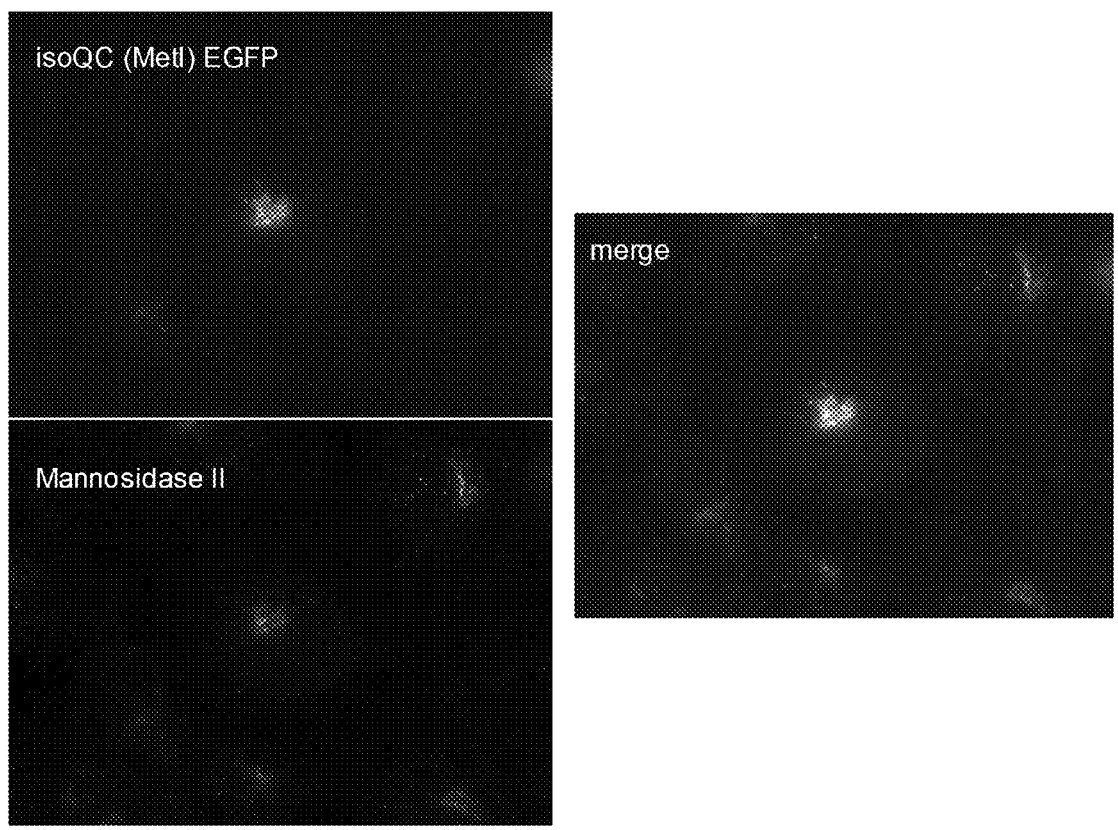
FIG. 11 shows the analysis of the subcellular localization of isoQC (Met I, SEQ ID NO: 11) by immunhistochemistry. Human isoQC starting at methionine I was expressed as a fusion protein with EGFP (isoQC (MetI) EGFP) in COS-7. Mannosidase II counterstaining was performed using AB3712 (Chemicon). Merge represents the overlay of isoQC (MetI)-EGFP and Mannosidase II staining.
Figure 13:
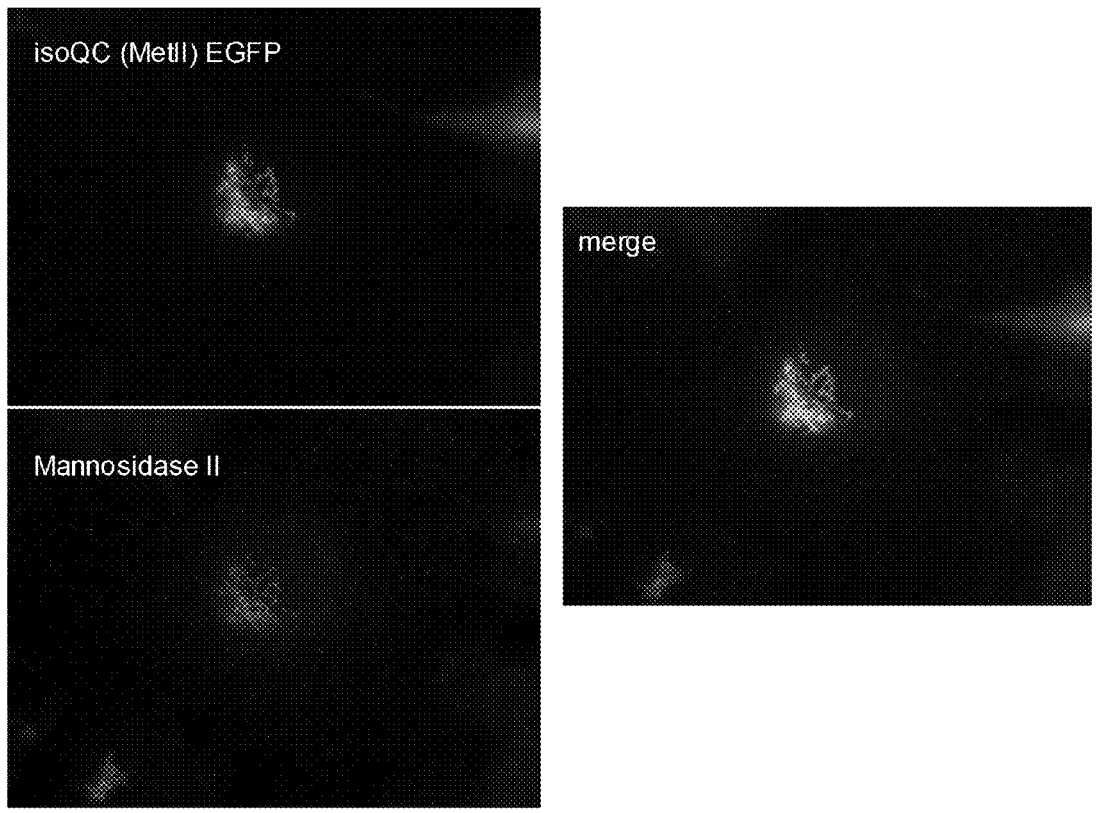
FIG. 13 shows the analysis of isoQC (Met II, SEQ ID NO: 12) subcellular localization by immunhistochemistry. Human isoQC starting at methionine II was expressed as a fusion protein with EGFP (isoQC (MetII) EGFP) in COS-7. Mannosidase II counterstaining was performed using AB3712 (Chemicon). Merge represents the overlay of isoQC (MetII)-EGFP and Mannosidase II staining.

In analogy to the expression of human isoQC-EGFP fusion protein starting with methionine I and methionine II in cell line LN405, leads the expression of human isoQC-EGFP fusion protein starting with methionine I and methionine II in COS-7 to a compartmentalization of the resulting protein (green fluorescence). Counterstaining of the golgi-zone of COS-7 cells using mannosidase II antibody (red fluorescence) and subsequent superimposition of human isoQC-EGFP with mannosidase II suggests a localization of human isoQC-EGFP fusion protein within the golgi-compartment of COS-7 (yellow coloration of the merged images) (FIGS. 11,13). Again, in COS-7 cells the expression of human isoQC-EGFP fusion protein starting at methionine II is sufficient to cause a golgi-localization.

Figure 12:
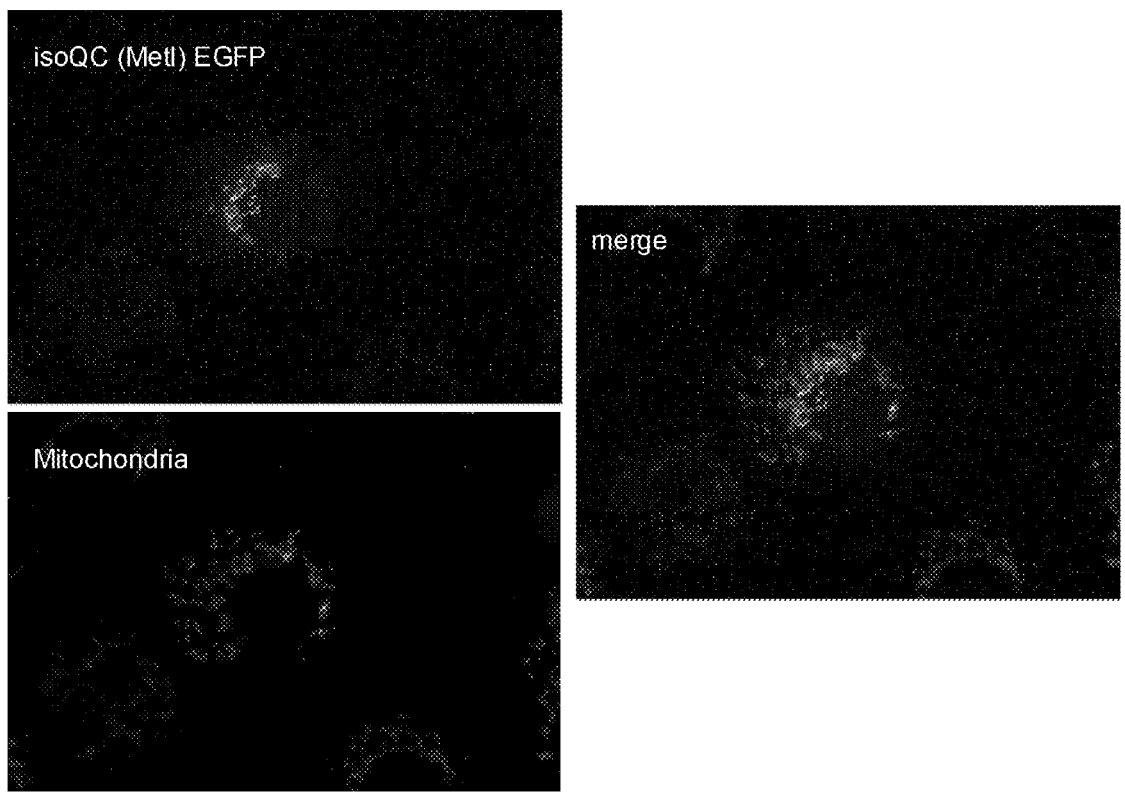
FIG. 12 shows the analysis of isoQC (Met I, SEQ ID NO: 11) subcellular localization by immunhistochemistry. Human isoQC starting at methionine I was expressed as a fusion protein with EGFP (isoQC (MetI) EGFP) in COS-7. Mitochondrial counterstaining was performed using MAB1273 (Chemicon). Merge represents the overlay of isoQC (MetI)-EGFP and mitochondrial staining.
Figure 14:
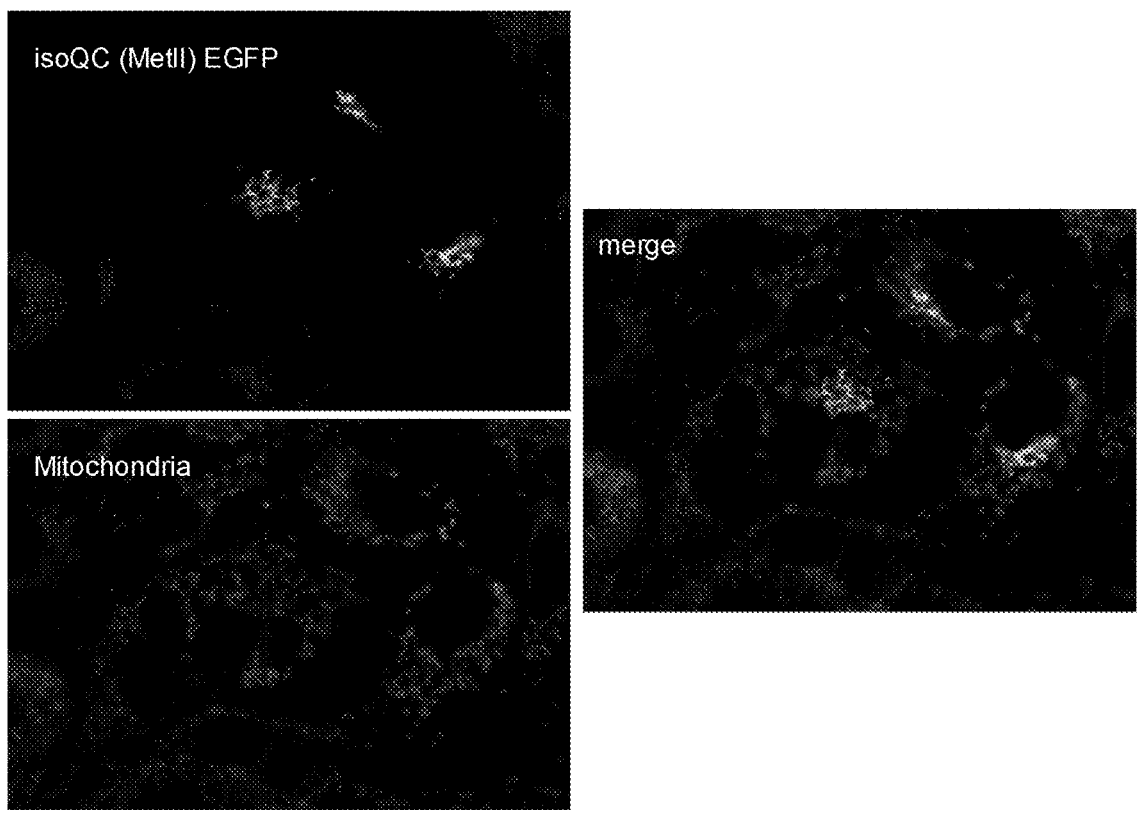
FIG. 14 shows the analysis of isoQC (Met II, SEQ ID NO: 12) subcellular localization by immunhistochemistry. Expression of human isoQC starting at methionine II as a fusion protein with EGFP (isoQC (MetII) EGFP) in COS-7. Mitochondrial counterstaining was performed using MAB1273 (Chemicon). Merge represents the overlay of isoQC (MetII)-EGFP and mitochondrial staining.

As expected, the expression of human isoQC-EGFP fusion protein starting with methionine I and II in COS-7 (green fluorescence) and counterstaining for mitochondria (red fluorescence) did not result in a localization of human isoQC-EGFP fusion protein starting with methionine I or II within the mitochondria due to the absence of a yellow coloration of the merged images after superimposition (FIGS. 12, 14).

EXAMPLE 4

Expression and Purification of Human isoQC in *E. Coli*

Host Strains and Media

*Escherichia coli* strain DH5α was used for propagation of plasmids and *E. coli* strain BL21 was used for the expression of human isoQC. *E. coli* strains were grown, transformed and analyzed according to the manufacturer's instructions (Qiagen(DH5α) Stratagene (BL21)). The media required for *E. coli*, i.e. Luria-Bertani (LB) medium, was prepared according to the manufacturer's recommendations.

Molecular Cloning of Plasmid Vectors Encoding the Human QC

All cloning procedures were done applying standard molecular biology techniques. For expression in *E. coli* BL21, the vector pET41a (Novagen) was used. The cDNA of the mature human isoQC starting with codon 30 (counting from methionine 11) was fused in frame with the plasmid encoded GST-tag. After amplification utilizing the primers hisoQC pET41a-1 (SEQ ID NO: 60) and hisoQC pET41a-2 (SEQ ID NO: 61) (Table 4) a N-terminal protease cleavage site for Enterokinase and a C-terminal (His)$_6$-tag was introduced. After subcloning, the fragment was inserted into the expression vector employing the restriction sites of Spe I and EcoR I.

Expression and Purification in *E. coli* BL21

The construct encoding the human isoQC was transformed into BL21 cells (Stratagene) and grown on selective LB agar plates at 37° C. Protein expression was carried out in LB medium containing 1% glucose at 37° C. After reaching an OD$_{600}$ of approximately 0.8, isoQC expression was induced with 20 µM IPTG for 4 h at 37° C. Cells were separated from the medium by centrigugation (4000×g, 20 min), resuspended in PBS (140 mM NaCl, 2.7 mM KCl, 10 mM Na$_2$HPO$_4$, 1.8 mM KH$_2$PO$_4$, pH 7.3) and lysed by one cycle of freezing and thawing followed by one cycle of French Press. The cell lysate was diluted to a final volume of 1.5 l using phosphate-containing buffer (50 mM Na$_2$HPO$_4$, 500 mM NaCl. pH 7.3) and centrifuged at 13.400×g at 4° C. for 1 h. After centrifugation, the protein concentration of the resulting supernatant was determined using the method of Bradford. If necessary, the solution was diluted again to obtain a final total protein concentration of 0.6 mg/ml. The GST-isoQC fusion protein was purified utilizing a 4-step protocol (Table 5). The purification is illustrated by SDS-PAGE analysis in FIG. 20.

EXAMPLE 5

Assays for Glutaminyl Cyclase Activity

Fluorometric Assays

All measurements were performed with a NovoStar reader for microplates (BMG Labtechnologies) at 30° C. QC activity was evaluated fluorometrically using H-Gln-βNA. The samples consisted of 0.2 mM fluorogenic substrate, 0.25 U pyroglutamyl aminopeptidase (Qiagen, Hilden, Germany) in 0.05 M Tris/HCl, pH 8.0 and an appropriately diluted aliquot of QC in a final volume of 250 µl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 µmol pGlu-βNA from H-Gln-βNA per minute under the described conditions.

In a second fluorometric assay, QC was activity was determined using H-Gln-AMC as substrate. Reactions were carried out at 30° C. utilizing the NOVOStar reader for microplates (BMG Labtechnologies). The samples consisted of varying concentrations of the fluorogenic substrate, 0.1 U pyroglutamyl aminopeptidase (Qiagen) in 0.05 M Tris/HCl, pH 8.0 and an appropriately diluted aliquot of QC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit software.

Spectrophotometric Assay of isoQC

This assay was used to determine the kinetic parameters for most of the QC substrates. QC activity was analyzed spectrophotometrically using a continuous method (Schilling, S. et al., 2003 Biol Chem 384, 1583-1592) utilizing glutamic dehydrogenase as auxiliary enzyme. Samples consisted of the respective QC substrate, 0.3 mM NADH, 14 mM α-Ketoglutaric acid and 30 U/ml glutamic dehydrogenase in a final volume of 250 µl. Reactions were started by addition of QC and pursued by monitoring of the decrease in absorbance at 340 nm for 8-15 min. The initial velocities were evaluated and the enzymatic activity was determined from a standard curve of ammonia under assay conditions. All samples were measured at 30° C., using the Sunrise reader for microplates. Kinetic data were evaluated using GraFit software.

Inhibitor Assay

For inhibitor testing, the sample composition was the same as described above, except of the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Results

A variety of different substrates was evaluated on conversion by human isoQC (Table 3). All analyzed substrates were converted by isoQC, indicating a relatively relaxed overall specificity similar to human QC (Schilling, S. et al., 2003 Biol Chem 384, 1583-1592). As observed previously for human QC (Schilling, S. et al., 2003 Biol Chem 384, 1583-1592), highest specificity constants ($k_{cat}/K_M$) were observed for substrates carrying large hydrophobic amino acids adjacent to the N-terminal glutaminyl residue, e.g. Gln-AMC. In contrast, negatively charged residues in that very position led to a drastic drop in specificity, as observed for Gln-Glu, indicating a negatively charged active site of isoQC. Compared to human QC, both recombinant iosQCs exerted a lower enzymatic activity (FIG. 21). The difference was up to one order of magnitude. According to the specificity of isoQC, it reasonable to assume that the enzyme is responsible for conversion of different substrates in vivo, i.e. isoQC is involved in the generation of many different physiological substrates.

Figure 15:
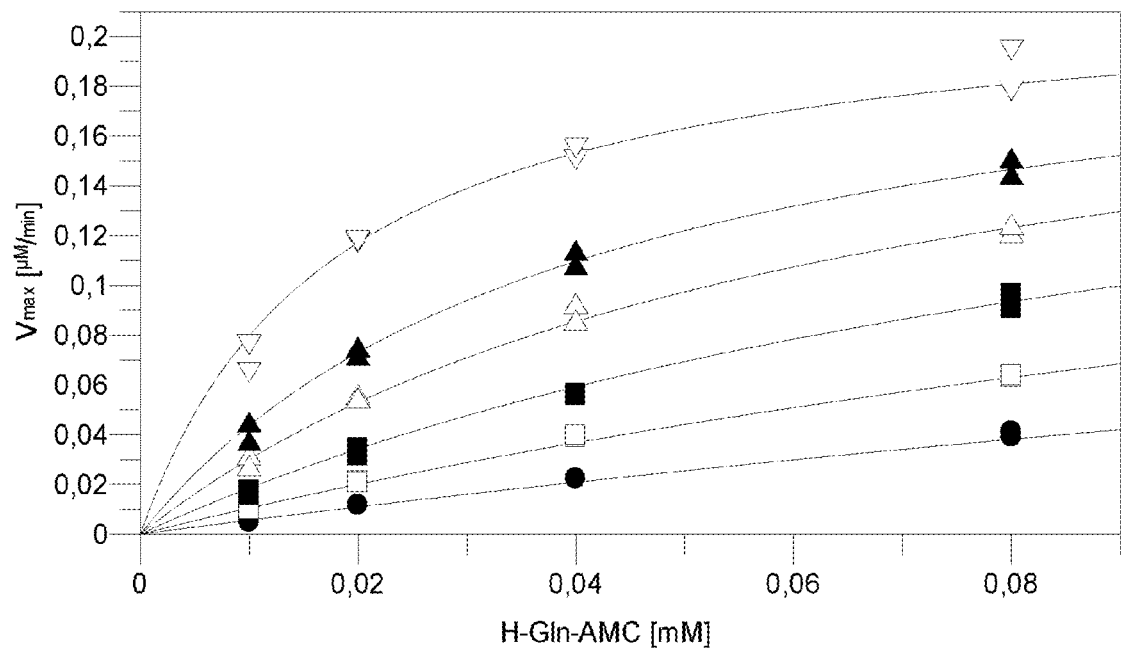
FIG. 15 shows the inhibition of human isoQC-catalyzed conversion of H-Gln-AMC into pGlu-AMC by the inhibitor P150/03. The data were evaluated according to the Michaelis-Menten kinetic model considering linear competitive inhibition. Inhibitor concentrations were as follows.

Human isoQC activity was competitively inhibited by imidazole derivatives (table 6, FIG. 15). The inhibition constants $K_i$ for imidazole and benzimidazole was very similar to the value which was obtained for human QC previously. A 10-fold drop in $K_i$, however, was observed for the potent QC inhibitor P150/03. Thus, the binding mode of the chelating part, i.e. the imidazole ring, appears to be very similar. Presumably, this results from complexation of the active site zinc ion of QC and isoQC by the imidazole basic nitrogen. The differences in the $K_i$-values for P150/03 clearly demonstrates that the active sites of both enzymes display subtle differences. Therefore, it is possible to generate inhibitors that exert selectivity for one enzymic isoform. Selective inhibitors are beneficial for the treatment of the diseases.

TABLE 3

Kinetic evaluation of peptide substrates of human QC and human isoQC.
Human isoQC was expressed in *E. coli* BL21 (hisoQCdt) or *P. pastoris* (YSShisoQC).
The substrates are displayed in the one-letter code of amino acids.

| Substrate | $K_M$ (mM) hisoQCdt | $K_M$ (mM) YSShisoQC | $k_{cat}$ (s$^{-1}$) hisoQCdt | $k_{cat}$ (s$^{-1}$) YSShisoQC | $k_{cat}/K_M$ (mM$^{-1}$ * s$^{-1}$) hisoQCdt | $k_{cat}/K_M$ (mM$^{-1}$ * s$^{-1}$) YSShisoQC |
|---|---|---|---|---|---|---|
| Q-βNA | 0.03 ± 0.002 | 0.035 ± 0.0005 | 3.37 ± 0.12 | 8.16 ± 0.87 | 93.26 ± 6.68 | 228.70 ± 22.22 |
| QAMC | 0.01 ± 0.0009 | 0.03 ± 0.0064 | 1.07 ± 0.03 | 3.72 ± 0.44 | 62.57 ± 5.68 | 102.87 ± 29.22 |
| QQ | 0.11 ± 0.027 | 0.11 ± 0.007 | 2.72 ± 0.25 | 6.08 ± 0.17 | 24.50 ± 4.009 | 54.32 ± 4.61 |
| QE | 0.7 ± 0.13 | 0.61 ± 0.064 | 2.64 ± 0.21 | 5.33 ± 0.43 | 3.85 ± 0.56 | 8.75 ± 0.87 |
| QG | 0.42 ± 0.04 | 0.36 ± 0.047 | 1.65 ± 0.04 | 3.24 ± 0.18 | 3.93 ± 0.31 | 9.01 ± 1.75 |
| QGP | 0.21 ± 0.016 | 0.23 ± 0.02 | 4.01 ± 0.14 | 8.98 ± 0.07 | 18.82 ± 1.26 | 38.42 ± 3.55 |
| QYA | 0.22 ± 0.01 | 0.08 ± 0.022 | 7.7 ± 0.4 | 16.47 ± 0.72 | 66.48 ± 13.07 | 206.9 ± 57.54 |
| QFA | 0.11 ± 0.016 | 0.104 ± 0.025 | 7.49 ± 0.28 | 11.68 ± 2.39 | 33.03 ± 2.38 | 116.99 ± 34.37 |
| QEYF | 0.03 ± 0.004 | 0.04 ± 0.004 | 3.34 ± 0.15 | 5.64 ± 0.39 | 109.57 ± 21.03 | 122.56 ± 5.6 |
| QEDL | 0.63 ± 0.052 | 0.16 ± 0.01 | 6.41 ± 0.15 | 9.24 ± 0.65 | 10.2 ± 0.84 | 55.04 ± 5.14 |

TABLE 4

Utilized primers

| Primer | Sequence 5' → 3' | Application |
|---|---|---|
| IsoQCh-1 (SEQ ID NO: 53) | GGTCTACACCATTTGGAGCGGCTGGC | Cell Line Screening |
| IsoQCh-2 (SEQ ID NO: 54) | GGGTTGGAAGTACATCACTTCCTGGGG | Cell Line Screening |
| IsoQChu-1 (SEQ ID NO: 55) | ACCATGCGTTCCGGGGGCCGCGGG | Isolation of hisoQC |
| IsoQChu-2 (SEQ ID NO: 56) | ACGCTAGAGCCCCAGGTATTCAGCCAG | Isolation of hisoQC |
| IsoQC EGFP-1 Met I (SEQ ID NO: 57) | ATATATGAATTCATGCGTTCCGGGGGCCGC | Cloning human isoQC (Met I) into vector pEGFN-N3 |
| IsoQC EGFP-2 Met II (SEQ ID NO: 58) | ATATATGAATTCATGGAGCCACTCTTGCCGCCG | Cloning human isoQC (Met II) into vector pEGFP-N3 |
| IsoQC EGFP-3 (SEQ ID NO: 59) | ATATATGTCGACGAGCCCCAGGTATTCAGCCAG | Cloning human isoQC (Met I and Met II) into vector pEGFP-N3 |
| HisoQC pET41a-1 (SEQ ID NO: 60) | ATATACTAGTGATGACGAC GACAAGTTCTACACCATTTGGAGCG | Cloning human isoQC into vector pET41a |
| HisoQC pET41a-2 (SEQ ID NO: 61) | TATAGAATTCCTAGTGATGGT GATGGTGATGGAGCCCCAGGTATTCAGC | Cloning human isoQC into vector pET41a |
| hisoQC HIS C-Term pPICZAA-1 (SEQ ID NO: 62) | ATA TGA ATT CTT CTA CAC CAT TTG GAG C | Cloning human isoQC into vector PPICZαA |

TABLE 4-continued

Utilized primers

| Primer | Sequence 5' → 3' | Application |
|---|---|---|
| hisoQC HIS N-Term pPICZAA-1 (SEQ ID NO: 63) | ATA TGA ATT CCA TCA CCA TCA CCA TCA CTT CTA CAC CAT TTG GAG CGG C | Cloning human isoQC into vecotr PPICZαA |
| hisoQC HIS N-TERM pPICZAA-2 (SEQ ID NO: 64) | 5'-ATA TAT GCG GCC GCC TAG AGC CCC AGG TAT TCA GC-3' | Cloning human isoQC into vector PPICZαA |
| isoQCm RT s (SEQ ID NO: 65) | CCA GGA TCC AGG CTA TTG AG | Real-time PCR analysis of isoQC |
| hisoQC HIS C-TERM pPICZAA-2 (SEQ ID NO: 66) | ATA TAT GCG GCC GCC TAG TGA TGG TGA TGG TGA TGG AGC CCC AGG TAT TCA GCC AG | Cloning human isoQC into vector PPICZαA |
| isoQCm RT as (SEQ ID NO: 67) | TTC CAC AGG GCC GGG GGG C | Real-time PCR analysis of isoQC |
| isoQCm MetI s (SEQ ID NO: 68) | ATG AGT CCC GGG AGC CGC | Cloning of murine isoQC cDNA |
| isoQCm MetI as (SEQ ID NO: 69) | CTA GAG TCC CAG GTA CTC | Cloning of murine isoQC cDNA |
| isoQCm kurz s (SEQ ID NO: 70) | AGT TCC TGC CCC TGC TGC TG | Cloning of murine isoQC cDNA |
| mQC RT s (SEQ ID NO: 71) | ATC AAG AGG CAC CAA CCA AC | Real-time PCR analysis of mQC |
| mQC RT as (SEQ ID NO: 72) | CTG GAT AAT ATT TCC ATA G | Real-time PCR analysis of mQC |
| mQC RT N-terminal s (SEQ ID NO: 73) | ACA GCT GGG AAT CTG AGT C | Real-time PCR analysis of mQC |
| mQC RT N-terminal as (SEQ ID NO: 74) | GAG CAG AAT AGC TTC CGG GCG | Real-time PCR analysis of mQC |
| Iso-I55Ns (SEQ ID NO: 75) | CTG CGG GTC CCA TTG AAC GGA AGC CTC CCC GAA | Site-directed mutagenesis hisoQC I55N |
| Iso-I55Nas (SEQ ID NO: 76) | TTC GGG GAG GCT TCC GTT CAA TGG GAC CCG CAG | Site-directed mutagenesis hisoQC I55N |
| Iso-C351As (SEQ ID NO: 77) | ACG GTA CAC AAC TTG GCC CGC ATT CTC GCT GTG | Site-directed mutagenesis hisoQC C351A |
| Iso-C351Aas (SEQ ID NO: 78) | CAC AGC GAG AAT GCG GGC CAA GTT GTG TAC CGT | Site-directed mutagenesis hisoQC C351A |
| hQC-1 (SEQ ID NO: 82) | ATATATAAGCTTATGGCAGGCGGAAGACAC | Insertion of native hQC into pcDNA 3.1 |
| hQC-2 (SEQ ID NO: 83) | ATATGCGGCCGCTTACAAATGAAGATATTCC | Insertion of navtive hQC into pcDNA 3.1 |
| hisoQC pcDNA as (SEQ ID NO: 84) | ATATATGCGGCCGCCTAGAGCCCCAGGTATTCAGC | Amplification hisoQC including the stop codon for |

TABLE 4-continued

Utilized primers

| Primer | Sequence 5' → 3' | Application |
|---|---|---|
| | | insertion into pcDNA 3.1 |
| EGFP-1 (SEQ ID NO: 85) | ATATCTCGAGTCCATCGCCACCATGGTGAGC | Amplification EGFP |
| EGFP-2 (SEQ ID NO: 86) | ATATCTCGAGTTACTTGTACAGCTCGTCCAT | Amplification EGFP |
| hisoQC SS EGFP pcDNA as (SEQ ID NO: 87) | ATATGCGGCCGCATGTCGACGCTCCAAATGGTGTAGAACGC | Amplification hisoQC N-terminal sequence |
| hQC C-FLAG pcDNA as (SEQ ID NO: 88) | ATATGCGGCCGCTTACTTGTCATCGTCATCCTTGTAATC CAAATGAAGATATTCCAA | Amplification |
| hisoQC C-FLAG pcDNA as (SEQ ID NO: 89) | ATATGCGGCCGCCTACTTGTCATCGTCATCCTTGTA ATCGAGCCCCAGGTATTCAGC | Amplification h-isoQC C-Flag |
| Hs_QPCT_1_SG | QuantiTect Primer Assay (200), Qiagen, Hilden | qPCR hQC |
| Hs_QPCTL_1_SG | QuantiTect Primer Assay (200), Qiagen, Hilden | qPCR h-isoQC |
| CCL2-F (SEQ ID NO: 90) | GCCTCCAGCATGAAAGTCTC | qPCR CCL2 |
| CCL2-R (SEQ ID NO: 91) | CAGATCTCCTTGGCCACAAT | |
| CCL7-F (SEQ ID NO: 92) | ATGAAAGCCTCTGCAGCACT | qPCR CCL7 |
| CCL7-R (SEQ ID NO: 93) | TGGCTACTGGTGGTCCTTCT | |
| CCL8-F (SEQ ID NO: 94) | TCACCTGCTGCTTTAACGTG | qPCR CCL8 |
| CCL8-R (SEQ ID NO: 95) | ATCCCTGACCCATCTCTCCT | |
| CCL13-F (SEQ ID NO: 96) | ATCTCCTTGCAGAGGCTGAA | qPCR CCL13 |
| CCL13-R (SEQ ID NO: 97) | AGAAGAGGAGGCCAGAGGAG | |
| HIF1α-F (SEQ ID NO: 98) | CACAGAAATGGCCTTGTGAA | qPCR HIF1α |
| HIF1α-R (SEQ ID NO: 99) | CCAAGCAGGTCATAGGTGGT | |
| AIM1-F (SEQ ID NO: 100) | TCCTTTCATCCTGGAACCTG | qPCR AIM1 |
| AIM1-R (SEQ ID NO: 101) | CGCCTCTTCTGTTTCACCTC | |
| AIM2-F (SEQ ID NO: 102) | AAGCGCTGTTTGCCAGTTAT | qPCR AIM2 |
| AIM2-R (SEQ ID NO: 103) | CACACGTGAGGCGCTATTTA | |
| MAGEA1-F (SEQ ID NO: 104) | GTCAACAGATCCTCCCCAGA | qPCR MAGEA1 |
| MAGEA1-R (SEQ ID NO: 105) | CAGCATTTCTGCCTTTGTGA | |
| MAGEA2-F (SEQ ID NO: 106) | AGGTGGAGAGCCTGAGGAAT | qPCR MAGEA2 |
| MAGEA2-R (SEQ ID NP: 107) | CTCGGGTCCTACTTGTCAGC | |
| MAGEA10-F (SEQ ID NO: 108) | AAGCGAGGTTCTCGTTCTGA | qPCR MAGEA10 |
| MAGEA10-R (SEQ ID NO: 109) | TGACCTCTTGCTCTCCCTGT | |

TABLE 4-continued

Utilized primers

| Primer | Sequence 5' → 3' | Application |
|---|---|---|
| MAGEB2-F (SEQ ID NO: 110) | CTTCAAGCTCTCCTGCTGCT | qPCR MAGEB2 |
| MAGEB2-R (SEQ ID NO: 111) | CGACCCTGACTTCCTGGTTA | |
| MART1-F (SEQ ID NO: 112) | GCTCATCGGCTGTTGGTATT | qPCR MART1 |
| MART1-R (SEQ ID NO: 113) | ATAAGCAGGTGGAGCATTGG | |
| MCL1-F (SEQ ID NO: 114) | ATGCTTCGGAAACTGGACAT | qPCR MCL1 |
| MCL1-R (SEQ ID NO: 115) | ATGGTTCGATGCAGCTTTCT | |
| TYR-F (SEQ ID NO: 116) | TACGGCGTAATCCTGGAAAC | qPCR TYR |
| TYR-R (SEQ ID NO: 117) | ATTGTGCATGCTGCTTTGAG | |
| TYRP1-F (SEQ ID NO: 118) | CCGAAACACAGTGGAAGGTT | qPCR TYRP1 |
| TYRP1-R (SEQ ID NO: 119) | TCTGTGAAGGTGTGCAGGAG | |
| TYRP2-F (SEQ ID NO: 120) | GGTTCCTTTCTTCCCTCCAG | qPCR TYRP2 |
| TYRP2-R (SEQ ID NO: 121) | AACCAAAGCCACCAGTGTTC | |

TABLE 5

Purification of GST-isoQC fusion protein following Expression in *E. coli*. The purified fusion protein was used for determination of QC activity.

| | Purification Step | | | |
|---|---|---|---|---|
| | 1 | 2 | 3 | 4 |
| Method | Ni$^{2+}$-IMAC (EBA) | GST-TAG AC | GF (Desalting) | IEX (UNO S) |
| Column type (Amersham Biosciences AB, Sweden) | Chelating Sepharose Fast Flow | Glutathion Sepharose 4 Fast Flow | Sephadex G-25 Fine | "continuous bed" matrix BIO-Rad |
| Column size | d = 2.5 cm l = 42 cm CV = 206 cm$^3$ | d = 1.6 cm l = 10 cm CV = 20 cm$^3$ | d = 2.6 cm l = 10 cm CV = 53 cm$^3$ | d = 1.2 cm l = 5.3 cm CV = 6 cm$^3$ |
| Equilibration | | | | |
| Buffer | PBS | PBS | 25 mM Mes | 25 mM Mes |
| pH | 7.3 | 7.3 | 6.0 | 6.0 |
| Volume | 10 CV | 10 CV | 10 CV | 10 CV |
| Intermediate (Wash) | | | | |
| Buffer | PBS 0.5 mM Histidin | PBS | — | 25 mM Mes |
| pH | 7.3 | 7.3 | | 6.0 |
| Volume | 10 CV | 10 CV | | 10 CV |
| Elution | | | | |
| Buffer | PBS 100 mM Histidin | 50 mM Tris 10 mM Glutathion (reduced) | 25 mM Mes | 25 mM Mes Gradient elution NaCl |
| pH | 7.3 | 8.0 | 6.0 | 6.0 |
| Volume | 1.5 CV | (reverse flow) | 1 CV | CV |

TABLE 6

K$_i$-values for competitive inhibition of human QC and human isoQC by imidazole derivatives. Human isoQC was expressed in *E. coli* BL21 (hisoQCdt) or *P. pastoris* (YSShisoQC).

| Inhibitor | Ki (μM) hisoQCdt | Ki (μM) YSShisoQC | Ki (μM) hQC |
|---|---|---|---|
| Imidazole | 220 ± 1 | 235 ± 13 | 103 ± 2 |
| Benzimidazole | 200 ± 8 | 250 ± 5 | 138 ± 4 |
| 1-Benzylimidazole | 7.3 ± 0.5 | 6.2 ± 0.2 | 7.1 ± 0.1 |
| 1-Methylimidazole | 80 ± 5 | 82 ± 3 | 39.7 ± 0.2 |
| PBD150 1-(3,4-Dimethoxy-phenyl)-3-(3-imidazole-1-yl-propyl)-thiourea | 0.48 ± 0.03 | 0.519 ± 0.001 | 0.0584 ± 0.0002 |

EXAMPLE 6

Expression and Purification of Human isoQC in *P. pastoris*

Host Strains and Media

*Escherichia coli* strain DH5α was used for propagation of plasmids and *P. pastoris* strain X-33 was used for the expression of human isoQC in yeast. *E. coli* and *P. pastoris* strains were grown, transformed and analyzed according to the manufacturer's instructions (Qiagen (DH5α), invitrogen (X-33)). The media required for *E. coli*, i.e. Luria-Bertani (LB) medium, was prepared according to the manufacturer's recommendations. The media required for *Pichia pastoris*, i.e. BMMY, BMGY, YPD, YPDS and the concentration of the antibiotics, i.e. Zeocin, were prepared as described in the *Pichia* manual (invitrogen, catalog. No. K1740-01). The manual also includes all relevant descriptions for the handling of yeast.

Molecular Cloning of Plasmid Vectors Encoding the Human Qc

All cloning procedures were done applying standard molecular biology techniques. For expression in *Pichia pastoris* X-33, the pPiCZαA (invitrogen) was used. The cDNA of the mature human isoQC starting with codon 30 (counting from methionine 11) was fused in frame with the plasmid encoded α-factor, directing the protein into the secretory pathway. After amplification utilizing the primers hisoQC HIS C-Term pPICZAA-1 (SEQ ID NO: 62) or hisoQC HIS N-Term pPICZAA-1 (SEQ ID NO: 63) as sense-Primers and hisoQC HIS N-Term pPICZAA-2 (SEQ ID NO: 64) and hisoQC HIS C-Term pPICZAA-2 (SEQ ID NO: 66) (Table 4) as antisense Primers, the fragment was inserted into the expression vector employing the restriction sites of NotI and EcoR I. Depending on the construct, Mutations were introduced in codons 55 (Ile) and 351 (Cys). The mutagenesis was performed according to standard PCR techniques followed by digestion of the parent DNA using DpnI (quik-change 11 site-directed mutagenesis kit, Stratagene, Catalog No. 200524). The generated constructs are illustrated schematically in FIG. 17.

Transformation of *P. pastoris* and Mini-Scale Expression 1-2 μg of plasmid DNA were applied for transformation of competent *P. pastoris* cells by electroporation according to the manufacturer's instructions (BioRad). Selection was done on plates containing 100 μg/ml Zeocin. In order to test the recombinant yeast clones upon is QC expression, recombinants were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h for about 72 h. Subsequently, QC activity in the supernatant was determined. Clones that displayed the highest activity were chosen for further experiments and fermentation. Depending on the expressed construct, the isoQC-activity in the medium differed (FIG. 18).

Expression and Purification of hisoQC in *P. pastoris*

For large scale-Expression of isoQC in *Pichia pastoris*, the condition were kept as described in the mini-scale expression, however, the total volume was 8 L. The expression was performed in shake-flasks. After expression, cells were separated from the medium by centrigugation (1500×g, 20 min), and the pellet discarded. The pH-value of the supernatant was adjusted to neutrality, centrifuged again and applied for the first purification step. The isoQC protein was purified utilizing a 3-step protocol (Table 7). The purfication is illustrated by SDS-PAGE analysis in FIG. 19.

TABLE 7

Purification of hisoQC (YSShisoQCN55IC351A C-His) following Expression in *P. pastoris*. The purified fusion protein was used for determination of Q activity and pH-dependence.

| | Purification Step | | |
|---|---|---|---|
| | 1 | 2 | 3 |
| Method | Ni$^{2+}$-IMAC | HIC | GF (Desalting) |
| Column type (Amersham Biosciences AB, Sweden) | Chelating Sepharose Fast Flow | Butyl Sepharose 4Fast Flow | Sephadex G-25 Fine |
| Column size | d = 2.5 cm<br>l = 42 cm<br>CV = 206 cm$^3$ | d = 1.6 cm<br>l = 15.5 cm<br>CV = 23 cm$^3$ | d = 2.6 cm<br>l = 10 cm<br>CV = 53 cm$^3$ |
| Equilibration | | | |
| Buffer | 50 mM NaH$_2$PO$_4$ | 30 mM NaH$_2$PO$_4$<br>1 M (NH$_4$)$_2$SO$_4$ | 50 mM Bis-Tris<br>100 mM NaCl |
| pH | 7.0 | 7.0 | 6.8 |
| Volume | 10 CV | 10 CV | 10 CV |
| Intermediate (Wash) | | | |
| Buffer | 50 mM NaH$_2$PO$_4$<br>0.5 mM Histidin | 30 mM NaH$_2$PO$_4$<br>1 M (NH$_4$)$_2$SO$_4$ | — |
| pH | 7.0 | 7.0 | |
| Volume | 10 CV | 6 CV | |
| Elution | | | |
| Buffer | 50 mM NaH$_2$PO$_4$<br>100 mM Histidin | 30 mM NaH$_2$PO$_4$ | 50 mM Bis-Tris<br>100 mM NaCl |
| pH | 7.0 | 7.0 | 6.8 |
| Volume | 1.5 CV | 5 CV | 1 CV |

Results

Human isoQC was expressed in the methylotrophic yeast P. pastoris successfully. Several different constructs were generated, in order to select the best expression conditions in yeast (FIG. 17). As illustrated in FIG. 18, the QC activity that is expressed and present in the medium of the expressing cells, varies depending on the expressed construct. Introduction of a glycosylation site resulted in proper secretion, as can be observed from constructs YSShisoQCN55IC35IA C-His and YSShisoQCN55I C-His. Due to the highest activity in the medium, construct YSShisoQCN55IC35IA C-His was expressed in large-scale and purified. The purification was carried out as described in Table 7, the yield of purification was 59%. The apparent homogeneous protein was glycosylated, as evidenced by a shift in migration to lower molecular mass (FIG. 19). Glycosylation did not influence the catalytic activity of the enzyme.

EXAMPLE 7

The pH-Dependence of hisoQC

The fluorometric assay using H-Gln-βNA (described in example 5) was applied to investigate the pH-dependence of the catalytic specificity. The reactions were carried out at substrate concentrations of 7 µM, i.e. at [S]<<$K_M$. Therefore, the observed specificity constants could be directly deduced from the initial velocity of the progress curves of substrate conversion. In these studies the reaction buffer consisted of 0.075 M acetic acid, 0.075 M Mes and 0.15 M Tris, adjusted to the desired pH using HCl or NaOH. The buffer assures a constant ionic strength over a very broad pH-range. Evaluation of the acquired enzyme kinetic data was performed using the following equation:

$$k_{cat}/K_M(pH)=k_{cat}/K_M(\text{limit})*1/(1+[H^+]/K_{HS}+K_{E1}/[H^+]+K_{E1}/[H^+]*K_{E2}/[H^+]),$$

in which $k_{cat}/K_M(pH)$ denotes the pH-dependent (observed) kinetic parameter. $k_{cat}/K_M(\text{limit})$ denotes the pH-independent ("limiting") value. $K_{HS}$, $K_{E1}$ and $K_{E2}$ denote the dissociation constants of an dissociating group in the acidic pH-range, and two dissociating groups of the enzyme, respectively. Evaluation of all kinetic data was performed using GraFit software (version 5.0.4. for windows, ERITHACUS SOFTWARE Ltd., Horley, UK).

Results

The hisoQC displays a pH-optimum of specificity at pH 7-8. Thus, the pH-optimum of catalysis is very similar to human QC. Fitting of the data according to a model which is based on three dissociating groups resulted in a well interpretation of the pH-dependence of hisoQC and hQC (FIG. 22). Thus, the catalysis of both enzymatic reactions is influenced by similar dissociating groups, suggesting a similar catalytic mechanism in general.

The determined pKa-values are displayed in Table 8. It is obvious, that only one pKa differs between hisoQC and hQC significantly. In hQC, the pKa corresponds to the pKa of the dissociation constant of the substrate. Possibly, the subtle difference between hQC and hisoQC is caused by structural changes occurring in isoQC catalysis (induced fit), influencing the pH-dependence.

EXAMPLE 8

Investigation of Glutamyl Cyclase Activity

It has been described for human QC, that the enzyme catalyses the cyclization of N-terminal glutamic acid into pyroglutamic acid. Therefore, QC is involved into the generation of pGlu-modified amyloid peptides.

In order to investigate the cyclization of glutamic acid, human QC and human isoQC were purified and the formation of pGlu-modified amyloid β(3-11) [pGlu-Aβ(3-11)] from Aβ(3-11) was monitored. Reactions consisted of 20 µl substrate (Aβ(3-11), 2.5 mM stock solution in 50 mM Mes buffer, pH 6.5) and 80 µl enzyme (0.62 mg/ml hQC stock solution; 0.61 mg/ml hisoQC stock solution in 50 mM Mes pH 6.5). Samples (15 µl) were removed after 0 h, 6 h, 24 h, 48 h and 72 h and boiled for 5 min in order to terminate the reaction. The analysis of substrate conversion was monitored by Maldi-T of mass spectrometry. Substrate and product differ in their molecular mass by 18 Da, the mass of water, which is released during cyclization.

As shown in FIG. 23, human QC and human isoQC (YSShisoQCI55NC351A C-His) catalyze the conversion of Aβ(3-11) into pGlu-Aβ(3-11). However, based on equal protein concentrations in both samples, one can conclude that the conversion of N-terminal glutamic acid by hisoQC is much slower compared with hQC. Thus, the lower specificity constants for conversion of glutaminyl substrates is also observed with glutamyl substrates. No cyclization was observed under these conditions with inactivated enzyme (Schilling, S. et al., 2004 FEBS Lett. 563, 191-196).

EXAMPLE 9

Tissue Specificity of Murine isoQC

The tissue distribution of murine QC and murine isoQC was investigated using quantitative real time PCR techniques. Prior to analysis of cDNA from several different organs and tissues, the murine isoQC open reading frame was isolated applying specific primers (isoQCm MetI s (SEQ ID NO: 68), isoQCm MetI as (SEQ ID NO: 69) (table 4), which were deduced from the chromosomal coding region of murine isoQC.

The open reading frame was cloned into vector pPCR-Script CAM SK (+) (PCR-Script CAM Cloning Kit, Stratagene) and used as a positive control in the real-time PCR determinations and for preparation of a standard curve under assay conditions. The characterization of the tissue specificity of misoQC expression was achieved applying cDNA from 3-6 month old mice. Total RNA was isolated from 30 mg tissue, using the RNA-isolation kit 11 (Macherey and Nagel). The RNA concentration and purity was assessed by gelelectrophoresis (agarose gel) and spectrophotometry. For synthesis of cDNA, 1 µg of RNA was used. The reaction was done applying the reverse Transcriptase Superscript II RT (Invitrogen) according to the recommendations of the supplier, the cDNA was stored at −80° C.

The quantitative analysis of the transcript concentration in different tissues was analysed using the "Light Cycler" (Corbett research), applying the "QuantiTect SYBR Green PCR" (Qiagen). The DNA standard (cloned cDNA isoQC mouse) was used for quantification. The copy number was calculated according to the following equation: $(X^g/_{\mu l}$ DNA)/(Plasmid length in bp*660)*6.022*1023=$Y^{Molecules}/_{\mu l}$. The DNA standard contained 4 concentrations in the range of $10^7$-$10^1$ $^{Molecules}/_{\mu l}$, and an limiting concentration (100). The reaction protocol is displayed in Table 8. The results are displayed in FIG. 24.

For amplification of murine QC, the same protocol was used, applying the primers mQC RT N-terminal s (SEQ ID NO: 73) and mQC RT N-terminal as (SEQ ID NO: 74).

TABLE 8

Reaction protocol of the quantitative real-time-PCR using the Roto-Gene RG 3000 (Corbett Research)

PCR-Cycles

| step | T in ° C. | t in sec. |
|---|---|---|
| 0 Denaturation | 95 | 900 |
| 1 Denaturation | 95 | 15 |
| 2 Primer Annealing | 55 | 20 |
| 3 Elongation | 72 | 20 |
| Cycles | | 45 |

Results

As shown in FIG. 24, murine QC and murine isoQC are expressed in all organs tested. In contrast to murine QC, the variances in expression of murine isoQC between different organs are smaller, indicating a lower stringency of regulation of transcription. The data for expression of mQC correspond to previous analyses of bovine QC, which was analyzed using Northern-Blot (Pohl, T. et al. 1991 Proc Natl Acad Sci USA 88, 10059-10063). Highest expression of QC was observed in Thalamus, Hippocampus and Cortex. Thus, QC-expression is primarily detected in neuronal tissue. Little QC-expression is detected in peripheral organs as spleen and kidney. Also misoQC is expressed in neuronal tissue, but at lower levels compared with mQC. In contrast, expression levels in peripheral organs is very similar between isoQC and QC.

Concluding, based on the results of transcript concentration, the combined activity (isoQC and QC) should be highest in brain. Thus, highest QC-protein levels are present in organs that are afflicted by amyloidoses like Alzheimers Disease, familial british dementia and familial danish dementia.

EXAMPLE 10

Inhibition of Human isoQC by Heterocyclic Chelators

Results

The time-dependent inhibition of QCs from different sources using heterocyclic chelators, such as 1,10-phenanthroline and dipicolinic acid has been investigated previously (6, 9). In analogy, h-isoQC is also time-dependently inactivated by the heterocyclic chelators 1,10-phenanthroline (FIG. 25) and dipicolinic acid (not shown), clearly pointing to a metal-dependent activity. Furthermore, EDTA also inhibited h-isoQC (FIG. 25). This is in sharp contrast to QCs, since neither human QC, porcine QC nor murine QC has shown discernible inhibition by EDTA. However, inhibition of hisoQC by EDTA even stronger suggests a metal-dependent catalysis.

EXAMPLE 11

Subcellular Localization of hisoQC Investigated Using Cell Fractionation

Cell Fractionation

The day following transfection, expressing HEK293 cells were washed with D-PBS and collected by centrifugation at 500×g for 5 min at 4° C. Subsequently, D-PBS was discarded and the cells were resuspended in 1 ml of disruption buffer (50 mM Tris, 50 mM KCl, 5 mM EDTA, 2 mM $MgCl_2$, pH 7.6 adjusted with HCl) and cracked by 30 crushes in a Potter cell homogenisator. The suspension was centrifuged at 700×g for 10 min at 4° C. The obtained pellet was resuspended in 300 µl disruption buffer and designated as debris fraction (D). The resulting supernatant was further centrifuged at 20.000×g for 30 min at 4° C. The pellet illustrated the heavy membrane fraction (HM) and was resuspended in 200 µl disruption buffer. The resulting supernatant was centrifuged at 100.000×g for 1 h at 4° C. using an ultracentrifuge (Beckmann). The obtained pellet was resuspended in 200 µl disruption buffer and was termed as light membrane fraction (LM). The supernatant was designated as soluble fraction (S). Debris, heavy membrane and light membrane fractions were sonicated for 10 sec and. the protein content of all fractions was determined using the method of Bradford. Subsequently, fractions were analyzed for QC activity and stained for marker proteins using Western Blot.

Results

For further corroboration, biochemical analysis of QC activity distribution, derived from hisoQC and hQC expression were performed. The native hisoQC beginning with methionine I and II and hQC were expressed in HEK293 cells, respectively. After cell fractionation the QC activity in the each fraction was determined using the fluorescence assay applying H-Gln-βNA as substrate. In cells, transfected with the empty vector (pcDNA), specific QC activity is hardly measurable. When expressing native hisoQC (MetI) and hisoQC (MetII), QC activity was readily detectable with the highest specific activity in the heavy membrane fraction (MetI: 40±2 µmole/min/g; MetII: 36±1.5 µmole/min/g) and the medium (MetI: 30±2 µmole/min/g; MetII: 54±3 µmole/min/g). In contrast, hQC shows the highest specific QC activity within the medium (1339±76 µmole/min/g) followed by the heavy membrane fraction (251±21 µmole/min/g) (FIG. 26A).

In addition the absolute activities were calculated, illustrating that the expression of hisoQC (MetI) and hisoQC (MetII) led mainly to an increase in the intracellular QC activity, namely within the debris (MetI: 1032±9 nM/min; MetII: 1110±10 nM/min) and heavy membrane fraction (MetI: 374±20 nM/min; MetII: 281±12 nM/min). Only little QC activity was found within the medium (MetI: 27±2 nM/min; MetII: 53±3 nM/min). In contrast, QC activity deduced by hQC expression shows high activity within the medium (1138±65 nM/min) and within intracellular compartments (debris: 1089±14 nM/min; heavy membrane fraction: 583±38 nM/min) supporting an Golgi localization of hisoQC as shown by histochemical analysis (FIG. 26B).

The data obtained by the expression of the native enzymes was further supported by expression of hisoQC (MetI and MetII) and hQC possessing a C-terminal FLAG-tag (FIG. 26C). Western Blot analysis of the resulting FLAG-tagged proteins in comparison to marker proteins of the Golgi complex and mitochondria revealed a mainly intracellular localization of hisoQC(MetI) and hisoQC (MetII) within the debris and heavy membrane fraction, whereas hQC is enriched within the medium but also found within the debris and heavy membrane fraction. Visualization of marker proteins of the Golgi complex (ST1GAL3) and mitochondria revealed the presence of these compartments within the debris and heavy membrane fraction. In addition the 65 kDa mitochondrial protein was also found to a smaller portion within the soluble fraction.

EXAMPLE 12

Analysis on the Golgi Retention Signal of hisoQC

In order to clarify, whether the predicted N-terminal transmembrane helix is responsible for the retention of hisoQC within the Golgi complex, the signal peptides starting at MetI and MetII, including the transmembrane helix, were cloned in frame with EGFP. The resulting vectors hisoQC (MetI) SS EGFP and hisoQC (MetII) SS EGFP were expressed in LN405 cells and examined in analogy to the full-length hisoQC EGFP fusion proteins using confocal laserscanning microscopy. The expression of hisoQC (MetI) SS EGFP led to the same Golgi complex localization observed for the full-length hisoQC (MetI) EGFP fusion protein. Again, a transport of hisoQC (MetI) SS EGFP to the mitochondria was not observed (FIG. 27A). In addition, the expression of the N-terminal truncated peptide hisoQC (MetII) SS EGFP also led to a enrichment of the protein within the Golgi complex. In analogy to hisoQC (MetI) SS EGFP, no mitochondrial EGFP fluorescence could be recorded (FIG. 27B). Consequently, the N-terminal sequence of hisoQC leads to the co-translational translocation of the protein to the ER membrane and to the retention within the Golgi complex. Furthermore, due to the expression of hisoQC (MetII) SS EGFP, the Golgi retention signal was grossly mapped to reside between methionine 19 and serine 53 (counting of amino acids beginning at MetI).

Additional topology analysis revealed the possibility for a functional homology of the hisoQC N-terminus to glycosyl-transferases. Glycosyltransferases are type II transmembrane proteins, possessing a short cytoplasmatic sequence, followed by the transmembrane helix and a large luminal catalytic domain. Clearly, this is essentially the same domain structure as found for misoQC and hisoQC (FIG. 28). For a number of glycosyltransferases, the Golgi retention signal was identified to reside within the transmembrane domain. Furthermore, for some of these enzymes truncation of the cytoplasmatic sequence was found to have no influence on the activity or the localization of the protein. In summary, evidence was provided, that hisoQC is a type II transmembrane protein showing a retention within the Golgi complex similar to glycosyltransferases.

EXAMPLE 12

Detection of QPCTL mRNA in Different Human Carcinoma Cell Lines and Tissues qPCR Analysis Analysis of human QPCTL expression in human carcinoma cell lines were performed using the quatitative real time PCR (qPCR) technique, essentially as described in example 9. For determining QPCTL mRNA, primers of the Quanti-Tect® primer assay were applied covering an exon/exon region for exclusion of co-amplification of genomic DNA. QPCR was performed following the manufacturers recommendations. The reaction mixture is depicted in Table 9 and the PCR program is illustrated in Table 8.

TABLE 9

Composition of the qPCR mixture

| component | Volume in μl |
|---|---|
| 2x QuantiTect SYBR Green PCR Master Mix (2.5 mM MgCl$_2$) | 7.5 |
| 10x QuantiTect Primer Assay | 1.5 |
| cDNA (≦100 ng/Reaktion) | 1 |
| Aqua bidest. | 5 |

The quantitative analysis of the transcript concentration in different tissues was analysed using the "Light Cycler" (Corbett research), applying the "QuantiTect SYBR Green PCR" (Qiagen). The DNA standard (cloned cDNA isoQC human) was used for quantification. The copy number was calculated according to the following equation: $(X^g/_{\mu l}$ DNA)/(Plasmid length in bp*660)*6.022*1023=$Y^{Molecules}/_{\mu l}$. The DNA standard contained 4 concentrations in the range of $10^7$-$10^{1\ Molecules}/_{\mu l}$, and an limiting concentration ($10^0$).

The results of qPCR were evaluated using the rotor-gene operating software (Corbett research).

Results

Expression of QPCTL in Different Carcinoma Cell Lines

Among the tested cancer cell lines, human melanoma cells show the highest expression of QPCTL transcripts (approx. 7000 copies/50 ng total-RNA), whereas the human soft tissue sarcoma cell lines show the lowest expression of QPCTL (365 copies/50 ng total-RNA). Pancreas carcinoma shows 2100 copies, thyroid carcinoma 3500 copies and gastric carcinoma possesses 4100 copies in the median (FIG. 29).

Expression of QPCTL in Different Melanoma Cell Lines

Recently it has been shown, that melanoma cells possess comparable high QPCT expression (Gillis, J. S., J. Transl. Med. 4 (2006), 4:27). Therefore, QPCTL expression in different melanoma cell lines was analyzed. As depicted in FIG. 30, QPCTL expression was detected in all melanoma cell lines, tested. The variation among the cell lines varied from 2025 copies/50 ng total-RNA in line Mel_ZL__11 to 18043 copies/50 ng total-RNA in line Mel_ZL12.

TABLE 10

Correlation of QPCT and QPCTL to tumor-associates antigens (taa) and correlation of taa among each other

| correlation | significance | correlation | significance |
|---|---|---|---|
| QPCT-MAGEB2 | 0.0436 | AIM1-MCL1 | 0.0163 |
| QPCT-MART1 | 0.0020 | MAGEA1-MAGEA2 | 0.00002 |
| QPCT-TYR | 0.0023 | MAGEA1-MAGEB2 | 0.0058 |
| QPCT-MAGEA1 | 0.0591 | TYRP2-MART1 | 0.0042 |
| QPCTL-MART1 | 0.0008 | TYR-MART1 | 0.0335 |
|  |  | TYR-TYRP2 | 0.0408 |
| AIM1-AIM2 | 0.0082 | TYR-MCL-1 | 0.0151 |

Furthermore, QPCT and QPCTL expression was correlated to the expression of tumor-associated antigens (taa). The melanoma-specific tumor-associated antigens were selected by data base mining and published results. Among others, AIM1 and AIM2 (absent in melanoma), MAGEA1, -A2, -A10 and MAGEB2 (melanoma antigen family A and B), MART1 (melanoma antigen recognized by T-cells), TYR (tyrosinase), TYRP1 and TYRP2 (tyrosinase related protein) and MCL-1 (myeloid cell leukemia) are tumor-associated antigens in melanoma. Data were compared using SPSS statistic software. Correlation between QPCT and MAGEB2 was significant (p=0.0436). Furthermore, correlation between QPCT and MART1 (p=0.002), QPCTL and MART1 (p=0.008) and QPCT and TYR (p=0.0023) was also statistically highly significant. The correlations show a direct dependence, which implies: the higher QPCT/QPCTL expression, the higher the expression of tumor-associated antigens. The only exception is the correlation between TYR and MCL1, which shows an indirect dependence.

Expression of QPCT and QPCTL in Different Tumor Tissues

The expression of QPCT and QPCTL was evaluated in tumor tissues of soft tissue sarcoma, gastric carcinoma and thyroid carcinoma. Highest expression of QPCT has been found in thyroid carcinoma followed by gastric carcinoma and soft tissue carcinoma (Table 11). The same order was observed for QPCTL expression, however, the copy number of QPCTL transcripts was always lower, than observed for QPCT transcripts as revealed by Student's t-test ($p_{soft\ tissues\ carcinoma}$=0.001; $p_{gastric\ carcinoma}$=4.8E-7; $p_{thyroid\ carcinoma}$=0.04) (Table 11; FIG. 31).

TABLE 11

Comparison of QPCT and QPCTL expression in different tumor tissues

|  | soft tissue sarcoma (119 samples) | gastric carcinoma (47 samples) | thyroid carcinoma (29 samples) |
| --- | --- | --- | --- |
| QPCT | 1293 | 2985 | 8303 |
| QPCTL | 170 | 469 | 2540 |

Further investigations on the expression level of QPCT and QPCTL revealed a two-sided significant correlation by Pearson in soft tissue sarcoma (p=2E-31) and gastric carcinoma (p=0.015). No correlation has been observed for QPCT and QPCTL expression level in thyroid carcinoma (p=0.46).

Expression of QPCTL Dependent on the Stage of Differentiation in Gastric Carcinoma For gastric carcinomas, QPCTL expression in samples representing different stages of tumor differentiation were investigated. As control served tumor-surrounding normal tissue. The comparison of normal with tumor tissue revealed a significantly higher QPCTL expression (p=0.04) in tumor tissues. Undifferentiated gastric carcinomas show higher QPCTL expression, than normal tissue. Poorly and well to moderate differentiated gastric carcinomas show no differences in the median compared to normal tissue (FIG. 32).

Expression of QPCT and QPCTL in Different Stages of Thyroid Carcinoma

Different stages of thyroid carcinoma were investigated concerning QPCT and QPCTL expression. The stages were classified according to nomenclature of the world health organisation (WHO) as follicular thyroid carcinoma (FTC), papillary thyroid carcinoma (PTC) and undifferentiated thyroid carcinoma (UTC). Samples from patients possessing goiter served as control.

The QPCT mRNA level (median) in differentiated thyroid carcinomas FTC (6700 copies/50 ng total-RNA) and PTC (16000 copies/50 ng total-RNA) were higher than in non-tumor tissue (goiter: 2100 copies/50 ng total-RNA). UTC possesses 5400 copies/50 ng total-RNA and is 2.5 times higher than observed in goiter. The mRNA copy number of QPCT is in all thyroid tumors significantly higher than in goiter (p=0.04, Student's t-test) (FIG. 33).

The QPCTL mRNA level in thyroid carcinoma is homogeneous. The samples from FTC (2600 copies/50 ng total-RNA) and UTC (2500 copies/50 ng total-RNA) are similar to goiter (2500 copies/50 ng total-RNA). The expression of QPCTL in PTC is slightly decreased to 1900 copies/50 ng total-RNA (FIG. 34).

In conclusion, QPCT and QPCTL are equally expressed in goiter. However, in tumor tissues the expression of QPCT increases, whereas the expression of QPCTL remains stable.

EXAMPLE 13

Investigations on the QPCT and QPCTL Expression in Human Cell Lines after Incubation with Different Stimuli Cell Lines and Media The stimulation experiments were performed using the human embryonal kidney cell line HEK293, human acute monocytic leukemia cell line THP-1 and the follicular thyroid carcinoma cell line FTC-133. Cells were grown in appropriate culture media (DMEM, 10% FBS for HEK293, RPMI1640, 10% FBS for THP-1 and DMEM/F12, 10% FBS for FTC-133) in a humidified atmosphere at 37° C. and 5% $CO_2$.

Stimulation Using Bioactive Peptides, Chemicals or LPS

HEK293 and FTC-133 cells were cultivated as adherent cultures and THP-1 cells were grown in suspension. For stimulation assay $2\times10^5$ cells of FTC-133 and HEK293 cells were transferred to 24 well plates. In case of HEK293, plates were coated with collagen I for ensuring proper adherence. In addition, $2\times10^6$ cells of THP-1 were grown in 24 well suspension plates. All stimulation experiments were applied under serum-free conditions. FTC-133 was grown over night. Afterwards, cells were adapted to serum-free media for another 24 h and the stimulation was started by replacing the conditioned media by fresh serum-free media. HEK293 cells were grown over night and afterwards the stimulation using respective agents was started without an adaption to serum-free conditions due to morphological changes in case of cultivation of HEK293 under serum-free conditions for more than 24 h. THP-1 cells were plated in serum-free media together with respective agent. The applied stimuli and final concentrations are listed in Table 12.

TABLE 12

Stimuli for investigations on the regulation of hQC and hisoQC in human cell lines

| Name | Final concentration |
| --- | --- |
| butyric acid (BA) | 2 mM |
| hepatocyte growth factor (HGF) | 10 ng/ml |
| lipopolysaccharide (LPS) | 1, 10 µg/ml |
| transforming growth factor β (TGFβ) | 10, 100 ng/ml |
| tumor necrosis factor α (TNFα) | 10, 100 ng/ml |

Cells were incubated with the respective stimulus for 24 h. Afterwards, total-RNA from the cells was isolated using the Nucleo-Spin® RNA II Kit (Macherey-Nagel) and stored until qPCR assay.

Stimulation Using Hypoxia

THP-1, HEK293 and FTC-133 cells were plated into two 25 cm² tissue culture flasks, respectively. Thereby, one flask of each cell line served as negative control, cultivated under normal growth conditions for 24 h. The other flasks were placed in a anaerobic bag together with an anaerobic reagent (Anaerocult® P, Merck) and an indicator. The bag was sealed to ensure air tight conditions. Cells were also grown for 24 h and subsequently, total-RNA was isolated using the Nucleo-Spin® RNA II Kit (Macherey-Nagel) and stored until qPCR assay.

Results

Basal Expression of QPCT and QPCTL in HEK293 FTC-133 and THP-1

The basal expression in the used cell lines HEK293, FTC-133 and THP-1 was evaluated in preparation for the following stimulation experiments. The copy number of QPCT and QPCTL transcripts is summarized in Table 13.

TABLE 13

Basal expression of QPCT and QPCTL in different cell lines

| cell line | Absolute mRNA copy numbers per 50 ng total RNA | |
|---|---|---|
| | QPCT | QPCTL |
| HEK-293 (8 samples) | 37196 ± 18928 | 3206 ± 855 |
| FTC-133 (8 samples) | 24790 ± 7605 | 10262 ± 1899 |
| THP-1 (8 samples) | 3588 ± 853 | 6725 ± 1763 |

Influence of Selected Stimuli on Expression of QPCT and QPCTL

Regulational binding sites of the promotors of QPCT and QPCTL and signal transduction pathways leading to their regulation are not described so far. Therefore, stimulation experiments using different cell lines and stimuli were conducted. QPCT mRNA levels in HEK293 cells were increased by stimulation using TNF-α, HGF and butyric acid. In addition the regulation of CCL2 as QPCT/QPCTL substrate has been investigated. TNF-α and butyric acid increased the amount of CCL2 transcripts in HEK293. HGF had no influence in CCL2 expression. In contrast QPCTL was not regulated by TNF-α, HGF and butyric acid (FIG. 35).

In addition FTC-133 was stimulated using LPS and TGF-β and the regulation of QPCT, QPCTL and CCL2 was monitored. In FTC-133, LPS and TGF-β stimulated the expression of QPCT mRNA, but failed to induce QPCTL and CCL2 expression (FIG. 36).

This experiments were further coroborated by stimulation of THP-1 cells using LPS (1 µg/ml), LPS (10 µg/ml), TGF-β and TNF-α. As observed for FTC-133 and HEK293, QPCT expression could be induced using different stimuli. In addition CCL2 expression was induced using LPS and TNF-α. Again, no induction or repression of QPCTL mRNA could be observed (FIG. 37).

In conclusion, the experiments revealed, that QPCT can be regulated by a set of stimuli in different cell lines (LPS, TNF-α, HGF, butyric acid and others). In contrast, QPCTL could neither stimulated nor repressed by the tested stimuli suggesting a house-keeping function of QPCTL.

Influence of Selected Stimuli on Expression of QPCT its Substrates

Since QPCT expression was induced by a number of stimuli, the question was raised, whether QPCT induction takes place in combination with an induction of the QPCT substrates CCL2, CCL7, CCL8 and CCL13. Therefore, the stimulation using LPS (1 µg/ml), LPS (10 µg/ml), TGF-β (100 ng/ml) and TNF-α (100 ng/ml), respectively, was performed using THP-1 monocytes. THP-1 expresses all chemokines at a basal level, important for comparison of stimulated cells with the negative control. LPS and TNF-α led to the reliable induction of all tested chemokines and QPCT in THP-1 cells. TGF-β was less effective as stimulus and induced the expression of QPCT, CCL2, CCL7 and CCL8 maximum 2fold. CCL13 was repressed by TGF-β stimulation (FIG. 38).

Stimulation of QPCT and QPCTL Expression by Hypoxia

QPCTL expression could not be regulated by chemical agents, bioactive pepitides or LPS. Therefore, we tested, whether QPCTL expression is regulated by hypoxia. As summarized in FIG. 39. Hypoxia selectively induced the expression of QPCTL but not of QPCT. In comparison, hypoxia induced factor 1a (HIF1a) was repressed by 15% (FIG. 39A) and 45% (FIG. 39C). The data suggest a connection of QPCTL to hypoxia.

Synthesis of the Inhibitors

Synthesis scheme 1: Synthesis of the examples 1-53, 96-102, 136-137

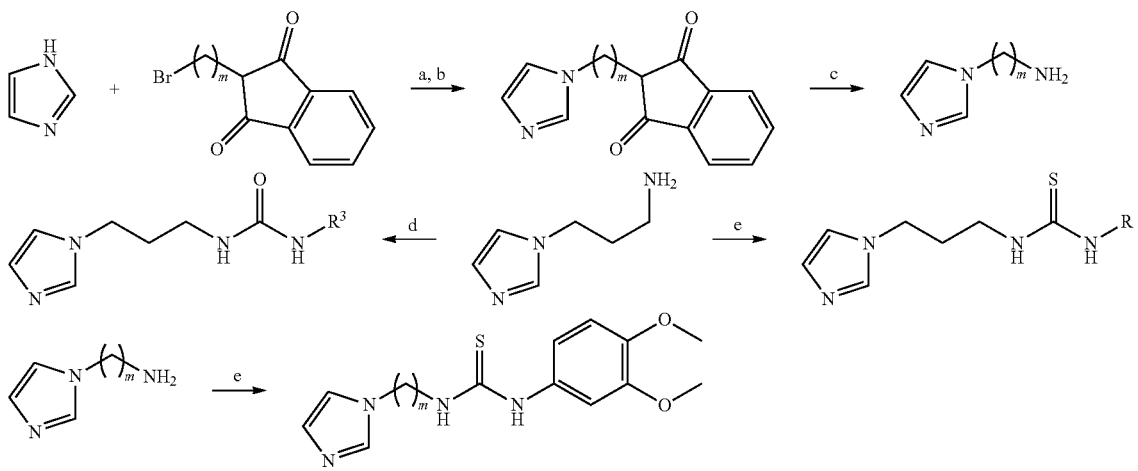

Reagents and conditions: (a) NaH, DMF, 4 h, rt.; (b), 8 h, 100° C.; (c) H₂N—NH₂, EtOH, 8 h, reflux then 4N HCl, 6 h, reflux, (d) R³—NCO, EtOH, 6 h, reflux, (e) 3,4 dimethoxy-phenyl-isothiocyanate, Synthesis scheme 2: Synthesis of the examples 54-95

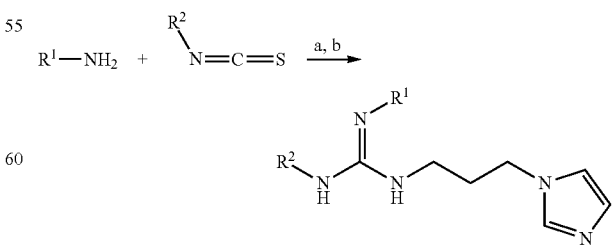

Reagents and conditions: (a) R—NCS, EtOH, 6 h, reflux; (b) WSCD, 1H-imidazole-1-propanamine, DMF, 2 h, r.t.

Synthesis scheme 3: Synthesis of the examples 103-105

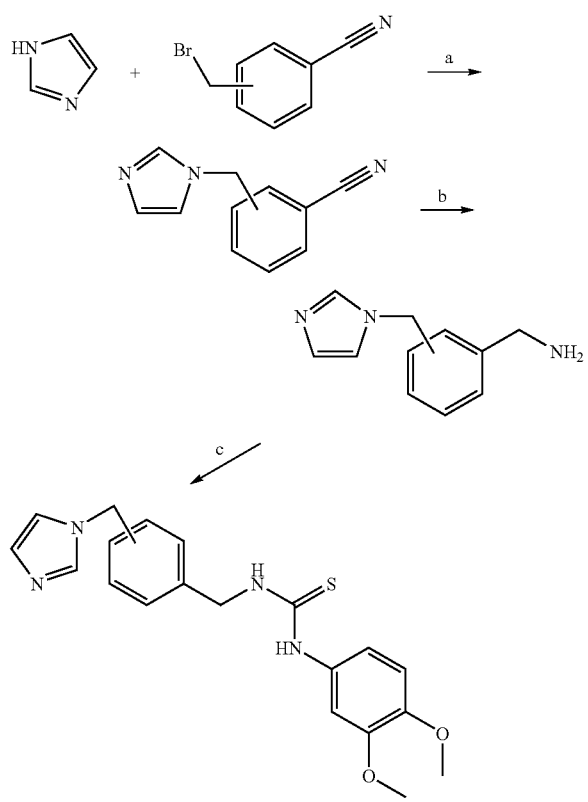

Reagents and conditions: (a) NaH, DMF, rt., 3 h; (b) LiAlH₄, dioxane, reflux, 1 h; (c) R-NCS, EtOH, reflux 6 h, Synthesis scheme 4: Synthesis of the examples 106-109

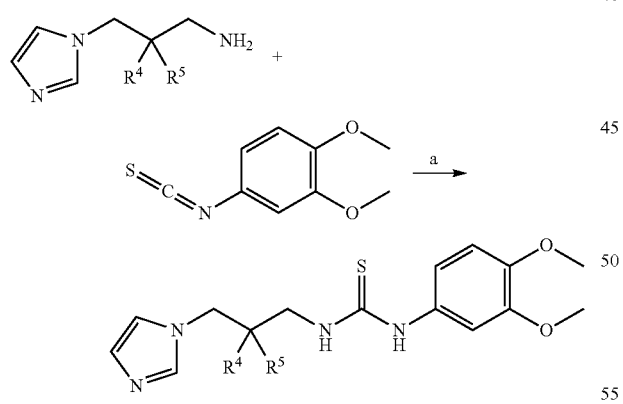

Reagents and conditions: (a) EtOH, 2 h, reflux

Synthesis scheme 5: Synthesis of the examples 110-112

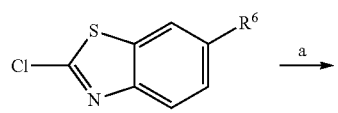

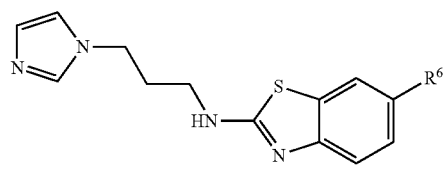

Reagents and conditions: (a) 1H-imidazole-1-propanamine, Triethylamine, Toluene, 12 h, reflux Synthesis scheme 6: Synthesis of the examples 113-132

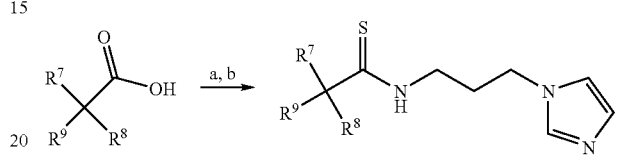

Reagents and conditions: (a) CAIBE, 1H-imidazole-1-propanamine, Dioxan, 0° C., 12 h; (b) Laweson's Reaent, EtOH, reflux, 8 h Synthesis scheme 7: Synthesis of the examples 133-135

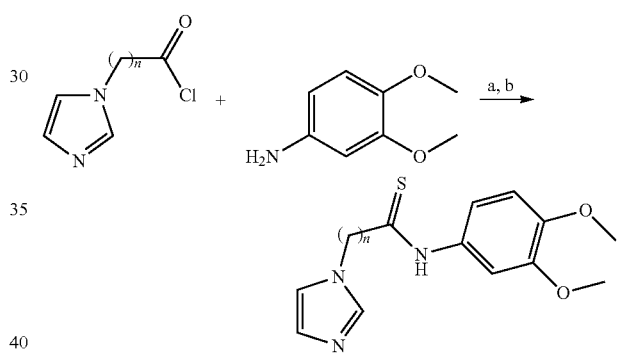

Reagents and conditions: (a) 1H-imidazole-1-propan acidic chloride, CH₂Cl₂, -10° C., 1 h; (b) Lawesson's Reagent, Dioxane, reflux, 8 h Synthesis scheme 8: Synthesis of the example 138

Reagents and conditions: (a) EtOH, reflux, 8 h

Synthesis scheme 9: Synthesis of the example 139

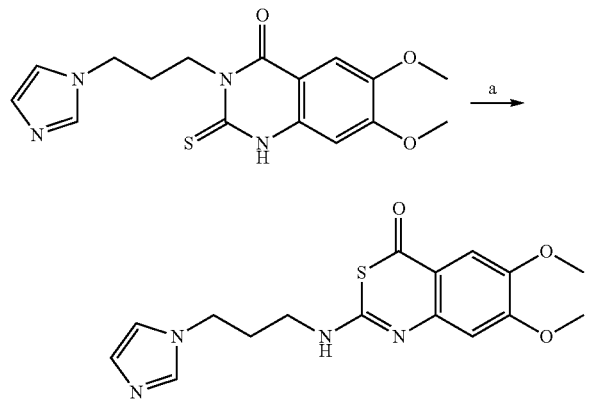

Reagents and conditions: (a) 75% conc. H₂SO₄, 4 h

Synthesis scheme 10: Synthesis of the example 140

Reagents and conditions: (a) Acetonitrile, reflux 2 h

Analytical Conditions

ESI-Mass spectra were obtained with a SCIEX API 365 spectrometer (Perkin Elmer). The $^1$H-NMR (500 MHz) data was recorded on a BRUKER AC 500, using DMSO-D$_6$ as solvent. Chemical shifts are expressed as parts per million downfield from tetramethylsilane. Splitting patterns have been designated as follows: s (singulet), d (doublet), dd (doublet of doublet), t (triplet), m (multiplet), and br (broad signal).

DETAILED SYNTHESIS DESCRIPTION

Examples 1-12 and 14-53

1H-imidazole-1-propanamine was reacted with the corresponding isothiocyanate in ethanol under reflux for 8 h. After that the solvent was removed and the remaining oil was dissolved in methylene chloride. The organic layer was washed twice with a saturated solution of NaHCO$_3$ followed by NaHSO$_4$ and brine, dried then evaporated. The remaining solid was re-crystallized from ethyl acetate, yielding the example thiourea in yields of 80-98%.

Example 13

1-(3-(1H-imidazol-1-yl)propyl)-3-(3,4-dimethoxyphenyl)thiourea 4.0 mmol of 3,4-dimethoxyphenyl isothiocyanate and 4.0 mmol of 3-(1H-imidazol-1-yl)alkyl-1-amine were dissolved in 10 mL of absolute ethanol. After stirring for 2 h under reflux, the solvent was evaporated and the resulting solid was recrystallized from ethanol.

Yield: 0.66 g (51.3%); mp: 160.0-161.0° C.
$^1$H NMR δ 1.8-2.0 (m, 2H), 3.4-3.5 (m, 2H), 3.75 (s, 6H), 3.9-4.0 (m, 2H), 6.7-6.8 (m, 1H), 6.9 (br m, 2H), 6.95 (s, 1H), 7.15 (s, 1H), 7.55 (br s, 1H), 7.6 (s, 1H), 9.3 (s, 1H); MS m/z 321.2 (M+H), 253.3 (M-C$_3$H$_3$N$_2$.)

Examples 96-102

1H-imidazole-1-propanamine was reacted with the corresponding isocyanate in ethanol under reflux for 8 h. After that

Synthesis scheme 11: Synthesis of the example 141

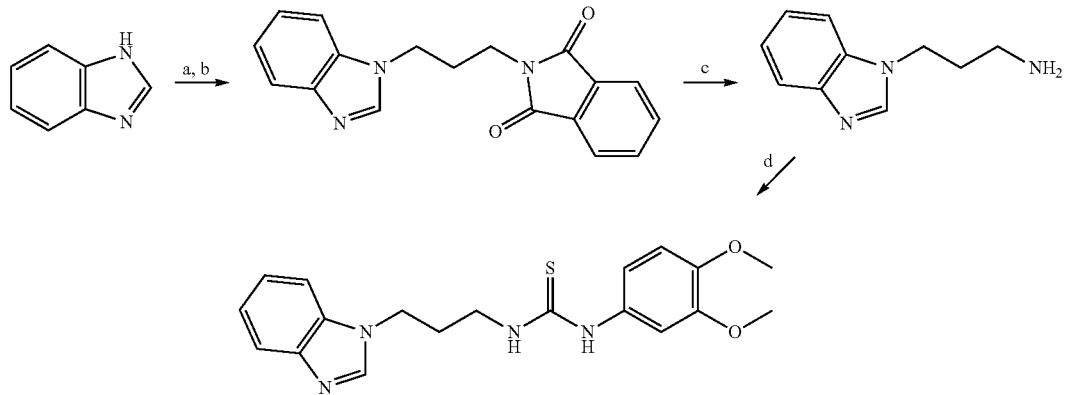

Reagents and conditions: (a) NaH, DMF, 4 h, rt.; (b), 8 h, 100° C.; (c)H₂N—NH₂, EtOH, 8 h, reflux then 4N HCl, 6 h, reflux, (d) 3,4 dimethoxy-phenyl-isothiocyanate, EtOH, 6 h, reflux the solvent was removed and the remaining oil was dissolved in methylene chloride. The organic layer was washed twice with a saturated solution of NaHCO$_3$ followed by NaHSO$_4$ and brine, dried then evaporated. The remaining solid was re-crystallized from ethyl acetate, yielding the example urea in yields of 85-90%.

Examples 136, 137

The 1H-imidazole-1-alkylamines were prepared according to the literature from -brom-alkyl-phthalimides and imidazolium salt and subsequent hydrazinolysis. The resulting products were transformed into the thioureas according to example 1-53 giving a 88% (example 136) and 95% (example 137) yield.

Examples 54-95

All examples were made from the corresponding thioureas by reacting with Water-soluble-carbodiimide (WSCD) and 1H-imidazole-1-propanamine in dry dimethyl form-amide for 2 h at r.t. giving the trisubstituted guanidines with yields from 40-87%.

Examples 103-105

Imidazole was reacted with the corresponding brommethylphenylcyanide in DMF, utilizing 1 equivalent of NaH for 3 h under rt., giving the 1H-imidazole-1-methylphenylcyanides. The solvent was removed and the resulting oil was re-dissolved in dioxane. The cyanides were converted in the corresponding amines using 1 equivalent of LiAlH$_4$. After adding a saturated solution of KHSO$_4$, dioxane was evaporated and the aqueous layer was extracted by means of CHCl$_3$. The organic layer was concentrated in vacuo and the amine was converted in the corresponding thioureas according to example 1-53 giving a 78% (example 103) and 65% (example 104) and 81% (example 105) yield.

Examples 106-109

Starting from the corresponding methansulfonate-2-methylpropyl-phthalimides the amines were synthesized as described for the amines in example 136-137. The resulting products were transformed into the thioureas according to example 1-53 giving example 106-109 in total yields of 25-30%.

Examples 110-112

1H-imidazole-1-propanamine was reacted with the corresponding 2-chlorobenzo[d] thiazole in toluol for 24 h at a temperature of 130° C. After removing the solvent and recrystallization from methanol example 110-112 was yielded in an amount of 55-65%.

Examples 113-118, 120-124 and 126-132

1H-imidazole-1-propanamine was reacted with the corresponding 2-phenyl acetic acid in dry dioxane by adding one equivalent of CAIBE and N-methylmorpholine at a temperature of 0° C. After 2 h the mixture was allowed to warm to r.t. and the mixture was stirred for 12 h. After removing the solvent the resulting oil was redissolved in methylene chloride and the organic layer was washed by means of an aqueous solution of NaHCO$_3$ and water, dried and the solvent was evaporated. The remaining oil was dissolved in dioxane adding Laweson's Reagent. After stirring for 12 h a saturated solution of NaHCO$_3$ was added. Dioxane was evaporated and the aqueous layer was extracted by means of ethyl acetate. The organic layer was separated, dried and the solvent was evaporated. The remaining solid was crystallized from acetyl acetate/ether, giving 113-118, 120-124 and 126-132 with total yields of 62-85%.

Example 119

N-(3-(1H-imidazol-1-yl)propyl)-2-(3,4-dimethoxyphenyl)ethanethioamide

A mixture of 4.0 mmol triethylamine and 4.0 mmol of 3-(1H-imidazol-1-yl)alkyl-1-amine 20 mL of dioxane was added drop wise to an ice cooled, stirred solution of 4.0 mmol of 2-(3,4-dimethoxyphenyl)acetyl chloride in 30 mL of dioxane. The mixture was allowed to warm to r.t., and then stirred for 1 h. After removing the solvent by reduced pressure, the residue was redissolved in 50 mL of dichloromethane. The organic layer was washed by means of 30 mL of saturated aqueous solution of NaHCO$_3$, and water. The organic solution was dried, filtered, and the solvent was removed under reduced pressure. After redissolving in 50 mL of dry dioxane 2.2 mmol of Lawesson's reagent was added, and the mixture was heated to 90° C. and stirred for 8 h. The solvent was removed by reduced pressure, and the residue was redissolved in 50 mL of dichloromethane. The organic layer was washed three times by means of a saturated aqueous solution of NaHCO$_3$, followed three times by water, dried, filtered, and then the organic solvent was removed. The compound was purified by chromatography using a centrifugal-force-chromatography device, (Harrison Research Ltd.) utilizing silica plates of a layer thickness of 2 mm, and a CHCl$_3$/MeOH gradient as eluting system.

Yield: 0.14 g (10.6%); melting point: 148.0-150.0° C.
$^1$H NMR δ 2.0-2.15 (br m, 2H), 3.4-3.5 (m, 2H), 3.7 (s, 6H), 6.75-6.8 (m, 2H), 4.1-4.2 (m, 2H), 6.8-6.9 (m, 2H), 6.95-7.0 (m, 1H), 7.4 (s, 1H), 7.75-7.85 (br m, 1H), 8.6 (s, 1H), 10.2 (s, 1H); MS m/z 320.2 (M+H), 252.2 (M-C$_3$H$_3$N$_2$.)

Example 125

N-(3-(1H-imidazol-1-yl)propyl)-1-(3,4-dimethoxyphenyl)cyclopropanecarbothioamide 11.06 mmol of 3,4-dimethoxyphenyl acetonitrile, 34.8 mmol of 2-Bromo-1-chloroethanole and 1.16 mmol of triethylbenzylammonium hydrochloride were dissolved in 10 mL of an aqueous solution of KOH (60%). The mixture was transferred into an ultrasonic bath and vigorously stirred for 3 h at room temperature. The resulting suspension was diluted with 40 mL of water and extracted three times by means of 20 mL of dichloromethane. The combined organic layers where washed by means of an aqueous solution of hydrochloric acid (1N), dried over Na$_2$SO$_4$ and the solvent was removed under reduced pressure. The remaining oil was purified by flash-chromatography using silica gel and ethyl acetate/heptane as eluting system, resulting in 0.81 g (34.4%) of 1-(3,4-dimethoxyphenyl)cyclopropanecarbonitrile 3.9 mmol of 1-(3,4-dimethoxyphenyl)cyclopropanecarbonitrile and 11.2 mmol of KOH were suspended in 80 mL of ethylene glycol. The mixture was stirred for 12 h under reflux. Then 80 mL of water were added and the aqueous layer was extracted two times with ether. After pH adjustment to a value of pH=4-5 using HCl (1N) the aqueous layer was extracted three times by means of ether, then the combined organic layers were dried over Na$_2$SO$_4$ and the solvent was removed, resulting in 0.81 g (93.5%) of 1-(3,4-dimethoxyphenyl)cyclopropanecarboxylic acid.

3.44 mmol of 1-(3,4-dimethoxyphenyl)cyclopropanecarboxylic acid, 3.5 mmol of N-Methyl morpholine, and 3.5 mmol of isobutyl chloroformate were dissolved in dry tetrahydrofurane and stirred for 15 min at −15° C. Then 3.5 mmol of 3-(1H-imidazol-1-yl)alkyl-1-amine was added and the mixture was allowed to warm to 0° C. and was stirred for 12 h. The solvent was removed under reduced pressure and the remaining oil was redissolved in chloroform. Then the organic layer was washed two times by means of a saturated aqueous solution of NaHCO$_3$, then dried over Na$_2$SO$_4$ and the solvent was removed. Purification was performed by means of centrifugal forced chromatography using a Chromatotron® device (Harrison Research Ltd.) utilizing silica plates of a layer thickness of 2 mm, and a CHCl$_3$/MeOH gradient as eluting system resulting in 0.671 g (59.3%) of N-(3-(1H-imidazol-1-yl)propyl)-1-(3,4-dimethoxyphenyl)cyclopropane-carboxamide.

After redissolving in 30 mL of dry dioxane 1.43 mmol of Lawesson's reagent were added, and the mixture was heated to 90° C. and stirred for 8 h. The solvent was removed by reduced pressure, and the residue was remains were dissolved in 50 mL of dichloromethane. The organic layer was washed three times by means of a saturated aqueous solution of NaHCO$_3$, followed three times by water, dried, filtered, and then the organic solvent was removed. The compound was purified by chromatography using a centrifugal-force-chromatography device, (Harrison Research Ltd.) utilizing silica plates of a layer thickness of 2 mm, and a CHCl$_3$/MeOH gradient as eluting system.

Yield: 0.33 g (46.2%); melting point: 127.0-127.5° C.

$^1$H NMR δ 1.1-1.2 (t, 2H), 1.55-1.6 (t, 2H), 2.0-2.1 (m, 2H), 3.5-3.6 (m, 2H), 3.7-3.8 (s, 6H), 4.1-4.2 (t, 2H), 6.8-6.9 (m, 3H), 7.65 (s, 1H), 7.75 (s, 1H), 8.8 (m, 1H), 9.05 (s, 1H); MS m/z 346.0 (M+H), 278.2 (M-C$_3$H$_3$N$_2$.), 177.1 (M-C$_6$H$_8$N$_3$S.)

Examples 133-135

A mixture of 1 equivalent triethylamine and 3,4-dimethoxyaniline in dioxane was added to an stirred solution of the corresponding ω-bromoalkyl acidic chloride at a temperature of 0° C. The solution was allowed to warm to r.t. and stirred for 2 h. The solvent was evaporated, and the remaining oil was redissolved in dichloromethane. The organic layer was washed by means of water, dried, filtered, and the solvent was removed under reduced pressure.

Imidazole and sodium hydride were suspended in and the mixture was stirred under inert conditions at r.t. for 3 h. ω-Bromo-N-(3,4-dimethoxy-phenyl)alkylamide was added and the mixture was heated to 100° C. and stirred for 8 h. After that, the solvent was evaporated, hot toluene were added and the solution was filtered. Then the solvent was removed under reduced pressure. The transformation into the thioamides was performed as described for example 113-132 by means of Laweson's reagent, giving 133-135 in total yields of 13-20%.

The analytical data for further examples, which were synthesized according to the general synthesis schemes described above, are as follows:

EXAMPLE 1

1-(3-(1H-imidazo/1-yl)propyl)-3-methylthiourea melting point: 122-122.5° C.

$^1$H NMR δ 1.85-1.95 (m, 2H), 2.8 (s, 3H), 3.2-3.5 (br d, 2H), 3.8-3.9 (m, 2H), 6.85 (d, 1H), 7.15 (d, 1H), 7.3-7.5 (br d, 2H), 7.65 (s, 1H); MS m/z 199.1 (M+H), 221.3 (M+Na), 131.0 (M-C$_3$H$_3$N$_2$.)

EXAMPLE 2

1-(3-(1H-imidazol-1-yl)propyl)-3-tert-butylthiourea melting point: 147.0-147.5° C.

$^1$H NMR δ 1.3-1.4 (s, 9H), 1.85-1.95 (m, 2H), 3.5 (t, 2H), 3.8 (t, 2H), 6.85 (d, 1H), 7.15 (d, 1H), 7.3-7.5 (br d, 2H), 7.65 (s, 1H); MS m/z 241.1 (M+H), 173.1 (M-C$_3$H$_3$N$_2$.)

EXAMPLE 3

1-(3-(1H-imidazol-1-yl)propyl)-3-benzylthiourea melting point: 127.0-128.0° C.

$^1$H NMR δ 1.85-1.95 (m, 2H), 3.2-3.5 (br d, 2H), 3.8-3.9 (m, 2H), 4.6 (s, 2H), 6.8 (d, 1H), 7.15 (d, 1H), 7.19-7.35 (m, 5H), 7.5-7.6 (br d, 2H), 7.85 (s, 1H); MS m/z 275.3 (M+H), 207.1 (M-C$_3$H$_3$N$_2$.)

EXAMPLE 5

1-(3-(1H-imidazol-1-yl)propyl)-3-phenylthiourea melting point: 166.5-167.0° C.

$^1$H NMR δ 1.95-2.05 (m, 2H), 3.3-3.5 (br d, 2H), 3.9-4.0 (m, 2H), 6.85 (d, 1H), 7.05 (m, 1H) 7.15 (d, 1H), 7.25 (m, 2H), 7.35 (m, 2H), 7.6 (s, 1H), 7.8 (br s, 1H), 9.5 (br s, 1H); MS m/z 261.1 (M+H), 193.2 (M-C$_3$H$_3$N$_2$.)

EXAMPLE 6

1-(3-(1H-imidazol-1-yl)propyl)-3-(4-fluorophenyl)thiourea melting point: 147.0-148.0° C.

$^1$H NMR δ 1.95-2.05 (m, 2H), 3.3-3.5 (br d, 2H), 3.9-4.05 (m, 2H), 6.85 (d, 1H), 7.05-7.15 (m, 3H), 7.3-7.4 (m, 2H), 7.6 (s, 1H), 7.7-7.8 (br s, 1H), 9.4 (br s, 1H); MS m/z 279.3 (M+H), 211.2 (M-C$_3$H$_3$N$_2$.)

EXAMPLE 7

1-(3-(1H-imidazol-1-yl)propyl)-3-(4-ethylphenyl)thiourea melting point: 100.0-100.5° C.

$^1$H NMR δ 1.15-1.2 (t, 3H), 1.9-2.0 (m, 2H), 2.5-2.6 (m, 2H), 3.3-3.5 (br d, 2H), 3.9-4.05 (m, 2H), 6.85 (d, 1H), 7.1-7.2 (m, 3H), 7.25-7.3 (m, 2H), 7.6 (s, 1H), 7.7-7.8 (br s, 1H), 9.4 (br s, 1H); MS m/z 289.3 (M+H), 221.1 (M-C$_3$H$_3$N$_2$.)

EXAMPLE 8

1-(3-(1H-imidazol-1-yl)propyl)-3-(4-(trifluoromethyl)phenyl)thiourea melting point: 154.5-155.0° C.
$^1$H NMR δ 1.9-2.1 (br m, 2H), 3.4-3.6 (br d, 2H), 3.95-4.1 (br m, 2H), 6.85 (d, 1H), 7.2 (d, 1H), 7.6-7.8 (m, 5H), 8.2 (br s, 1H), 9.9 (br s, 1H); MS m/z 329.3 (M+H), 261.2 (M-C$_3$H$_3$N$_2$.)

EXAMPLE 10

1-(3-(1H-imidazol-1-yl)propyl)-3-(4-acetylphenyl)thiourea melting point: 170.0-171.0° C.
$^1$H NMR δ 1.9-2.1 (br m, 2H), 2.4-2.5 (s, 3H), 3.2-3.5 (br m, 2H), 3.9-4.1 (m, 2H), 6.85 (d, 1H), 7.15 (d, 1H), 7.5-7.65 (br m, 3H), 7.8-7.9 (m, 2H), 8.1 (m, 2H), 9.8 (br s, 1H); MS m/z 303.2 (M+H), 235.1 (M-C$_3$H$_3$N$_2$.)

EXAMPLE 11

1-(3-(1H-imidazol-1-yl)propyl)-3-(4-methoxyphenyl)thiourea melting point: 125.0-125.5° C.
$^1$H NMR δ 1.8-2.0 (br m, 2H), 3.2-3.5 (br m, 2H), 3.7 (s, 3H), 3.9-4.0 (m, 2H), 6.7-6.9 (m, 3H), 7.1-7.2 (m, 3H), 7.5 (s, 1H), 7.6 (s, 1H), 9.2 (s, 1H); MS m/z 291.1 (M+H), 223.2 (M-C$_3$H$_3$N$_2$.)

EXAMPLE 14

1-(3-(1H-imidazol-1-yl)propyl)-3-(2,4-dimethoxyphenyl)thiourea melting point: 120.0-120.5° C.
$^1$H NMR δ 1.8-2.0 (br m, 2H), 3.4-3.5 (br m, 2H), 3.75 (s, 6H), 3.9-4.0 (m, 2H), 6.5 (d, 1H), 6.6 (s, 1H), 6.9 (s, 1H), 7.15 (s, 1H), 7.3 (d, 1H), 7.5 (br s, 1H), 7.6 (s, 1H), 9.75 (s, 1H); MS m/z 321.2 (M+H), 253.3 (M-C$_3$H$_3$N$_2$.)

EXAMPLE 15

1-(3-(1H-imidazol-1-yl)propyl)-3-(3,5-dimethoxyphenyl)thiourea melting point: 142.0-143.0° C.
$^1$H NMR δ 1.8-2.0 (br m, 2H), 3.4-3.5 (br m, 2H), 3.6 (s, 6H), 3.95-4.0 (m, 2H), 6.25 (m, 1H), 6.6 (m, 2H), 6.9 (s, 1H), 7.2 (s, 1H), 7.6 (s, 1H), 7.8 (s, 1H), 9.5 (s, 1H); MS m/z 321.2 (M+H), 253.3 (M-C$_3$H$_3$N$_2$.)

EXAMPLE 23

1-(3-(1H-imidazol-1-yl)propyl)-3-(2,3-dihydrobenzo[b][1,4]dioxin-7-yl)-thiourea melting point: 103.0-103.5° C.
$^1$H NMR δ 1.9-2.0 (br m, 2H), 3.3-3.5 (br d, 2H), 3.9-4.0 (m, 2H), 4.2-4.3 (m, 4H), 6.7 (m, 1H), 6.8-6.8 (m, 1H), 6.9 (m, 2H), 7.2 (s, 1H), 7.6 (m, 1H), 9.3 (s, 1H); MS m/z 319.3 (M+H), 251.3 (M-C$_3$H$_3$N$_2$.)

EXAMPLE 24

1-(3-(1H-imidazol-1-yl)propyl)-3-(benzo[d][1,3]dioxol-6-yl)thiourea melting point: 115.0-115.6° C.
$^1$H NMR δ 1.9-2.1 (br m, 2H), 3.4-3.5 (br d, 2H), 4.05-4.15 (m, 2H), 6.0 (s, 2H), 6.7 (m, 1H), 6.8-6.85 (m, 1H), 6.95 (d, 1H), 7.25 (s, 1H), 7.45 (s, 1H), 7.7 (br s, 1H), 8.5 (br s, 1H), 9.4 (br s, 1H); MS m/z 305.2 (M+H), 237.2 (M-C$_3$H$_3$N$_2$.)

EXAMPLE 25

1-(3-(1H-imidazol-1-yl)propyl)-3-(3, 4, 5-trimethoxyphenyl)thiourea melting point: 124.5-125.5° C.
$^1$H NMR δ 1.8-2.0 (m, 2H), 3.4-3.5 (br m, 2H), 3.6 (s, 3H), 3.7 (s, 6H), 3.9-4.0 (m, 2H), 6.65 (m, 2H), 6.85 (s, 1H), 7.2 (s, 1H), 7.6 (s, 1H), 7.7 (br s, 1H), 9.4 (s, 1H); MS m/z 351.3 (M+H), 283.2 (M-C$_3$H$_3$N$_2$.)

EXAMPLE 26

1-(3-(1H-imidazol-1-yl)propyl)-3-(3-methoxyphenyl)thiourea melting point: 89.5-90.0° C.
$^1$H NMR δ 1.9-2.1 (br m, 2H), 3.4-3.5 (br m, 2H), 3.7 (s, 3H), 3.9-4.0 (m, 2H), 6.6-6.7 (m, 1H), 6.8-6.9 (m, 2H), 7.1 (m, 2H), 7.15-7.25 (br m, 1H), 7.6 (s, 1H), 7.8 (br s, 1H), 9.5 (s, 1H); MS m/z 291.1 (M+H), 223.2 (M-C$_3$H$_3$N$_2$.)

EXAMPLE 27

1-(3-(1H-imidazol-1-yl)propyl)-3-(4-ethoxyphenyl)thiourea melting point: 126.0-126.5° C.
$^1$H NMR δ 1.5 (br m, 3H), 1.9-2.0 (br m, 2H), 3.4-3.5 (br m, 2H), 3.9-4.0 (br m, 4H), 6.8-6.9 (m, 2H), 6.95 (s, 1H), 7.15-7.2 (m, 2H), 7.25 (s, 1H), 7.55-7.6 (br s, 1H), 7.8 (s, 1H), 9.3 (s, 1H); MS m/z 305.2 (M+H), 237.2 (M-C$_3$H$_3$N$_2$.)

EXAMPLE 33

1-(3-(1H-imidazol-1-yl)propyl)-3-(4-(methylthio)phenyl)thiourea melting point: 140.0-140.5° C.
$^1$H NMR δ 1.8-2.05 (br m, 2H), 2.5 (s, 3H), 3.3-3.5 (br m, 2H), 3.9-4.1 (m, 2H), 6.9 (m, 1H), 7.1-7.3 (br m, 5H), 7.6 (s, 1H), 7.75 (br s, 1H), 9.4 (s, 1H); MS m/z 307.2 (M+H), 239.2 (M-C$_3$H$_3$N$_2$.)

EXAMPLE 42

1-(3-(1H-imidazol-1-yl)propyl)-3-(4-nitrophenyl)thiourea melting point: 165.0. 166.0° C.
$^1$H NMR δ 1.9-2.05 (m, 2H), 3.3-3.5 (br d, 2H), 3.95-4.05 (m, 2H), 6.85 (d, 1H), 7.15 (d, 1H), 7.6 (d, 1H), 7.7 (m, 2H), 8.1 (m, 2H), 8.3 (br s, 1H), 10.1 (br s, 1H); MS m/z 306.2 (M+H), 237.9 (M-C$_3$H$_3$N$_2$.)

EXAMPLE 50

1-(3-(1H-imidazol-1-yl)propyl)-3-(4-(dimethylamino)phenyl)thiourea melting point: 146.5-147.0° C.
$^1$H NMR δ 1.9-2.0 (m, 2H), 2.9 (s, 6H), 3.4 (m, 2H), 3.9-4.0 (m, 2H), 6.7 (m, 2H), 6.9 (s, 1H), 7.05-7.1 (m, 2H), 7.15 (s, 1H), 7.4 (br s, 1H), 7.6 (s, 1H), 9.2 (s, 1H); MS m/z 304.2 (M+H), 236.0 (M-$C_3H_3N_2$.)

EXAMPLE 102

1-(3-(1H-imidazol-1-yl)propyl)-3-(3,4-dimethoxyphenyl)urea melting point: 114.5-115.0° C.
$^1$H NMR δ 1.7-1.9 (m, 2H), 2.9-3.1 (m, 2H), 3.7 (2s, 6H), 3.9-4.0 (m, 2H), 6.1 (t, 1H), 6.7 (s, 2H), 6.8 (s, 1H), 7.15 (d, 2H), 7.6 (s, 1H), 8.2 (s, 1H); MS m/z 321.2 (M+H), 253.3 (M-$C_3H_3N_2$.)

EXAMPLE 106

1-((S)-3-(1H-imidazol-1-yl)-2-methylpropyl)-3-(3,4-dimethoxyphenyl)-thiourea melting point: 150.5-151.5° C.
$^1$H NMR δ 0.9 (d, 3H), 2.3-2.4 (m, 2H), 2.5 (s, 1H), 3.7 (d, 6H), 4.0-4.1 (br m, 1H), 4.15-4.25 (br m, 1H), 6.75-6.8 (m, 1H), 6.85 (m, 1H), 6.9-7.0 (m, 1H), 7.65 (s, 1 H), 7.75 (s, 2H), 9.1 (s, 1H), 9.5 (s, 1H); MS m/z 335.6 (M+H), 267.1 (M-$C_3H_3N_2$.)

EXAMPLE 107

1-((R)-3-(1H-imidazol-1-yl)-2-methylpropyl)-3-(3,4-dimethoxyphenyl)-thiourea melting point: 155.0-157.5° C.
$^1$H NMR δ 0.9 (d, 3H), 2.3-2.4 (m, 2H), 2.5 (s, 1H), 3.7 (d, 6H), 4.0-4.1 (br m, 1H), 4.15-4.25 (br m, 1H), 6.75-6.8 (m, 1H), 6.85 (m, 1H), 6.9-7.0 (m, 1H), 7.65 (s, 1H), 7.75 (s, 2H), 9.1 (s, 1H), 9.5 (s, 1H); MS m/z 335.4 (M+H), 267.2 (M-$C_3H_3N_2$.)

EXAMPLE 109

1-((1-((1H-imidazol-1-yl)methyl)cyclopropyl)methyl)-3-(3,4-dimethoxy-phenyl)thiourea melting point: 166.5-168.5° C.
$^1$H NMR δ 0.7-0.8 (br m, 2H), 1.85-1.9 (m, 1H), 2.15-2.2 (m, 1H), 2.2-2.3 (m, 1H), 3.4-3.5 (m, 1H), 3.7 (d, 6H), 4.2 (s, 1H), 4.95 (s, 1H), 6.75-6.8 (br m, 1H), 6.85-6.9 (br m, 1H), 7.0 (s, 1H), 7.5 (m, 1H), 7.6 (m, 1H), 7.7 (s, 0.5H), 7.8 (s, 0.5H), 8.85 (s, 0.5 H), 9.1 (s, 0.5H), 9.35 (s, 0.5H), 9.45 (s, 0.5H); MS m/z 347.2 (M+H), 279.2 (M-$C_3H_3N_2$.), 137.5 (M-$C_9H_{13}N_4S$.)

EXAMPLE 110

N-(3-(1H-imidazol-1-yl)propyl)benzo[d]thiazol-2-amine $^1$H NMR δ 1.95-2.15 (m, 2H), 3.25-3.35 (m, 2H), 4.0-4.1 (t, 2H), 6.9 (s, 1H), 6.95-7.05 (t, 1H), 7.15-7.2 (m, 2H), 7.35-7.4 (d, 1H), 7.60-7.70 (m, 2H), 8.0-8.1 (br s, 1H); MS m/z 259.4 (M+H), 191.3 (M-$C_3H_3N_2$.)

EXAMPLE 111

N-(3-(1H-imidazol-1-yl)propyl)-6-chlorobenzo[d]thiazol-2-amine $^1$H NMR δ 1.95-2.15 (m, 2H), 3.25-3.35 (m, 2H), 4.0-4.1 (t, 2H), 6.9 (s, 1H), 7.1-7.2 (d, 2H), 7.3-7.4 (d, 1H), 7.65 (s, 1H), 7.8 (s, 1H), 8.2 (s, 1H); MS m/z 293.3 (M+H), 225.3 (M-$C_3H_3N_2$.)

EXAMPLE 112

N-(3-(1H-imidazol-1-yl)propyl)-6-methoxybenzo[d]thiazol-2-amine $^1$H NMR δ 1.9-2.05 (m, 2H), 3.2-3.3 (m, 2H), 3.7 (s, 3H), 4.0-4.1 (t, 2H), 6.7-6.8 (d, 1H), 6.9 (s, 1H), 7.15-7.2 (s, 1H), 7.2-7.3 (m, 2H), 7.65 (s, 1H), 7.8 (s, 1H); MS m/z 289.1 (M+H), 221.4 (M-$C_3H_3N_2$.)

EXAMPLE 115

(R)—N-(3-(1H-imidazol-1-yl)propyl)-2-phenylpropanethioamide melting point: 82.0-82.5° C.
$^1$H NMR δ 1.4-1.55 (d, 3H), 1.9-2.0 (m, 2H), 3.4-3.5 (m, 2H), 3.85-3.95 (m, 2H), 4.0-4.1 (q, 1H), 6.8-6.9 (s, 1H), 7.1 (s, 1H), 7.15-7.2 (m, 1H), 7.2-7.3 (m, 2H), 7.35-7.4 (m, 2H), 7.55 (s, 1H), 10.1 (s, 1H); MS m/z 274.4 (M+H), 206.3 (M-$C_3H_3N_2$.)

EXAMPLE 116

(S)—N-(3-(1H-imidazol-1-yl)propyl)-2-phenylpropanethioamide melting point: 82.5-83.5° C.
$^1$H NMR δ 1.4-1.55 (d, 3H), 1.9-2.0 (m, 2H), 3.4-3.5 (m, 2H), 3.85-3.95 (m, 2H), 4.0-4.1 (q, 1H), 6.8-6.9 (s, 1H), 7.1 (s, 1H), 7.15-7.2 (m, 1H), 7.2-7.3 (m, 2H), 7.35-7.4 (m, 2H), 7.55 (s, 1H), 10.1 (s, 1H); MS m/z 274.4 (M+H), 206.3 (M-$C_3H_3N_2$.)

EXAMPLE 121

N-(3-(1H-imidazol-1-yl)propyl)-1-(4-chlorophenyl)cyclobutanecarbo-thioamide melting point: 137.5-139.0° C.
$^1$H NMR δ 1.55-1.75 (br m, 2H), 1.85-1.95 (br m, 2H), 2.4-2.5 (br m, 2H), 2.7-2.85 (br m, 2H), 3.3-3.5 (br m, 2H), 3.8 (m, 2H), 6.9 (s, 1H), 7.0 (s, 1H), 7.3 (m, 2H), 7.45 (s, 1H), 7.5 (m, 2H), 9.6 (t, 1H); MS m/z 334.3 (M+H), 266.1 (M-$C_3H_3N_2$.)

EXAMPLE 122

N-(3-(1H-imidazol-1-yl)propyl)-1-(4-chlorophenyl)cyclopentanecarbo-thioamide melting point: 140.0-141.0° C.
$^1$H NMR δ 1.5-1.65 (br m, 4H), 1.8-1.9 (m, 2H), 2.0-2.1 (m, 2H), 2.6 (m, 2H), 3.4-3.5 (m, 2H), 3.7-3.8 (m, 2H), 6.85

(s, 1H), 7.0 (s, 1H), 7.35 (m, 2H), 7.4 (m, 2H), 7.5 (s, 1H), 9.4 (t, 1H); MS m/z 348.2 (M+H), 280.2 (M-$C_3H_3N_2$.)

EXAMPLE 123

N-(3-(1H-imidazol-1-yl)propyl)-1-(4-methoxyphenyl)cyclohexanecarbo-thioamide melting point: 162.5-164.0° C.
$^1$H NMR δ 1.2-1.3 (m, 1H), 1.35-1.5 (br m, 5H), 1.85-2.0 (br m, 4H), 2.4-2.6 (br m, 2H), 3.4-3.5 (m, 2H), 3.7 (s, 3H), 3.8 (m, 2H), 6.8 (m, 3H), 7.0 (s, 1H), 7.3 (m, 2H), 7.5 (s, 1H), 9.2 (t, 1H); MS m/z 358.3 (M+H), 290.3 (M-$C_3H_3N_2$.)

EXAMPLE 124

N-(3-(1H-imidazol-1-yl)propyl)-1-(4-methoxyphenyl)cyclopropanecarbothioamide melting point: 129.0-129.5° C.
$^1$H NMR δ 1.0-1.1 (m, 2H), 1.5-1.6 (m, 2H), 1.9-2.0 (br m, 2H), 3.4-3.5 (m, 2H), 3.7 (s, 3H), 3.9 (m, 2H), 6.9 (m, 3H), 7.1 (s, 1H), 7.2-7.3 (m, 2H), 7.6 (s, 1H), 8.9 (br s, 1H); MS m/z 316.0 (M+H), 248.4 (M-$C_3H_3N_2$.)

EXAMPLE 134

5-(1H-imidazol-1-yl)-N-(3,4-dimethoxyphenyl)pentanethioamide melting point: 128.0-128.5° C.
$^1$H NMR δ 1.65-1.70 (m, 2H), 1.75-1.80 (m, 2H), 2.7-2.75 (m, 2H), 3.7 (s, 3H), 3.75 (s, 3H), 4.0-4.05 (t, 2H), 6.9-7.0 (m, 2H), 7.2 (s, 1H), 7.3 (d, 1H), 7.5 (s, 1H), 7.75 (s, 1H), 11.0 (s, 1H); MS m/z 320.2 (M+H), 252.2 (M-$C_3H_3N_2$.)

EXAMPLE 136

1-(2-(1H-imidazol-1-yl)ethyl)-3-(3,4-dimethoxyphenyl)thiourea melting point: 157.5-159.0° C.
$^1$H NMR δ 3.7 (2 s, 6H), 3.8 (m, 2H), 4.2 (m, 2H), 6.7 (m, 1H), 6.85 (m, 1H), 6.9 (m, 2H), 7.15 (s, 1H), 7.5 (br s, 1H), 7.6 (s, 1H), 9.5 (s, 1H); MS m/z 307.2 (M+H), 239.1 (M-$C_3H_3N_2$.)

ABBREVIATIONS

° C. degree Celsius
A, Ala alanine
Aβ amyloid-β peptide
ABri amyloid peptide in familial british dementia
AC adenylyl cyclase
ADan amyloid peptide in familial danish dementia
AIM absent in melanoma
AMC amino methyl coumarine
as antisense
Asp aspartate
βNA beta-naphtylamine
BA butyric acid
bp basepair
BSA bovine serum albumin
C cysteine
CAT chloramphenicol acetyl transferase
cAMP cyclic adenosine monophsphate
CCL2 MCP-1, monocyte chemoattractant protein 1
CCL7 MCP-3, monocyte chemoattractant protein 3
CCL8 MCP-2, monocyte chemoattractant protein 2
CCL13 MCP-4, monocyte chemoattractant protein 4
cDNA copy-DNA
C-His C-terminal histidine tag
CIDP Chronic inflammatory demyelinizing polyradiculoneuropathy
Cl chlorine
CSF cerebor-spinal fluid (liquor cerebrospinalis)
C-terminus carboxy-terminus
CTL cytotoxic T-lymphocyte
CV column volume
d diameter
Da Dalton
DMSO dimethyl sulphoxide
DNA desoxyribonucleic acid
E enzyme
EBV Epstein Barr virus
ECL enterochromaffin-like
E. coli Escherichia coli
EC glutamyl cyclase
ED effective dose
EGFP enhanced green fluorescent protein
ES enzyme-substrate complex
FPP fertilization promoting peptide
FTC follicular thyroid carcinoma
g relative centrifugal force
GBS Guillain-Barré syndrome
GF gel filtration
Gln glutamine
Glu glutamic acid
GnRH gonadotropin-releasing hormone (gonadoliberin)
GST glutathion S-transferase
H hydrogen
h human, hour
HGF hepatocyte growth factor
HIC hydrophobic interaction chromatography
HIF1a hypoxia induced factor 1a
His histidine
HPLC high performance liquid chromatography
I inhibitor, isoleucine
ID identification
IMAC immobilized metal affinity chromatography
IPTG Isopropyl-β-D-thiogalactopyranosid
K potassium
k constant
kDA kilo-dalton
$k_i$ inhibitor constant
KLH Keyhole limpet hemocyanin
l length
LB Luria-Bertani
LD lethal dose
LPS lipopolysaccharide
M molar
μl micro-liter
μM micro-molar
MAGEA melanoma antigen family A
MAGEB melanoma antigen family B
Maldi-tof matrix assisted laser desorption/ionization time-of-flight
MART 1 melanoma antigen recognized by T-cells 1
max maximum
MCL-1 myeloid cell leukemia 1
Met methionine
min minutes
mM milli-molar
MS Multiple Sclerosis mRNA messenger-RNA
N asparagine
Na sodium
NADH nicotinamide adenine dinucleotide
nm nanometer
NO number
NT Neurotensin
N-terminus amino terminus
O oxygen
OD optical density
P product, phosphor
PBS phosphate-buffered saline
PCR polymerase chain reaction
pGlu pyroglutamic acid
pH pondus hydrogenii
Pro proline
PTC papillary thyroid carcinoma
Pyr pyroglutamate
QC glutaminyl cyclase (glutaminyl-peptide cyclotransferase)
qPCR quantitative real-time polymerase chain reaction
QPCTL glutaminyl-peptide cyclotransferase-like
RNA ribonucleic acid
RT reverse transcription; reverse transcriptase
S substrate
s sense
SAGE serial analysis of gene expression
SDS sodium dodecly sulfate
SDS-PAGE SDS-polyacrylamid gelelectrophoresis
SGAP *Streptomyces griseus* amino peptidase
SEQ sequence
SNP single nucleotide polymorphism
taa tumor-associated antigen
TGF-β transforming growth factor beta
TNF-α tumor necrosis factor alpha
TRH thyreotropin-releasing hormone (thyreoliberin)
TSH thyroidea-stimulating-hormone
TYR tyrosinase
TYRP tyrosinase related protein
U unit
UTC undifferentiated thyroid carcinoma
UV ultraviolet
V velocity
VpAP *Vibrio proteolytica* amino peptidase
YSS yeast signal sequence
Zn zinc

---

What is claimed is:

1. A method of screening for a compound capable of inhibiting an enzymatic activity, comprising:
   incubating at least a first polypeptide and a suitable substrate for the at least a first polypeptide in the presence of at least one test compound or salt thereof;
   measuring an enzymatic activity of the at least a first polypeptide;
   comparing said activity with enzymatic activity determined in the absence of the at least one test compound or salt thereof; and
   selecting a test compound that reduces the enzymatic activity of the at least a first polypeptide;
   wherein the at least a first polypeptide comprises:
   (a) an amino acid sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 21, and SEQ ID NO: 22, or an amino acid sequence having at least about 95% sequence identity thereto and having glutaminyl cyclase activity;
   (b) an amino acid sequence encoded by a nucleic acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 19, and SEQ ID NO: 20; or
   (c) a fragment of (a) or (b) wherein said fragment is immunologically reactive and has glutaminyl cyclase activity.

2. The method of claim 1, wherein the at least a first polypeptide comprises an amino acid sequence having at least about 95% sequence identity to an amino acid sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 21, or SEQ ID NO: 22 and has glutaminyl cyclase activity.

3. The method of claim 1 wherein the enzymatic activity is glutaminyl cyclase activity.

4. The method of claim 3 further comprising:
   incubating a polypeptide comprising SEQ ID NO: 10 (wild type human glutaminyl cyclase) and a suitable substrate for wild type human glutaminyl cyclase in the presence of the at least one test compound or salt thereof;
   measuring the glutaminyl cyclase activity of the polypeptide comprising SEQ ID NO: 10; and
   selecting a test compound that reduces the glutaminyl cyclase activity of the at least a first polypeptide but does not reduce the glutaminyl cyclase activity of the polypeptide comprising SEQ ID NO: 10.

5. The method of claim 1 wherein the at least a first polypeptide comprises:
   the amino acid sequence of SEQ ID NO: 21, or an amino acid sequence having at least about 95% sequence identity to SEQ ID NO: 21 and having glutaminyl cyclase activity;
   the amino acid sequence encoded by a nucleic acid sequence of SEQ ID NO: 19, or at least about 95% sequence identity to SEQ ID NO: 19 and having glutaminyl cyclase activity; or
   a fragment thereof wherein said fragment is immunologically reactive and has glutaminyl cyclase activity.

6. The method of claim 1 wherein the at least a first polypeptide comprises:
   the amino acid sequence of SEQ ID NO: 21;
   the amino acid sequence having at least about 95% sequence identity to SEQ ID NO: 21 and having glutaminyl cyclase activity; or
   a fragment thereof wherein said fragment is immunologically reactive and has glutaminyl cyclase activity.

7. The method of claim 6 wherein the at least a first polypeptide comprises a fragment of SEQ ID NO: 21, said fragment comprises amino acid residues 11 through 392 of SEQ ID NO: 21, and said fragment is immunologically reactive and has glutaminyl cyclase activity; or an amino acid sequence having at least about 95% sequence identity to said fragment and having glutaminyl cyclase activity.

8. The method of claim 1 wherein the at least a first polypeptide comprises:
   the amino acid sequence of SEQ ID NO: 21;
   the amino acid sequence having at least about 99% sequence identity to SEQ ID NO: 21 and having glutaminyl cyclase activity; or
   a fragment thereof wherein said fragment is immunologically reactive and has glutaminyl cyclase activity.

9. The method of claim 1 wherein the at least a first polypeptide is glycosylated.

10. The method of claim 1 wherein the at least a first polypeptide is free in solution; affixed to a solid support; borne on a cell surface; or located intracellularly.

11. The method of claim 1 wherein measuring the enzymatic activity of the at least a first polypeptide comprises measuring glutaminyl cyclase activity of the at least a first polypeptide.

12. The method of claim 1 wherein selecting a test compound that reduces the enzymatic activity of the at least a first polypeptide comprises selecting a test compound with a Ki for glutaminyl cyclase activity inhibition of 10 μM or less.

13. The method of claim 1 wherein selecting a test compound that reduces the enzymatic activity of the at least a first polypeptide comprises selecting a test compound with a Ki for glutaminyl cyclase activity inhibition of 1 µM or less.

14. The method of claim 1 wherein selecting a test compound that reduces the enzymatic activity of the at least a first polypeptide comprises selecting a test compound with a Ki for glutaminyl cyclase activity inhibition of 0.1 µM or less.

15. The method of claim 1 wherein selecting a test compound that reduces the enzymatic activity of the at least a first polypeptide comprises selecting a test compound with a Ki for glutaminyl cyclase activity inhibition of 0.01 µM or less.

16. The method of claim 1, wherein the suitable substrate comprises Glu$^1$-A Bri (SEQ ID NO: 33), Glu$^1$-ADan (SEQ ID NO: 34), Gln$^1$-Gastrin 17 (SEQ ID NO: 35), Gln$^1$-Gastrin 34 (SEQ ID NO: 36), Gln$^1$-neurotensin (SEQ ID NO: 41), Gln$^1$-fertilization promoting peptide (FPP) (QEP amino acid sequence), Gln$^1$-thyrotrophin releasing hormone (TRH) (QHP amino acid sequence), Gln$^1$-CCL2 (SEQ ID NO: 45), Gln$^1$-CCL7 (SEQ ID NO: 48), Gln$^1$-CCL8 (SEQ ID NO: 44), Gln$^1$-CCL16 (SEQ ID NO: 43), Gln$^1$-CCL18 (SEQ ID NO: 46), Gln$^1$-fractalkine (SEQ ID NO: 47), Gln$^1$-orexin A (SEQ ID NO: 49) or peptide QYNAD (SEQ ID NO: 51).

17. The method of claim 1, wherein measuring an enzymatic activity of the at least a first polypeptide comprises a fluorometric assay.

18. The method of claim 1, wherein measuring an enzymatic activity of the at least a first polypeptide comprises a mass spectrophotometric assay.

19. The method of claim 1, wherein measuring an enzymatic activity of the at least a first polypeptide occurs at a pH of 7 to 8.

* * * * *